(12) United States Patent
Guerry et al.

(10) Patent No.: US 10,202,368 B2
(45) Date of Patent: Feb. 12, 2019

(54) CXCR7 RECEPTOR MODULATORS

(71) Applicant: IDORSIA PHARMACEUTICALS LTD, Allschwil (CH)

(72) Inventors: Philippe Guerry, Allschwil (CH); Francois Lehembre, Allschwil (CH); Julien Pothier, Allschwil (CH); Hervé Siendt, Allschwil (CH)

(73) Assignee: IDORSIA PHARMACEUTICALS LTD., Allschwil (CH)

( * ) Notice: Subject to any disclaimer, the term of this patent is extended or adjusted under 35 U.S.C. 154(b) by 0 days.

(21) Appl. No.: 15/526,983

(22) PCT Filed: Nov. 30, 2015

(86) PCT No.: PCT/EP2015/078058
§ 371 (c)(1),
(2) Date: May 15, 2017

(87) PCT Pub. No.: WO2016/087370
PCT Pub. Date: Jun. 9, 2016

(65) Prior Publication Data
US 2017/0327493 A1 Nov. 16, 2017

(30) Foreign Application Priority Data
Dec. 1, 2014 (WO) .................. PCT/EP2014/076126

(51) Int. Cl.
| | | |
|---|---|---|
| A61K 31/553 | (2006.01) |
| C07D 267/14 | (2006.01) |
| C07D 401/12 | (2006.01) |
| C07D 401/14 | (2006.01) |
| C07D 403/12 | (2006.01) |
| C07D 405/12 | (2006.01) |
| C07D 413/12 | (2006.01) |
| C07D 413/14 | (2006.01) |
| C07D 417/12 | (2006.01) |
| C07D 223/16 | (2006.01) |
| C07D 243/14 | (2006.01) |
| A61K 45/06 | (2006.01) |
| C07D 405/14 | (2006.01) |

(52) U.S. Cl.
CPC .......... *C07D 417/12* (2013.01); *A61K 31/553* (2013.01); *A61K 45/06* (2013.01); *C07D 223/16* (2013.01); *C07D 243/14* (2013.01); *C07D 267/14* (2013.01); *C07D 405/12* (2013.01); *C07D 405/14* (2013.01)

(58) Field of Classification Search
CPC .. A61K 31/553; C07D 267/14; C07D 401/12; C07D 401/14; C07D 403/12; C07D 405/12; C07D 413/12; C07D 413/14; C07D 417/12
USPC ................ 514/211.05, 211.09; 540/490, 552
See application file for complete search history.

(56) References Cited

U.S. PATENT DOCUMENTS

| | | | |
|---|---|---|---|
| 5,639,748 | A | 6/1997 | DeMarinis et al. |
| 9,428,456 | B2 | 8/2016 | Fretz et al. |
| 2005/0192272 | A1 | 9/2005 | Marshall |
| 2016/0107997 | A1 | 4/2016 | Fretz et al. |

FOREIGN PATENT DOCUMENTS

| | | |
|---|---|---|
| JP | 2002-371042 A | 12/2002 |
| WO | WO 99/42456 A2 | 8/1999 |
| WO | WO 02/46164 A1 | 6/2002 |
| WO | WO 2004/056705 A2 | 7/2004 |
| WO | WO 2007/059108 A2 | 5/2007 |
| WO | WO 2008/039420 A2 | 4/2008 |
| WO | WO 2008/051547 A1 | 5/2008 |
| WO | WO 2009/076404 A1 | 6/2009 |
| WO | WO 2009/080725 A1 | 7/2009 |
| WO | WO 2014/191929 A1 | 12/2014 |
| WO | WO 2013/190508 A2 | 12/2015 |

OTHER PUBLICATIONS

Brown,. "Inhibiting Vasculogenesis After Radiation: A New Paradigm to Improve Local Control by Radiotherapy," Seminars in Radiation Oncol., vol. 23(4), pp. 261-287.
Burns et al., "A novel Chemokine receptor for SDF-1 and I-TAC involved in cell survival, cell adhesion, and tumor development," Journal of Experimental and Clinical Cancer Research, 2006, vol. 203(9), pp. 2201-2213.
Calatozzolo et al., "Expression of the new CXCL12 receptor, CXCR7, in gliomas," Cancer Biology and Therapy, 2011, vol. 11(2), pp. 1-12.

(Continued)

*Primary Examiner* — Brenda L Coleman
(74) *Attorney, Agent, or Firm* — Arent Fox LLP

(57) ABSTRACT

The present invention relates to derivatives of formula (I)

Formula (I)

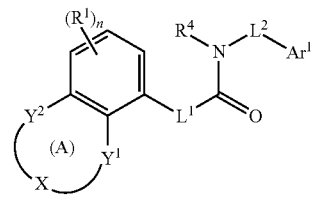

wherein $(R^1)_n$, ring (A), $Y^1$, $Y^2$, X, $R^4$, $L^1$, $L^2$, and $Ar^1$ are as described in the description, to their preparation, to pharmaceutically acceptable salts thereof, and to their use as pharmaceuticals, to pharmaceutical compositions containing one or more compounds of formula (I), and especially to their use as CXCR7 receptor modulators.

16 Claims, No Drawings

(56) References Cited

OTHER PUBLICATIONS

Cruz-Orengo et al., "CXCR7 influence leukocyte entry into the CNS parenchyma by controlling abluminal CXCL12 abundance during autoimmunity," Journal of Experimental Medicine, 2011, vol. 208(2), pp. 1-18.
Ding et al., "Divergent angiocrine signals from vascular ninche balance liver regeneration and fibrosis," Nature, 2004, vol. 505(7481), pp. 97-102.
Duda et al., "CXCL12 (SDF1beta)—CXCR4/CXCR7 Pathway Inhibition: An Emerging sensitizer for Anti-Cancer Therapy?" Clin. Cancer Res., 2011, vol. 17(8), pp. 1-24.
Ebsworth et al., "The effect of the CXCR7 inhibitor CCX662 on survival in the ENU rat model of glioblastoma," J. Clin. Oncol., 2012, vol. 30, suppl., abstract e13580 (1 page).
Ebsworth et al., Neuro-Oncology, vol. 15, 2013, pp. iii37-iii6.
Greene et al., Protective Groups in Organic Synthesis, Wiley-Interscience, 1999, pp. 1-3.
Hattermann et al., "CXCL12 mediates apoptosis resistance in rat C6 glioma cells." Oncology Reports, vol. 27, 2012, pp. 1348-1352.
Hattermann et al., "The Chenmokine Receptor CXCR7 Is Highly Expressed in Human Glioma Cells and Mediates Antiapoptotic Effects," Caner Research, 2010, vol. 70(8), pp. 3299-3308.
Ikeda et al., Modulation of Circadian Glucocorticoid Oscillation via Adrenal Opiod-CXCR7 Signaling Alters Emotional Behavior, Cell 2013, vol. 155(6), pp. 1323-1336.
International Search Report and Written Opinion issued in International Patent Application No. PCT/EP2015/078058 dated Feb. 2, 2016 (9 pages).
Kioi et al., "Inhibition of vasculogenesis, but not angiogenesis, prevents the recurrence of glioblastoma after irradiation in mice," J. Clin. Invest, 2010, vol. 120(3), pp. 694-705.
Liu et al., Neuro-Oncology, vol. 15, 2013, pp. iii189-iii190, doi: 10.1093/neuonc/not188.
Liu et al., Neuro-Oncology, vol. 16, 2014, pp. 21-26, doi: 10.1093/neuonc/not149.
Miao et al., "CXCR7 (RDC1) promotes breast and lung tumor growth in vivo and is expressed on tumor-associated vasculature," PNAS, vol. 104 (40), Oct. 2007, pp. 15735-15740.
Naumann et al., "CXCR7 Functions as a scavenger for CXCL12 and CXCL11, " PLoS One, vol. 5(2), 2010, pp. 1-11.
Remington, The Science and Practice of Pharmacy, 21st Ed. 2005, Part 5, Pharmaceutical Manufacturing [published by Lippincott Williams & Wilkins] (5 pages).
Salmaggi et al., "CXCL12, CXCR4 and CXCR7 expression in brain metastases," Cancer Biology & Therapy, vol. 8, Sep. 2009, pp. 1-7.
Sartina et al., "Antagonism of CXCR7 attenuates chronic hypoxia-induced pulmonary hypertension," Pediatric Res., 2012, vol. 71(6), pp. 682-688.
Stahl et al., IUPAC, Handbook of Pharmaceutical Salts Properties, Selection, and Use, Wiley-VCH, 2008, pp. 329-350.
Sun et al., "CXCL12/CXCR4/CXCR7 Chemokine Axis and Cancer," Cancer Metastasis Rev. Dec. 2010, vol. 29(4), pp. 709-722.
Walters et al., "Inhibition of CXCR7 extends survival following irradiation of brain tumors in mice and rats," British Journal of Cancer, 2014, vol. 110, pp. 1179-1188.
Wang et al., "The Role of CXCR7/RDC1 as a Chemokine Receptor for CXCL12/SDF-1 in Prostate Cancer," The Journal of Biological Chemistry, vol. 283(7), Feb. 2008, pp. 4283-4294.
Watanabe et al., "Pathogenic Role of CXCR7 in Rheumatoid Arthritis, " Arthritis & Rheumatism, vol. 62(11), Nov. 2010, pp. 3211-3220.
Wouters et al., Pharmaceuticals Salts and Co-crystals, RSC Publishing, 2012, 10 pages.
Zheng et al., "Cherrokine receptor CXCR7 regulated the invasion, angiogenesis and tumor growth of human hepatocellular carcinoma cells," J. of Experimental & Clinical Cancer Research, 2010, vol. 29(31), pp. 1-14.

CXCR7 RECEPTOR MODULATORS

CROSS REFERENCE TO RELATED APPLICATION

This application is a 35 U.S.C. 371 National Phase of PCT Application No. PCT/EP2015/078058 filed Nov. 30, 2015 which claims priority to PCT Application No. PCT/EP2014/076126 filed Dec. 1, 2014, The disclosure of these prior applications are hereby incorporated in their entirety by reference.

The present invention relates to novel CXCR7 receptor modulators of formula (I) and their use as pharmaceuticals. The invention also concerns related aspects including processes for the preparation of the compounds, pharmaceutical compositions containing one or more compounds of formula (I), and their use as CXCR7 receptor modulators. The invention further relates to the compounds of formula (I) and their use as pharmaceuticals in combination with one or more therapeutic agents and/or radiotherapy in the treatment of cancers, especially in the treatment of malignant glioma, in particular glioblastoma multiforme.

Chemokine receptors are a group of G-protein coupled receptors (GPCRs) that bind peptidic chemokine ligands with high affinity. The predominant function of chemokine receptors is to guide leukocyte trafficking to lymphoid organs and tissues under resting conditions as well as during inflammation, but a role for certain chemokine receptors on non-hematopoietic cells and their progenitors has also been recognized.

Signaling networks and metabolic profiles of cancer cells differ in a microenvironment dependent manner. This is a major reason for lack of therapeutic response of tumors at certain organ sites and of tumor metastases in comparison to primary tumors. CXCL12 (alias stromal cell-derived factor 1, SDF-1; alias Pre-B cell growth stimulating factor, PBSF), a stroma-derived chemo-attractant, exerts anti-apoptotic effects, displays pro-angiogenic properties and plays a key role in seeding circulating tumor cells to metastatic sites. CXCL12 binds and activates two receptors, CXCR7 (alias ACKR3, alias RDC1, alias CMKOR1, alias GPR159) and CXCR4 (alias Fusin, alias Leukocyte-derived seven-trans-membrane-domain receptor; LESTR, alias D2S201E, alias seven-transmembrane-segment receptor, alias HM89, alias lipopolysaccharide-associated protein 3; lap3, alias LPS-associated protein 3).

The expression of the CXCL12 receptor CXCR7 correlates with diseases progression in cancer (among others in hormone refractory prostate cancer, in renal cell carcinoma, cervical cancer, papillary thyroid carcinoma, bladder cancer, Ewing's sarcoma, colorectal cancers, lung cancer, meningiomas, MALT lymphoma and in tumors in the brain). CXCR7 is also expressed in hepatocellular carcinoma, breast cancer, osteosarcoma, leukemia, gallbladder cancers, alveolar rhabdomyosarcoma, myeloma, non-small cell lung cancer, oral cancers and pancreas cancer (for review see Sun et al.; CXCL12/CXCR4/CXCR7 Chemokine Axis and Cancer Progression; Cancer Metastasis Rev. 2010, 29(4), 709-722).

CXCR7 silencing and targeting have been shown to reduce tumor growth in experimental disease models as single agents, or in combination with cytotoxic therapies [Wang et al.; The role of CXCR7/RDC1 as a chemokine Receptor for CXCL12/SDF-1 in prostate cancer; Journal of Biochemical Chemistry 2008, 293(7), 4283-4294; Ebsworth et al.; The effect of the CXCR7 inhibitor CCX662 on survival in the ENU rat model of gliobastoma; J Clin Oncol 2012, 30, (suppl; abstr e13580); Zheng et al.; Chemokine receptor CXCR7 regulates the invasion, angiogenesis and tumor growth of human hepatocellular carcinoma cells; Journal of Experimental and Clinical Cancer Research. 2010, 29: 31; Miao et al.; CXCR7 (RDC1) promotes breast and lung tumor growth in vivo and is expressed on tumor associated vasculature; PNAS 2007, 104(40), 15735-15740; Burns et al.; A novel chemokine receptor for SDF-1 and I-TAC involved in cell survival, cell adhesion, and tumor development; Journal of Experimental Medicine 2006, 203 (9), 2201-2213; Walters et al.; "Inhibition of CXCR7 extends survival following irradiation of brain tumours in mice and rats", British Journal of Cancer (2014), 1-10|doi: 10.1038/bjc.2013.830], including among others hepatocellular carcinoma, Kaposi's sarcoma, T cell leukemia, lymphoma, lung carcinomas, breast cancer, rhabdomyosarcoma, prostate cancer, pancreatic cancer and glioblastoma; to alter tumor-associated blood vessels; to reduce tumor cell seeding; to reduce rheumatoid arthritis clinical scores; to decrease the clinical severity of experimental autoimmune encephalomyelitis; to attenuate chronic hypoxia induced pulmonary hypertension, to induce anxiolytic-like behaviour, to trigger an angiocrine response to initiate liver regeneration and resolve fibrosis, and to improve beneficial effects of mesenchymal stem cells based therapies for renal ischemia/reperfusion injury [Cruz-Orengo et al.; CXCR7 influences leukocyte entry into the CNS parenchyma by controlling abluminal CXCL12 abundance during autoimmunity; Journal of Experimental Medicine 2011, 208(2), 327-339; Sartina et al.; Antagonism of CXCR7 attenuates chronic hypoxia-induced pulmonary hypertension; Pediatric Research 2012, 71(6), 682-688; Watanabe et al.; Pathogenic role of CXCR7 in rheumatoid arthritis; Arthritis and Rheumatism 2010, 62(11), 3211-3220; Ding et al, Divergent angiocrine signals from vascular niche balance liver regeneration and fibrosis; Nature 2014; 505(7481):97-102; Ikeda et al, Modulation of Circadian Glucocorticoid Oscillation via Adrenal Opioid-CXCR7 Signaling Alters Emotional Behavior; Cell 2013, 155(6):1323-36].

Recent studies have provided increasing evidence that activation of the CXCL12 pathway is a potential mechanism of tumor resistance to both conventional therapies and biological agents via multiple complementary actions: (i) by directly promoting cancer cell survival, invasion, and the cancer stem and/or tumor-initiating cell phenotype; (ii) by recruiting "distal stroma" (i.e., myeloid bone marrow-derived cells) to indirectly facilitate tumor recurrence and metastasis; and (iii) by promoting angiogenesis directly or in a paracrine manner. Duda D G et al (Clin Cancer Res; 2011, 17(8); 2074-80) recently discussed preclinical and clinical data that support the potential use of anti-CXCL12 agents including CXCR7 modulators as sensitizers to currently available therapies in cancer treatments.

Specifically, the potential role of CXCR7 in brain tumors, malignant glioma and in glioblastoma multiforme is known from the literature. Modulators of the CXCL12 pathway including CXCR7 modulators have been mentioned as potential therapeutic agents for treating brain cancer in combination with chemotherapeutic agents or radiotherapy. For example, Hattermann et al (Cancer research, 2010, 70 (8):3299-3308) teach that CXCL12 "stimulation prevented camptothecin- and temozolomide-induced apoptosis and that a CXCR7 antagonist reduced the antiapoptotic effect of CXCL12". The authors concluded that "CXCR7 is a functional receptor for CXCL12 in astrocytomas/glioblastomas and mediates resistance to drug-induced apoptosis". Furthermore, Hattermann et al (Oncology reports, 27: 1348-

1352, 2012) teach that "CXCL12 abrogates the antiproliferative effect of temozolomide". The authors also teach that this effect could be almost completely abolished by a CXCR7 specific antagonist, "indicating that the anti-apoptotic effect of CXCL12 is mainly mediated via CXCR7". Ebsworth et al (Neuro Oncol (2013) 15 (suppl 3):iii37-iii61. ET-023) teach that a CXCR7 antagonist significantly prolongs survival when administered in combination with radiotherapy in a rat model of glioblastoma. This finding is supported by other studies (e.g. Ebsworth et al (J Clin Oncol 30, 2012, suppl; abstr e13580; Walters et al.; British Journal of Cancer 2014, 1-10 I doi: 10.1038/bjc.2013.830) disclosing that in vivo inhibition of CXCR7 in concert with radiotherapy results in a significant extension of survival time in another rat model of glioblastoma. In addition, Liu S C et al (Neuro-Oncology 2014; 16(1):21-28) teach that inhibition of CXCL12 after irradiation inhibits tumor recurrence in autochtonous brain tumors in rats. Liu S C et al (Neuro Oncol (2013) 15 (suppl 3):iii189-iii190. RB-002. doi: 10.1093/neuonc/not188) also teach that inhibition of CXCL12 in a brain metastasis model after irradiation produced a marked inhibition of tumor growth and prolongation of lifespan compared to irradiation alone. Calatozzolo C et al (Cancer Biology and Therapy 2011, 11:2, 1-12) teach in in vitro experiments that CXCR7 antagonists showed complete inhibition of glioma proliferation.

CXCR7 is also reported to be expressed in brain metastases (Salmaggi et al, Cancer Biology and therapy 2009, 8:17, 1-7). The authors concluded that the CXCL12/CXCR4/CXCR7 pathway could be an interesting target for further researches investigating the role of these molecules in invasion and proliferation of metastatic cells.

Furthermore, CXCL12 depletion sensitizes cancer cells to chemotherapy in vivo and CXCL12 treatment blocks colonic carcinoma metastasis. CXCR7 is also a receptor for CXCL11 (alias small inducible cytokine subfamily b, member 11; scyb11, alias interferon-gamma-inducible protein 9; ip9, alias small inducible cytokine subfamily b, member 9b; scyb9b) and therefore modulators of CXCR7 activity can also be used in indications with CXCL11-associated pathology. CXCR7 functions also as a receptor for the opioid peptide BAM22 and its related peptides (peptide E, peptides BAM12, BAM14, BAM18) and therefore modulators of CXCR7 activity possibly may also be used in indications with opioid peptides associated pathologies (Ikeda et al Cell 155, 1323-1336, Dec. 5, 2013). CXCR7 has also been shown to function as a scavenger receptor for CXCL12. Thus, CXCR7 targeting has been shown to alter CXCL12 local concentration leading to a deregulation of the CXCL12 concentration gradient. The biological properties of CXCR7 modulators thus include, but are not limited to, any physiological function and/or cellular function linked and/or controlled by CXCL12 (Duda et al.; CXCL12 (SDF1alpha)-CXCR4/CXCR7 pathway inhibition: an emerging sensitizer for anticancer therapies?; Clin. Cancer Res. 2011 17(8) 2074-2080; Naumann et al.; CXCR7 function as a scavenger for CXCL12 and CXCL11; Plos One 2010, 5(2) e9175).

CXCR7 modulation (using small molecules antagonizing CXCL12 binding on CXCR7, or anti-CXCR7 antibodies, or RNA interference techniques to silence CXCR7 expression), CXCL12 modulation of activity/expression, or CXCR7 expression is, thus, associated with diseases and disorders including cancer, notably carcinomas, leukemias, adenocarcinomas, malignant gliomas, glioblastoma multiforme, brain metastases, multiple myelomas, renal clear cell carcinoma, prostate cancer, pancreatic adenocarcinoma, melanoma, metastatic melanoma, rhabdomyosarcoma, hepatocellular carcinoma, colon tumors, breast cancer, non-small cell lung cancer, oral tumors, adult T-cell leukemia, gallbladder cancer, brain tumors, esophageal cancer, Ewing's sarcoma, bladder cancer, meningiomas, lymphoma, viral-induced tumors, Burkitt's lymphoma, Hodgkin's lymphoma, MALT lymphoma, papillary thyroid carcinoma, cervical cancer, osteosarcoma, lymphoproliferative disease, Kaposi's sarcoma, and choriocarcinoma; primary intra-ocular B-cell lymphoma; inflammation; multiple sclerosis; renal allograft rejection; rheumatoid arthritis; auto-immune encephalomyelitis; demyelinating diseases; systemic lupus erythematosus; osteoarthritis; pulmonary vascular diseases; acute renal failure; ischemia; acute coronary syndrome; inflammatory bowel disease; injured central nervous system; HSCs transplantation; cerebral ischemia; hypertension; pulmonary hypertension; Shiga-toxin-associated heomolytic uremic syndrome; preeclampsia; chronic rhinosinusitis; HIV/AIDS; atherosclerosis; acute lung injury; asthma; liver fibrosis, cirrhosis; stress-related disorders; proliferative diabetic retinopathy; West Nile virus encephalitis; vascular injury; pulmonary fibrosis; diseases involving opioid peptides; and diseases involving CXCR7 and/or CXCL12 and/or CXCL11 mediated metastasis, chemotaxis, cell adhesion, trans-endothelial migration, cell proliferation and/or survival.

WO2009/076404 discloses certain carboxamide compounds comprising a bicyclic ring, which are antagonists of the chemokine CCR2 receptor. WO1999/042456 and WO2002/046164 disclose certain tetrahydroisoquinoline compounds which are active as positive AMPA receptor modulators, respectively, as estrogen receptor-β ligands.

The present invention provides novel fused seven-membered ring derivatives of formula (I) which are modulators of the CXCR7 receptor, and are useful for the prevention or treatment of diseases which respond to the activation of the CXCL12 receptors and/or CXCL11 receptors, especially cancer. In the prevention or treatment of cancers the compounds of formula (I) may also be used in combination with anti-neoplastic therapeutic agents and/or radiotherapy.

1) A first aspect of the invention relates to compounds of the formula (I)

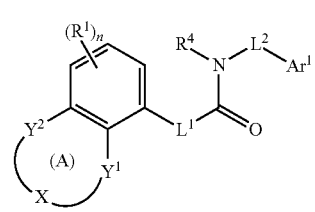

Formula (I)

wherein ring (A) represents a seven-membered ring, wherein

Y$^1$ and Y$^2$ both represent CH$_2$; and

X represents —CH$_2$—NR$^5$—CH$_2$—, or

X represents *—CO—NR$^5$—CH$_2$—, or

X represents *—CH$_2$—NR$^5$—CO—; or

Y$^1$ represents O, CH$_2$, or NR$^{Y1}$ wherein R$^{Y1}$ represents hydrogen or (C$_{1-3}$)alkyl;

Y$^2$ represents CH$_2$ or CO; and

X represents *—CH$_2$—CH$_2$—NR$^5$—; or

X represents *—CH$_2$—CO—NR$^5$—; or $Y^1$ represents $CH_2$ or $CO$;

$Y^2$ represents $O$, $CH_2$, or $NR^{Y2}$ wherein $R^{Y2}$ represents hydrogen or $(C_{1-3})$alkyl; and X represents *—$NR^5$—$CH_2$—$CH_2$—; or X represents *—$NR^5$—$CO$—$CH_2$—;

wherein the asterisks indicate the bond which is attached to the group $Y^1$;

$R^5$ represents $(C_{1-6})$alkyl;

$(C_{1-4})$alkyl mono-substituted with $(C_{1-3})$alkoxy, cyano, vinyl; ethynyl; or $(C_{1-3})$alkoxy-carbonyl;

—$CO$—$R^{10}$ wherein $R^{10}$ represents $(C_{1-5})$alkyl; $(C_{1-5})$alkoxy; $(C_{3-6})$cycloalkyl-$(C_{1-3})$alkyl; $(C_{3-4})$alkenoxy; $(C_{3-4})$alkynoxy; $(C_{1-3})$fluoroalkyl; $(C_{1-3})$fluoroalkoxy; $(C_{1-3})$alkoxy-$(C_{2-3})$alkoxy; hydroxy-$(C_{1-5})$alkyl; $(C_{1-3})$alkoxy-$(C_{1-5})$alkyl; $(C_{3-6})$cycloalkyl optionally containing one ring oxygen atom, wherein said cycloalkyl is optionally mono- or di-substituted wherein the substituents independently are fluoro or $(C_1)$fluoroalkyl; or —$NR^{10a}R^{10b}$ wherein $R^{10a}$ and $R^{10b}$ independently represent hydrogen, $(C_{1-4})$alkyl or $(C_{3-6})$cycloalkyl, or $R^{10a}$ and $R^{10b}$ together with the nitrogen to which they are attached to form a 5- to 7-membered saturated ring;

$(C_{2-4})$fluoroalkyl;

$(C_{3-6})$cycloalkyl optionally containing one ring oxygen atom;

$(C_{3-6})$cycloalkyl-$(C_{1-3})$alkyl, wherein the $(C_{3-6})$cycloalkyl group optionally contains one ring oxygen atom; wherein said cycloalkyl is optionally substituted with one or two methyl substituents;

$(R^1)_n$ represents one or two optional substituents (i.e. n represents the integer 0, 1, or 2) independently selected from $(C_{1-4})$alkyl (especially methyl), $(C_{1-4})$alkoxy (especially methoxy), halogen, $(C_{1-3})$fluoroalkyl (especially trifluoromethyl), $(C_{1-3})$fluoroalkoxy (especially trifluoromethoxy), and cyano;

$L^1$ represents a two-membered linker group selected from —$NH$—$CH_2$—*; —$O$—$CH_2$—*; —$CH_2$—$CH_2$—; and —$CH$=$CH$—; wherein the asterisks indicate the bond with which the group $L^1$ is attached to the carbonyl group;

$L^2$ represents —$(C_{1-3})$alkylene-(especially a linker group selected from —$CH_2$—, —$CH(CH_3)$—, —$CH_2$—$CH_2$—, and —$CH_2$—$CH_2$—$CH_2$—, preferably —$CH_2$—);

$Ar^1$ represents phenyl, or 5- or 6-membered heteroaryl (especially pyridinyl); wherein said phenyl or 5- or 6-membered heteroaryl independently is unsubstituted, mono-, di-, or tri-substituted, wherein the substituents are independently selected from $(C_{1-4})$alkyl (especially methyl); $(C_{1-4})$alkoxy (especially methoxy); $(C_{1-3})$fluoroalkyl (especially trifluoromethyl); $(C_{1-3})$fluoroalkoxy (especially trifluoromethoxy); halogen; or cyano; and $R^4$ represents $(C_{2-6})$alkyl;

$(C_{2-5})$alkyl which is mono-substituted with $(C_{1-4})$alkoxy, cyano, or hydroxy; or di-substituted wherein the substituents are independently selected from $(C_{1-3})$alkoxy, or hydroxy;

$(C_{2-3})$fluoroalkyl which is optionally further substituted with one hydroxy;

—$(C_{2-4})$alkylene-$NR^6R^7$, wherein $R^6$ and $R^7$ independently represent hydrogen; $(C_{1-4})$alkyl; —$CO$—$(C_{1-4})$alkoxy; —$SO_2$—$(C_{1-3})$alkyl; $(C_{2-3})$fluoroalkyl; $(C_{3-6})$cycloalkyl or $(C_{3-6})$cycloalkyl-$(C_{1-3})$alkyl, wherein in the above groups independently the $(C_{3-6})$cycloalkyl group optionally contains one ring oxygen atom, and wherein said $(C_{3-6})$cycloalkyl group independently is optionally substituted with methyl;

—$(C_{1-3})$alkylene-$CO$—$R^8$, wherein $R^8$ represents $(C_{1-4})$alkoxy (especially ethoxy); or $R^8$ represents $NR^{81}R^{82}$ wherein $R^{81}$ and $R^{82}$ independently represent hydrogen or $(C_{1-4})$alkyl, or $R^{81}$ and $R^{82}$ together with the nitrogen to which they are attached to form a 4- to 6-membered saturated ring optionally substituted with two fluoro substituents (especially such $NR^{81}R^{82}$ represents amino, 3,3-difluoroazetidinyl);

$(C_{3-6})$cycloalkyl or $(C_{3-6})$cycloalkyl-$(C_{1-3})$alkyl, wherein in the above groups the cycloalkyl group independently is optionally mono-substituted with hydroxy;

$(C_{4-7})$heterocyclyl or $(C_{4-7})$heterocyclyl-$(C_{1-3})$alkyl, wherein in the above groups the $(C_{4-7})$heterocyclyl independently contains one or two ring heteroatoms independently selected from nitrogen, sulfur and oxygen; wherein in the above groups said $(C_{4-7})$heterocyclyl independently is unsubstituted, or mono-, or di-substituted, wherein the substituents are independently selected from:

one oxo substituent attached to a ring carbon atom in alpha position to a ring nitrogen (thus forming together with the nitrogen an amide group, or, in case a ring oxygen is additionaly adjacent, a carbamate group, or, in case second ring nitrogen is additionaly adjacent, a urea group); and/or two oxo substituents at a ring sulfur ring atom (thus forming a —$SO_2$— group); and/or $(C_{1-4})$alkyl (especially methyl) attached to a ring nitrogen atom having a free valency; and/or two fluoro substituents attached to a ring carbon atom; and/or in case of a $(C_{4-7})$heterocyclyl-$(C_{1-3})$alkyl group, methyl attached to a ring carbon atom which is attached to the linking $(C_{1-3})$alkyl group.

The compounds of formula (I) may contain one or more stereogenic or asymmetric centers, such as one or more asymmetric carbon atoms. The compounds of formula (I) may thus be present as mixtures of stereoisomers or preferably as pure stereoisomers. Mixtures of stereoisomers may be separated in a manner known to a person skilled in the art.

It is understood that the nitrogen atom of $NR^5$ will not be directly bound to more than two CO or $SO_2$ groups; especially it is bound to a maximum of two CO groups, or of one $SO_2$ group and no CO group; preferably it is bound to a maximum of a) one CO group or b) one $SO_2$ group.

The present invention also includes isotopically labelled, especially $^2H$ (deuterium) labelled compounds of formula (I) according to embodiments 1) to 28), which compounds are identical to the compounds of formula (I) except that one or more atoms have each been replaced by an atom having the same atomic number but an atomic mass different from the atomic mass usually found in nature. Isotopically labelled, especially $^2H$ (deuterium) labelled compounds of formula (I) and salts thereof are within the scope of the present invention. Substitution of hydrogen with the heavier isotope $^2H$ (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

In this patent application, a bond drawn as a dotted line shows the point of attachment of the radical drawn. For example, the radical drawn below

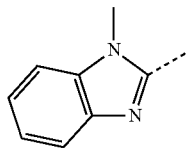

is the 1-methyl-1H-benzoimidazol-2-yl group.

Where the plural form is used for compounds, salts, pharmaceutical compositions, diseases and the like, this is intended to mean also a single compound, salt, or the like.

Any reference to compounds of formula (I) according to embodiments 1) to 28) is to be understood as referring also to the salts (and especially the pharmaceutically acceptable salts) of such compounds, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example "Handbook of Phramaceutical Salts. Properties, Selection and Use.", P. Heinrich Stahl, Camille G. Wermuth (Eds.), Wiley-VCH, 2008; and "Pharmaceutical Salts and Co-crystals", Johan Wouters and Luc Quéré (Eds.), RSC Publishing, 2012.

Definitions provided herein are intended to apply uniformly to the compounds of formula (I), as defined in any one of embodiments 1) to 26), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein.

The term "halogen" means fluorine, chlorine, or bromine, preferably fluorine or chlorine. For substituents of the group $Ar^1$ the term preferably means chlorine or bromine.

The term "alkyl", used alone or in combination, refers to a saturated straight or branched chain hydrocarbon group containing one to six carbon atoms. The term "$(C_{x-y})$alkyl" (x and y each being an integer), refers to an alkyl group as defined before, containing x to y carbon atoms. For example a $(C_{1-6})$alkyl group contains from one to six carbon atoms. Examples of alkyl groups are methyl, ethyl, propyl, isopropyl, butyl, isobutyl, tert-butyl, 3-methyl-butyl, 2,2-dimethyl-propyl and 3,3-dimethyl-butyl. For avoidance of any doubt, in case a group is referred to as e.g. propyl or butyl, it is meant to be n-propyl, respectively n-butyl. Preferred are methyl and ethyl. Most preferred is methyl. Examples of $(C_{2-6})$alkyl groups as used for $R^4$ are ethyl, 3-methyl-butyl and 3,3-dimethyl-butyl. Examples of $(C_{1-6})$alkyl groups as used for $R^5$ are methyl, ethyl, propyl, isopropyl, isobutyl, 2,2-dimethyl-propyl, 3,3-dimethyl-butyl, 1-methyl-propyl, and 1,2-dimethyl-propyl; preferred $R^5$ alkyl groups are ethyl, propyl, and isobutyl. Examples of $(C_{1-5})$alkyl groups as used for $R^{10}$ are methyl, ethyl, propyl, isopropyl, isobutyl, tert-butyl, and 2,2-dimethyl-propyl; preferred are methyl and ethyl.

Examples of substituted $(C_{2-5})$alkyl groups as used for $R^4$ are 2-methoxy-ethyl, 2-hydroxy-ethyl, 2-hydroxy-propyl, 2-hydroxy-2-methyl-propyl, 3-hydroxy-3-methyl-butyl, and 2-hydroxy-3-methoxy-propyl; especially 2-hydroxy-3-methoxy-propyl and 2-hydroxy-2-methyl-propyl. Preferred are $(C_{2-4})$alkyl groups mono-substituted with hydroxy, such as especially 2-hydroxy-2-methyl-propyl.

The term "—$(C_{x-y})$alkylene-", used alone or in combination, refers to bivalently bound alkyl group as defined before containing x to y carbon atoms. Preferably, the points of attachment of a —$(C_{1-y})$alkylene group are in 1,1-diyl, in 1,2-diyl, or in 1,3-diyl arrangement. Preferably, the points of attachment of a —$(C_{2-y})$alkylene group are in 1,2-diyl or in 1,3-diyl arrangement. For the linker $L^2$, examples of —$(C_{1-3})$alkylene-groups are methylene, ethylene, ethane-1,1-diyl, and propylene. For the substituent —$(C_{2-4})$alkylene-$NR^6R^7$ as used for $R^4$ examples of —$(C_{2-4})$alkylene-groups are notably ethylene and propylene, preferred is ethylene.

Examples of —$(C_{1-3})$alkylene-CO—$R^8$ groups as used for $R^4$ are ethoxycarbonyl-methyl, 3-amino-3-oxopropyl, and (3,3-difluoroazetidinyl)-3-oxo-propyl.

Examples of —$(C_{2-4})$alkylene-$NR^6R^7$ groups as used for $R^4$ are 2-amino-ethyl, 2-methylamino-ethyl, 2-dimethylamino-ethyl, 2-diethylamino-ethyl, 2-(butylmethylamino)-ethyl, 3-dimethylamino-propyl, 2-[(tert-butoxycarbonyl)-amino]-ethyl, 2-[(tert-butoxycarbonyl)-methylamino]-ethyl, 2-[(tert-butoxycarbonyl)-ethylamino]-ethyl, 2-[(tert-butoxycarbonyl)-isopropylamino]-ethyl, 2-ethylamino-ethyl, 2-(ethyl-methylamino)-ethyl, 2-(isopropylamino)-ethyl, 2-(isopropyl-methylamino)-ethyl, 2-(diisopropylamino)-ethyl, 2-[(tert-butyl)-amino]-ethyl, 2-(allyl-methylamino)-ethyl, 2-(methyl-prop-2-ynyl-amino)-ethyl, 2-[(2-fluoro-ethyl)-methylamino]-ethyl, 2-[(2,2,2-trifluoroethyl)-amino]-ethyl, 2-[methyl-(2,2,2-trifluoroethyl)-amino]-ethyl, 2-[(2-fluoro-1-methylethyl)-methylamino]-ethyl, 2-methanesulfonylamino-ethyl, 2-[(cyclopropyl)-methylamino]-ethyl, 2-[(cyclopropylmethyl)-methylamino]-ethyl, 2-[(cyclobutyl)-methylamino]-ethyl, 2-[(cyclopentyl)-methylamino]-ethyl, 2-[methyl-(tetrahydrofuran-3-yl)-amino]-ethyl, 2-[ethyl-(3-methyl-oxetan-3-yl-methyl)-amino]-ethyl. Preferred are 2-methylamino-ethyl, 2-dimethylamino-ethyl, 2-ethylamino-ethyl, 2-(isopropylamino)-ethyl, 2-[(tert-butyl)-amino]-ethyl, and 2-[(cyclopropyl)-methylamino]-ethyl; notably 2-methylamino-ethyl, 2-dimethylamino-ethyl, 2-ethylamino-ethyl, and 2-[(cyclopropyl)-methylamino]-ethyl; especially 2-dimethylamino-ethyl.

The term "alkoxy", used alone or in combination, refers to an alkyl-O— group wherein the alkyl group is as defined before. The term "$(C_{x-y})$alkoxy" (x and y each being an integer) refers to an alkoxy group as defined before containing x to y carbon atoms. For example a $(C_{1-4})$alkoxy group means a group of the formula $(C_{1-4})$alkyl-O— in which the term "$(C_{1-4})$alkyl" has the previously given significance. Examples of alkoxy groups are methoxy, ethoxy, n-propoxy, isopropoxy, n-butoxy, isobutoxy, sec-butoxy and tert-butoxy. Preferred are ethoxy and especially methoxy. Examples of (Cis)alkoxy groups as used for $R^{10}$ are methoxy, ethoxy, propoxy, isopropoxy, isobutoxy, tert-butoxy, and 2,2-dimethyl-propoxy.

The term "alkenyl", used alone or in combination, refers to a straight or branched hydrocarbon chain containing two to five carbon atoms and one carbon-carbon double bond. The term "$(C_{x-y})$alkenyl" (x and y each being an integer), refers to an alkenyl group as defined before containing x to y carbon atoms. For example a $(C_2-C_5)$alkenyl group contains from two to five carbon atoms. Examples of alkenyl groups are vinyl, prop-1-en-1-yl, 2-methylprop-1-en-1-yl, but-2-en-2-yl, buta-1,3-dien-1-yl, and especially allyl.

The term "alkynyl", used alone or in combination, refers to a straight or branched hydrocarbon chain containing two to five carbon atoms and one carbon-carbon triple bond. The term "$(C_{x-y})$alkynyl" (x and y each being an integer), refers to an alkynyl group as defined before containing x to y carbon atoms. For example a $(C_2-C_5)$alkynyl group contains from two to five carbon atoms. An example of an alkynyl group is prop-2-yn-1-yl.

The term "fluoroalkyl", used alone or in combination, refers to an alkyl group as defined before containing one to three carbon atoms in which one or more (and possibly all) hydrogen atoms have been replaced with fluorine. The term "$(C_{x-y})$fluoroalkyl" (x and y each being an integer) refers to a fluoroalkyl group as defined before containing x to y carbon atoms. For example a $(C_{1-3})$fluoroalkyl group contains from one to three carbon atoms in which one to seven hydrogen atoms have been replaced with fluorine. Representative examples of fluoroalkyl groups include trifluoromethyl, 2-fluoroethyl, 2,2-difluoroethyl and 2,2,2-trifluoroethyl. Preferred are $(C_1)$fluoroalkyl groups such as trifluoromethyl. Examples of $(C_{2-4})$fluoroalkyl groups as used for $R^5$ are 2,2,2-trifluoroethyl, 2-fluoroethyl and 3-fluoropropyl. Examples of $(C_{1-3})$fluoroalkyl as used for the substituent $R^{10}$ are trifluoromethyl, and 1,1-difluoroethyl. Examples of optionally substituted $(C_{2-3})$fluoroalkyl groups as used for $R^4$ are 3,3,3-trifluoro-propyl and 2-hydroxy-3,3,3-trifluoro-propyl.

The term "fluoroalkoxy", used alone or in combination, refers to an alkoxy group as defined before containing one to three carbon atoms in which one or more (and possibly all) hydrogen atoms have been replaced with fluorine. The term "$(C_{x-y})$fluoroalkoxy" (x and y each being an integer) refers to a fluoroalkoxy group as defined before containing x to y carbon atoms. For example a $(C_{1-3})$fluoroalkoxy group contains from one to three carbon atoms in which one to seven hydrogen atoms have been replaced with fluorine. Representative examples of fluoroalkoxy groups include trifluoromethoxy, difluoromethoxy, 2-fluoroethoxy, 2,2-difluoroethoxy and 2,2,2-trifluoroethoxy. Preferred are $(C_1)$ fluoroalkoxy groups such as trifluoromethoxy and difluoromethoxy.

The term "cyano" refers to a group —CN.

The term "cycloalkyl", used alone or in combination, refers to a saturated monocyclic hydrocarbon ring containing three to six carbon atoms. The term "$(C_{x-y})$cycloalkyl" (x and y each being an integer), refers to a cycloalkyl group as defined before containing x to y carbon atoms. For example a $(C_{3-6})$cycloalkyl group contains from three to six carbon atoms. Examples of cycloalkyl groups are cyclopropyl, cyclobutyl, cyclopentyl, cyclohexyl, and cycloheptyl. Preferred are cyclopropyl, cyclopentyl and cyclohexyl; especially cyclopropyl. Examples of $(C_{3-6})$cycloalkyl groups as used for the group $R^5$ are cyclobutyl and cyclopentyl; especially cyclobutyl. In case the $(C_{3-6})$cycloalkyl group as used for the group $R^4$ is optionally mono-substituted with hydroxy, an example is 4-hydroxy-cyclohexyl.

The term "$(C_{x-y})$cycloalkyl-$(C_{x-y})$alkyl" refers to a $(C_{x-y})$cycloalkyl group as defined before, which is linked through a $(C_{x-y})$alkylene group as defined before to the rest of the molecule. A particular example of such groups is cyclopropyl-methyl. Examples of $(C_{3-6})$cycloalkyl-$(C_{1-3})$ alkyl groups as used for the group $R^5$ are cyclopropyl-methyl and cyclohexyl-methyl; preferred is cyclopropyl-methyl. An example of $(C_{3-6})$cycloalkyl-$(C_{1-3})$alkyl groups as used for the group $R^{10}$ is cyclohexyl-methyl. An example of $(C_{3-6})$cycloalkyl-$(C_{1-3})$alkyl groups as used for the group $R^4$ is cyclopropyl-methyl. In case the cycloalkyl of a $(C_{3-6})$cycloalkyl-$(C_{1-3})$alkyl group as used for the group $R^4$ is optionally mono-substituted with hydroxy, an example is (1-hydroxy-cyclopentyl)-methyl.

The term "cycloalkyl optionally containing one ring oxygen atom", used alone or in combination, refers to a cycloalkyl group as defined before. In addition, one ring carbon atom of said cycloalkyl may be replaced by an oxygen atom. Examples of such groups are especially cycloalkyl groups such as cyclopropyl, cyclobutyl, cyclopentyl, cyclohexyl, and cycloheptyl; as well as oxygen containing groups such as oxetanyl, tetrahydrofuranyl, and tetrahydro-2H-pyranyl. As used for the substituent $R^5$ (i.e. said cycloalkyl optionally containing one ring oxygen atom is attached to a nitrogen atom) a ring oxygen atom, if present, is preferably separated from said nitrogen atom by at least two ring carbon atoms. Examples of such groups as used for the substituent $R^5$ are especially cycloalkyl groups such as cyclobutyl and cyclopentyl; as well as oxetan-3-yl, and tetrahydrofuran-3-yl. Preferred is cyclobutyl. Examples of optionally substituted cycloalkyl optionally containing one ring oxygen atom as used for the group $R^{10}$ are cyclopropyl, cyclobutyl, 2-fluorocyclopropyl, 2,2-difluorocyclopropyl, 1-trifluoromethyl-cyclopropyl, and tetrahydrofuran-3-yl. Preferred are 2-fluorocyclopropyl, and 2,2-difluorocyclopropyl.

Examples of optionally substituted $(C_{3-6})$cycloalkyl-$(C_{1-3})$alkyl groups optionally containing one ring oxygen atom as used for the substituent $R^5$ are cyclopropyl-methyl, cyclobutylmethyl, cyclohexyl-methyl, and 1-cyclopropylethyl; especially cyclopropyl-methyl and cyclobutylmethyl.

The term "heterocyclyl", used alone or in combination, and if not explicitly defined in a more narrow way, refers to a saturated monocyclic hydrocarbon ring containing one or two (especially one) ring heteroatoms independently selected from nitrogen, sulfur, and oxygen (especially one nitrogen atom, two nitrogen atoms, or one nitrogen atom and one oxygen atom; preferably such heterocyclyl contains one ring nitrogen atom). The term "$(C_{x-y})$heterocyclyl" refers to such a heterocyclyl group containing x to y ring atoms. Heterocyclyl groups are unsubstituted or substituted as explicitly defined. Examples of heterocyclyl groups as used for the group $R^4$ are pyrrolidin-3-yl, 1-methyl-pyrrolidin-3-yl, piperidin-3-yl, 1-methyl-piperidin-3-yl, piperidin-4-yl, 1-methyl-piperidin-4-yl, tetrahydro-pyran-4-yl, and 1,1-dioxo-tetrahydrothiophen-3-yl. Preferred are 1-methyl-pyrrolidin-3-yl, 1-methyl-piperidin-3-yl, 1-methyl-piperidin-4-yl, and especially pyrrolidin-3-yl.

The term "$(C_{x-y})$ heterocyclyl-$(C_{x-y})$alkyl" refers to a $(C_{x-y})$heterocyclyl group as defined before, which is linked through a $(C_{x-y})$alkylene group as defined before to the rest of the molecule. For the $(C_{4-6})$heterocyclyl-$(C_{1-3})$alkyl groups as used for $R^4$ examples of —$(C_{1-3})$alkylene-groups are especially methylene, and ethylene. Examples of heterocyclyl groups part of such $(C_{4-6})$heterocyclyl-$(C_{1-3})$alkyl groups as used for the group $R^4$ are pyrrolidin-1-yl, 1-methyl-pyrrolidin-2-yl, 1-methyl-pyrrolidin-3-yl, 2-oxopyrrolidin-1-yl, 2-oxo-imidazolidin-1-yl, piperidin-1-yl, 1-methyl-piperidin-2-yl, 1-methyl-piperidin-3-yl, 1-methylpiperidin-4-yl, morpholin-4-yl, 3-methyl-oxetan-3-yl, pyrrolidin-3-yl, [1,4]dioxan-2-yl, piperazin-1-yl, azepan-1-yl, 3,3-difluoroazetidin-1-yl, 3,3-difluoropyrrolidin-1-yl, 3,3-difluoropiperidin-1-yl, and 4,4-difluoropiperidin-1-yl. Particular examples of $(C_{4-6})$heterocyclyl-$(C_{1-3})$alkyl groups as used for $R^4$ are 2-(pyrrolidin-1-yl)-ethyl, 2-(2-oxo-imidazolidin-1-yl)-ethyl, 2-(1-methyl-pyrrolidin-2-yl)-ethyl, 2-(2-oxo-pyrrolidin-1-yl)-ethyl, 2-(morpholin-4-yl)-ethyl, 3-methyl-oxetan-3-yl-methyl, pyrrolidin-3-yl-methyl, 3-(pyrrolidin-1-yl)-propyl, [1,4]dioxan-2-yl-methyl, 2-(piperazin-1-yl)-ethyl, 2-(piperidin-1-yl)-ethyl, 2-(azepan-1-yl)-ethyl, 2-(3,3-difluoroazetidin-1-yl)-ethyl, 2-(3,3-difluoropyrrolidin-1-yl)-ethyl, 2-(3,3-difluoropiperidin-1-yl)-ethyl, and 2-(4,4-difluoropiperidin-1-yl)-ethyl. Preferred are 2-(pyrrolidin-1-yl)-ethyl, 2-(morpholin-4-yl)-ethyl, 2-(piperazin-1-yl)-ethyl, and 2-(4,4-difluoropiperidin-1-yl)-ethyl; especially 2-(pyrrolidin-1-yl)-ethyl.

The term "aryl", used alone or in combination, means phenyl or naphthyl, especially phenyl. The above-mentioned aryl groups are unsubstituted or substituted as explicitly defined.

Examples of the substituent $Ar^1$ representing phenyl are especially those which are unsubstituted or mono-, or di-substituted (especially mono-, or di-substituted) wherein the substituents are independently selected from $(C_{1-4})$alkyl; $(C_{1-4})$alkoxy; $(C_{1-3})$fluoroalkyl; $(C_{1-3})$fluoroalkoxy; halogen; and cyano. In a sub-embodiment, the substituents are independently selected from $(C_{1-4})$alkyl; $(C_{1-4})$alkoxy; $(C_{1-3})$fluoroalkyl; and halogen; especially from $(C_{1-3})$fluoroalkyl; and halogen. Particular examples are phenyl, 2-fluoro-phenyl, 3-fluoro-phenyl, 4-fluoro-phenyl, 2,4-difluoro-phenyl, 2,6-difluoro-phenyl, 2-chloro-phenyl, 3-chloro-phenyl, 4-chloro-phenyl, 2-chloro-4-fluoro-phenyl, 2,3-dichloro-phenyl, 2,6-dichloro-phenyl, 2-bromo-phenyl, 3-bromo-phenyl, 4-bromo-phenyl, 2-methyl-phenyl, 3-methyl-phenyl, 4-methyl-phenyl, 2,3-dimethyl-phenyl, 2-methoxy-phenyl, 3-methoxy-phenyl, 4-methoxy-phenyl, 3,4-dimethoxy-phenyl, 2-trifluoromethyl-phenyl, 3-trifluoromethyl-phenyl, 4-trifluoromethyl-phenyl, 4-fluoro-2-trifluoromethyl-phenyl, 2-trifluoromethoxy-phenyl, 3-trifluoromethoxy-phenyl, 4-trifluoromethoxy-phenyl. Preferred are 2,4-difluoro-phenyl, 2,6-difluoro-phenyl, 2-chloro-phenyl, 2,3-dichloro-phenyl, 2,6-dichloro-phenyl, 2-bromo-phenyl, 3-bromo-phenyl, 2-trifluoromethyl-phenyl, 3-trifluoromethyl-phenyl, and 4-fluoro-2-trifluoromethyl-phenyl; especially 2-chloro-phenyl, 2-trifluoromethyl-phenyl, and 2-bromo-phenyl.

The term "aryl-$(C_{x-y})$alkyl-" refers to an aryl group as defined before; in the particular case of a "phenyl-$(C_{x-y})$alkyl-" group it refers to a phenyl group, which is linked to the rest of the molecule through a $(C_{x-y})$alkylene group as defined before (especially through a methylene or ethylene group). The aryl/phenyl group part of aryl/phenyl-$(C_{x-y})$alkyl- is unsubstituted or substituted as explicitly defined. Examples of phenyl-$(C_{1-3})$alkyl- groups as used for the substituent $R^4$ are benzyl, 2-trifluoromethyl-benzyl, and 2-(4-fluoro-phenyl)-ethyl.

The term "heteroaryl", used alone or in combination, means a 5- to 10-membered monocyclic or bicyclic aromatic ring containing one to a maximum of four heteroatoms, each independently selected from oxygen, nitrogen and sulfur. Examples of such heteroaryl groups are furanyl, oxazolyl, isoxazolyl, oxadiazolyl, thiophenyl, thiazolyl, isothiazolyl, thiadiazolyl, pyrrolyl, imidazolyl, pyrazolyl, triazolyl, pyridinyl, pyrimidinyl, pyridazinyl, pyrazinyl, indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzoxadiazolyl, benzothiadiazolyl, quinolinyl, isoquinolinyl, naphthyridinyl, cinnolinyl, quinazolinyl, quinoxalinyl, phthalazinyl, pyrrolopyridinyl, pyrazolopyridinyl, pyrazolopyrimidinyl, pyrrolopyrazinyl, imidazopyridinyl, imidazopyridazinyl, and imidazothiazolyl. The above-mentioned heteroaryl groups are unsubstituted or substituted as explicitly defined. In case $Ar^1$ represents "5- or 6-membered heteroaryl", the term means the above-mentioned 5- or 6-membered groups. Notably, the term refers to 5-membered heteroaryl containing at least one nitrogen atom and optionally one further heteroatom selected from nitrogen, oxygen or sulfur such as pyrazolyl, imidazolyl, or thiazolyl; or to 6-membered heteroaryl containing one or two nitrogen atoms such as pyrimidinyl, pyrazinyl, or pyridinyl. Especially the term refers to pyridinyl. For the substituent $Ar^1$, such 5- or 6-membered heteroaryl group is unsubstituted or mono-, or di-substituted (especially mono-, or di-substituted) wherein the substituents are independently selected from $(C_{1-4})$alkyl; $(C_{1-4})$alkoxy; $(C_{1-3})$fluoroalkyl; $(C_{1-3})$fluoroalkoxy; halogen; and cyano. In a sub-embodiment, the substituents are independently selected from $(C_{1-4})$alkyl; $(C_{1-4})$alkoxy; $(C_{1-3})$fluoroalkyl; and halogen; especially $(C_{1-4})$alkyl; $(C_{1-3})$fluoroalkyl; and halogen. Examples are 1-methyl-imidazol-2-yl, 1-ethyl-1H-pyrazol-3-yl, 5-chloro-1-methyl-3-trifluoromethyl-pyrazol-4-yl, 4-methyl-thiazol-2-yl, 2-trifluoromethyl-thiazol-5-yl, thiazol-2-yl, isoxazol-5-yl, 5-methyl-isoxazol-3-yl, 1-methyl-1H-pyrazol-5-yl; pyrimidin-2-yl, pyrimidin-4-yl, pyridin-2-yl, 3-chloro-pyridin-2-yl, 3-trifluoromethyl-pyridin-2-yl, 6-trifluoromethyl-pyridin-2-yl, pyridin-3-yl, pyridin-4-yl, 3-fluoro-pyridin-2-yl, 5-fluoro-pyridin-2-yl, 3-chloro-pyridin-5-yl, 5-chloro-pyridin-2-yl, 3-bromo-pyridin-2-yl, 3-bromo-pyridin-4-yl, 3-methyl-pyridin-2-yl, 4-methyl-pyridin-2-yl, 5-methyl-pyridin-2-yl, 6-methyl-pyridin-2-yl, 4-methoxy-pyridin-2-yl; preferred are 3-chloro-pyridin-2-yl, 3-trifluoromethyl-pyridin-2-yl, 6-trifluoromethyl-pyridin-2-yl, 3-bromo-pyridin-2-yl, 3-methyl-pyridin-2-yl, 6-methyl-pyridin-2-yl.

The term "heteroaryl-$(C_{x-y})$alkyl-" refers to a heteroaryl group as defined before which is linked to the rest of the molecule through a $(C_{x-y})$alkylene group as defined before (especially through a methylene or ethylene group). The heteroaryl group part of heteroaryl-$(C_{x-y})$alkyl- is unsubstituted or substituted as explicitly defined. Especially it is unsubstituted or mono-substituted with $(C_{1-4})$alkyl. Examples of heteroaryl-$(C_{1-3})$alkyl- groups as used for the substituent $R^4$ are (1-methyl-imidazol-2-yl)-methyl, 1-(1-ethyl-1H-pyrazol-3-yl)-ethan-1-yl, (4-methyl-thiazol-2-yl)-methyl, (pyridin-2-yl)-methyl and isoxazol-5-ylmethyl.

Further embodiments of the invention are presented hereinafter:

2) A second embodiment relates to compounds according to embodiment 1), wherein ring (A) represents a seven-membered ring, wherein
   $Y^1$ and $Y^2$ both represent $CH_2$; and
      X represents —$CH_2$—$NR^5$—$CH_2$—, or
      X represents *—CO—$NR^5$—$CH_2$—, or
      X represents *—$CH_2$—$NR^5$—CO—; or
   $Y^1$ represents O, $CH_2$, or $NR^{Y1}$ wherein $R^{Y1}$ represents hydrogen or $(C_{1-3})$alkyl;
   $Y^2$ represents $CH_2$; and
      X represents *—$CH_2$—$CH_2$—$NR^5$—; or
      X represents *—$CH_2$—CO—$NR^5$—; or
   $Y^1$ represents O, $CH_2$, or $NR^{Y1}$ wherein $R^{Y1}$ represents hydrogen or $(C_{1-3})$alkyl;
   $Y^2$ represents CO; and
      X represents *—$CH_2$—$CH_2$—$NR^5$—; or
   $Y^1$ represents $CH_2$;
   $Y^2$ represents O, $CH_2$, or $NR^{Y2}$ wherein $R^{Y2}$ represents hydrogen or $(C_{1-3})$alkyl; and
      X represents *—$NR^5$—$CH_2$—$CH_2$—; or
      X represents *—$NR^5$—CO—$CH_2$—; or
   $Y^1$ represents CO;
   $Y^2$ represents O, $CH_2$, or $NR^{Y2}$ wherein $R^{Y2}$ represents hydrogen or $(C_{1-3})$alkyl; and
      X represents *—$NR^5$—$CH_2$—$CH_2$—;

wherein the asterisks indicate the bond which is attached to the group $Y^1$.

3) Another embodiment relates to compounds according to embodiment 1), wherein ring (A) represents a seven-membered ring, wherein $Y^1$ and $Y^2$ both represent $CH_2$; and X represents —$CH_2$—$NR^5$—$CH_2$—, or $Y^1$ and $Y^2$ both represent $CH_2$; and X represents *—CO—$NR^5$—$CH_2$—, or $Y^1$ and $Y^2$ both represent $CH_2$; and X represents *—$CH_2$—$NR^5$—CO—; or $Y^1$ represents O, $CH_2$, or $NR^{Y1}$ wherein $R^{Y1}$ represents hydrogen or $(C_{1-3})$alkyl;

$Y^2$ represents $CH_2$; and X represents *—$CH_2$—$CH_2$—$NR^5$—; or $Y^1$ represents O, $CH_2$, or $NR^{Y1}$ wherein $R^{Y1}$ represents hydrogen or $(C_{1-3})$alkyl;

$Y^2$ represents $CH_2$; and X represents *—$CH_2$—CO—$NR^5$—; or $Y^1$ represents O, $CH_2$, or $NR^{Y1}$ wherein $R^{Y1}$ represents hydrogen or $(C_{1-3})$alkyl;

$Y^2$ represents CO; and X represents *—$CH_2$—$CH_2$—$NR^5$—; or $Y^1$ represents $CH_2$; $Y^2$ represents $CH_2$, O, or $NR^{Y2}$ wherein $R^{Y2}$ represents hydrogen or $(C_{1-3})$alkyl; and X represents *—$NR^5$—$CH_2$—$CH_2$—; or $Y^1$ represents $CH_2$; $Y^2$ represents $CH_2$; and X represents *—$NR^5$—CO—$CH_2$—; or $Y^1$ represents CO; $Y^2$ represents $CH_2$, O, or $NR^{Y2}$ wherein $R^{Y2}$ represents hydrogen $(C_{1-3})$alkyl; and X represents *—$NR^5$—$CH_2$—$CH_2$—;

wherein the asterisks indicate the bond which is attached to the group $Y^1$;

wherein in a sub-embodiment ring (A) especially represents a seven-membered ring, wherein $Y^1$ and $Y^2$ both represent $CH_2$; and X represents —$CH_2$—$NR^5$—$CH_2$—, or $Y^1$ represents O, $CH_2$, NH, or $NR^{Y1}$ wherein $R^{Y1}$ represents $(C_{1-3})$alkyl;

$Y^2$ represents $CH_2$; and X represents *—$CH_2$—$CH_2$—$NR^5$—; or $Y^1$ represents O, $Y^2$ represents $CH_2$; and X represents *—$CH_2$—CO—$NR^5$—; or $Y^1$ represents O, or $NR^{Y1}$ wherein $R^{Y1}$ represents $(C_{1-3})$alkyl; $Y^2$ represents CO; and X represents *—$CH_2$—$CH_2$—$NR^5$—; or $Y^1$ represents $CH_2$; $Y^2$ represents O, or $CH_2$; and X represents *—$NR^5$—$CH_2$—$CH_2$—; or $Y^1$ represents CO; $Y^2$ represents O; and X represents *—$NR^5$—$CH_2$—$CH_2$—;

wherein the asterisks indicate the bond which is attached to the group $Y^1$.

4) Another embodiment relates to compounds according to embodiment 1), wherein $Y^1$ and $Y^2$ both represent $CH_2$; and X represents —$CH_2$—$NR^5$—$CH_2$—, or $Y^1$ represents O, $CH_2$, NH, or; $Y^2$ represents $CH_2$; and X represents *—$CH_2$—$CH_2$—$NR^5$—; or $Y^1$ represents O; $Y^2$ represents CO; and X represents *—$CH_2$—$CH_2$—$NR^5$—; or $Y^1$ represents $CH_2$; $Y^2$ represents O, or $CH_2$; and X represents *—$NR^5$—$CH_2$—$CH_2$—; or $Y^1$ represents CO; $Y^2$ represents O; and X represents *—$NR^5$—$CH_2$—$CH_2$—;

wherein the asterisks indicate the bond which is attached to the group $Y^1$.

5) Another embodiment relates to compounds according to any one of embodiments 1) to 4), wherein $R^5$ represents $(C_{1-6})$alkyl [in particular methyl, ethyl, propyl, isopropyl, isobutyl, 1-methyl-propyl, 1,2-dimethyl-propyl, 2,2-dimethyl-propyl, 3,3-dimethyl-butyl];

$(C_{1-4})$alkyl mono-substituted with $(C_{1-3})$alkoxy [in particular 2-methoxy-ethyl, 2-methoxy-1-methyl-ethyl];

—CO—$R^{10}$ wherein $R^{10}$ represents $(C_{1-5})$alkyl; $(C_{1-5})$alkoxy; $(C_{3-6})$cycloalkyl-$(C_{1-3})$alkyl; $(C_{1-3})$fluoroalkyl; $(C_{1-3})$fluoroalkoxy; $(C_{1-3})$alkoxy-$(C_{2-3})$alkoxy; hydroxy-$(C_{1-5})$alkyl; $(C_{1-3})$alkoxy-$(C_{1-3})$alkyl; $(C_{3-6})$cycloalkyl optionally containing one ring oxygen atom, wherein said cycloalkyl is optionally mono- or di-substituted with fluoro; or —$NR^{10a}R^{10b}$ wherein $R^{10a}$ and $R^{10b}$ independently represent hydrogen, $(C_{1-4})$alkyl or $(C_{3-6})$cycloalkyl, or $R^{10a}$ and $R^{10b}$ together with the nitrogen to which they are attached to form a 5- to 7-membered saturated ring; [in particular such —CO—$R^{10}$ is methyl-carbonyl, ethyl-carbonyl, propyl-carbonyl, isopropyl-carbonyl, isobutyl-carbonyl, tert-butyl-carbonyl, (2,2-dimethyl-propyl)-carbonyl, hydroxymethyl-carbonyl, methoxymethyl-carbonyl, cyclopropyl-carbonyl, cyclobutyl-carbonyl, (2-fluoro-cyclopropyl)-carbonyl, (cyclohexyl-methyl)-carbonyl, (2,2-difluorocyclopropyl)-carbonyl, (tetrahydrofuran-3-yl)-carbonyl, trifluoromethyl-carbonyl, (1,1-difluoroethyl)-carbonyl, carbamoyl, methylcarbamoyl, ethylcarbamoyl, isopropylcarbamoyl, butyl-carbamoyl, tert-butyl-carbamoyl, cyclohexyl-carbamoyl, dimethylcarbamoyl, (pyrrolidin-1-yl)-carbonyl, methoxycarbonyl, ethoxycarbonyl, propoxycarbonyl, isopropoxycarbonyl, isobutoxycarbonyl, tert-butoxycarbonyl, (2,2-dimethyl-propoxy)-carbonyl, (2-fluoro-ethoxy)-carbonyl, (2-methoxy-ethoxy)-carbonyl]

$(C_{2-4})$fluoroalkyl [in particular 2-fluoroethyl, 2,2,2-trifluoroethyl, 3-fluoropropyl];

$(C_{3-6})$cycloalkyl optionally containing one ring oxygen atom [in particular cyclobutyl, oxetan-3-yl, cyclopentyl, tetrahydrofuran-3-yl];

$(C_{3-6})$cycloalkyl-$(C_{1-3})$alkyl, wherein the $(C_{3-6})$cycloalkyl group optionally contains one ring oxygen atom [in particular such $(C_{3-6})$cycloalkyl-$(C_{1-3})$alkyl is cyclopropyl-methyl, cyclobutyl-methyl, cyclohexyl-methyl, 1-cyclopropyl-ethyl];

wherein in a sub-embodiment $R^5$ especially represents ethyl, propyl, isobutyl, methyl-carbonyl, methoxymethyl-carbonyl, trifluoromethyl-carbonyl, or cyclopropyl-methyl.

6) Another embodiment relates to compounds according to any one of embodiments 1) to 4), wherein $R^5$ represents $(C_{1-6})$alkyl [in particular methyl, ethyl, propyl, isopropyl, isobutyl, 1-methyl-propyl, 1,2-dimethyl-propyl, 2,2-dimethyl-propyl, 3,3-dimethyl-butyl];

$(C_{1-4})$alkyl mono-substituted with $(C_{1-3})$alkoxy [in particular 2-methoxy-ethyl, 2-methoxy-1-methyl-ethyl];

—CO—$R^{10}$ wherein $R^{10}$ represents $(C_{1-5})$alkyl; $(C_{1-5})$alkoxy; $(C_{3-6})$cycloalkyl-$(C_{1-3})$alkyl; $(C_{1-3})$fluoroalkyl; $(C_{1-3})$fluoroalkoxy; $(C_{1-3})$alkoxy-$(C_{2-3})$alkoxy; hydroxy-$(C_{1-3})$alkyl; $(C_{1-3})$alkoxy-$(C_{1-3})$alkyl; or $(C_{3-6})$cycloalkyl optionally containing one ring oxygen atom, wherein said cycloalkyl is optionally mono- or di-substituted with fluoro; [especially $R^{10}$ represents $(C_{1-5})$alkyl, $(C_{1-3})$fluoroalkyl, or $(C_{1-3})$alkoxy-$(C_{1-3})$alkyl; in particular such —CO—$R^{10}$ is methyl-carbonyl, ethyl-carbonyl, propyl-carbonyl, isopropyl-carbonyl, isobutyl-carbonyl, tert-butyl-carbonyl, (2,2-dimethyl-propyl)-carbonyl, hydroxymethyl-carbonyl, methoxymethyl-carbonyl, cyclopropyl-carbonyl, cyclobutyl-carbonyl, (2-fluorocyclopropyl)-carbonyl, (2,2-difluorocyclopropyl)-carbonyl, (tetrahydrofuran-3-yl)-carbonyl, trifluoromethyl-carbonyl, (1,1-difluoroethyl)-carbonyl; especially methyl-carbonyl, ethyl-carbonyl, hydroxymethyl-carbonyl, methoxymethyl-carbonyl, (2-fluorocyclopropyl)-carbonyl, or (2,2-difluorocyclopropyl)-carbonyl];

($C_{2-4}$)fluoroalkyl [in particular 2-fluoroethyl, 2,2,2-trifluoroethyl, 3-fluoropropyl];

($C_{3-6}$)cycloalkyl optionally containing one ring oxygen atom [in particular cyclobutyl, oxetan-3-yl, cyclopentyl, tetrahydrofuran-3-yl];

($C_{3-6}$)cycloalkyl-($C_{1-3}$)alkyl, wherein the ($C_{3-6}$)cycloalkyl group optionally contains one ring oxygen atom [in particular such ($C_{3-6}$)cycloalkyl-($C_{1-3}$)alkyl is cyclopropyl-methyl, cyclobutyl-methyl, cyclohexyl-methyl, 1-cyclopropyl-ethyl];

wherein in a sub-embodiment $R^5$ especially represents ethyl, propyl, isobutyl, methyl-carbonyl, methoxymethyl-carbonyl, trifluoromethyl-carbonyl, or cyclopropyl-methyl.

7) Another embodiment relates to compounds according to any one of embodiments 1) to 4), wherein $R^5$ represents
($C_{1-6}$)alkyl; [in particular methyl, ethyl, propyl, isopropyl, isobutyl, 1-methyl-propyl, 1,2-dimethyl-propyl, 2,2-dimethyl-propyl, 3,3-dimethyl-butyl; especially ethyl, propyl, or isobutyl];

—CO—$R^{10}$ wherein $R^{10}$ represents ($C_{1-5}$)alkyl; hydroxy-($C_{1-3}$)alkyl; ($C_{1-3}$)alkoxy-($C_{1-3}$)alkyl; or ($C_{3-6}$)cycloalkyl optionally containing one ring oxygen atom, wherein said cycloalkyl is unsubstituted, or mono- or di-substituted with fluoro; [especially $R^{10}$ represents ($C_{1-5}$)alkyl or ($C_{1-3}$)alkoxy-($C_{1-3}$)alkyl; in particular such —CO—$R^{10}$ is methyl-carbonyl, ethyl-carbonyl, propyl-carbonyl, isopropyl-carbonyl, isobutyl-carbonyl, tert-butyl-carbonyl, (2,2-dimethyl-propyl)-carbonyl, hydroxymethyl-carbonyl, methoxymethyl-carbonyl, cyclopropyl-carbonyl, cyclobutyl-carbonyl, (2-fluorocyclopropyl)-carbonyl, (2,2-difluorocyclopropyl)-carbonyl, (tetrahydrofuran-3-yl)-carbonyl, (1,1-difluoroethyl)-carbonyl; especially methyl-carbonyl, ethyl-carbonyl, hydroxymethyl-carbonyl, methoxymethyl-carbonyl, (2-fluorocyclopropyl)-carbonyl, or (2,2-difluorocyclopropyl)-carbonyl];

($C_{2-4}$)fluoroalkyl; [in particular 2-fluoroethyl, 2,2,2-trifluoroethyl, 3-fluoropropyl; especially 3-fluoropropyl];

($C_{3-6}$)cycloalkyl optionally containing one ring oxygen atom; [in particular cyclobutyl, oxetan-3-yl, cyclopentyl, tetrahydrofuran-3-yl; especially cyclobutyl]; or ($C_{3-6}$)cycloalkyl-($C_{1-3}$)alkyl [in particular cyclopropyl-methyl, cyclobutylmethyl, cyclohexyl-methyl, 1-cyclopropyl-ethyl; especially cyclopropyl-methyl, or cyclobutyl-methyl];

wherein in a sub-embodiment $R^5$ especially represents ethyl, propyl, isobutyl, methyl-carbonyl, methoxymethyl-carbonyl, or cyclopropyl-methyl.

8) Another embodiment relates to compounds according to any one of embodiments 1) to 7), wherein $(R')_n$ represents one optional substituent (i.e. n represents the integer 0, or 1) independently selected from ($C_{1-4}$)alkyl (especially methyl), ($C_{1-4}$)alkoxy (especially methoxy), halogen, ($C_{1-3}$)fluoroalkyl (especially trifluoromethyl), ($C_{1-3}$)fluoroalkoxy (especially trifluoromethoxy), and cyano; (especially $(R^1)_n$ is absent, or it represents one methyl, methoxy, halogen, or trifluoromethyl substituent; preferably $(R^1)_n$ is absent).

9) Another embodiment relates to compounds according to any one of embodiments 1) to 8), wherein $(R^1)_n$ is absent.

10) Another embodiment relates to compounds according to any one of embodiments 1) to 8), wherein $L^1$ represents a two-membered linker group selected from —NH—$CH_2$—*, —O—$CH_2$—*, and —$CH_2CH_2$— (notably $L^1$ represents —NH—$CH_2$—*); wherein the asterisks indicate the bond with which the group $L^1$ is attached to the carbonyl group.

11) Another embodiment relates to compounds according to any one of embodiments 1) to 8), wherein $L^1$ represents —NH—$CH_2$—*; wherein the asterisk indicates the bond with which the group $L^1$ is attached to the carbonyl group.

12) Another embodiment relates to compounds according to any one of embodiments 1) to 11), wherein $L^2$ represents a linker group selected from —$CH_2$—, —CH($CH_3$)—, —$CH_2$—$CH_2$—, and —$CH_2$—$CH_2$—$CH_2$— (notably —$CH_2$—).

13) Another embodiment relates to compounds according to any one of embodiments 1) to 11), wherein $L^2$ represents a linker group selected from —$CH_2$—, —CH($CH_3$)—, and —$CH_2$—$CH_2$— (notably —$CH_2$—).

14) Another embodiment relates to compounds according to any one of embodiments 1) to 11), wherein $L^2$ represents —$CH_2$—.

15) Another embodiment relates to compounds according to any one of embodiments 1) to 14), wherein $Ar^1$ represents phenyl, or 5- or 6-membered heteroaryl (especially pyridinyl); wherein said phenyl or 5- or 6-membered heteroaryl independently is unsubstituted, mono-, or di-substituted, wherein the substituents are independently selected from ($C_{1-4}$)alkyl (especially methyl); ($C_{1-4}$)alkoxy (especially methoxy); ($C_{1-3}$)fluoroalkyl (especially trifluoromethyl); ($C_{1-3}$)fluoroalkoxy (especially trifluoromethoxy); halogen; or cyano;

[in particular $Ar^1$ represents phenyl, 2-fluoro-phenyl, 3-fluoro-phenyl, 4-fluoro-phenyl, 2,4-difluoro-phenyl, 2,6-difluoro-phenyl, 2-chloro-phenyl, 3-chloro-phenyl, 4-chloro-phenyl, 2-chloro-4-fluoro-phenyl, 2,3-dichloro-phenyl, 2,6-dichloro-phenyl, 2-bromo-phenyl, 3-bromo-phenyl, 4-bromo-phenyl, 2-methyl-phenyl, 3-methyl-phenyl, 4-methyl-phenyl, 2,3-dimethyl-phenyl, 2-methoxy-phenyl, 3-methoxy-phenyl, 4-methoxy-phenyl, 3,4-dimethoxy-phenyl, 2-trifluoromethyl-phenyl, 3-trifluoromethyl-phenyl, 4-trifluoromethyl-phenyl, 4-fluoro-2-trifluoromethyl-phenyl, 2-trifluoromethoxy-phenyl, 3-trifluoromethoxy-phenyl, 4-trifluoromethoxy-phenyl; or $Ar^1$ represents pyrimidin-2-yl, pyrimidin-4-yl, pyridin-2-yl, pyridin-3-yl, pyridin-4-yl, 3-chloro-pyridin-2-yl, 3-trifluoromethyl-pyridin-2-yl, 6-trifluoromethyl-pyridin-2-yl, 3-fluoro-pyridin-2-yl, 5-fluoro-pyridin-2-yl, 3-chloro-pyridin-5-yl, 5-chloro-pyridin-2-yl, 3-bromo-pyridin-2-yl, 3-bromo-pyridin-4-yl, 3-methyl-pyridin-2-yl, 4-methyl-pyridin-2-yl, 5-methyl-pyridin-2-yl, 6-methyl-pyridin-2-yl, 4-methoxy-pyridin-2-yl].

16) Another embodiment relates to compounds according to any one of embodiments 1) to 14), wherein $Ar^1$ represents phenyl which is unsubstituted, mono-, or di-substituted, wherein the substituents are independently selected from ($C_{1-4}$)alkyl; ($C_{1-4}$)alkoxy; ($C_{1-3}$)fluoroalkyl; ($C_{1-3}$)fluoroalkoxy; halogen; and cyano (especially mono-substituted with methyl; methoxy; trifluoromethyl, trifluoromethoxy; or halogen); [in particular such $Ar^1$ represents phenyl, 2-fluoro-phenyl, 3-fluoro-phenyl, 4-fluoro-phenyl, 2,4-difluoro-phenyl, 2,6-difluoro-phenyl, 2-chloro-phenyl, 3-chloro-phenyl, 4-chloro-phenyl, 2-chloro-4-fluoro-phenyl, 2,3-dichloro-phenyl, 2,6-dichloro-phenyl, 2-bromo-phenyl, 3-bromo-phenyl, 4-bromo-phenyl, 2-methyl-phenyl, 3-methyl-phenyl, 4-methyl-phenyl, 2,3-dimethyl-phenyl, 2-methoxy-phenyl, 3-methoxy-phenyl, 4-methoxy-phenyl, 3,4-dimethoxy-phenyl, 2-trifluoromethyl-phenyl, 3-trifluoromethyl-phenyl, 4-trifluoromethyl-phenyl, 4-fluoro-2-trifluoromethyl-phenyl, 2-trifluoromethoxy-phenyl, 3-trifluoromethoxy-phenyl, 4-trifluoromethoxy-phenyl; especially 2-chloro-phenyl, 2-bromo-phenyl, 2-trifluoromethyl-phenyl]; or
- 6-membered heteroaryl (in particular pyridinyl); which is unsubstituted, mono-, or di-substituted, wherein the substituents are independently selected from $(C_{1-4})$alkyl; $(C_{1-4})$alkoxy; $(C_{1-3})$fluoroalkyl; $(C_{1-3})$fluoroalkoxy; halogen; and cyano (especially mono-substituted with methyl, trifluoromethyl or halogen); [in particular such $Ar^1$ represents pyrimidin-2-yl, pyrimidin-4-yl, pyridin-2-yl, pyridin-3-yl, pyridin-4-yl, 3-chloro-pyridin-2-yl, 3-trifluoromethyl-pyridin-2-yl, 6-trifluoromethyl-pyridin-2-yl, 3-fluoro-pyridin-2-yl, 5-fluoro-pyridin-2-yl, 3-chloro-pyridin-5-yl, 5-chloro-pyridin-2-yl, 3-bromo-pyridin-2-yl, 3-bromo-pyridin-4-yl, 3-methyl-pyridin-2-yl, 4-methyl-pyridin-2-yl, 5-methyl-pyridin-2-yl, 6-methyl-pyridin-2-yl, 4-methoxy-pyridin-2-yl; especially 3-chloro-pyridin-2-yl, 3-trifluoromethyl-pyridin-2-yl, 6-trifluoromethyl-pyridin-2-yl, 3-bromo-pyridin-2-yl, 3-methyl-pyridin-2-yl, 6-methyl-pyridin-2-yl]; or
- 5-membered heteroaryl (in particular imidazolyl, pyrazolyl, thiazolyl or isoxazolyl); which is unsubstituted, mono-, di- or tri-substituted, wherein the substituents are independently selected from $(C_{1-4})$alkyl; $(C_{1-4})$alkoxy; $(C_{1-3})$fluoroalkyl; $(C_{1-3})$fluoroalkoxy; halogen; and cyano (especially mono-substituted with $(C_{1-2})$alkyl); [in particular such $Ar^1$ represents 5-chloro-1-methyl-3-trifluoromethyl-pyrazol-4-yl, 2-trifluoromethyl-thiazol-5-yl, 1-methyl-imidazol-2-yl, 1-ethyl-1H-pyrazol-3-yl, 4-methyl-thiazol-2-yl, thiazol-2-yl, isoxazol-5-yl, 5-methyl-isoxazol-3-yl, 1-methyl-1H-pyrazol-5-yl];

wherein in a sub-embodiment $Ar^1$ especially represents 2,4-difluoro-phenyl, 2,6-difluoro-phenyl, 2-chloro-phenyl, 2-bromo-phenyl, 3-bromo-phenyl, 2,3-dichloro-phenyl, 2,6-dichloro-phenyl, 2-trifluoromethyl-phenyl, 3-trifluoromethyl-phenyl, 4-fluoro-2-trifluoromethyl-phenyl, 3-chloro-pyridin-2-yl, 3-trifluoromethyl-pyridin-2-yl, 6-trifluoromethyl-pyridin-2-yl, 3-bromo-pyridin-2-yl, 3-methyl-pyridin-2-yl, 4-methyl-pyridin-2-yl, 6-methyl-pyridin-2-yl, or 4-methoxy-pyridin-2-yl.

17) Another embodiment relates to compounds according to any one of embodiments 1) to 15), wherein $Ar^1$ represents phenyl which is mono-, or di-substituted, wherein the substituents are independently selected from $(C_{1-4})$alkyl; $(C_{1-4})$alkoxy; $(C_{1-3})$fluoroalkyl; $(C_{1-3})$fluoroalkoxy; halogen; and cyano (especially mono- or di-substituted with methyl; methoxy; trifluoromethyl, trifluoromethoxy; or halogen; preferably trifluoromethyl or halogen); [in particular such $Ar^1$ represents 2-fluoro-phenyl, 3-fluoro-phenyl, 4-fluoro-phenyl, 2,4-difluoro-phenyl, 2,6-difluoro-phenyl, 2-chloro-phenyl, 3-chloro-phenyl, 4-chloro-phenyl, 2-chloro-4-fluoro-phenyl, 2,3-dichloro-phenyl, 2,6-dichloro-phenyl, 2-bromo-phenyl, 3-bromo-phenyl, 4-bromo-phenyl, 2-methyl-phenyl, 3-methyl-phenyl, 4-methyl-phenyl, 2,3-dimethyl-phenyl, 2-methoxy-phenyl, 3-methoxy-phenyl, 4-methoxy-phenyl, 3,4-dimethoxy-phenyl, 2-trifluoromethyl-phenyl, 3-trifluoromethyl-phenyl, 4-trifluoromethyl-phenyl, 4-fluoro-2-trifluoromethyl-phenyl, 2-trifluoromethoxy-phenyl, 3-trifluoromethoxy-phenyl, 4-trifluoromethoxy-phenyl; especially 2-chloro-phenyl, 2-bromo-phenyl, 2-trifluoromethyl-phenyl]; or
- 6-membered heteroaryl (in particular pyridinyl); which is mono-, or di-substituted, wherein the substituents are independently selected from $(C_{1-4})$alkyl; $(C_{1-4})$alkoxy; $(C_{1-3})$fluoroalkyl; $(C_{1-3})$fluoroalkoxy; halogen; and cyano (especially mono-substituted with methyl, trifluoromethyl or halogen); [in particular such $Ar^1$ represents 3-chloro-pyridin-2-yl, 3-trifluoromethyl-pyridin-2-yl, 6-trifluoromethyl-pyridin-2-yl, 3-fluoro-pyridin-2-yl, 5-fluoro-pyridin-2-yl, 3-chloro-pyridin-5-yl, 5-chloro-pyridin-2-yl, 3-bromo-pyridin-2-yl, 3-bromo-pyridin-4-yl, 3-methyl-pyridin-2-yl, 4-methyl-pyridin-2-yl, 5-methyl-pyridin-2-yl, 6-methyl-pyridin-2-yl, 4-methoxy-pyridin-2-yl; especially 3-chloro-pyridin-2-yl, 3-trifluoromethyl-pyridin-2-yl, 6-trifluoromethyl-pyridin-2-yl, 3-bromo-pyridin-2-yl, 3-methyl-pyridin-2-yl, 6-methyl-pyridin-2-yl];

wherein in a sub-embodiment $Ar^1$ especially represents 2,4-difluoro-phenyl, 2,6-difluoro-phenyl, 2-chloro-phenyl, 2-bromo-phenyl, 3-bromo-phenyl, 2,3-dichloro-phenyl, 2,6-dichloro-phenyl, 2-trifluoromethyl-phenyl, 3-trifluoromethyl-phenyl, 4-fluoro-2-trifluoromethyl-phenyl, 3-chloro-pyridin-2-yl, 3-trifluoromethyl-pyridin-2-yl, 6-trifluoromethyl-pyridin-2-yl, 3-bromo-pyridin-2-yl, 3-methyl-pyridin-2-yl, 4-methyl-pyridin-2-yl, 6-methyl-pyridin-2-yl, or 4-methoxy-pyridin-2-yl; in particular 2-chloro-phenyl, 2-bromo-phenyl, 2-trifluoromethyl-phenyl, 3-chloro-pyridin-2-yl, 3-trifluoromethyl-pyridin-2-yl, 6-trifluoromethyl-pyridin-2-yl, 3-bromo-pyridin-2-yl, 3-methyl-pyridin-2-yl, or 6-methyl-pyridin-2-yl.

18) Another embodiment relates to compounds according to any one of embodiments 1) to 17), wherein $R^4$ represents
- $(C_{2-5})$alkyl which is mono-substituted with $(C_{1-4})$alkoxy, cyano, or hydroxy; or di-substituted wherein the substituents are independently selected from $(C_{1-3})$alkoxy or hydroxy (especially mono-substituted with hydroxy; or disubstituted wherein the substituents are independently methoxy or hydroxy); [in particular such substituted $(C_{2-5})$alkyl is 2-methoxy-ethyl, 2-hydroxy-ethyl, 2-hydroxy-propyl, 2-hydroxy-2-methyl-propyl, 3-hydroxy-3-methyl-butyl, 2-hydroxy-3-methoxy-propyl];
- —$(C_{2-4})$alkylene-$NR^6R^7$, wherein $R^6$ and $R^7$ independently represent hydrogen; $(C_{1-4})$alkyl; $(C_{2-3})$fluoroalkyl; $(C_{3-6})$cycloalkyl; or $(C_{3-6})$cycloalkyl-$(C_{1-3})$alkyl; [in particular such —$(C_{2-4})$alkylene-$NR^6R^7$ is 2-amino-ethyl, 2-methylamino-ethyl, 2-dimethylamino-ethyl, 2-diethylamino-ethyl, 3-(dimethylamino)-propyl, 2-ethylamino-ethyl, 2-(ethyl-methylamino)-ethyl, 2-(isopropylamino)-ethyl, 2-(isopropylmethylamino)-ethyl, 2-(diisopropylamino)-ethyl, 2-(butyl-methylamino)-ethyl, 2-(tert-butylamino)-ethyl, 2-[(2-fluoroethyl)-methylamino]-ethyl, 2-[(2,2,2-trifluoroethyl)-amino]-ethyl, 2-[methyl-(2,2,2-trifluoroethyl)-amino]-ethyl, 2-[(2-fluoro-1-methylethyl)-methylamino]-ethyl, 2-[(cyclopropyl)-methylamino]-ethyl, 2-[(cyclopropylmethyl)-methylamino]-ethyl, 2-[(cyclobutyl)-methylamino]-ethyl, 2-[(cyclopentyl)-methylamino]-ethyl];
- $(C_{3-6})$cycloalkyl optionally mono-substituted with hydroxy; [in particular cyclopropyl, or 4-hydroxy-cyclohexyl];

$(C_{3-6})$cycloalkyl-$(C_{1-3})$alkyl, wherein the cycloalkyl group is optionally mono-substituted hydroxy; [in particular cyclopropyl-methyl, (1-hydroxy-cyclopentyl)-methyl]; or $(C_{4-7})$heterocyclyl or $(C_{4-7})$heterocyclyl-$(C_{1-3})$alkyl, wherein in the above groups the $(C_{4-7})$heterocyclyl independently contains one or two ring heteroatoms independently selected from nitrogen and oxygen; wherein in the above groups said $(C_{4-7})$heterocyclyl independently is unsubstituted, or mono-, or di-substituted, wherein the substituents are independently selected from:

one oxo substituent attached to a ring carbon atom in alpha position to a ring nitrogen (thus forming together with the nitrogen an amide group, or, in case a ring oxygen is additionaly adjacent, a carbamate group, or, in case second ring nitrogen is additionaly adjacent, a urea group); and/or $(C_{1-4})$alkyl (especially methyl) attached to a ring nitrogen atom having a free valency; or two fluoro substituents attached to a ring carbon atom;

[in particular such $(C_{4-7})$heterocyclyl is pyrrolidin-3-yl, 1-methyl-pyrrolidin-3-yl, piperidin-3-yl, 1-methyl-piperidin-3-yl, piperidin-4-yl, 1-methyl-piperidin-4-yl, tetrahydro-pyran-4-yl; and such $(C_{4-7})$heterocyclyl-$(C_{1-3})$alkyl is 2-(pyrrolidin-1-yl)-ethyl, 2-(2-oxo-imidazolidin-1-yl)-ethyl, 2-(1-methyl-pyrrolidin-2-yl)-ethyl, 2-(2-oxo-pyrrolidin-1-yl)-ethyl, 2-(morpholin-4-yl)-ethyl, pyrrolidin-3-yl-methyl, 3-(pyrrolidin-1-yl)-propyl, [1,4]dioxan-2-yl-methyl, 2-(piperazin-1-yl)-ethyl, 2-(piperidin-1-yl)-ethyl, 2-(azepan-1-yl)-ethyl, 2-(3,3-difluoroazetidin-1-yl)-ethyl, 2-(3,3-difluoropyrrolidin-1-yl)-ethyl, 2-(3,3-difluoropiperidin-1-yl)-ethyl, 2-(4,4-difluoropiperidin-1-yl)-ethyl].

19) Another embodiment relates to compounds according to any one of embodiments 1) to 17), wherein $R^4$ represents $(C_{2-5})$alkyl which is mono-substituted with hydroxy; or disubstituted wherein the substituents are independently methoxy or hydroxy; [in particular such substituted $(C_{2-5})$alkyl is 2-hydroxy-ethyl, 2-hydroxy-propyl, 2-hydroxy-2-methyl-propyl, 3-hydroxy-3-methyl-butyl, 2-hydroxy-3-methoxy-propyl];

—$(C_{2-4})$alkylene-$NR^6R^7$, wherein $R^6$ represents hydrogen or $(C_{1-4})$alkyl (especially methyl); and $R^7$ represents $(C_{1-4})$alkyl (especially methyl); $(C_{2-3})$fluoroalkyl (especially 2,2,2-trifluoroethyl); $(C_{3-6})$cycloalkyl (especially cyclopropyl); or $(C_{3-6})$cycloalkyl-$(C_{1-3})$alkyl (especially cyclopropylmethyl); [in particular such —$(C_{2-4})$alkylene-$NR^6R^7$ is 2-amino-ethyl, 2-methylamino-ethyl, 2-dimethylamino-ethyl, 2-diethylamino-ethyl, 3-(dimethylamino)-propyl, 2-ethylamino-ethyl, 2-(ethyl-methylamino)-ethyl, 2-(isopropylamino)-ethyl, 2-(isopropyl-methylamino)-ethyl, 2-(diisopropylamino)-ethyl, 2-(tert-butylamino)-ethyl, 2-(butyl-methylamino)-ethyl, 2-[(2-fluoroethyl)-methylamino]-ethyl, 2-[(2,2,2-trifluoroethyl)-amino]-ethyl, 2-[methyl-(2,2,2-trifluoroethyl)-amino]-ethyl, 2-[(2-fluoro-1-methylethyl)-methylamino]-ethyl, 2-[(cyclopropyl)-methylamino]-ethyl, 2-[(cyclopropylmethyl)-methylamino]-ethyl, 2-[(cyclobutyl)-methylamino]-ethyl, 2-[(cyclopentyl)-methylamino]-ethyl];

$(C_{3-6})$cycloalkyl-$(C_{1-3})$alkyl, wherein the cycloalkyl group is optionally mono-substituted with hydroxy; [in particular cyclopropyl-methyl, or (1-hydroxy-cyclopentyl)-methyl]; or $(C_{4-7})$heterocyclyl or $(C_{4-7})$heterocyclyl-$(C_{1-3})$alkyl, wherein in the above groups the $(C_{4-7})$heterocyclyl independently contains one or two ring heteroatoms independently selected from nitrogen and oxygen (especially one ring nitrogen atom); wherein in the above groups said $(C_{4-7})$heterocyclyl independently is unsubstituted, or mono-, or di-substituted, wherein the substituents are independently selected from:

one oxo substituent attached to a ring carbon atom in alpha position to a ring nitrogen (thus forming together with the nitrogen an amide group, or, in case a ring oxygen is additionaly adjacent, a carbamate group, or, in case second ring nitrogen is additionaly adjacent, a urea group); and/or $(C_{1-4})$alkyl (especially methyl) attached to a ring nitrogen atom having a free valency; or two fluoro substituents attached to a ring carbon atom;

[in particular such $(C_{4-7})$heterocyclyl is pyrrolidin-3-yl, 1-methyl-pyrrolidin-3-yl, piperidin-3-yl, 1-methyl-piperidin-3-yl, piperidin-4-yl, 1-methyl-piperidin-4-yl, tetrahydro-pyran-4-yl; and such $(C_{4-7})$heterocyclyl-$(C_{1-3})$alkyl is 2-(pyrrolidin-1-yl)-ethyl, 2-(2-oxo-imidazolidin-1-yl)-ethyl, 2-(1-methyl-pyrrolidin-2-yl)-ethyl, 2-(2-oxo-pyrrolidin-1-yl)-ethyl, 2-(morpholin-4-yl)-ethyl, pyrrolidin-3-yl-methyl, 3-(pyrrolidin-1-yl)-propyl, 2-(piperazin-1-yl)-ethyl, 2-(piperidin-1-yl)-ethyl, 2-(azepan-1-yl)-ethyl, 2-(3,3-difluoroazetidin-1-yl)-ethyl, 2-(3,3-difluoropyrrolidin-1-yl)-ethyl, 2-(3,3-difluoropiperidin-1-yl)-ethyl, 2-(4,4-difluoropiperidin-1-yl)-ethyl];

wherein in a sub-embodiment $R^4$ especially represents 2-methylamino-ethyl, 2-dimethylamino-ethyl, 2-(isopropylamino)-ethyl, 2-(tert-butylamino)-ethyl, 2-[(cyclopropyl)-methylamino]-ethyl, 2-(pyrrolidin-1-yl)-ethyl, 2-(morpholin-4-yl)-ethyl, or 2-(4,4-difluoropiperidin-1-yl)-ethyl.

20) Another embodiment relates to compounds according to any one of embodiments 1) to 17), wherein $R^4$ represents $(C_{2-5})$alkyl which is mono-substituted with hydroxy (in particular 2-methoxy-ethyl, 2-hydroxy-ethyl, 2-hydroxy-propyl, 2-hydroxy-2-methyl-propyl, 3-hydroxy-3-methyl-butyl, 2-methoxy-ethyl, especially 2-hydroxy-2-methyl-propyl];

$(C_{2-5})$alkyl which is disubstituted wherein the substituents are independently methoxy or hydroxy; [in particular 2-hydroxy-3-methoxy-propyl];

—$(C_{2-4})$alkylene-$NR^6R^7$, wherein $R^6$ represents hydrogen or $(C_{1-4})$alkyl (especially methyl); and $R^7$ represents $(C_{1-4})$alkyl (especially methyl); $(C_{2-3})$fluoroalkyl (especially 2,2,2-trifluoroethyl); $(C_{3-6})$cycloalkyl (especially cyclopropyl); or $(C_{3-6})$cycloalkyl-$(C_{1-3})$alkyl (especially cyclopropylmethyl); [in particular such —$(C_{2-4})$alkylene-$NR^6R^7$ is 2-amino-ethyl, 2-methylamino-ethyl, 2-dimethylamino-ethyl, 2-diethylamino-ethyl, 3-(dimethylamino)-propyl, 2-ethylamino-ethyl, 2-(ethyl-methylamino)-ethyl, 2-(isopropylamino)-ethyl, 2-(isopropyl-methylamino)-ethyl, 2-(diisopropylamino)-ethyl, 2-(tert-butylamino)-ethyl, 2-(butyl-methylamino)-ethyl, 2-[(2-fluoroethyl)-methylamino]-ethyl, 2-[(2,2,2-trifluoroethyl)-amino]-ethyl, 2-[methyl-(2,2,2-trifluoroethyl)-amino]-ethyl, 2-[(2-fluoro-1-methylethyl)-methylamino]-ethyl, 2-[(cyclopropyl)-methylamino]-ethyl, 2-[(cyclopropylmethyl)-methylamino]-ethyl, 2-[(cyclobutyl)-methylamino]-ethyl, 2-[(cyclopentyl)-methylamino]-ethyl; especially 2-methylamino-ethyl, 2-dimethylamino-ethyl, or 2-ethylamino-ethyl];

$(C_{3-6})$cycloalkyl-$(C_{1-3})$alkyl, wherein the cycloalkyl group is mono-substituted with hydroxy; [in particular (1-hydroxy-cyclopentyl)-methyl];

($C_{4-7}$)heterocyclyl wherein the ($C_{4-7}$)heterocyclyl contains one ring heteroatom selected from nitrogen or oxygen (especially one ring nitrogen atom); wherein in the above groups said ($C_{4-7}$)heterocyclyl independently is unsubstituted, or mono-substituted with ($C_{1-4}$)alkyl (especially methyl) attached to a ring nitrogen atom having a free valency; [in particular pyrrolidin-3-yl, 1-methyl-pyrrolidin-3-yl, piperidin-3-yl, 1-methyl-piperidin-3-yl, piperidin-4-yl, 1-methyl-piperidin-4-yl, or tetrahydro-pyran-4-yl; especially pyrrolidin-3-yl];

($C_{4-7}$)heterocyclyl-($C_{1-3}$)alkyl, wherein the ($C_{4-7}$)heterocyclyl contains one or two ring heteroatoms independently selected from nitrogen and oxygen (especially one ring nitrogen atom); wherein in the above groups said ($C_{4-7}$)heterocyclyl independently is unsubstituted, or mono-, or di-substituted, wherein the substituents are selected from:

($C_{1-4}$)alkyl (especially methyl) attached to a ring nitrogen atom having a free valency; or two fluoro substituents attached to a ring carbon atom;

[in particular 2-(pyrrolidin-1-yl)-ethyl, 2-(1-methyl-pyrrolidin-2-yl)-ethyl, 2-(morpholin-4-yl)-ethyl, pyrrolidin-3-yl-methyl, 3-(pyrrolidin-1-yl)-propyl, 2-(piperazin-1-yl)-ethyl, 2-(piperidin-1-yl)-ethyl, 2-(azepan-1-yl)-ethyl, 2-(3,3-difluoroazetidin-1-yl)-ethyl, 2-(3,3-difluoropyrrolidin-1-yl)-ethyl, 2-(3,3-difluoropiperidin-1-yl)-ethyl, or 2-(4,4-difluoropiperidin-1-yl)-ethyl; especially 2-(pyrrolidin-1-yl)-ethyl, 2-(morpholin-4-yl)-ethyl, pyrrolidin-3-yl-methyl, 2-(piperazin-1-yl)-ethyl, 2-(4,4-difluoropiperidin-1-yl)-ethyl].

wherein in a sub-embodiment $R^4$ especially represents 2-methylamino-ethyl, 2-dimethylamino-ethyl, 2-(isopropylamino)-ethyl, 2-(tert-butylamino)-ethyl, 2-[(cyclopropyl)-methylamino]-ethyl, 2-(pyrrolidin-1-yl)-ethyl, 2-(morpholin-4-yl)-ethyl, or 2-(4,4-difluoropiperidin-1-yl)-ethyl.

21) Another embodiment relates to compounds according to any one of embodiments 1) to 17), wherein $R^4$ represents 2-hydroxy-ethyl, 2-hydroxy-propyl, 2-hydroxy-2-methyl-propyl, 3-hydroxy-3-methyl-butyl, or 2-methoxy-ethyl (especially 2-hydroxy-2-methyl-propyl);

2-hydroxy-3-methoxy-propyl;

—($C_{2-4}$)alkylene-$NR^6R^7$ selected from 2-amino-ethyl, 2-methylamino-ethyl, 2-dimethylamino-ethyl, 2-diethylamino-ethyl, 3-(dimethylamino)-propyl, 2-ethylamino-ethyl, 2-(ethyl-methylamino)-ethyl, 2-(isopropylamino)-ethyl, 2-(isopropyl-methylamino)-ethyl, 2-(diisopropylamino)-ethyl, 2-(tert-butylamino)-ethyl, 2-(butyl-methylamino)-ethyl, 2-[(2-fluoroethyl)-methylamino]-ethyl, 2-[(2,2,2-trifluoroethyl)-amino]-ethyl, 2-[methyl-(2,2,2-trifluoroethyl)-amino]-ethyl, 2-[(2-fluoro-1-methylethyl)-methylamino]-ethyl, 2-[(cyclopropyl)-methylamino]-ethyl, 2-[(cyclopropylmethyl)-methylamino]-ethyl, 2-[(cyclobutyl)-methylamino]-ethyl, and 2-[(cyclopentyl)-methylamino]-ethyl; especially 2-methylamino-ethyl, 2-dimethylamino-ethyl, or 2-ethylamino-ethyl;

(1-hydroxy-cyclopentyl)-methyl;

($C_{4-7}$)heterocyclyl selected from pyrrolidin-3-yl, 1-methyl-pyrrolidin-3-yl, piperidin-3-yl, 1-methyl-piperidin-3-yl, piperidin-4-yl, 1-methyl-piperidin-4-yl, and tetrahydro-pyran-4-yl; especially pyrrolidin-3-yl;

($C_{4-7}$)heterocyclyl-($C_{1-3}$)alkyl selected from 2-(pyrrolidin-1-yl)-ethyl, 2-(1-methyl-pyrrolidin-2-yl)-ethyl, 2-(morpholin-4-yl)-ethyl, pyrrolidin-3-yl-methyl, 3-(pyrrolidin-1-yl)-propyl, 2-(piperazin-1-yl)-ethyl, 2-(piperidin-1-yl)-ethyl, 2-(azepan-1-yl)-ethyl, 2-(3,3-difluoroazetidin-1-yl)-ethyl, 2-(3,3-difluoropyrrolidin-1-yl)-ethyl, 2-(3,3-difluoropiperidin-1-yl)-ethyl, and 2-(4,4-difluoropiperidin-1-yl)-ethyl; especially 2-(pyrrolidin-1-yl)-ethyl, 2-(morpholin-4-yl)-ethyl, pyrrolidin-3-yl-methyl, [1,4]dioxan-2-yl-methyl, 2-(piperazin-1-yl)-ethyl, or 2-(4,4-difluoropiperidin-1-yl)-ethyl;

wherein in a sub-embodiment $R^4$ especially represents 2-methylamino-ethyl, 2-dimethylamino-ethyl, 2-(isopropylamino)-ethyl, 2-(tert-butylamino)-ethyl, 2-[(cyclopropyl)-methylamino]-ethyl, 2-(pyrrolidin-1-yl)-ethyl, 2-(morpholin-4-yl)-ethyl, or 2-(4,4-difluoropiperidin-1-yl)-ethyl.

22) The invention, thus, relates to compounds of the formula (I) as defined in embodiment 1), or to such compounds further limited by the characteristics of any one of embodiments 2) to 21), under consideration of their respective dependencies; to pharmaceutically acceptable salts thereof; and to the use of such compounds as medicaments especially in the treatment of disorders relating to a dysfunction of the CXCR7 receptor or its ligands as described herein below. For avoidance of any doubt, especially the following embodiments relating to the compounds of formula (I) are thus possible and intended and herewith specifically disclosed in individualized form:

1, 3+1, 6+1, 6+3+1, 8+1, 8+3+1, 8+6+1, 8+6+3+1, 10+1, 10+3+1, 10+6+1, 10+6+3+1, 10+8+1, 10+8+3+1, 10+8+6+1, 10+8+6+3+1, 13+1, 13+3+1, 13+6+1, 13+6+3+1, 13+8+1, 13+8+3+1, 13+8+6+1, 13+8+6+3+1, 13+10+1, 13+10+3+1, 13+10+6+1, 13+10+6+3+1, 13+10+8+1, 13+10+8+3+1, 13+10+8+6+1, 13+10+8+6+3+1, 17+1, 17+3+1, 17+6+1, 17+6+3+1, 17+8+1, 17+8+3+1, 17+8+6+1, 17+8+6+3+1, 17+10+1, 17+10+3+1, 17+10+6+1, 17+10+6+3+1, 17+10+8+1, 17+10+8+3+1, 17+10+8+6+1, 17+10+8+6+3+1, 17+13+1, 17+13+3+1, 17+13+6+1, 17+13+6+3+1, 17+13+8+1, 17+13+8+3+1, 17+13+8+6+1, 17+13+8+6+3+1, 17+13+10+1, 17+13+10+3+1, 17+13+10+6+1, 17+13+10+6+3+1, 17+13+10+8+1, 17+13+10+8+3+1, 17+13+10+8+6+1, 17+13+10+8+6+3+1, 19+1, 19+3+1, 19+6+1, 19+6+3+1, 19+8+1, 19+8+3+1, 19+8+6+1, 19+8+6+3+1, 19+10+1, 19+10+3+1, 19+10+6+1, 19+10+6+3+1, 19+10+8+1, 19+10+8+3+1, 19+10+8+6+1, 19+10+8+6+3+1, 19+13+1, 19+13+3+1, 19+13+6+1, 19+13+6+3+1, 19+13+8+1, 19+13+8+3+1, 19+13+8+6+1, 19+13+8+6+3+1, 19+13+10+1, 19+13+10+3+1, 19+13+10+6+1, 19+13+10+6+3+1, 19+13+10+8+1, 19+13+10+8+3+1, 19+13+10+8+6+1, 19+13+10+8+6+3+1, 19+17+1, 19+17+3+1, 19+17+6+1, 19+17+6+3+1, 19+17+8+1, 19+17+8+3+1, 19+17+8+6+1, 19+17+8+6+3+1, 19+17+10+1, 19+17+10+3+1, 19+17+10+6+1, 19+17+10+6+3+1, 19+17+10+8+1, 19+17+10+8+3+1, 19+17+10+8+6+1, 19+17+10+8+6+3+1, 19+17+13+1, 19+17+13+3+1, 19+17+13+6+1, 19+17+13+6+3+1, 19+17+13+8+1, 19+17+13+8+3+1, 19+17+13+8+6+1, 19+17+13+8+6+3+1, 19+17+13+10+1, 19+17+13+10+3+1, 19+17+13+10+6+1, 19+17+13+10+6+3+1, 19+17+13+10+8+1, 19+17+13+10+8+3+1, 19+17+13+10+8+6+1, 19+17+13+10+8+6+3+1, 21+1, 21+3+1, 21+6+1, 21+6+3+1, 21+8+1, 21+8+3+1, 21+8+6+1, 21+8+6+3+1, 21+10+1, 21+10+3+1, 21+10+6+1, 21+10+6+3+1, 21+10+8+1, 21+10+8+3+1, 21+10+8+6+1, 21+10+8+6+3+1, 21+13+1, 21+13+3+1, 21+13+6+1, 21+13+6+3+1, 21+13+8+1, 21+13+8+3+1, 21+13+8+6+1, 21+13+8+6+3+1, 21+13+10+1, 21+13+10+3+1, 21+13+10+6+1, 21+13+10+6+3+1, 21+13+10+8+1, 21+13+10+8+3+1, 21+13+10+8+6+1, 21+13+10+8+6+3+1, 21+17+1, 21+17+3+1, 21+17+6+1, 21+17+6+3+1, 21+17+8+1,

21+17+8+3+1, 21+17+8+6+1, 21+17+8+6+3+1, 21+17+10+1, 21+17+10+3+1, 21+17+10+6+1, 21+17+10+6+3+1, 21+17+10+8+1, 21+17+10+8+3+1, 21+17+10+8+6+1, 21+17+10+8+6+3+1, 21+17+13+1, 21+17+13+3+1, 21+17+13+6+1, 21+17+13+6+3+1, 21+17+13+8+1, 21+17+13+8+3+1, 21+17+13+8+6+1, 21+17+13+8+6+3+1, 21+17+13+10+1, 21+17+13+10+3+1, 21+17+13+10+6+1, 21+17+13+10+6+3+1, 21+17+13+10+8+1, 21+17+13+10+8+3+1, 21+17+13+10+8+6+1, 21+17+13+10+8+6+3+1.

In the list above the numbers refer to the embodiments according to their numbering provided hereinabove whereas "+" indicates the dependency from another embodiment. The different individualized embodiments are separated by commas. In other words, "17+13+3+1" for example refers to embodiment 17) depending on embodiment 13), depending on embodiment 3), depending on embodiment 1), i.e. embodiment "17+13+3+1" corresponds to the compounds of formula (I) according to embodiment 1) further limited by all the features of the embodiments 3), 13), and 17).

23) A second aspect of the invention relates to compounds of the formula (I) according to embodiment 1) which are also compounds of the formula (II)

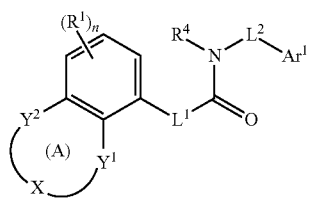

Formula (II)

wherein
Y$^1$ and Y$^2$ both represent CH$_2$; and
X represents —CH$_2$—NR$^5$—CH$_2$—, or
X represents *—CO—NR$^5$—CH$_2$—, or
X represents *—CH$_2$—NR$^5$—CO—; or
Y$^1$ represents O, CH$_2$, or NR$^{Y1}$ wherein R$^{Y1}$ represents hydrogen or (C$_{1-3}$)alkyl;
Y$^2$ represents CH$_2$; and
X represents *—CH$_2$—CH$_2$—NR$^5$—; or
X represents *—CH$_2$—CO—NR$^5$—; or
Y$^1$ represents O, CH$_2$, or NR$^{Y1}$ wherein R$^{Y1}$ represents hydrogen or (C$_{1-3}$)alkyl;
Y$^2$ represents CO; and
X represents *—CH$_2$—CH$_2$—NR$^5$—; or
Y$^1$ represents CH$_2$;
Y$^2$ represents O, CH$_2$, or NR$^{Y2}$ wherein R$^{Y2}$ represents hydrogen or (C$_{1-3}$)alkyl; and
X represents *—NR$^5$—CH$_2$—CH$_2$—; or
X represents *—NR$^5$—CO—CH$_2$—; or
Y$^1$ represents CO;
Y$^2$ represents O, CH$_2$, or NR$^{Y2}$ wherein R$^{Y2}$ represents hydrogen or (C$_{1-3}$)alkyl; and
X represents *—NR$^5$—CH$_2$—CH$_2$—;
wherein the asterisks indicate the bond which is attached to the group Y$^1$;
R$^5$ represents
(C$_{1-6}$)alkyl [in particular methyl, ethyl, propyl, isopropyl, isobutyl, 1-methyl-propyl, 1,2-dimethyl-propyl, 2,2-dimethyl-propyl, 3,3-dimethyl-butyl];
(C$_{1-4}$)alkyl mono-substituted with (C$_{1-3}$)alkoxy [in particular 2-methoxy-ethyl, 2-methoxy-1-methyl-ethyl];
—CO—R$^{10}$ wherein R$^{10}$ represents (C$_{1-5}$)alkyl; (C$_{1-5}$)alkoxy; (C$_{3-6}$)cycloalkyl-(C$_{1-3}$)alkyl; (C$_{1-3}$)fluoroalkyl; (C$_{1-5}$)fluoroalkoxy; hydroxy-(C$_{1-5}$)alkyl; (C$_{1-3}$)alkoxy-(C$_{2-3}$)alkoxy; (C$_{1-3}$)alkoxy-(C$_{1-3}$)alkyl; (C$_{3-6}$)cycloalkyl optionally containing one ring oxygen atom, wherein said cycloalkyl is optionally mono- or di-substituted with fluoro; or —NR$^{10a}$R$^{10b}$ wherein R$^{10a}$ and R$^{10b}$ independently represent hydrogen, (C$_{1-4}$)alkyl or (C$_{3-6}$)cycloalkyl, or R$^{10a}$ and R$^{10b}$ together with the nitrogen to which they are attached to form a 5- to 7-membered saturated ring; [in particular such —CO—R$^{10}$ is methyl-carbonyl, ethyl-carbonyl, propyl-carbonyl, isopropyl-carbonyl, isobutyl-carbonyl, tert-butyl-carbonyl, (2,2-dimethyl-propyl)-carbonyl, hydroxymethyl-carbonyl, methoxymethyl-carbonyl, cyclopropyl-carbonyl, cyclobutyl-carbonyl, (2-fluoro-cyclopropyl)-carbonyl, (cyclohexyl-methyl)-carbonyl, (2,2-difluorocyclopropyl)-carbonyl, (1-trifluoromethyl-cyclopropyl)-carbonyl, (tetrahydrofuran-3-yl)-carbonyl, trifluoromethyl-carbonyl, (1,1-difluoro-ethyl)-carbonyl, carbamoyl, methylcarbamoyl, ethylcarbamoyl, isopropylcarbamoyl, butyl-carbamoyl, tert-butyl-carbamoyl, cyclohexyl-carbamoyl, dimethyl-carbamoyl, (pyrrolidin-1-yl)-carbonyl, methoxycarbonyl, ethoxycarbonyl, propoxycarbonyl, isopropoxycarbonyl, isobutoxycarbonyl, tert-butoxycarbonyl, (2,2-dimethyl-propoxy)-carbonyl, (2-fluoro-ethoxy)-carbonyl, (2-methoxy-ethoxy)-carbonyl]
(C$_{2-4}$)fluoroalkyl [in particular 2-fluoroethyl, 2,2,2-trifluoroethyl, 3-fluoropropyl];
(C$_{3-6}$)cycloalkyl optionally containing one ring oxygen atom [in particular cyclobutyl, oxetan-3-yl, cyclopentyl, tetrahydrofuran-3-yl];
(C$_{3-6}$)cycloalkyl-(C$_{1-3}$)alkyl, wherein the (C$_{3-6}$)cycloalkyl group optionally contains one ring oxygen atom [in particular such (C$_{3-6}$)cycloalkyl-(C$_{1-3}$)alkyl is cyclopropyl-methyl, cyclobutylmethyl, cyclohexyl-methyl, 1-cyclopropyl-ethyl];
(R$^1$)$_n$ is absent;
L$^1$ represents a two-membered linker group selected from —NH—CH$_2$—*, —O—CH$_2$—*, and —CH$_2$CH$_2$— (notably L$^1$ represents —NH—CH$_2$—*); wherein the asterisks indicate the bond with which the group L$^1$ is attached to the carbonyl group;
L$^2$ represents a linker group selected from —CH$_2$—, —CH(CH$_3$)—, and —CH$_2$—CH$_2$— (notably —CH$_2$—);
Ar$^1$ represents
phenyl which is mono-, or di-substituted, wherein the substituents are independently selected from (C$_{1-4}$)alkyl; (C$_{1-4}$)alkoxy; (C$_{1-5}$)fluoroalkyl; (C$_{1-3}$)fluoroalkoxy; halogen; and cyano (especially mono- or di-substituted with methyl; methoxy; trifluoromethyl, trifluoromethoxy; or halogen; preferably trifluoromethyl or halogen); [in particular such Ar$^1$ represents 2-fluoro-phenyl, 3-fluoro-phenyl, 4-fluoro-phenyl, 2,4-difluoro-phenyl, 2,6-difluoro-phenyl, 2-chloro-phenyl, 3-chloro-phenyl, 4-chloro-phenyl, 2-chloro-4-fluoro-phenyl, 2,3-dichloro-phenyl, 2,6-dichloro-phenyl, 2-bromo-phenyl, 3-bromo-phenyl, 4-bromo-phenyl, 2-methyl-phenyl, 3-methyl-phenyl, 4-methyl-phenyl, 2,3-dimethyl-phenyl, 2-methoxy-phenyl, 3-methoxy-phenyl, 4-methoxy-phenyl, 3,4-dimethoxy-phenyl, 2-trifluoromethyl-phenyl, 3-trifluoromethyl-phenyl, 4-trifluoromethyl-phenyl, 4-fluoro-2-trifluoromethyl-phenyl, 2-trifluoromethoxy-phenyl, 3-trifluoromethoxy-phenyl, 4-trifluoromethoxy-phenyl; especially 2-chloro-phenyl, 2-bromo-phenyl, 2-trifluoromethyl-phenyl]; or
6-membered heteroaryl (in particular pyridinyl); which is mono-, or di-substituted, wherein the substituents are independently selected from $(C_{1-4})$alkyl; $(C_{1-4})$alkoxy; $(C_{1-3})$fluoroalkyl; $(C_{1-3})$fluoroalkoxy; halogen; and cyano (especially mono-substituted with methyl, trifluoromethyl or halogen); [in particular such $Ar^1$ represents 3-chloro-pyridin-2-yl, 3-trifluoromethyl-pyridin-2-yl, 6-trifluoromethyl-pyridin-2-yl, pyrimidin-2-yl, pyrimidin-4-yl, pyridin-3-yl, pyridin-4-yl, 3-fluoro-pyridin-2-yl, 5-fluoro-pyridin-2-yl, 3-chloro-pyridin-5-yl, 5-chloro-pyridin-2-yl, 3-bromo-pyridin-2-yl, 3-bromo-pyridin-4-yl, 3-methyl-pyridin-2-yl, 4-methyl-pyridin-2-yl, 5-methyl-pyridin-2-yl, 6-methyl-pyridin-2-yl, 4-methoxy-pyridin-2-yl; especially 3-chloro-pyridin-2-yl, 3-trifluoromethyl-pyridin-2-yl, 6-trifluoromethyl-pyridin-2-yl, 3-bromo-pyridin-2-yl, 3-methyl-pyridin-2-yl, 6-methyl-pyridin-2-yl]; and $R^4$ represents
$(C_{2-5})$alkyl which is mono-substituted with $(C_{1-4})$alkoxy, cyano, or hydroxy; or di-substituted wherein the substituents are independently selected from $(C_{1-3})$alkoxy or hydroxy (especially mono-substituted with hydroxy; or disubstituted wherein the substituents are independently methoxy or hydroxy); [in particular such substituted $(C_{2-5})$alkyl is 2-methoxy-ethyl, 2-hydroxy-ethyl, 2-hydroxy-propyl, 2-hydroxy-2-methyl-propyl, 3-hydroxy-3-methyl-butyl, 2-hydroxy-3-methoxy-propyl];
—$(C_{2-4})$alkylene-$NR^6R^7$, wherein $R^6$ and $R^7$ independently represent hydrogen; $(C_{1-4})$alkyl; $(C_{2-3})$fluoroalkyl; $(C_{3-6})$cycloalkyl; or $(C_{3-6})$cycloalkyl-$(C_{1-3})$alkyl; [in particular such —$(C_{2-4})$alkylene-$NR^6R^7$ is 2-amino-ethyl, 2-methylamino-ethyl, 2-dimethylamino-ethyl, 2-diethylamino-ethyl, 3-(dimethylamino)-propyl, 2-ethylamino-ethyl, 2-(ethyl-methylamino)-ethyl, 2-(isopropylamino)-ethyl, 2-(isopropylmethylamino)-ethyl, 2-(diisopropylamino)-ethyl, 2-(butyl-methylamino)-ethyl, 2-(tert-butylamino)-ethyl, 2-[(2-fluoroethyl)-methylamino]-ethyl, 2-[(2,2,2-trifluoroethyl)-amino]-ethyl, 2-[methyl-(2,2,2-trifluoroethyl)-amino]-ethyl, 2-[(2-fluoro-1-methylethyl)-methylamino]-ethyl, 2-[(cyclopropyl)-methylamino]-ethyl, 2-[(cyclopropylmethyl)-methylamino]-ethyl, 2-[(cyclobutyl)-methylamino]-ethyl, 2-[(cyclopentyl)-methylamino]-ethyl];
$(C_{3-6})$cycloalkyl optionally mono-substituted with hydroxy; [in particular cyclopropyl, or 4-hydroxy-cyclohexyl];
$(C_{3-6})$cycloalkyl-$(C_{1-3})$alkyl, wherein the cycloalkyl group is optionally mono-substituted hydroxy; [in particular cyclopropyl-methyl, (1-hydroxy-cyclopentyl)-methyl]; or
$(C_{4-7})$heterocyclyl or $(C_{4-7})$heterocyclyl-$(C_{1-3})$alkyl, wherein in the above groups the $(C_{4-7})$heterocyclyl independently contains one or two ring heteroatoms independently selected from nitrogen and oxygen; wherein in the above groups said $(C_{4-7})$heterocyclyl independently is unsubstituted, or mono-, or di-substituted, wherein the substituents are independently selected from:
one oxo substituent attached to a ring carbon atom in alpha position to a ring nitrogen (thus forming together with the nitrogen an amide group, or, in case a ring oxygen is additionaly adjacent, a carbamate group, or, in case second ring nitrogen is additionaly adjacent, a urea group); and/or
$(C_{1-4})$alkyl (especially methyl) attached to a ring nitrogen atom having a free valency; or
two fluoro substituents attached to a ring carbon atom;
[in particular such $(C_{4-7})$heterocyclyl is pyrrolidin-3-yl, 1-methyl-pyrrolidin-3-yl, piperidin-3-yl, 1-methyl-piperidin-3-yl, piperidin-4-yl, 1-methyl-piperidin-4-yl, tetrahydro-pyran-4-yl; and such $(C_{4-7})$heterocyclyl-$(C_{1-3})$alkyl is 2-(pyrrolidin-1-yl)-ethyl, 2-(2-oxo-imidazolidin-1-yl)-ethyl, 2-(1-methyl-pyrrolidin-2-yl)-ethyl, 2-(2-oxo-pyrrolidin-1-yl)-ethyl, 2-(morpholin-4-yl)-ethyl, pyrrolidin-3-yl-methyl, 3-(pyrrolidin-1-yl)-propyl, [1,4]dioxan-2-yl-methyl, 2-(piperazin-1-yl)-ethyl, 2-(piperidin-1-yl)-ethyl, 2-(azepan-1-yl)-ethyl, 2-(3,3-difluoroazetidin-1-yl)-ethyl, 2-(3,3-difluoropyrrolidin-1-yl)-ethyl, 2-(3,3-difluoropiperidin-1-yl)-ethyl, 2-(4,4-difluoropiperidin-1-yl)-ethyl];

wherein the characteristics disclosed in embodiments 2) to 22) are intended to apply mutatis mutandis also to the compounds formula (II) according to embodiment 23); wherein especially the following embodiments are thus possible and intended and herewith specifically disclosed in individualized form:
23, 23+3, 23+6+3, 23+6, 23+7+3, 23+7, 23+11+3, 23+11+6+3, 23+11+6, 23+11+7+3, 23+11+7, 23+11, 23+14+3, 23+14+6+3, 23+14+6, 23+14+7+3, 23+14+7, 23+14+11+3, 23+14+11+6+3, 23+14+11+6, 23+14+11+7+3, 23+14+11+7, 23+14+11, 23+14, 23+19+3, 23+19+6+3, 23+19+6, 23+19+7+3, 23+19+7, 23+19+11+3, 23+19+11+6+3, 23+19+11+6, 23+19+11+7+3, 23+19+11+7, 23+19+11, 23+19+14+3, 23+19+14+6+3, 23+19+14+6, 23+19+14+7+3, 23+19+14+7, 23+19+14+11+3, 23+19+14+11+6+3, 23+19+14+11+6, 23+19+14+11+7+3, 23+19+14+11+7, 23+19+14+11, 23+19+14, 23+19+17, 23+19, 23+21+3, 23+21+6+3, 23+21+6, 23+21+7+3, 23+21+7, 23+21+11+3, 23+21+11+6+3, 23+21+11+6, 23+21+11+7+3, 23+21+11+7, 23+21+11, 23+21+14+3, 23+21+14+6+3, 23+21+14+6, 23+21+14+7+3, 23+21+14+7, 23+21+14+11+3, 23+21+14+11+6+3, 23+21+14+11+6, 23+21+14+11+7+3, 23+21+14+11+7, 23+21+14+11, 23+21+14, 23+21+17, 23+21.

In the list above the numbers refer to the embodiments according to their numbering provided hereinabove whereas "+" indicates the limitations as outlined above.

24) A third aspect of the invention relates to compounds of the formula (I) according to embodiment 1) which are also compounds of the formula (III)

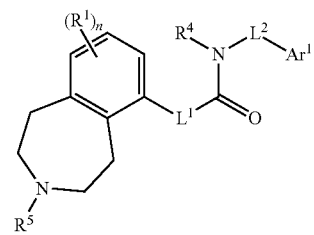

Formula (III)

wherein
$R^5$ represents
$(C_{1-6})$alkyl [in particular methyl, ethyl, propyl, isopropyl, isobutyl, 1-methyl-propyl, 1,2-dimethyl-propyl, 2,2-dimethyl-propyl, 3,3-dimethyl-butyl];

($C_{1-4}$)alkyl mono-substituted with ($C_{1-3}$)alkoxy [in particular 2-methoxy-ethyl, 2-methoxy-1-methyl-ethyl];
—CO—$R^{10}$ wherein $R^{10}$ represents ($C_{1-5}$)alkyl; ($C_{1-5}$) alkoxy; ($C_{3-6}$)cycloalkyl-($C_{1-3}$)alkyl; ($C_{1-3}$)fluoroalkyl; ($C_{1-3}$)fluoroalkoxy; hydroxy-($C_{1-3}$)alkyl; ($C_{1-3}$)alkoxy-($C_{2-3}$)alkoxy; ($C_{1-3}$)alkoxy-($C_{1-3}$)alkyl; ($C_{3-6}$)cycloalkyl optionally containing one ring oxygen atom, wherein said cycloalkyl is optionally mono- or di-substituted with fluoro; or —$NR^{10a}R^{10b}$ wherein $R^{10a}$ and $R^{10b}$ independently represent hydrogen, ($C_{1-4}$)alkyl or ($C_{3-6}$)cycloalkyl, or $R^{10a}$ and $R^{10b}$ together with the nitrogen to which they are attached to form a 5- to 7-membered saturated ring; [in particular such —CO—$R^{10}$ is methyl-carbonyl, ethyl-carbonyl, propyl-carbonyl, isopropyl-carbonyl, isobutyl-carbonyl, tert-butyl-carbonyl, (2,2-dimethyl-propyl)-carbonyl, hydroxymethyl-carbonyl, methoxymethyl-carbonyl, cyclopropyl-carbonyl, cyclobutyl-carbonyl, (2-fluoro-cyclopropyl)-carbonyl, (cyclohexyl-methyl)-carbonyl, (2,2-difluorocyclopropyl)-carbonyl, (1-trifluoromethyl-cyclopropyl)-carbonyl, (tetrahydrofuran-3-yl)-carbonyl, trifluoromethyl-carbonyl, (1,1-difluoro-ethyl)-carbonyl, carbamoyl, methylcarbamoyl, ethylcarbamoyl, isopropylcarbamoyl, butyl-carbamoyl, tert-butyl-carbamoyl, cyclohexyl-carbamoyl, dimethyl-carbamoyl, (pyrrolidin-1-yl)-carbonyl, methoxycarbonyl, ethoxycarbonyl, propoxycarbonyl, isopropoxycarbonyl, isobutoxycarbonyl, tert-butoxycarbonyl, (2,2-dimethyl-propoxy)-carbonyl, (2-fluoro-ethoxy)-carbonyl, (2-methoxy-ethoxy)-carbonyl]
($C_{2-4}$)fluoroalkyl [in particular 2-fluoroethyl, 2,2,2-trifluoroethyl, 3-fluoropropyl];
($C_{3-6}$)cycloalkyl optionally containing one ring oxygen atom [in particular cyclobutyl, oxetan-3-yl, cyclopentyl, tetrahydrofuran-3-yl];
($C_{3-6}$)cycloalkyl-($C_{1-3}$)alkyl, wherein the ($C_{3-6}$)cycloalkyl group optionally contains one ring oxygen atom [in particular such ($C_{3-6}$)cycloalkyl-($C_{1-3}$)alkyl is cyclopropyl-methyl, cyclobutylmethyl, cyclohexyl-methyl, 1-cyclopropyl-ethyl];

($R^1$)$_n$ represents one or two optional substituents (i.e. n represents the integer 0, 1, or 2) independently selected from ($C_{1-4}$)alkyl (especially methyl), ($C_{1-4}$)alkoxy (especially methoxy), halogen, ($C_{1-3}$)fluoroalkyl (especially trifluoromethyl), ($C_{1-3}$)fluoroalkoxy (especially trifluoromethoxy), and cyano;

$L^1$ represents a two-membered linker group selected from —NH—$CH_2$—*; —O—$CH_2$—*; —$CH_2$—$CH_2$—; and —CH=CH—; wherein the asterisks indicate the bond with which the group $L^1$ is attached to the carbonyl group;

$L^2$ represents —($C_{1-3}$)alkylene-(especially a linker group selected from —$CH_2$—, —CH($CH_3$)—, —$CH_2$—$CH_2$—, —$CH_2$—$CH_2$—$CH_2$—, preferably —$CH_2$—);

$Ar^1$ represents phenyl, or 5- or 6-membered heteroaryl (especially pyridinyl); wherein said phenyl or 5- or 6-membered heteroaryl independently is unsubstituted, mono-, di- or tri-substituted, wherein the substituents are independently selected from ($C_{1-4}$)alkyl (especially methyl); ($C_{1-4}$)alkoxy (especially methoxy); ($C_{1-3}$)fluoroalkyl (especially trifluoromethyl); ($C_{1-3}$)fluoroalkoxy (especially trifluoromethoxy); halogen; or cyano; and $R^4$ represents
($C_{2-5}$)alkyl which is mono-substituted with ($C_{1-4}$)alkoxy, cyano, or hydroxy; or di-substituted wherein the substituents are independently selected from ($C_{1-3}$)alkoxy or hydroxy (especially mono-substituted with hydroxy; or disubstituted wherein the substituents are independently methoxy or hydroxy); [in particular such substituted ($C_{2-5}$)alkyl is 2-methoxy-ethyl, 2-hydroxy-ethyl, 2-hydroxy-propyl, 2-hydroxy-2-methyl-propyl, 3-hydroxy-3-methyl-butyl, 2-hydroxy-3-methoxy-propyl];

—($C_{2-4}$)alkylene-$NR^6R^7$, wherein $R^6$ and $R^7$ independently represent hydrogen; ($C_{1-4}$)alkyl; ($C_{2-3}$)fluoroalkyl; ($C_{3-6}$)cycloalkyl; or ($C_{3-6}$)cycloalkyl-($C_{1-3}$) alkyl; [in particular such —($C_{2-4}$)alkylene-$NR^6R^7$ is 2-amino-ethyl, 2-methylamino-ethyl, 2-dimethylamino-ethyl, 2-diethylamino-ethyl, 3-(dimethylamino)-propyl, 2-ethylamino-ethyl, 2-(ethyl-methyl-amino)-ethyl, 2-(isopropylamino)-ethyl, 2-(isopropylmethylamino)-ethyl, 2-(diisopropylamino)-ethyl, 2-(butyl-methylamino)-ethyl, 2-(tert-butylamino)-ethyl, 2-[(2-fluoroethyl)-methylamino]-ethyl, 2-[(2,2,2-trifluoroethyl)-amino]-ethyl, 2-[methyl-(2,2,2-trifluoroethyl)-amino]-ethyl, 2-[(2-fluoro-1-methylethyl)-methylamino]-ethyl, 2-[(cyclopropyl)-methylamino]-ethyl, 2-[(cyclopropylmethyl)-methylamino]-ethyl, 2-[(cyclobutyl)-methylamino]-ethyl, 2-[(cyclopentyl)-methylamino]-ethyl];

($C_{3-6}$)cycloalkyl optionally mono-substituted with hydroxy; [in particular cyclopropyl, or 4-hydroxy-cyclohexyl];

($C_{3-6}$)cycloalkyl-($C_{1-3}$)alkyl, wherein the cycloalkyl group is optionally mono-substituted hydroxy; [in particular cyclopropyl-methyl, (1-hydroxy-cyclopentyl)-methyl]; or ($C_{4-7}$)heterocyclyl or ($C_{4-7}$)heterocyclyl-($C_{1-3}$)alkyl, wherein in the above groups the ($C_{4-7}$)heterocyclyl independently contains one or two ring heteroatoms independently selected from nitrogen and oxygen; wherein in the above groups said ($C_{4-7}$)heterocyclyl independently is unsubstituted, or mono-, or di-substituted, wherein the substituents are independently selected from:
one oxo substituent attached to a ring carbon atom in alpha position to a ring nitrogen (thus forming together with the nitrogen an amide group, or, in case a ring oxygen is additionaly adjacent, a carbamate group, or, in case second ring nitrogen is additionaly adjacent, a urea group); and/or
($C_{1-4}$)alkyl (especially methyl) attached to a ring nitrogen atom having a free valency; or
two fluoro substituents attached to a ring carbon atom;
[in particular such ($C_{4-7}$)heterocyclyl is pyrrolidin-3-yl, 1-methyl-pyrrolidin-3-yl, piperidin-3-yl, 1-methyl-piperidin-3-yl, piperidin-4-yl, 1-methyl-piperidin-4-yl, tetrahydro-pyran-4-yl; and such ($C_{4-7}$)heterocyclyl-($C_{1-3}$)alkyl is 2-(pyrrolidin-1-yl)-ethyl, 2-(2-oxo-imidazolidin-1-yl)-ethyl, 2-(1-methyl-pyrrolidin-2-yl)-ethyl, 2-(2-oxo-pyrrolidin-1-yl)-ethyl, 2-(morpholin-4-yl)-ethyl, pyrrolidin-3-yl-methyl, 3-(pyrrolidin-1-yl)-propyl, [1,4]dioxan-2-yl-methyl, 2-(piperazin-1-yl)-ethyl, 2-(piperidin-1-yl)-ethyl, 2-(azepan-1-yl)-ethyl, 2-(3,3-difluoroazetidin-1-yl)-ethyl, 2-(3,3-difluoropyrrolidin-1-yl)-ethyl, 2-(3,3-difluoropiperidin-1-yl)-ethyl, 2-(4,4-difluoropiperidin-1-yl)-ethyl];

wherein the characteristics disclosed in embodiments 2) to 21) are intended to apply mutatis mutandis also to the compounds formula (III) according to embodiment 24); wherein especially the following embodiments are thus possible and intended and herewith specifically disclosed in individualized form:
24+7, 24+8+7, 24+8, 24+10+7, 24+10+8+7, 24+10+8, 24+10, 24+13+7, 24+13+8+7, 24+13+8, 24+13+10+7, 24+13+10+8+7, 24+13+10+8, 24+13+10, 24+13, 24+17+7, 24+17+8+7, 24+17+8, 24+17+10+7, 24+17+10+8+7, 24+17+10+8, 24+17+10, 24+17+13+7, 24+17+13+8+7, 24+17+13+8, 24+17+13+10+7, 24+17+13+10+8+7, 24+17+13+10+8, 24+17+13+10, 24+17+13, 24+17, 24+19+7, 24+19+8+7, 24+19+8, 24+19+10+7, 24+19+10+8+7, 24+19+10+8, 24+19+10, 24+19+13+7, 24+19+13+8+7, 24+19+13+8, 24+19+13+10+7, 24+19+13+10+8+7, 24+19+13+10+8, 24+19+13+10, 24+19+13, 24+19+17+7, 24+19+17+8+7, 24+19+17+8, 24+19+17+10+7, 24+19+17+10+8+7, 24+19+17+10+8, 24+19+17+10, 24+19+17+13+7, 24+19+17+13+8+7, 24+19+17+13+8, 24+19+17+13+10+7, 24+19+17+13+10+8+7, 24+19+17+13+10+8, 24+19+17+13+10, 24+19+17+13, 24+19+17, 24+19, 24+21+7, 24+21+8+7, 24+21+8, 24+21+10+7, 24+21+10+8+7, 24+21+10+8, 24+21+10, 24+21+13+7, 24+21+13+8+7, 24+21+13+8, 24+21+13+10+7, 24+21+13+10+8+7, 24+21+13+10+8, 24+21+13+10, 24+21+13, 24+21+17+7, 24+21+17+8+7, 24+21+17+8, 24+21+17+10+7, 24+21+17+10+8+7, 24+21+17+10+8, 24+21+17+10, 24+21+17+13+7, 24+21+17+13+8+7, 24+21+17+13+8, 24+21+17+13+10+7, 24+21+17+13+10+8+7, 24+21+17+13+10+8, 24+21+17+13+10, 24+21+17+13, 24+21+17, 24+21, 24.

In the list above the numbers refer to the embodiments according to their numbering provided hereinabove whereas "+" indicates the limitations as outlined above.

25) A further aspect of the invention relates to compounds of the formula (I) which are also compounds of the formula (IV), Formula (IV)

wherein $Y^1$ represents O, $CH_2$, NH, or $NR^{Y1}$ wherein $R^{Y1}$ represents $(C_{1-3})$alkyl;
$Y^2$ represents $CH_2$; and $X^2$ represents $CH_2$; or
$Y^1$ represents O, $CH_2$, or NH;
$Y^2$ represents $CH_2$; and $X^2$ represents CO; or
$Y^1$ represents O, $CH_2$, NH, or $NR^{Y1}$ wherein $R^{Y1}$ represents $(C_{1-3})$alkyl;
$Y^2$ represents CO; and $X^2$ represents $CH_2$; or
$R^5$ represents
- $(C_{1-6})$alkyl [in particular methyl, ethyl, propyl, isopropyl, isobutyl, 1-methyl-propyl, 1,2-dimethyl-propyl, 2,2-dimethyl-propyl, 3,3-dimethyl-butyl];
- $(C_{1-4})$alkyl mono-substituted with $(C_{1-3})$alkoxy [in particular 2-methoxy-ethyl, 2-methoxy-1-methyl-ethyl];
- —CO—$R^{10}$ wherein $R^{10}$ represents $(C_{1-5})$alkyl; $(C_{1-5})$alkoxy; $(C_{3-6})$cycloalkyl-$(C_{1-3})$alkyl; $(C_{1-3})$fluoroalkyl; $(C_{1-3})$fluoroalkoxy; hydroxy-$(C_{1-3})$alkyl; $(C_{1-3})$alkoxy-$(C_{2-3})$alkoxy; $(C_{1-3})$alkoxy-$(C_{1-3})$alkyl; $(C_{3-6})$cycloalkyl optionally containing one ring oxygen atom, wherein said cycloalkyl is optionally mono- or di-substituted with fluoro; or —$NR^{10a}R^{10b}$ wherein $R^{10a}$ and $R^{10b}$ independently represent hydrogen, $(C_{1-4})$alkyl or $(C_{3-6})$cycloalkyl, or $R^{10a}$ and $R^{10b}$ together with the nitrogen to which they are attached to form a 5- to 7-membered saturated ring; [in particular such —CO—$R^{10}$ is methyl-carbonyl, ethyl-carbonyl, propyl-carbonyl, isopropyl-carbonyl, isobutyl-carbonyl, tert-butyl-carbonyl, (2,2-dimethyl-propyl)-carbonyl, hydroxymethyl-carbonyl, methoxymethyl-carbonyl, cyclopropyl-carbonyl, cyclobutyl-carbonyl, (2-fluoro-cyclopropyl)-carbonyl, (cyclohexyl-methyl)-carbonyl, (2,2-difluorocyclopropyl)-carbonyl, (1-trifluoromethyl-cyclopropyl)-carbonyl, (tetrahydrofuran-3-yl)-carbonyl, trifluoromethyl-carbonyl, (1,1-difluoro-ethyl)-carbonyl, carbamoyl, methylcarbamoyl, ethylcarbamoyl, isopropylcarbamoyl, butyl-carbamoyl, tert-butyl-carbamoyl, cyclohexyl-carbamoyl, dimethyl-carbamoyl, (pyrrolidin-1-yl)-carbonyl, methoxycarbonyl, ethoxycarbonyl, propoxycarbonyl, isopropoxycarbonyl, isobutoxycarbonyl, tert-butoxycarbonyl, (2,2-dimethyl-propoxy)-carbonyl, (2-fluoro-ethoxy)-carbonyl, (2-methoxy-ethoxy)-carbonyl]
- $(C_{2-4})$fluoroalkyl [in particular 2-fluoroethyl, 2,2,2-trifluoroethyl, 3-fluoropropyl];
- $(C_{3-6})$cycloalkyl optionally containing one ring oxygen atom [in particular cyclobutyl, oxetan-3-yl, cyclopentyl, tetrahydrofuran-3-yl];
- $(C_{3-6})$cycloalkyl-$(C_{1-3})$alkyl, wherein the $(C_{3-6})$cycloalkyl group optionally contains one ring oxygen atom [in particular such $(C_{3-6})$cycloalkyl-$(C_{1-3})$alkyl is cyclopropyl-methyl, cyclobutylmethyl, cyclohexyl-methyl, 1-cyclopropyl-ethyl];

$(R^1)_n$ represents one or two optional substituents (i.e. n represents the integer 0, 1, or 2) independently selected from $(C_{1-4})$alkyl (especially methyl), $(C_{1-4})$alkoxy (especially methoxy), halogen, $(C_{1-3})$fluoroalkyl (especially trifluoromethyl), $(C_{1-3})$fluoroalkoxy (especially trifluoromethoxy), and cyano;

$L^1$ represents a two-membered linker group selected from —NH—$CH_2$—*; —O—$CH_2$—*; —$CH_2$—$CH_2$—; and —CH=CH—; wherein the asterisks indicate the bond with which the group $L^1$ is attached to the carbonyl group;

$L^2$ represents —$(C_{1-3})$alkylene-(especially a linker group selected from —$CH_2$—, —CH($CH_3$)—, —$CH_2$—$CH_2$—, —$CH_2$—$CH_2$—$CH_2$—, preferably —$CH_2$—);

$Ar^1$ represents phenyl, or 5- or 6-membered heteroaryl (especially pyridinyl); wherein said phenyl or 5- or 6-membered heteroaryl independently is unsubstituted, mono-, di- or tri-substituted, wherein the substituents are independently selected from $(C_{1-4})$alkyl (especially methyl); $(C_{1-4})$alkoxy (especially methoxy); $(C_{1-3})$fluoroalkyl (especially trifluoromethyl); $(C_{1-3})$fluoroalkoxy (especially trifluoromethoxy); halogen; or cyano; and $R^4$ represents
- $(C_{2-5})$alkyl which is mono-substituted with $(C_{1-4})$alkoxy, cyano, or hydroxy; or di-substituted wherein the substituents are independently selected from $(C_{1-3})$alkoxy or hydroxy (especially mono-substituted with hydroxy; or disubstituted wherein the substituents are independently methoxy or hydroxy); [in particular such substituted $(C_{2-5})$alkyl is 2-methoxy-ethyl, 2-hydroxy-ethyl, 2-hydroxy-propyl, 2-hydroxy-2-methyl-propyl, 3-hydroxy-3-methyl-butyl, 2-hydroxy-3-methoxy-propyl];
- —$(C_{2-4})$alkylene-$NR^6R^7$, wherein $R^6$ and $R^7$ independently represent hydrogen; $(C_{1-4})$alkyl; $(C_{2-3})$fluoroalkyl; $(C_{3-6})$cycloalkyl; or $(C_{3-6})$cycloalkyl-$(C_{1-3})$alkyl; [in particular such —$(C_{2-4})$alkylene-$NR^6R^7$ is 2-amino-ethyl, 2-methylamino-ethyl, 2-dimethyl-amino-ethyl, 2-diethylamino-ethyl, 3-(dimethyl-amino)-propyl, 2-ethylamino-ethyl, 2-(ethyl-methylamino)-ethyl, 2-(isopropylamino)-ethyl, 2-(isopropyl-methylamino)-ethyl, 2-(diisopropylamino)-ethyl, 2-(butyl-methylamino)-ethyl, 2-(tert-butylamino)-ethyl, 2-[(2-fluoroethyl)-methylamino]-ethyl, 2-[(2,2,2-trifluoroethyl)-amino]-ethyl, 2-[methyl-(2,2,2-trifluoroethyl)-amino]-ethyl, 2-[(2-fluoro-1-methylethyl)-methylamino]-ethyl, 2-[(cyclopropyl)-methylamino]-ethyl, 2-[(cyclopropylmethyl)-methylamino]-ethyl, 2-[(cyclobutyl)-methylamino]-ethyl, 2-[(cyclopentyl)-methylamino]-ethyl];

($C_{3-6}$)cycloalkyl optionally mono-substituted with hydroxy; [in particular cyclopropyl, or 4-hydroxy-cyclohexyl];

($C_{3-6}$)cycloalkyl-($C_{1-3}$)alkyl, wherein the cycloalkyl group is optionally mono-substituted hydroxy; [in particular cyclopropyl-methyl, (1-hydroxy-cyclopentyl)-methyl]; or ($C_{4-7}$)heterocyclyl or ($C_{4-7}$)heterocyclyl-($C_{1-3}$)alkyl, wherein in the above groups the ($C_{4-7}$)heterocyclyl independently contains one or two ring heteroatoms independently selected from nitrogen and oxygen; wherein in the above groups said ($C_{4-7}$)heterocyclyl independently is unsubstituted, or mono-, or di-substituted, wherein the substituents are independently selected from:
  one oxo substituent attached to a ring carbon atom in alpha position to a ring nitrogen (thus forming together with the nitrogen an amide group, or, in case a ring oxygen is additionaly adjacent, a carbamate group, or, in case second ring nitrogen is additionaly adjacent, a urea group); and/or
  ($C_{1-4}$)alkyl (especially methyl) attached to a ring nitrogen atom having a free valency; or
  two fluoro substituents attached to a ring carbon atom;
[in particular such ($C_{4-7}$)heterocyclyl is pyrrolidin-3-yl, 1-methyl-pyrrolidin-3-yl, piperidin-3-yl, 1-methyl-piperidin-3-yl, piperidin-4-yl, 1-methyl-piperidin-4-yl, tetrahydro-pyran-4-yl; and such ($C_{4-7}$)heterocyclyl-($C_{1-3}$)alkyl is 2-(pyrrolidin-1-yl)-ethyl, 2-(2-oxo-imidazolidin-1-yl)-ethyl, 2-(1-methyl-pyrrolidin-2-yl)-ethyl, 2-(2-oxo-pyrrolidin-1-yl)-ethyl, 2-(morpholin-4-yl)-ethyl, pyrrolidin-3-yl-methyl, 3-(pyrrolidin-1-yl)-propyl, [1,4]dioxan-2-yl-methyl, 2-(piperazin-1-yl)-ethyl, 2-(piperidin-1-yl)-ethyl, 2-(azepan-1-yl)-ethyl, 2-(3,3-difluoroazetidin-1-yl)-ethyl, 2-(3,3-difluoropyrrolidin-1-yl)-ethyl, 2-(3,3-difluoropiperidin-1-yl)-ethyl, 2-(4,4-difluoropiperidin-1-yl)-ethyl];

wherein the characteristics disclosed in embodiments 2) to 21) are intended to apply mutatis mutandis also to the compounds formula (IV) according to embodiment 25); wherein especially the following embodiments are thus possible and intended and herewith specifically disclosed in individualized form:

25+7, 25+8+7, 25+8, 25+10+7, 25+10+8+7, 25+10+8, 25+10, 25+13+7, 25+13+8+7, 25+13+8, 25+13+10+7, 25+13+10+8+7, 25+13+10+8, 25+13+10, 25+13, 25+17+7, 25+17+8+7, 25+17+8, 25+17+10+7, 25+17+10+8+7, 25+17+10+8, 25+17+10, 25+17+13+7, 25+17+13+8+7, 25+17+13+8, 25+17+13+10+7, 25+17+13+10+8+7, 25+17+13+10+8, 25+17+13+10, 25+17+13, 25+17, 25+19+7, 25+19+8+7, 25+19+8, 25+19+10+7, 25+19+10+8+7, 25+19+10+8, 25+19+10, 25+19+13+7, 25+19+13+8+7, 25+19+13+8, 25+19+13+10+7, 25+19+13+10+8+7, 25+19+13+10+8, 25+19+13+10, 25+19+13, 25+19+17+7, 25+19+17+8+7, 25+19+17+8, 25+19+17+10+7, 25+19+17+10+8+7, 25+19+17+10+8, 25+19+17+10, 25+19+17+13+7, 25+19+17+13+8+7, 25+19+17+13+8, 25+19+17+13+10+7, 25+19+17+13+10+8+7, 25+19+17+13+10+8, 25+19+17+13+10, 25+19+17+13, 25+19+17, 25+19, 25+21+7, 25+21+8+7, 25+21+8, 25+21+10+7, 25+21+10+8+7, 25+21+10+8, 25+21+10, 25+21+13+7, 25+21+13+8+7, 25+21+13+8, 25+21+13+10+7, 25+21+13+10+8+7, 25+21+13+10+8, 25+21+13+10, 25+21+13, 25+21+17+7, 25+21+17+8+7, 25+21+17+8, 25+21+17+10+7, 25+21+17+10+8+7, 25+21+17+10+8, 25+21+17+10, 25+21+17+13+7, 25+21+17+13+8+7, 25+21+17+13+8, 25+21+17+13+10+7, 25+21+17+13+10+8+7, 25+21+17+13+10+8, 25+21+17+13+10, 25+21+17+13, 25+21+17, 25+21, 25.

In the list above the numbers refer to the embodiments according to their numbering provided hereinabove whereas "+" indicates the limitations as outlined above.

26) A further aspect of the invention relates to compounds of the formula (I) according to embodiment 1) which are also compounds of the formula (V)

Formula (V)

wherein
$Y^1$ represents $CH_2$; $Y^2$ represents $CH_2$, O, or NH; and $X^1$ represents $CH_2$; or
$Y^1$ represents CO; $Y^2$ represents $CH_2$, O, or NH; and $X^1$ represents $CH_2$; or
$Y^1$ represents $CH_2$; $Y^2$ represents $CH_2$; and $X^1$ represents CO;

$R^5$ represents
  ($C_{1-6}$)alkyl [in particular methyl, ethyl, propyl, isopropyl, isobutyl, 1-methyl-propyl, 1,2-dimethyl-propyl, 2,2-dimethyl-propyl, 3,3-dimethyl-butyl];
  ($C_{1-4}$)alkyl mono-substituted with ($C_{1-3}$)alkoxy [in particular 2-methoxy-ethyl, 2-methoxy-1-methyl-ethyl];
  —CO—$R^{10}$ wherein $R^{10}$ represents ($C_{1-5}$)alkyl; ($C_{1-5}$)alkoxy; ($C_{3-6}$)cycloalkyl-($C_{1-3}$)alkyl; ($C_{1-3}$)fluoroalkyl; ($C_{1-3}$)fluoroalkoxy; hydroxy-($C_{1-3}$)alkyl; ($C_{1-3}$)alkoxy-($C_{2-3}$)alkoxy; ($C_{1-3}$)alkoxy-($C_{1-3}$)alkyl; ($C_{3-6}$)cycloalkyl optionally containing one ring oxygen atom, wherein said cycloalkyl is optionally mono- or di-substituted with fluoro; or —$NR^{10a}R^{10b}$ wherein $R^{10a}$ and $R^{10b}$ independently represent hydrogen, ($C_{1-4}$)alkyl or ($C_{3-6}$)cycloalkyl, or $R^{10a}$ and $R^{10b}$ together with the nitrogen to which they are attached to form a 5- to 7-membered saturated ring; [in particular such —CO—$R^{10}$ is methyl-carbonyl, ethyl-carbonyl, propyl-carbonyl, isopropyl-carbonyl, isobutyl-carbonyl, tert-butyl-carbonyl, (2,2-dimethyl-propyl)-carbonyl, hydroxymethyl-carbonyl, methoxymethyl-carbonyl, cyclopropyl-carbonyl, cyclobutyl-carbonyl, (2-fluorocyclopropyl)-carbonyl, (cyclohexyl-methyl)-carbonyl, (2,2-difluorocyclopropyl)-carbonyl, (1-trifluoromethyl-cyclopropyl)-carbonyl, (tetrahydrofuran-3-yl)-carbonyl, trifluoromethyl-carbonyl, (1,1-difluoroethyl)-carbonyl, carbamoyl, methylcarbamoyl, ethylcarbamoyl, isopropylcarbamoyl, butyl-carbamoyl, tert-butyl-carbamoyl, cyclohexyl-carbamoyl, dimethylcarbamoyl, (pyrrolidin-1-yl)-carbonyl, methoxycarbonyl, ethoxycarbonyl, propoxycarbonyl, isopropoxycarbonyl, isobutoxycarbonyl, tert-butoxycarbonyl, (2,2-dimethyl-propoxy)-carbonyl, (2-fluoro-ethoxy)-carbonyl, (2-methoxy-ethoxy)-carbonyl]

$(C_{2-4})$fluoroalkyl [in particular 2-fluoroethyl, 2,2,2-trifluoroethyl, 3-fluoropropyl];

$(C_{3-6})$cycloalkyl optionally containing one ring oxygen atom [in particular cyclobutyl, oxetan-3-yl, cyclopentyl, tetrahydrofuran-3-yl];

$(C_{3-6})$cycloalkyl-$(C_{1-3})$alkyl, wherein the $(C_{3-6})$cycloalkyl group optionally contains one ring oxygen atom [in particular such $(C_{3-6})$cycloalkyl-$(C_{1-3})$alkyl is cyclopropyl-methyl, cyclobutylmethyl, cyclohexyl-methyl, 1-cyclopropyl-ethyl];

$(R^1)_n$ represents one or two optional substituents (i.e. n represents the integer 0, 1, or 2) independently selected from $(C_{1-4})$alkyl (especially methyl), $(C_{1-4})$alkoxy (especially methoxy), halogen, $(C_{1-3})$fluoroalkyl (especially trifluoromethyl), $(C_{1-3})$fluoroalkoxy (especially trifluoromethoxy), and cyano;

$L^1$ represents a two-membered linker group selected from —NH—CH$_2$—*; —O—CH$_2$—*; —CH$_2$—CH$_2$—; and —CH═CH—; wherein the asterisks indicate the bond with which the group $L^1$ is attached to the carbonyl group;

$L^2$ represents —$(C_{1-3})$alkylene-(especially a linker group selected from —CH$_2$—, —CH(CH$_3$)—, —CH$_2$—CH$_2$—, —CH$_2$—CH$_2$—CH$_2$—, preferably —CH$_2$—);

$Ar^1$ represents phenyl, or 5- or 6-membered heteroaryl (especially pyridinyl); wherein said phenyl or 5- or 6-membered heteroaryl independently is unsubstituted, mono-, di- or tri-substituted, wherein the substituents are independently selected from $(C_{1-4})$alkyl (especially methyl); $(C_{1-4})$alkoxy (especially methoxy); $(C_{1-3})$fluoroalkyl (especially trifluoromethyl); $(C_{1-3})$fluoroalkoxy (especially trifluoromethoxy); halogen; or cyano; and $R^4$ represents $(C_{2-5})$alkyl which is mono-substituted with $(C_{1-4})$alkoxy, cyano, or hydroxy; or di-substituted wherein the substituents are independently selected from $(C_{1-3})$alkoxy or hydroxy (especially mono-substituted with hydroxy; or disubstituted wherein the substituents are independently methoxy or hydroxy); [in particular such substituted $(C_{2-5})$alkyl is 2-methoxy-ethyl, 2-hydroxy-ethyl, 2-hydroxy-propyl, 2-hydroxy-2-methyl-propyl, 3-hydroxy-3-methyl-butyl, 2-hydroxy-3-methoxy-propyl];

—$(C_{2-4})$alkylene-NR$^6$R$^7$, wherein R$^6$ and R$^7$ independently represent hydrogen; $(C_{1-4})$alkyl; $(C_{2-3})$fluoroalkyl; $(C_{3-6})$cycloalkyl; or $(C_{3-6})$cycloalkyl-$(C_{1-3})$alkyl; [in particular such —$(C_{2-4})$alkylene-NR$^6$R$^7$ is 2-amino-ethyl, 2-methylamino-ethyl, 2-dimethylamino-ethyl, 2-diethylamino-ethyl, 3-(dimethylamino)-propyl, 2-ethylamino-ethyl, 2-(ethyl-methyl-amino)-ethyl, 2-(isopropylamino)-ethyl, 2-(isopropyl-methylamino)-ethyl, 2-(diisopropylamino)-ethyl, 2-(butyl-methylamino)-ethyl, 2-(tert-butylamino)-ethyl, 2-[(2-fluoroethyl)-methylamino]-ethyl, 2-[(2,2,2-trifluoroethyl)-amino]-ethyl, 2-[methyl-(2,2,2-trifluoroethyl)-amino]-ethyl, 2-[(2-fluoro-1-methylethyl)-methylamino]-ethyl, 2-[(cyclopropyl)-methylamino]-ethyl, 2-[(cyclopropylmethyl)-methylamino]-ethyl, 2-[(cyclobutyl)-methylamino]-ethyl, 2-[(cyclopentyl)-methylamino]-ethyl];

$(C_{3-6})$cycloalkyl optionally mono-substituted with hydroxy; [in particular cyclopropyl, or 4-hydroxy-cyclohexyl];

$(C_{3-6})$cycloalkyl-$(C_{1-3})$alkyl, wherein the cycloalkyl group is optionally mono-substituted hydroxy; [in particular cyclopropyl-methyl, (1-hydroxy-cyclopentyl)-methyl]; or $(C_{4-7})$heterocyclyl or $(C_{4-7})$heterocyclyl-$(C_{1-3})$alkyl, wherein in the above groups the $(C_{4-7})$heterocyclyl independently contains one or two ring heteroatoms independently selected from nitrogen and oxygen; wherein in the above groups said $(C_{4-7})$heterocyclyl independently is unsubstituted, or mono-, or di-substituted, wherein the substituents are independently selected from:

one oxo substituent attached to a ring carbon atom in alpha position to a ring nitrogen (thus forming together with the nitrogen an amide group, or, in case a ring oxygen is additionaly adjacent, a carbamate group, or, in case second ring nitrogen is additionaly adjacent, a urea group); and/or $(C_{1-4})$alkyl (especially methyl) attached to a ring nitrogen atom having a free valency; or two fluoro substituents attached to a ring carbon atom; [in particular such $(C_{4-7})$heterocyclyl is pyrrolidin-3-yl, 1-methyl-pyrrolidin-3-yl, piperidin-3-yl, 1-methyl-piperidin-3-yl, piperidin-4-yl, 1-methyl-piperidin-4-yl, tetrahydro-pyran-4-yl; and such $(C_{4-7})$heterocyclyl-$(C_{1-3})$alkyl is 2-(pyrrolidin-1-yl)-ethyl, 2-(2-oxo-imidazolidin-1-yl)-ethyl, 2-(1-methyl-pyrrolidin-2-yl)-ethyl, 2-(2-oxo-pyrrolidin-1-yl)-ethyl, 2-(morpholin-4-yl)-ethyl, pyrrolidin-3-yl-methyl, 3-(pyrrolidin-1-yl)-propyl, [1,4]dioxan-2-yl-methyl, 2-(piperazin-1-yl)-ethyl, 2-(piperidin-1-yl)-ethyl, 2-(azepan-1-yl)-ethyl, 2-(3,3-difluoroazetidin-1-yl)-ethyl, 2-(3,3-difluoropyrrolidin-1-yl)-ethyl, 2-(3,3-difluoropiperidin-1-yl)-ethyl, 2-(4,4-difluoropiperidin-1-yl)-ethyl];

wherein the characteristics disclosed in embodiments 2) to 21) are intended to apply mutatis mutandis also to the compounds formula (V) according to embodiment 26); wherein especially the following embodiments are thus possible and intended and herewith specifically disclosed in individualized form:

26+7, 26+8+7, 26+8, 26+10+7, 26+10+8+7, 26+10+8, 26+10, 26+13+7, 26+13+8+7, 26+13+8, 26+13+10+7, 26+13+10+8+7, 26+13+10+8, 26+13+10, 26+13, 26+17+7, 26+17+8+7, 26+17+8, 26+17+10+7, 26+17+10+8+7, 26+17+10+8, 26+17+10, 26+17+13+7, 26+17+13+8+7, 26+17+13+8, 26+17+13+10+7, 26+17+13+10+8+7, 26+17+13+10+8, 26+17+13+10, 26+17+13, 26+17, 26+19+7, 26+19+8+7, 26+19+8, 26+19+10+7, 26+19+10+8+7, 26+19+10+8, 26+19+10, 26+19+13+7, 26+19+13+8+7, 26+19+13+8, 26+19+13+10+7, 26+19+13+10+8+7, 26+19+13+10+8, 26+19+13+10, 26+19+13, 26+19+17+7, 26+19+17+8+7, 26+19+17+8, 26+19+17+10+7, 26+19+17+10+8+7, 26+19+17+10+8, 26+19+17+10, 26+19+17+13+7, 26+19+17+13+8+7, 26+19+17+13+8, 26+19+17+13+10+7, 26+19+17+13+10+8+7, 26+19+17+13+10+8, 26+19+17+13+10, 26+19+17+13, 26+19+17, 26+19, 26+21+7, 26+21+8+7, 26+21+8, 26+21+10+7, 26+21+10+8+7, 26+21+10+8, 26+21+10, 26+21+13+7, 26+21+13+8+7, 26+21+13+8, 26+21+13+10+7, 26+21+13+10+8+7, 26+21+13+10+8, 26+21+13+10, 26+21+13, 26+21+17+7, 26+21+17+8+7, 26+21+17+8, 26+21+17+10+7, 26+21+17+10+8+7, 26+21+17+10+8, 26+21+17+13+7, 26+21+17+13+8+7, 26+21+17+13+8, 26+21+17+13+10+7, 26+21+17+13+10+8+7, 26+21+17+13+10+8, 26+21+17+13+10, 26+21+17+13, 26+21+17, 26+21, 26.

In the list above the numbers refer to the embodiments according to their numbering provided hereinabove whereas "+" indicates the limitations as outlined above.

27) Another embodiment relates to compounds according to embodiment 1) which are selected from the following compounds:

N-(2-Dimethylamino-ethyl)-2-(4-isobutyl-2,3,4,5-tetrahydro-benzo[f][1,4]oxazepin-9-ylamino)-N-(2-trifluoromethyl-benzyl)-acetamide;

N-(2-Dimethylamino-ethyl)-2-(4-isobutyl-2,3,4,5-tetrahydro-benzo[f][1,4]oxazepin-9-ylamino)-N-(3-trifluoromethyl-pyridin-2-ylmethyl)-acetamide;

N-(3-Chloro-pyridin-2-ylmethyl)-N-(2-dimethylamino-ethyl)-2-(4-isobutyl-2,3,4,5-tetrahydro-benzo[f][1,4]oxazepin-9-ylamino)-acetamide;

N-(3-Chloro-pyridin-2-ylmethyl)-N-(2-dimethylamino-ethyl)-2-(4-ethyl-2,3,4,5-tetrahydro-benzo[f][1,4]oxazepin-9-ylamino)-acetamide;

N-(2-Dimethylamino-ethyl)-2-(4-ethyl-2,3,4,5-tetrahydro-benzo[f][1,4]oxazepin-9-ylamino)-N-(2-trifluoromethyl-benzyl)-acetamide;

N-(3-Chloro-pyridin-2-ylmethyl)-N-(2-dimethylamino-ethyl)-2-(4-propyl-2,3,4,5-tetrahydro-benzo[f][1,4]oxazepin-9-ylamino)-acetamide;

N-(2-Dimethylamino-ethyl)-2-(4-propyl-2,3,4,5-tetrahydro-benzo[f][1,4]oxazepin-9-ylamino)-N-(2-trifluoromethyl-benzyl)-acetamide;

N-(3-Bromo-benzyl)-N-(2-dimethylamino-ethyl)-2-(4-isobutyl-2,3,4,5-tetrahydro-benzo[f][1,4]oxazepin-9-ylamino)-acetamide;

N-(2-Dimethylamino-ethyl)-2-(4-isobutyl-2,3,4,5-tetrahydro-benzo[f][1,4]oxazepin-9-ylamino)-N-(4-methoxy-pyridin-2-ylmethyl)-acetamide;

N-[2-(Cyclopropyl-methyl-amino)-ethyl]-2-(4-isobutyl-2,3,4,5-tetrahydro-benzo[f][1,4]oxazepin-9-ylamino)-N-(2-trifluoromethyl-benzyl)-acetamide;

2-(4-Isobutyl-2,3,4,5-tetrahydro-benzo[f][1,4]oxazepin-9-ylamino)-N-[2-(2-oxo-pyrrolidin-1-yl)-ethyl]-N-(2-trifluoromethyl-benzyl)-acetamide;

N-(2,4-Difluoro-benzyl)-2-(4-isobutyl-2,3,4,5-tetrahydro-benzo[f][1,4]oxazepin-9-ylamino)-N-(2-pyrrolidin-1-yl-ethyl)-acetamide;

N-(3-Chloro-pyridin-2-ylmethyl)-N-[2-(4,4-difluoro-piperidin-1-yl)-ethyl]-2-(4-isobutyl-2,3,4,5-tetrahydro-benzo[f][1,4]oxazepin-9-ylamino)-acetamide;

N-(2-Dimethylamino-ethyl)-2-(4-isobutyl-2,3,4,5-tetrahydro-benzo[f][1,4]oxazepin-9-ylamino)-N-(4-methyl-pyridin-2-ylmethyl)-acetamide;

N-(2-Chloro-benzyl)-2-(4-isobutyl-2,3,4,5-tetrahydro-benzo[f][1,4]oxazepin-9-ylamino)-N-(2-pyrrolidin-1-yl-ethyl)-acetamide;

2-(4-Isobutyl-2,3,4,5-tetrahydro-benzo[f][1,4]oxazepin-9-ylamino)-N-(2-morpholin-4-yl-ethyl)-N-(2-trifluoromethyl-benzyl)-acetamide;

N-(2-Dimethylamino-ethyl)-N-(4-fluoro-2-trifluoromethyl-benzyl)-2-(4-isobutyl-2,3,4,5-tetrahydro-benzo[f][1,4]oxazepin-9-ylamino)-acetamide;

N-(2-Dimethylamino-ethyl)-2-(4-isobutyl-2,3,4,5-tetrahydro-benzo[f][1,4]oxazepin-9-ylamino)-N-(3-trifluoromethyl-benzyl)-acetamide;

N-(2,6-Difluoro-benzyl)-N-(2-dimethylamino-ethyl)-2-(4-isobutyl-2,3,4,5-tetrahydro-benzo[f][1,4]oxazepin-9-ylamino)-acetamide;

2-(4-Acetyl-2,3,4,5-tetrahydro-benzo[f][1,4]oxazepin-9-ylamino)-N-(2-dimethylamino-ethyl)-N-(2-trifluoromethyl-benzyl)-acetamide;

N-(2-Dimethylamino-ethyl)-2-(4-ethyl-2,3,4,5-tetrahydro-1H-benzo[e][1,4]diazepin-9-ylamino)-N-(2-trifluoromethyl-benzyl)-acetamide;

2-(4-Cyclopropylmethyl-2,3,4,5-tetrahydro-benzo[f][1,4]oxazepin-6-ylamino)-N-(2-dimethylamino-ethyl)-N-(2-trifluoromethyl-benzyl)-acetamide;

2-(3-Cyclopropylmethyl-2,3,4,5-tetrahydro-1H-benzo[d]azepin-6-yloxy)-N-(2-dimethylamino-ethyl)-N-(2-trifluoromethyl-benzyl)-acetamide;

N-(2-Dimethylamino-ethyl)-2-[3-(2-methoxy-acetyl)-2,3,4,5-tetrahydro-1H-benzo[d]azepin-6-yloxy]-N-(2-trifluoromethyl-benzyl)-acetamide;

2-(3-Acetyl-2,3,4,5-tetrahydro-1H-benzo[d]azepin-6-yloxy)-N-(2-dimethylamino-ethyl)-N-(2-trifluoromethyl-benzyl)-acetamide;

N-(2-Dimethylamino-ethyl)-2-[3-(2,2,2-trifluoro-acetyl)-2,3,4,5-tetrahydro-1H-benzo[d]azepin-6-ylamino]-N-(2-trifluoromethyl-benzyl)-acetamide;

2-(3-Cyclopropylmethyl-2,3,4,5-tetrahydro-1H-benzo[d]azepin-6-ylamino)-N-(2-dimethylamino-ethyl)-N-(2-trifluoromethyl-benzyl)-acetamide;

2-(2-Cyclopropylmethyl-2,3,4,5-tetrahydro-1H-benzo[c]azepin-6-ylamino)-N-(2-dimethylamino-ethyl)-N-(2-trifluoromethyl-benzyl)-acetamide;

N-(2-tert-Butylamino-ethyl)-2-(4-cyclopropylmethyl-5-oxo-2,3,4,5-tetrahydro-benzo[f][1,4]oxazepin-6-ylamino)-N-(2-trifluoromethyl-benzyl)-acetamide;

2-(4-Cyclopropylmethyl-5-oxo-2,3,4,5-tetrahydro-benzo[f][1,4]oxazepin-6-ylamino)-N-(2,3-dichloro-benzyl)-N-(2-dimethylamino-ethyl)-acetamide;

2-(4-Cyclopropylmethyl-5-oxo-2,3,4,5-tetrahydro-benzo[f][1,4]oxazepin-6-ylamino)-N-(2,6-dichloro-benzyl)-N-(2-dimethylamino-ethyl)-acetamide;

N-(2-Chloro-benzyl)-2-(4-cyclopropylmethyl-5-oxo-2,3,4,5-tetrahydro-benzo[f][1,4]oxazepin-6-ylamino)-N-(2-dimethylamino-ethyl)-acetamide;

2-(4-Cyclopropylmethyl-5-oxo-2,3,4,5-tetrahydro-benzo[f][1,4]oxazepin-6-ylamino)-N-(2-dimethylamino-ethyl)-N-(6-methyl-pyridin-2-ylmethyl)-acetamide;

2-(4-Cyclopropylmethyl-5-oxo-2,3,4,5-tetrahydro-benzo[f][1,4]oxazepin-6-ylamino)-N-(2-isopropylamino-ethyl)-N-(2-trifluoromethyl-benzyl)-acetamide;

{2-[[2-(4-Cyclopropylmethyl-5-oxo-2,3,4,5-tetrahydro-benzo[f][1,4]oxazepin-6-ylamino)-acetyl]-(2-trifluoromethyl-benzyl)-amino]-ethyl}-isopropyl-carbamic acid tert-butyl ester;

2-(4-Cyclopropylmethyl-5-oxo-2,3,4,5-tetrahydro-benzo[f][1,4]oxazepin-6-ylamino)-N-(2-methylamino-ethyl)-N-(2-trifluoromethyl-benzyl)-acetamide;

{2-[[2-(4-Cyclopropylmethyl-5-oxo-2,3,4,5-tetrahydro-benzo[f][1,4]oxazepin-6-ylamino)-acetyl]-(2-trifluoromethyl-benzyl)-amino]-ethyl}-methyl-carbamic acid tert-butyl ester;

2-(4-Cyclopropylmethyl-5-oxo-2,3,4,5-tetrahydro-benzo[f][1,4]oxazepin-6-ylamino)-N-(2-dimethylamino-ethyl)-N-(2-trifluoromethyl-benzyl)-acetamide;

N-(2-Dimethylamino-ethyl)-2-(4-ethyl-5-oxo-2,3,4,5-tetrahydro-benzo[f][1,4]oxazepin-9-ylamino)-N-(3-methyl-pyridin-2-ylmethyl)-acetamide;

N-(2-tert-Butylamino-ethyl)-2-(4-ethyl-5-oxo-2,3,4,5-tetrahydro-benzo[f][1,4]oxazepin-9-ylamino)-N-(2-trifluoromethyl-benzyl)-acetamide; and N-(2-Dimethylamino-ethyl)-2-(4-ethyl-5-oxo-2,3,4,5-tetrahydro-benzo[f][1,4]oxazepin-9-ylamino)-N-(2-trifluoromethyl-benzyl)-acetamide.

28) In addition to the compounds listed in embodiment 27), further compounds according to embodiment 1) are selected from the following compounds:

2-(4-Cyclopropylmethyl-1-methyl-5-oxo-2,3,4,5-tetrahydro-1H-benzo[e][1,4]diazepin-9-ylamino)-N-(2-dimethylamino-ethyl)-N-(2-trifluoromethyl-benzyl)-acetamide;

N-(2-tert-Butylamino-ethyl)-2-(4-cyclopropylmethyl-1-methyl-5-oxo-2,3,4,5-tetrahydro-1H-benzo[e][1,4]diazepin-9-ylamino)-N-(2-trifluoromethyl-benzyl)-acetamide;

2-(4-Cyclopropylmethyl-1-methyl-5-oxo-2,3,4,5-tetrahydro-1H-benzo[e][1,4]diazepin-9-ylamino)-N-(2-dimethylamino-ethyl)-N-(3-methyl-pyridin-2-ylmethyl)-acetamide;

N-(3-Chloro-pyridin-2-ylmethyl)-2-(4-cyclopropylmethyl-1-methyl-5-oxo-2,3,4,5-tetrahydro-1H-benzo[e][1,4]diazepin-9-ylamino)-N-(2-dimethylamino-ethyl)-acetamide;

2-(4-Cyclopropylmethyl-1-methyl-5-oxo-2,3,4,5-tetrahydro-1H-benzo[e][1,4]diazepin-9-ylamino)-N-(2-isopropylamino-ethyl)-N-(2-trifluoromethyl-benzyl)-acetamide;

2-(1,4-Diethyl-5-oxo-2,3,4,5-tetrahydro-1H-benzo[e][1,4]diazepin-9-ylamino)-N-(2-morpholin-4-yl-ethyl)-N-(3-trifluoromethyl-pyridin-2-ylmethyl)-acetamide;

2-(1,4-Diethyl-5-oxo-2,3,4,5-tetrahydro-1H-benzo[e][1,4]diazepin-9-ylamino)-N-(2-pyrrolidin-1-yl-ethyl)-N-(3-trifluoromethyl-pyridin-2-ylmethyl)-acetamide;

2-(4-Cyclopropylmethyl-1-methyl-2,3,4,5-tetrahydro-1H-benzo[e][1,4]diazepin-9-ylamino)-N-(2-dimethylamino-ethyl)-N-(2-trifluoromethyl-benzyl)-acetamide;

{2-[[2-(4-Cyclopropylmethyl-1-methyl-2,3,4,5-tetrahydro-1H-benzo[e][1,4]diazepin-9-ylamino)-acetyl]-(2-trifluoromethyl-benzyl)-amino]-ethyl}-isopropyl-carbamic acid tert-butyl ester;

2-(4-Cyclopropylmethyl-1-methyl-2,3,4,5-tetrahydro-1H-benzo[e][1,4]diazepin-9-ylamino)-N-(2-pyrrolidin-1-yl-ethyl)-N-(3-trifluoromethyl-pyridin-2-ylmethyl)-acetamide;

2-(4-Cyclopropylmethyl-1-methyl-2,3,4,5-tetrahydro-1H-benzo[e][1,4]diazepin-9-ylamino)-N-(2-isopropylamino-ethyl)-N-(2-trifluoromethyl-benzyl)-acetamide;

2-(4-Cyclopropylmethyl-1-methyl-2,3,4,5-tetrahydro-1H-benzo[e][1,4]diazepin-9-ylamino)-N-(2-morpholin-4-yl-ethyl)-N-(3-trifluoromethyl-pyridin-2-ylmethyl)-acetamide;

2-(4-Ethyl-5-oxo-2,3,4,5-tetrahydro-benzo[f][1,4]oxazepin-9-ylamino)-N-(2-isopropylamino-ethyl)-N-(2-trifluoromethyl-benzyl)-acetamide;

2-(4-Ethyl-5-oxo-2,3,4,5-tetrahydro-benzo[f][1,4]oxazepin-9-ylamino)-N-(2-pyrrolidin-1-yl-ethyl)-N-(3-trifluoromethyl-pyridin-2-ylmethyl)-acetamide;

N-(2-Dimethylamino-ethyl)-2-(4-ethyl-5-oxo-2,3,4,5-tetrahydro-benzo[f][1,4]oxazepin-9-ylamino)-N-(3-trifluoromethyl-pyridin-2-ylmethyl)-acetamide;

N-(3-Chloro-pyridin-2-ylmethyl)-2-(4-ethyl-5-oxo-2,3,4,5-tetrahydro-benzo[f][1,4]oxazepin-9-ylamino)-N-(2-pyrrolidin-1-yl-ethyl)-acetamide;

N-(3-Chloro-pyridin-2-ylmethyl)-N-(2-dimethylamino-ethyl)-2-(4-ethyl-5-oxo-2,3,4,5-tetrahydro-benzo[f][1,4]oxazepin-9-ylamino)-acetamide;

2-(4-Cyclopropylmethyl-5-oxo-2,3,4,5-tetrahydro-benzo[f][1,4]oxazepin-9-ylamino)-N-(2-dimethylamino-ethyl)-N-(2-trifluoromethyl-benzyl)-acetamide;

2-(4-Cyclopropylmethyl-5-oxo-2,3,4,5-tetrahydro-benzo[f][1,4]oxazepin-9-ylamino)-N-(2-isopropylamino-ethyl)-N-(2-trifluoromethyl-benzyl)-acetamide;

N-(2-tert-Butylamino-ethyl)-2-(4-cyclopropylmethyl-5-oxo-2,3,4,5-tetrahydro-benzo[f][1,4]oxazepin-9-ylamino)-N-(2-trifluoromethyl-benzyl)-acetamide;

2-(4-Cyclopropylmethyl-5-oxo-2,3,4,5-tetrahydro-benzo[f][1,4]oxazepin-9-ylamino)-N-(2-pyrrolidin-1-yl-ethyl)-N-(3-trifluoromethyl-pyridin-2-ylmethyl)-acetamide;

2-(4-Cyclopropylmethyl-3-oxo-2,3,4,5-tetrahydro-benzo[f][1,4]oxazepin-9-ylamino)-N-(2-pyrrolidin-1-yl-ethyl)-N-(3-trifluoromethyl-pyridin-2-ylmethyl)-acetamide;

N-(2-tert-Butylamino-ethyl)-2-(4-cyclopropylmethyl-3-oxo-2,3,4,5-tetrahydro-benzo[f][1,4]oxazepin-9-ylamino)-N-(2-trifluoromethyl-benzyl)-acetamide;

2-(4-Cyclopropylmethyl-3-oxo-2,3,4,5-tetrahydro-benzo[f][1,4]oxazepin-9-ylamino)-N-(2-dimethylamino-ethyl)-N-(2-trifluoromethyl-benzyl)-acetamide;

2-(4-Cyclopropylmethyl-3-oxo-2,3,4,5-tetrahydro-benzo[f][1,4]oxazepin-9-ylamino)-N-(2-isopropylamino-ethyl)-N-(2-trifluoromethyl-benzyl)-acetamide;

{2-[[2-(4-Ethyl-2,3,4,5-tetrahydro-benzo[f][1,4]oxazepin-9-ylamino)-acetyl]-(2-trifluoromethyl-benzyl)-amino]-ethyl}-isopropyl-carbamic acid tert-butyl ester;

N-(2-tert-Butylamino-ethyl)-2-(4-ethyl-2,3,4,5-tetrahydro-benzo[f][1,4]oxazepin-9-ylamino)-N-(2-trifluoromethyl-benzyl)-acetamide;

2-(4-Ethyl-2,3,4,5-tetrahydro-benzo[f][1,4]oxazepin-9-ylamino)-N-(2-isopropylamino-ethyl)-N-(2-trifluoromethyl-benzyl)-acetamide;

N-(2-Dimethylamino-ethyl)-2-(4-ethyl-2,3,4,5-tetrahydro-benzo[f][1,4]oxazepin-9-ylamino)-N-(3-trifluoromethyl-pyridin-2-ylmethyl)-acetamide;

N-(2-Dimethylamino-ethyl)-2-(4-ethyl-2,3,4,5-tetrahydro-benzo[f][1,4]oxazepin-9-ylamino)-N-(3-methyl-pyridin-2-ylmethyl)-acetamide;

2-(4-Ethyl-2,3,4,5-tetrahydro-benzo[f][1,4]oxazepin-9-ylamino)-N-(2-pyrrolidin-1-yl-ethyl)-N-(3-trifluoromethyl-pyridin-2-ylmethyl)-acetamide;

N-(3-Chloro-pyridin-2-ylmethyl)-2-(4-ethyl-2,3,4,5-tetrahydro-benzo[f][1,4]oxazepin-9-ylamino)-N-(2-pyrrolidin-1-yl-ethyl)-acetamide;

N-(2-Dimethylamino-ethyl)-2-(4-ethyl-2,3,4,5-tetrahydro-benzo[f][1,4]oxazepin-9-ylamino)-N-(2-trifluoromethyl-thiazol-5-ylmethyl)-acetamide;

N-(5-Chloro-1-methyl-3-trifluoromethyl-1H-pyrazol-4-ylmethyl)-N-(2-dimethylamino-ethyl)-2-(4-ethyl-2,3,4,5-tetrahydro-benzo[f][1,4]oxazepin-9-ylamino)-acetamide;

(2-{(3-Chloro-pyridin-2-ylmethyl)-[2-(4-ethyl-2,3,4,5-tetrahydro-benzo[f][1,4]oxazepin-9-ylamino)-acetyl]-amino}-ethyl)-methyl-carbamic acid tert-butyl ester;

2-(4-Cyclopropylmethyl-2,3,4,5-tetrahydro-benzo[f][1,4]oxazepin-9-ylamino)-N-(2-pyrrolidin-1-yl-ethyl)-N-(3-trifluoromethyl-pyridin-2-ylmethyl)-acetamide;

N-(2-tert-Butylamino-ethyl)-2-(4-cyclopropylmethyl-2,3,4,5-tetrahydro-benzo[f][1,4]oxazepin-9-ylamino)-N-(2-trifluoromethyl-benzyl)-acetamide;

2-(4-Cyclopropylmethyl-2,3,4,5-tetrahydro-benzo[f][1,4]oxazepin-9-ylamino)-N-(2-dimethylamino-ethyl)-N-(2-trifluoromethyl-benzyl)-acetamide;

2-(4-Cyclopropylmethyl-2,3,4,5-tetrahydro-benzo[f][1,4]oxazepin-9-ylamino)-N-(2-isopropylamino-ethyl)-N-(2-trifluoromethyl-benzyl)-acetamide;

N-(2-Chloro-benzyl)-2-(4-cyclopropylmethyl-2,3,4,5-tetrahydro-benzo[f][1,4]oxazepin-6-ylamino)-N-(2-dimethylamino-ethyl)-acetamide;

2-(4-Cyclopropylmethyl-2,3,4,5-tetrahydro-benzo[f][1,4]
oxazepin-6-ylamino)-N-(2-dimethylamino-ethyl)-N-(3-
methyl-pyridin-2-ylmethyl)-acetamide;
2-(4-Cyclopropylmethyl-2,3,4,5-tetrahydro-benzo[f][1,4]
oxazepin-6-ylamino)-N-(2,3-dichloro-benzyl)-N-(2-dim-
ethylamino-ethyl)-acetamide;
2-(4-Cyclopropylmethyl-2,3,4,5-tetrahydro-benzo[f][1,4]
oxazepin-6-ylamino)-N-(2-isopropylamino-ethyl)-N-(2-
trifluoromethyl-benzyl)-acetamide;
2-(4-Cyclopropylmethyl-2,3,4,5-tetrahydro-benzo[f][1,4]
oxazepin-6-ylamino)-N-(2-isopropylamino-ethyl)-N-(3-
trifluoromethyl-pyridin-2-ylmethyl)-acetamide;
N-(2-tert-Butylamino-ethyl)-N-(2-chloro-benzyl)-2-(4-cy-
clopropylmethyl-2,3,4,5-tetrahydro-benzo[f][1,4]oxaze-
pin-6-ylamino)-acetamide;
N-(2-tert-Butylamino-ethyl)-N-(3-chloro-pyridin-2-ylm-
ethyl)-2-(4-cyclopropylmethyl-2,3,4,5-tetrahydro-benzo
[f][1,4]oxazepin-6-ylamino)-acetamide;
N-(2-tert-Butylamino-ethyl)-2-(4-cyclopropylmethyl-2,3,4,
5-tetrahydro-benzo[f][1,4]oxazepin-6-ylamino)-N-(2-tri-
fluoromethyl-benzyl)-acetamide; and
N-(2-tert-Butylamino-ethyl)-2-(4-cyclopropylmethyl-2,3,4,
5-tetrahydro-benzo[f][1,4]oxazepin-6-ylamino)-N-(3-tri-
fluoromethyl-pyridin-2-ylmethyl)-acetamide.

The compounds of formula (I) according to embodiments 1) to 28) and their pharmaceutically acceptable salts can be used as medicaments, e.g. in the form of pharmaceutical compositions for enteral (such especially oral) or parenteral administration (including topical application or inhalation).

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) according to embodiments 1) to 28).

In a preferred embodiment of the invention, the administered amount is comprised between 1 mg and 1000 mg per day, particularly between 5 mg and 500 mg per day, more particularly between 25 mg and 400 mg per day, especially between 50 mg and 200 mg per day.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

For avoidance of any doubt, if compounds are described as useful for the prevention or treatment of certain diseases, such compounds are likewise suitable for use in the preparation of a medicament for the prevention or treatment of said diseases.

The compounds of formula (I) according to embodiments 1) to 28) are useful for the prevention or treatment of disorders relating to the CXCR7 receptor or its ligands which are especially to disorders relating to a dysfunction of the CXCR7 receptor, or dysfunction of ligands signalling through CXCR7, or dysfunction of CXCR7 ligands (CXCL12 and CXCL11) signalling through their other receptors (CXCR4 and CXCR3).

Diseases or disorders relating to the CXCR7 receptor or its ligands are especially selected from the group consisting of cancer (notably carcinomas, leukemias, adenocarcinomas, malignant glioma, glioblastoma multiforme, brain metastases, multiple myelomas, renal clear cell carcinoma, prostate cancer, pancreatic adenocarcinoma, melanoma, metastatic melanoma, hepatocellular carcinoma, colon tumors, breast cancer, non-small cell lung cancer, colorectal cancer, brain tumors, Ewing's sarcoma, lymphoma, Burkitt's lymphoma, Hodgkin's lymphoma, adult T-cell leukemia, lymphoproliferative disease, and Kaposi's sarcoma; especially malignant glioma, glioblastoma multiforme, brain metastases, pancreatic adenocarcinoma, lymphoma, Burkitt's lymphoma, and Hodgkin's lymphoma);

inflammatory diseases (notably chronic rhinosinusitis, asthma, chronic obstructive pulmonary disorder, atherosclerosis, myocarditis, and sarcoidosis; especially chronic rhinosinusitis, asthma, and atherosclerosis);

autoimmune disorders (notably multiple sclerosis, rheumatoid arthritis, inflammatory bowel disease, systemic lupus erythematosus, lupus nephritis, interstitial cystitis, celiac disease, auto-immune encephalomyelitis, demyelinating diseases, osteoarthritis, and type I diabetes; especially multiple sclerosis, rheumatoid arthritis, inflammatory bowel disease, and auto-immune encephalomyelitis);

transplant rejection (notably renal allograft rejection, cardiac allograft rejection, and graft-versus-host diseases brought about by hematopoietic stem cell transplantation); and fibrosis (notably liver fibrosis, liver cirrhosis, and idiopathic pulmonary fibrosis).

Notably such diseases or disorders relating to the CXCR7 receptor or its ligands are cancers and autoimmune disorders.

In addition, further diseases or disorders relating to the CXCR7 receptor or its ligands are diseases involving CXCR7 and/or CXCL12 and/or CXCL11 mediated metastasis, chemotaxis, cell adhesion, trans-endothelial migration, cell proliferation and/or survival.

In addition, further particular diseases or disorders relating to the CXCR7 receptor or its ligands are proliferative diabetic retinopathy; West Nile virus encephalitis; pulmonary vascular diseases, acute renal failure, ischemia including cerebral ischemia, acute coronary syndrome, injured central nervous system, hypertension, pulmonary hypertension, Shiga-toxin-associated heomolytic uremic syndrome, preeclampsia, vascular injury, HIV/AIDS, angiogenesis, and brain and neuronal dysfunctions (such as inflammatory components of Alzheimer's disease), stress-related disorders (such as anxiety, depression, and posttraumatic stress disorder), and diseases involving opioid receptors. In a sub-embodiment, such a further particular disease or disorder relating to the CXCR7 receptor or its ligands is especially pulmonary hypertension.

The term "cancer" refers to all sorts of cancers such as carcinomas, leukemias, adenocarcinomas, malignant glioma, glioblastoma multiforme, brain metastases, multiple myelomas, renal clear cell carcinoma, prostate cancer, pancreatic adenocarcinoma, melanoma, metastatic melanoma, rhabdomyosarcoma, hepatocellular carcinoma, colon tumors, breast cancer, non-small cell lung cancer, oral tumors, colorectal cancer, gallbladder cancer, brain tumors, esophageal cancer, Ewing's sarcoma, bladder cancer, meningiomas, lymphoma, viral-induced tumors, Burkitt's lymphoma, Hodgkin's lymphoma, adult T-cell leukemia, lymphoproliferative disease, Kaposi's sarcoma, MALT lymphoma, papillary thyroid carcinoma, cervical cancer, and osteosarcoma, choriocarcinoma, primary intra-ocular B-cell lymphoma, and diseases involving CXCR7 and/or CXCL12 and/or CXCL11 mediated metastasis. In addition, cancer furthermore comprises mesotheliomas, ovarian cancer, cervical cancer, head and neck cancer, small cell lung cancer, cancer of the esophagus, stomach cancer, hepatobiliary cancer, cancer of the small intestine, *recta* cancer, kidney cancer, bladder cancer, penile cancer, urethral cancer, testicular cancer, cervical cancer, vaginal cancer, uterine cancer, thyroid cancer, parathyroid cancer, adrenal cancer, pancreatic endocrine cancer, carcinoid cancer, bone cancer, skin cancer, retinoblastomas, non-Hodgkin's lymphoma, multicentric Castleman's disease or AIDS-associated cancer, primary effusion lymphoma, and neuroectodermal tumors. Preferably the term "cancer" refers to carcinomas, leukemias, adenocarcinomas, malignant glioma, glioblastoma multiforme, brain metastases, multiple myelomas, renal clear cell carcinoma, prostate cancer, pancreatic adenocarcinoma, melanoma, metastatic melanoma, hepatocellular carcinoma, colon tumors, breast cancer, non-small cell lung cancer, colorectal cancer, brain tumors, Ewing's sarcoma, lymphoma, Burkitt's lymphoma, Hodgkin's lymphoma, adult T-cell leukemia, lymphoproliferative disease, and Kaposi's sarcoma; especially to malignant glioma, glioblastoma multiforme, brain metastases, pancreatic adenocarcinoma, lymphoma, Burkitt's lymphoma, and Hodgkin's lymphoma.

The compounds of formula (I) according to any one of embodiments 1) to 28) are in particular useful as therapeutic agents for the prevention or treatment of a cancer. They can be used as single therapeutic agents or in combination with one or more chemotherapy agents and/or radiotherapy and/or targeted therapy. In a sub-embodiment, when a compound of formula (I) is used for the prevention or treatment of a cancer in combination with one or more chemotherapy agents and/or radiotherapy, such cancer is especially a malignant glioma, in particular a glioblastoma multiforme. Such combined treatment may be effected simultaneously, separately, or over a period of time.

The invention, thus, also relates to pharmaceutical compositions comprising a pharmaceutically acceptable carrier material, and:
 a compound of formula (I) according to any one of embodiments 1) to 28);
 and one or more cytotoxic chemotherapy agents.

The invention, thus, further relates to a kit comprising a pharmaceutical composition, said composition comprising a pharmaceutically acceptable carrier material, and:
 a compound of formula (I) according to any one of embodiments 1) to 28);
 and instructions how to use said pharmaceutical composition for the prevention or the treatment of a cancer (especially of a malignant glioma, in particular of a glioblastoma multiforme), in combination with chemotherapy and/or radiotherapy and/or targeted therapy.

The terms "radiotherapy" or "radiation therapy" or "radiation oncology", refer to the medical use of ionizing radiation in the prevention (adjuvant therapy) and/or treatment of cancer; including external and internal radiotherapy.

The term "targeted therapy" refers to the prevention (adjuvant therapy) and/or treatment of cancer with one or more anti-neoplastic agents such as small molecules or antibodies which attack specific types of cancer cells with less harm to normal cells. Some targeted therapies block the action of certain enzymes, proteins, or other molecules involved in the growth and spread of cancer cells. Other types of targeted therapies help the immune system kill cancer cells (immunotherapies); or deliver toxic substances directly to cancer cells and kill them.

The term "chemotherapy" refers to the treatment of cancer with one or more cytotoxic anti-neoplastic agents ("cytotoxic chemotherapy agents"). Chemotherapy is often used in conjunction with other cancer treatments, such as radiation therapy or surgery. The term especially refers to conventional chemotherapeutic agents which act by killing cells that divide rapidly, one of the main properties of most cancer cells. Chemotherapy may use one drug at a time (single-agent chemotherapy) or several drugs at once (combination chemotherapy or polychemotherapy). Chemotherapy using drugs that convert to cytotoxic activity only upon light exposure is called photochemotherapy or photodynamic therapy.

The term "cytotoxic chemotherapy agent" or "chemotherapy agent" as used herein refers to an active anti-neoplastic agent inducing apoptosis or necrotic cell death. When used in combination with the compounds of formula (I), the term especially refers to conventional cytotoxic chemotherapy agents such as:
 a) alkylating agents (for example mechlorethamine, chlorambucil, cyclophosphamide, ifosfamide, streptozocin, carmustine, lomustine, melphalan, busulfan, dacarbazine, temozolomide, thiotepa or altretamine);
 b) platinum drugs (for example cisplatin, carboplatin or oxaliplatin);
 c) antimetabolite drugs (for example 5-fluorouracil, capecitabine, 6-mercaptopurine, methotrexate, gemcitabine, cytarabine, fludarabine or pemetrexed);
 d) anti-tumor antibiotics (for example daunorubicin, doxorubicin, epirubicin, idarubicin, actinomycin-D, bleomycin, mitomycin-C or mitoxantrone);
 e) mitotic inhibitors (for example paclitaxel, docetaxel, ixabepilone, vinblastine, vincristine, vinorelbine, vindesine or estramustine); or
 f) topoisomerase inhibitors (for example etoposide, teniposide, topotecan, irinotecan, diflomotecan or elomotecan).

When used in combination with the compounds of formula (I), preferred cytotoxic chemotherapy agents are the above-mentioned alkylating agents (notably mechlorethamine, chlorambucil, cyclophosphamide, ifosfamide, streptozocin, carmustine, lomustine, melphalan, busulfan, dacarbazine, 3-methyl-(triazen-1-yl)imidazole-4-carboxamide (MTIC) and prodrugs thereof such as especially temozolomide, thiotepa, altretamine; or pharmaceutically acceptable salts of these compounds; in particular temozolomide); and mitotic inhibitors (notably paclitaxel, docetaxel, ixabepilone, vinblastine, vincristine, vinorelbine, vindesine, estramustine; or pharmaceutically acceptable salts of these compounds; in particular paclitaxel). Most preferred cytotoxic chemotherapy agents to be used in combination with the compounds of formula (I) are those routinely used in the treatment of glioblastoma multiforme, in particular temozolomide. Equally preferred is radiotherapy.

Chemotherapy may be given with a curative intent or it may aim to prolong life or to palliate symptoms.
a) Combined modality chemotherapy is the use of drugs with other cancer treatments, such as radiation therapy or surgery.
b) Induction chemotherapy is the first line treatment of cancer with a chemotherapeutic drug. This type of chemotherapy is used for curative intent.
c) Consolidation chemotherapy is the given after remission in order to prolong the overall disease free time and improve overall survival. The drug that is administered is the same as the drug that achieved remission.
d) Intensification chemotherapy is identical to consolidation chemotherapy but a different drug than the induction chemotherapy is used.
e) Combination chemotherapy involves treating a patient with a number of different drugs simultaneously. The drugs differ in their mechanism and side effects. The biggest advantage is minimising the chances of resistance developing to any one agent. Also, the drugs can often be used at lower doses, reducing toxicity.
f) Neoadjuvant chemotherapy is given prior to a local treatment such as surgery, and is designed to shrink the primary tumor. It is also given to cancers with a high risk of micrometastatic disease.
g) Adjuvant chemotherapy is given after a local treatment (radiotherapy or surgery). It can be used when there is little evidence of cancer present, but there is risk of recurrence. It is also useful in killing any cancerous cells that have spread to other parts of the body. These micrometastases can be treated with adjuvant chemotherapy and can reduce relapse rates caused by these disseminated cells.
h) Maintenance chemotherapy is a repeated low-dose treatment to prolong remission.
i) Salvage chemotherapy or palliative chemotherapy is given without curative intent, but simply to decrease tumor load and increase life expectancy. For these regimens, a better toxicity profile is generally expected.

When combined with the compounds of formula (I), preventive or curative forms of chemotherapy (or mutatis mutandis: radiotherapy) such as those listed under a), b) c), d), e), and especially g) and/or h) above are preferred.

"Simultaneously" or "simultaneous", when referring to an administration type, means in the present application that the administration type concerned consists in the administration of two or more active ingredients by the same route and at approximately the same time. When administered simultaneously, said two or more active ingredients may be administered in a fixed dose combination, or equivalent (e.g. by using two or more different pharmaceutical compositions, in general to be administered by the same route of administration at approximately the same time), "Fixed dose combination", when referring to an administration type, means in the present application that the administration type concerned consists in the administration of one single pharmaceutical composition comprising the two or more active ingredients.

"Separately" or "separate", when referring to an administration type, means in the present application that the administration type concerned consists in the administration of two or more active ingredients at approximately the same time by at least two different routes. It is understood that a separate administration will lead to a treatment phase where for a certain period of time (e.g. at least one day) the subject is exposed to only one of the two or more active ingredients and/or treatments, and to a treatment phase where the subject is exposed to the two or more active ingredients and/or treatments at the same time. Separate administration especially refers to situations wherein at least one of the active ingredients and/or treatments is given with a periodicity substantially different from daily (such as once or twice daily) administration (e.g. wherein one active ingredient and/or treatment is given once or twice a day, and another is given once a week). For example when used in combination with radiotherapy, the present CXCR7 modulators would be used "separately".

By administration "over a period of time" is meant in the present application the administration of two or more active ingredients/or of one or more active ingredients in combination with radiotherapy treatment, at different times. In a sub-embodiment, the term refers to an administration method according to which the entire administration of one of the active ingredients and/or of the radiotherapy treatment, is completed before the administration of the other/the others begins. In this way it is possible to administer one of the active ingredients/to use radiotherapy, for several months before administering the other active ingredient or ingredients. Administration "over a period of time" encompasses situations wherein the active ingredients are not given with the same periodicity (e.g. wherein one active ingredient is given once a day and another is given once a week).

Administration "over a period of time" also encompasses situations wherein the CXCR7 modulators of formula (I) would be used in a treatment that starts after an initial chemotherapeutic or radiotherapeutic treatment (for example an induction chemotherapy), optionally in combination with a further/an ongoing chemotherapeutic or radiotherapeutic treatment (for example in combination with a consolidation chemotherapy, an intensification chemotherapy, an adjuvant chemotherapy, or a maintenance chemotherapy; or radiotherapeutic equivalents thereof); wherein such further/ongoing chemotherapeutic or radiotherapeutic treatment would be simultaneously, separately, or over a period of time in the sense of "not given with the same periodicity".

Autoimmune disorders may be defined as comprising rheumatoid arthritis (RA); multiple sclerosis (MS); autoimmune encephalomyelitis; and inflammatory bowel disease (IBD, especially comprising Crohn's disease and ulcerative colitis). In addition, autoimmune diseases further comprise disorders such as systemic lupus erythematosus (SLE); psoriasis; psoriatic arthritis; lupus nephritis; interstitial cystitis; celiac disease; auto-immune encephalomyelitis; demyelinating diseases; osteoarthritis; antiphospholipid syndrome; thyroiditis such as Hashimoto's thyroiditis; lymphocytic thyroiditis; myasthenia gravis; type I diabetes; uveitis; episcleritis; scleritis; Kawasaki's disease; uveoretinitis; posterior uveitis; uveitis associated with Behcet's disease; uveomeningitis syndrome; allergic encephalomyelitis; atopic diseases such as rhinitis, conjunctivitis, dermatitis; and post-infectious autoimmune diseases including rheumatic fever and post-infectious glomerulonephritis. In a sub-embodiment, autoimmune disorders include rheumatoid arthritis (RA); multiple sclerosis (MS); and inflammatory bowel disease (comprising Crohn's disease and ulcerative colitis); as well as systemic lupus erythematosus (SLE);

lupus nephritis; interstitial cystitis; celiac disease; autoimmune encephalomyelitis; demyelinating diseases; osteoarthritis; and type I diabetes.

Inflammatory diseases may be defined as comprising especially chronic rhinusitis, as well as asthma, chronic obstructive pulmonary disorder (COPD), atherosclerosis, myocarditis, dry eye disease, sarcoidosis, inflammatory myopathies, and acute lung injury.

Transplant rejection may be defined as comprising rejection of transplanted organs such as kidney, liver, heart, lung, pancreas, cornea, and skin; graft-versus-host diseases brought about by hematopoietic stem cell transplantation; chronic allograft rejection and chronic allograft vasculopathy.

Fibrosis may be defined as comprising especially liver fibrosis, liver cirrhosis, idiopathic pulmonary fibrosis, renal fibrosis, endomyocardial fibrosis, and arthrofibrosis.

The compounds of formula (I) according to embodiments 1) to 28) are also useful in method of treating tumors comprising administering an effective amount of the compound of formula (I) wherein said effective amount leads to a change of tumor properties, and wherein said modification is achieved by modulating the CXCL12 receptor pathway; wherein said treatment may optionally be effected in combination with a conventional chemotherapeutic or radiotherapeutic treatment (in which case the tumor is notably a malignant glioma, in particular a glioblastoma multiforme). Such combined treatment may be effected simultaneously, separately, or over a period of time.

The compounds of formula (I) are also useful in method of modulating an immune response comprising the administration of an effective amount of the compound of formula (I) wherein said effective amount modulates an inflammatory disease and wherein said response is mediated by the CXCL12 receptor pathway.

Besides, any preferences, (sub-)embodiments, and uses indicated for the compounds of formula (I) (whether for the compounds themselves, salts thereof, compositions containing the compounds or salts thereof, or uses of the compounds or salts thereof, etc.) apply mutatis mutandis to compounds of formula (II), (III), (IV), and (V).

Preparation of Compounds of Formula (I)

A further aspect of the invention is a process for the preparation of compounds of Formula (I). Compounds of Formula (I) can be prepared from commercially available or well-known starting materials according to the methods described in the experimental part, by analogous methods; or according to the general sequence of reactions outlined below, wherein $R^1$, $R^4$, $L^1$, $L^2$, X, $Y^1$, $Y^2$ and $Ar^1$ are as defined for Formula (I). Optimum reaction conditions may vary with the particular reactants or solvents used, but such conditions can be determined by a person skilled in the art by routine optimisation procedures. Other abbreviations used herein are explicitly defined, or are as defined in the experimental section. In some instances the generic groups $R^1$, $R^4$, $L^1$, $L^2$, X, $Y^1$, $Y^2$ and $Ar^1$ might be incompatible with the assembly illustrated in the schemes below and so will require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as necessary are in place. In some cases the final product may be further modified, for example, by manipulation of substituents to give a new final product. These manipulations may include, but are not limited to, reduction, oxidation, alkylation, acylation, and hydrolysis reactions which are commonly known to those skilled in the art. The compounds obtained may also be converted into salts, especially pharmaceutically acceptable salts, in a manner known per se.

Preparation of Compounds of Formula (I)

Generally compounds of Formula (I) can be obtained by reaction of a compound of Structure A with an amine of Structure B in a typical amide coupling reaction, using HATU or another coupling agent in a solvent such as DCM or DMF or a combination of both at a temperature of 0° C. or at RT or at elevated temperature.

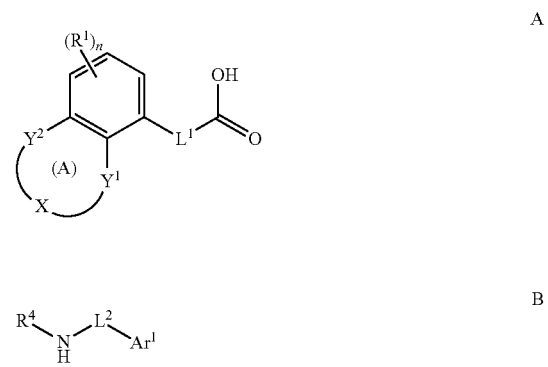

Preparation of Compounds of Formula (III)

Compounds of Formula (I) can generally also be obtained by derivatization of a free amine precursor. For example compounds of Formula (I) wherein the seven-membered ring is as in the compounds of Formula (III) can be obtained from a free amine precursor of Structure 1 and an aldehyde of Structure 2 in the conditions of a typical reductive amination reaction. In this particular case, $R^5$ represents $R^{5a)}CH_2$. For example a compound of Structure 1 is reacted with an aldehyde of Structure 2 in a solvent such as DCM, THF or MeOH using $NaBH_3CN$, $NaBH(OAc)_3$ or $NaBH_4$ as the reducing agent.

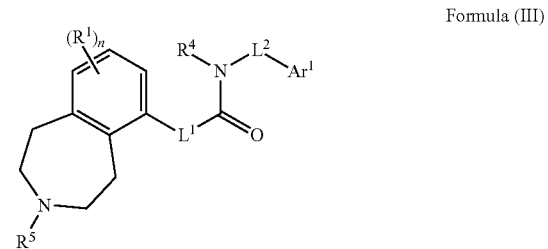

Similarly, examples of Formula (III) wherein $R^5$ represents $R^{5b)}CO$ can be obtained by reaction of a compound of Structure 1, preferably in presence of a base such as TEA or DIPEA, with:

a carboxylic acid of Structure 3 in presence of a coupling reagent such as HATU or like in a solvent such as DCM or DMF at 0° C. or RT; or a carboxylic acid derivative of Structure 3' wherein the group LG represents a leaving group such as Cl or the like in a solvent such as THF, DCM or the like preferably at 0° C.

Structure 1

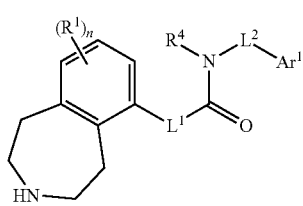

Structure 2

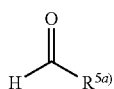

Structure 3

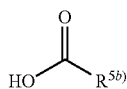

Structure 3'

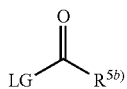

Depending on the compatibility of the generic groups $R^4$, $L^1$, $L^2$, $R^5$, and $Ar^1$ a final deprotection step according to conditions well known in the art may be required for reaching the final compound of Formula (III).

Compounds of Structure 3A which are a particular case of compounds of Structure 1 can be made in a four steps procedure from compounds of Structure 3A-1 which are commercially available or easily made by a person skilled in the art, e.g. as shown in Scheme 1 below.

In a first step a compound of Structure 3A-1 may be alkylated with ethyl- or methylbromoacetate in an alkylation reaction in a polar solvent such as MeCN, DMF or THF in presence of an organic base such as DIPEA, TEA or of an inorganic base such as $K_2CO_3$ to yield an ester of Structure 3A-2. This ester can be then saponified using a base such as LiOH, NaOH or the like in a solvent such as THF, EtOH, MeOH or a mixture of those, typically at RT to yield the corresponding acid 3A-3. This acid can be reacted in an amide coupling reaction with a base of Structure B with HATU or a similar amide coupling reagent in a solvent such as DCM or DMF or a combination of those in presence of a base such as DIPEA or TEA to yield an amide of Structure 3A-4. Finally the protecting group can be removed using well-known methods to give a compound of Structure 3A.

Scheme 1

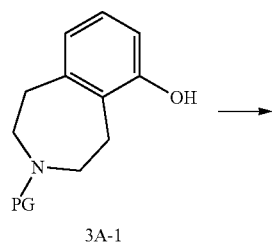

3A-1

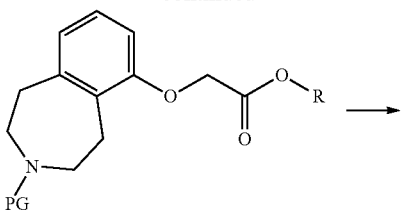

3A-2

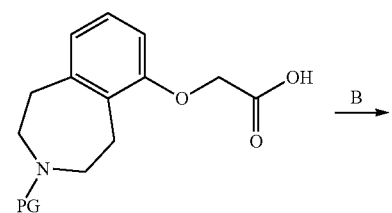

3A-3

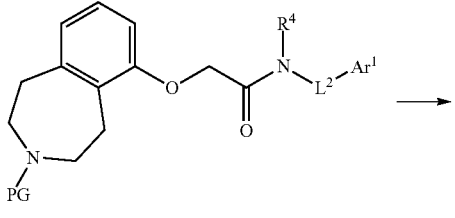

3A-4

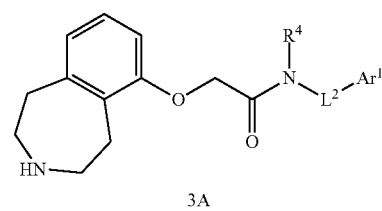

3A

Compounds of Structure 3B which are a particular case of compounds of Structure 1 can be prepared following the Scheme 2 below. In the first step a trifluoromethanesulfonate of Structure 3B-1 is synthesized from a compound of Structure 3A-1 by reaction of the phenol moiety with trifluormethane-sulfonic anhydride at a temperature below 0° C. in a solvent such as DCM. Then the compound of Structure 3B-1 is reacted with the amine of Structure 5A-2 (which synthesis is described below) under typical conditions of a Buchwald-Hartwig reaction. In this reaction a mixture of the compound of Structure 3B-1 and an amine of Structure C are heated to a temperature between 80° C. to 140° C. in a flask or a sealed tube under inert atmosphere in the presence of a palladium catalyst, for example $Pd_2(dba)_3$ or $Pd(PPh_3)_4$ with a base such as tert-BuOH, KOH or preferentially $Cs_2CO_3$ in a solvent such as dioxane, DMF or toluene in presence of a ligand, preferentially Brettphos®. Removal of the protecting group from compound of Structure 3B-2 allows for the formation of a compound of Structure 3B.

Scheme 2

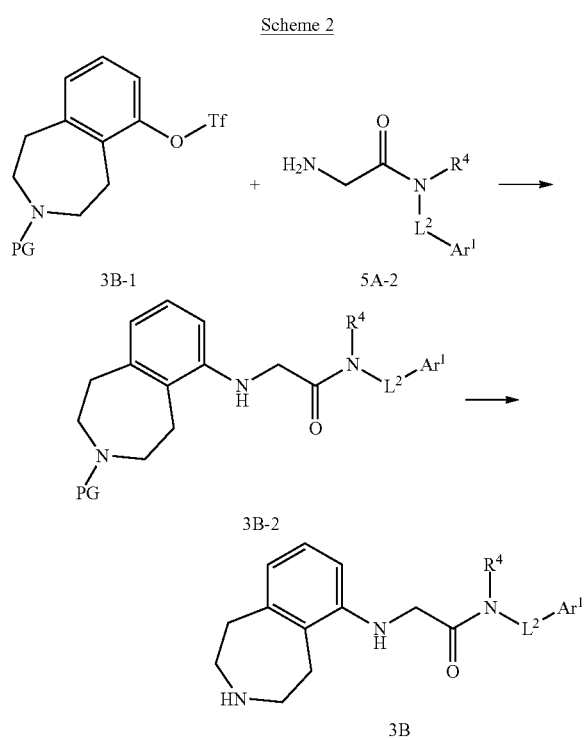

Preparation of Compounds of Formula (IV)

Compounds of Formula (I) wherein the seven-membered ring is as in the compounds of Formula (IV) can be prepared according to the general sequence of reactions outlined below.

Formula (IV)

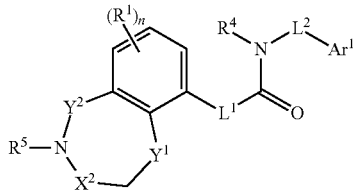

Generally examples of Formula (IV) are obtained from a carboxylic acid precursor of Structure 4 and an amine of Structure B using HATU or another amide coupling reagent in a solvent such as DCM or DMF at RT or 0° C. in the presence of a base like TEA or DIPEA. Depending on the compatibility of the generic groups $R^4$, $L^1$, $L^2$, $R^5$, $Y^1$ and $Ar^1$ a final deprotection step according to conditions well known in the art may be required for reaching the final derivative of Formula (IV).

Structure 4

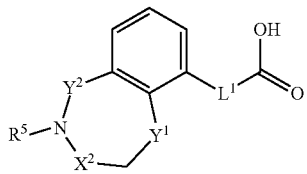

Preparation of Compounds of Structure 4

Compounds of Structure 4A which represent a particular case of compounds of Structure 4 can be prepared by one of the synthetic pathways described below.

Structure 4A

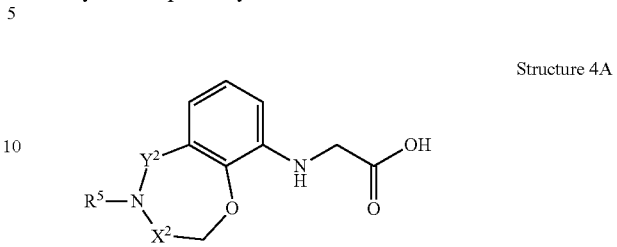

Compounds of Structure 4A wherein $Y^2$ represents $CH_2$ may be prepared by the procedure illustrated in Scheme 3. A commercially available amine 4A-1 is alkylated by treatment with 2-hydroxy-3-nitrobenzaldehyde in the presence of a reductive reagent like $NaBH_4$, $NaBH_3CN$, $NaBH(OAc)_3$ in a solvent like DCM, MeOH, THF to give the corresponding amine 4A-2. Compound 4A-2 can be reacted with a glycolic acid derivative (with or without protecting group) in presence of an amide coupling reagent such as HATU or HBTU in a solvent such as DCM or DMF at RT or 0° C. in the presence of a base like TEA or DIPEA to yield compound 4A-3 after a last deprotection step if required. Cyclization to yield derivative 4A-5 requires activation of the alcohol of the glycolic acid moiety which can be achieved in numerous ways: the alcohol 4A-3 can be treated under Mitsunobu reaction conditions ($PPh_3$, DEAD) in a compatible solvent such as THF at RT or 0° C.; or derivatives 4A-3 can be converted into compounds 4A-4 where the alcohol is activated through transformation into well-known leaving groups; either halides such as Cl, Br or I upon treatment with thionyl or oxalyl halide reagent or the like, or Appel reaction condition; or into sulfonic esters such as methyl- or 4-methylphenyl-sulfonate upon treatment with the appropriate sulfonyl chloride, in a solvent such as DCM or THF and in presence of a base such as TEA, Pyridine or DIPEA; alternatively compound 4A-4 can be obtained directly from derivative 4A-2 upon treatment with glycolic acid derivatives such as 2-chloroacetyl chloride or 2-bromoacetyl chloride in a solvent such as toluene or DMF at RT or 0° C. in the presence of a base like pyridine, TEA or DIPEA. Compounds 4A-5 can then be obtained through displacement of these leaving groups by the phenolate anion, formed in situ by basic treatment such as addition of $K_2CO_3$ or NaOH aqueous solution, in a solvent such as EtOH or DMF, at RT or up to reflux temperature.

Compounds 4A-6 can be obtained through reduction of the lactam function: in a typical experiment, a derivative 4A-5 is reacted with excess (such as 2 to 20 eq.) of a borane reagent such as $BH_3$.THF complex in a solvent such as THF at RT or reflux; partial or complete reduction of the nitro to yield derivative 4A-7 along with 4A-6 can be observed depending on the compound and reaction conditions, but the mixture can be carried on into the next step as such. Derivatives 4A-6 can then be reduced into the compounds 4A-7: in a typical experiment a compound 4A-6 is reduced with Pd/C in a solvent such as EtOH, THF, EtOAc or the like at RT in presence of $H_2$ or with the help of an H-Cube® hydrogen generator; alternatively a compound 4A-7 can be obtained from a compound 4A-6 by reaction at 0° C. or RT with a metal powder such as Zn or Fe in presence of a mild acid proton source such as NH₄Cl in a solvent such as acetone. Similarly, by selective reduction of the nitro group, the compounds of structure 4A-5 can be converted directly to compounds of structure 4A-7 wherein $X^2$ represents CO. Compounds of Structure 4A can then be made by reaction of a compound 4A-7 with glyoxylic acid monohydrate in presence of $NaBH_3CN$ in a solvent such as MeOH or the like; alternatively the mixture of compound 4A-7 and glyoxylic acid can be treated with Pd/C in a solvent such as MeOH, EtOH, EtOAc or the like at RT in presence of $H_2$ or with the help of an H-Cube® hydrogen generator to yield Structure 4A.

Scheme 4

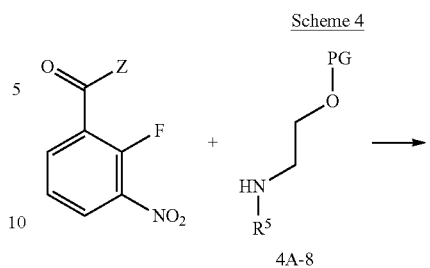

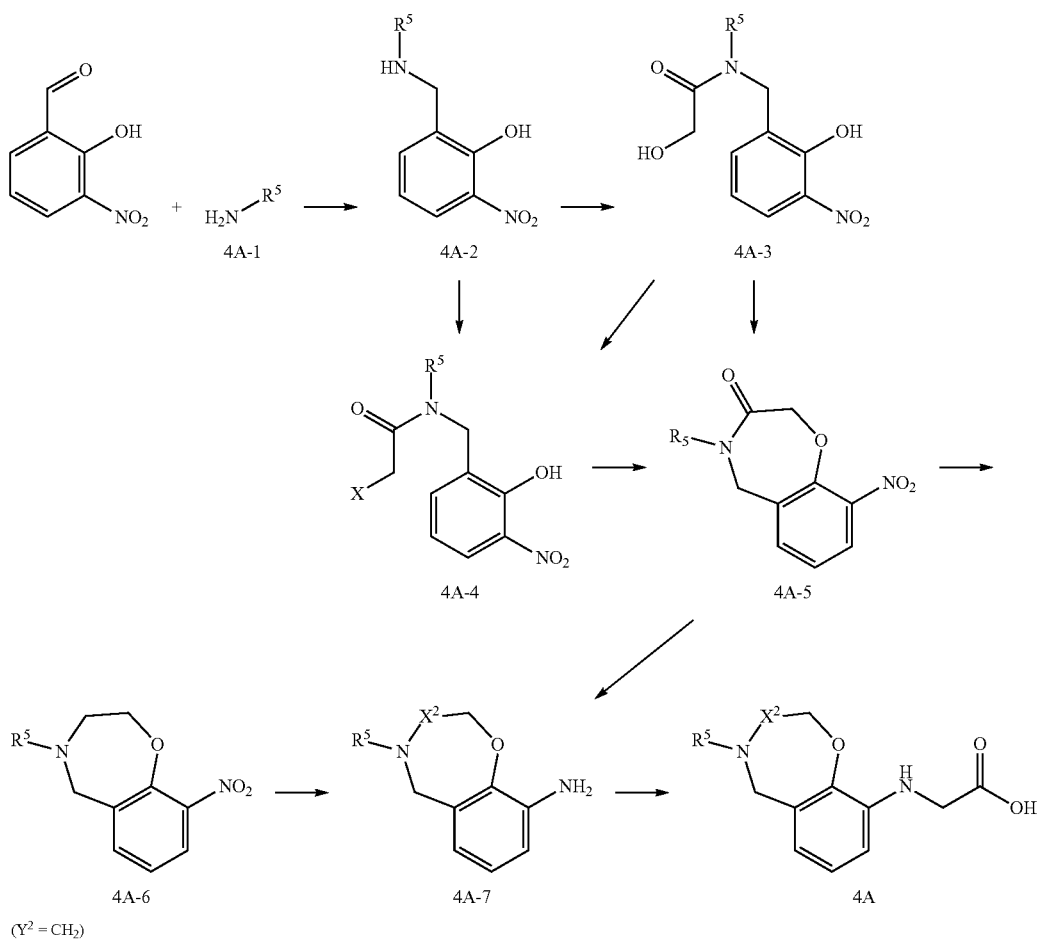

Alternatively the intermediates of structure 4A-6 can be synthesized according to the procedure illustrated in Scheme 4.

Compounds 4A-9 are obtained by reacting an aminoethanol derivative 4A-8 with the commercially available 2-fluoro-3-nitrobenzoyl chloride in presence of a base such as pyridine or (10%) NaOH aqueous solution, in a solvent such as DCM or DMF, at 0° C. or RT; aminoethanol derivatives 4A-8, with PG standing for any compatible protecting group such as TBDMS or Benzyl or even H if not protecting group is necessary, are extensively reported in literature.

-continued

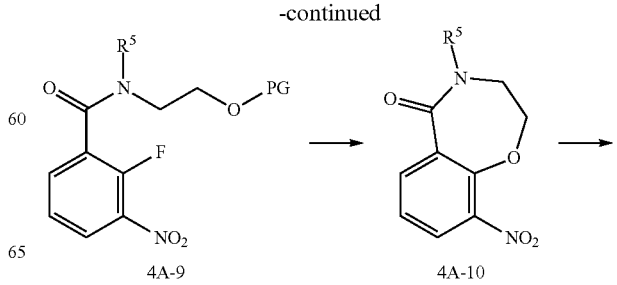

-continued

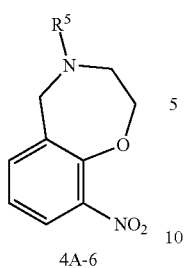
4A-6

Alternatively 2-fluoro-3-nitrobenzoic acid can be reacted with 4A-8 using HATU or another amide coupling reagent in a solvent such as DCM or DMF at RT or 0° C. in the presence of a base like TEA or DIPEA to yield 4A-9. After deprotection step if required, the alcohol in 4A-9 (PG=H) can cyclize in basic conditions to yield the derivatives 4A-10: in a typical experiment, the TBDMS alcohol protection in 4A-9 is selectively removed by treatment with a fluorine source such as TBAF (catalytic or stoichiometric amounts) in THF or the like at 0° C. or RT and the in situ generated alkoxide anion cyclizes spontaneously to yield the derivative 4A-10. Compounds 4A-6 can be obtained through reduction of the lactam function: in a typical experiment, a derivative 4A-10 is reacted with excess of borane reagent such as $BH_3$-THF complex in a solvent such as THF at RT or reflux. Partial or complete reduction of the nitro group to yield derivative 4A-7 along with 4A-6 can be observed depending on the compound and reaction conditions, but the mixture can be carried on into the next step as such. Alternatively compounds 4A-6 can be obtained through reduction of the lactam function: in a typical experiment, a derivative 4A-10 is reacted at RT with an excess of a reduction agent prepared by treatment of lithium aluminium hydride with 0.5 equivalent of concentrated sulphuric acid at 0° C. in a solvent such as THF. Compounds of Structure 4B which represent a particular case of compounds of Structure 4 can be prepared by the procedure illustrated in Scheme 5.

Structure 4B

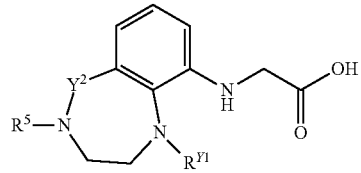

Derivatives 4B-1 wherein R may be $R^{Y1}$ as defined for formula (I), or a suitable protecting group (PG), are commercially available or their syntheses are extensively reported in literature (see for example the patent WO2008/039420, for the synthesis of the compound with R=PMB). Derivatives 4B-1 can be oxidized into the aldehyde 4B-2 by numerous ways for whoever is skilled in the art, such as submitting compound 4B-1 to Swern oxidation or its like or by treating 4B-1 with hypervalent iodine reagent such as IBX or well-known Dess-Martin reagent in a solvent such as DCM or EtOAc at 0° C. or RT. A commercially available amine 4B-3 is alkylated by treatment with compound 4B-2 in the presence of a reductive reagent like $NaBH_4$, $NaBH_3CN$, $NaBH(OAc)_3$ in a solvent like DCM, MeOH, THF to give the corresponding ethylenediamine derivative 4B-4.

Scheme 5

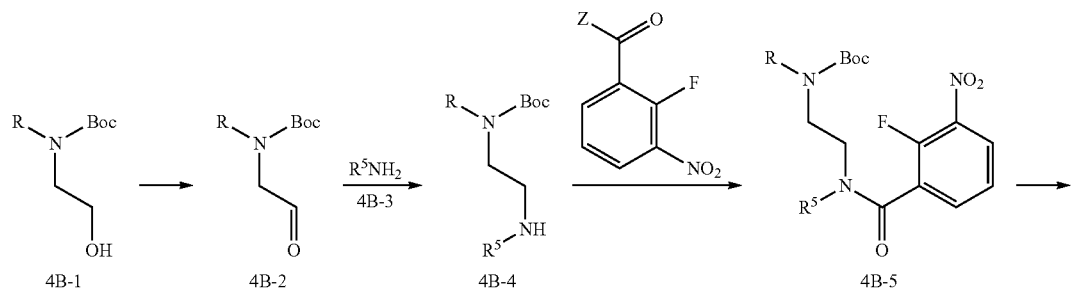

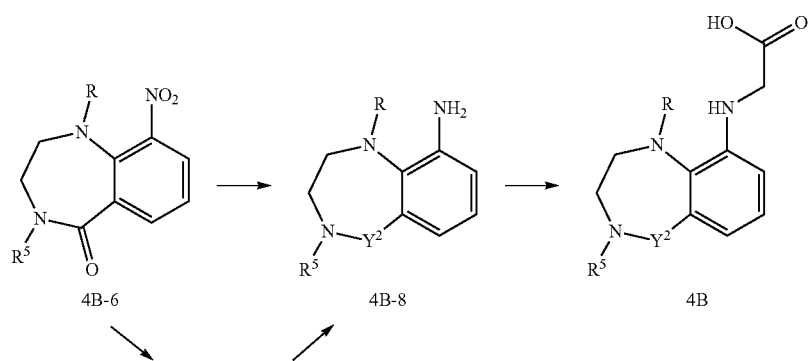

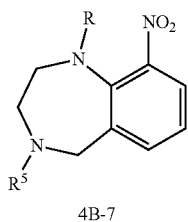

4B-7

Compounds 4B-5 are obtained by reacting derivative 4B-4 with 2-fluoro-3-nitrobenzoic acid or derivatives (Z=OH, a leaving group), e.g. commercially available 2-fluoro-3-nitrobenzoyl chloride in presence of a base such as pyridine or (10%) aq. NaOH solution, in solvent such as DCM or DMF, at 0° C. or RT. Alternatively, 2-fluoro-3-nitrobenzoic acid can be reacted with 4B-4 using HATU or another amide coupling reagent in a solvent such as DCM or DMF at RT or 0° C. in the presence of a base like TEA or DIPEA to yield 4B-5. After standard Boc deprotection, the amine in 4B-5 can cyclize in basic conditions to yield the derivatives 4B-6: in a typical experiment, the Boc protecting group in 4B-5 is selectively removed by treatment with a strong acid such as HCl in organic solution or TFA in a solvent such as DCM, EtOAc or Dioxane at 0° C. or RT; at the end of the deprotection step, excess of acid reagent is removed and the mixture is treated with a base such as TEA or DIPEA in a solvent such as DMF or toluene at RT or up to reflux to promote cyclization and yield the corresponding derivative 4B-6. Compounds 4B-7 can be obtained through reduction of the lactam function: in a typical experiment, a derivative 4B-6 is reacted with excess (such as 2 to 20 eq.) of borane reagent such as $BH_3$.THF complex in a solvent such as THF at RT or reflux; partial or complete reduction of the nitro group to yield derivative 4B-8 along with 4B-7 can be observed depending on the compound and reaction conditions, but the mixture can be carried on into the next step as such. Derivatives 4B-7 can then be reduced into the compounds 4B-8 wherein $Y^2$ represents $CH_2$: in a typical experiment, a compound 4B-8 can be obtained from a compound 4B-7 by reaction at 0° C. or RT with a metal powder such as Zn or Fe in presence of a mild acid proton source such as ammonium chloride in a solvent such as acetone according to a reaction well known by a person skilled in the art. Similarly, by selective reduction of the nitro group, the compounds of structure 4B-6 can be converted directly to compounds of structure 4B-8 wherein $Y^2$ represents CO. Compounds of Structure 4B can then be obtained by reaction of a compound 4B-8 with glyoxylic acid monohydrate in presence of $NaBH_3CN$ in a solvent such as MeOH or the like; alternatively the mixture of compound 4B-8 and glyoxylic acid can be treated with Pd/C in a solvent such as MeOH, EtOH, EtOAc or the like at RT in presence of $H_2$ or with the help of an H-Cube® hydrogen generator to yield Structure 4B.

In case R represents a protecting group compatible with the entire reaction sequence such as PMB or allyl moieties, after the general coupling step between Structure 4B and the amine of Structure B, a last well-known deprotection step will be required to yield the corresponding compounds of Formula (IV) wherein $Y^1$ is NH and $X^2$ is $CH_2$ (scheme 6).

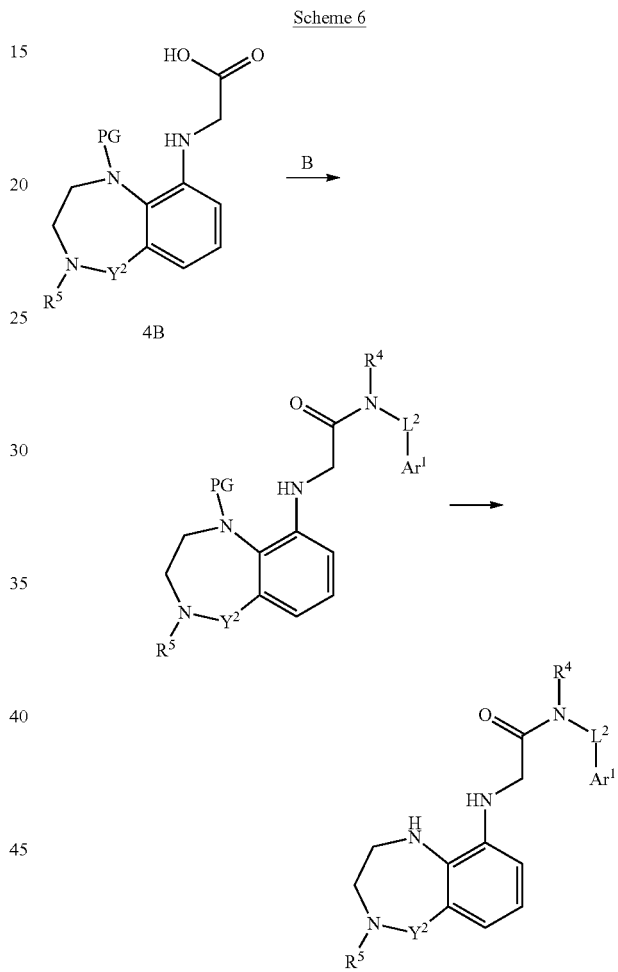

Scheme 6

In a particular case, wherein $Y^1$, $Y^2$ and $X^2$ represent a $CH^2$ group, and $L^1$ is —$NHCH_2$—, Example compounds can be obtained from intermediates of Formula 4C. The synthesis of a compound of Formula 4C starts with commercially available 6-methoxy-2,3,4,5-tetrahydro-1H-benzo[c]azepine and follows a synthetic pathway in close analogy to the synthesis of compounds of Structure 3B.

In an alternative approach to compounds of Formula (IV), in case the $R^5$ group used in the Schemes 3, 4 and 5 represents a protecting group compatible with the entire reaction sequence such as PMB or allyl moieties, after deprotection of such group according to conditions well-known in the art, the final $R^5$ groups may be introduced to generate the final compounds of Formula (IV): in a typical experiment, the PMB group is cleaved off by treatment with Pd/C in a solvent such as MeOH, EtOH, EtOAc or the like at RT in presence of H$_2$ or with the help of an H-Cube® hydrogen generator and then the resulting scaffold can be further functionalized into final compounds of Formula (IV) wherein Y$^1$ is NR$^Y$ and X$^2$ is CH$_2$; these manipulations may include, but are not limited to, alkylation, acylation, carbamate or urea formation which are commonly known to those skilled in the art.

Scheme 7

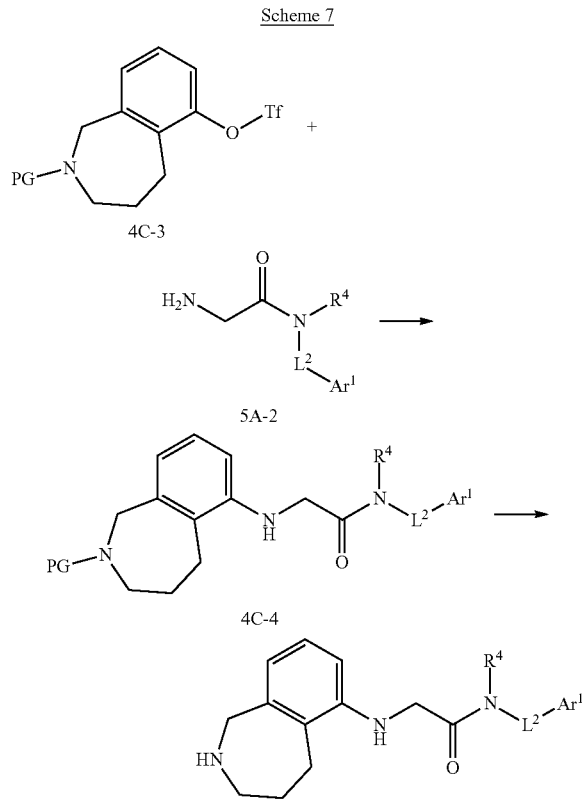

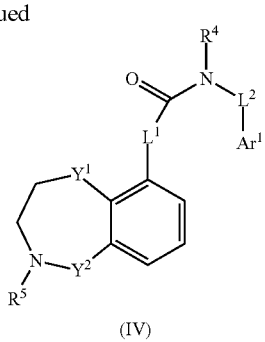

(IV)

Compounds of Structure 4D which represent a particular case of compounds of Structure 4 can be prepared by the synthetic pathways described below.

Structure 4D

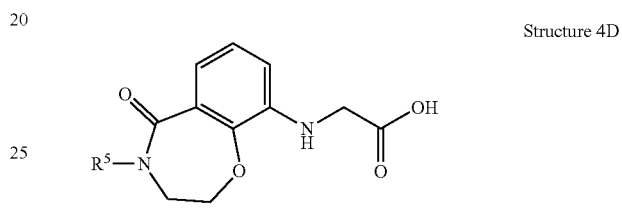

Compounds of Structure 4D may be prepared by the procedure illustrated in Scheme 9, using the intermediate 4A-10 described in Scheme 4. Derivatives 4D-10 can be reduced into the compounds 4D-1 wherein: in a typical experiment, a compound 4D-1 can be obtained from a compound 4A-10 by reaction at 0° C. or RT with a metal powder such as Zn or Fe in presence of a mild acid proton source such as ammonium chloride in a solvent such as acetone according to a reaction well known by a person skilled in the art. Compound 4D-1 can also be obtained by treatment of a Compound of Structure 4A-10 with stannous chloride in a solvent like MeOH at refluxing temperature. Compounds of Structure 4D-2 can then be obtained by reaction of a compound 4D-1 with benzylbromoacetate in a solvent like DMF at temperature between RT and 100° C. Removal of the protective group according to conditions well-known in the art, like treatment with H$_2$ of 4D-2 in a solvent like MeOH, EtOH, Ethylacetate or THF in the presence of an hydrogenation catalyst like Pd/C delivers Compounds 4D. Alternatively compounds 4D can be obtained by treatment of 4D-1 with glyoxylic acid monohydrate in presence of NaBH$_3$CN in a solvent such as MeOH or the like; alternatively the mixture of compound 4D-1 and glyoxylic acid can be treated with Pd/C in a solvent such as MeOH, EtOH, EtOAc or the like at RT in presence of H$_2$ or with the help of an H-Cube® hydrogen generator to yield Structure 4D.

Scheme 8

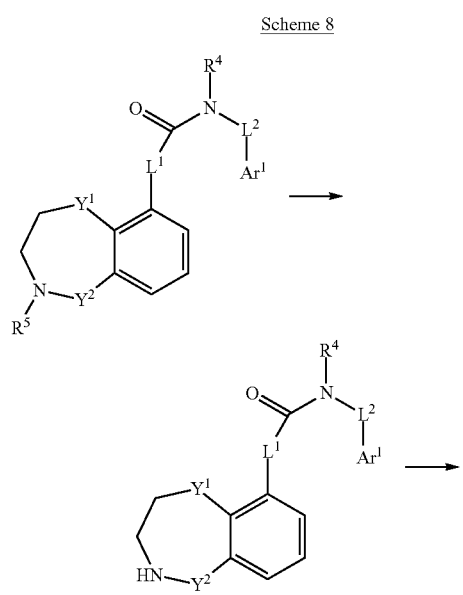

Scheme 9

4A-10

-continued

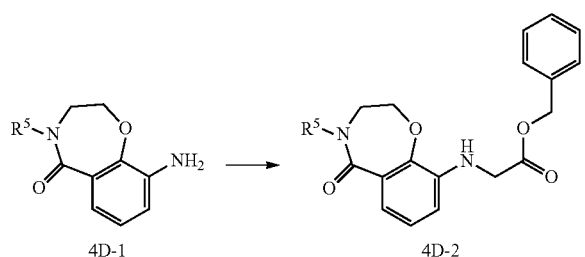

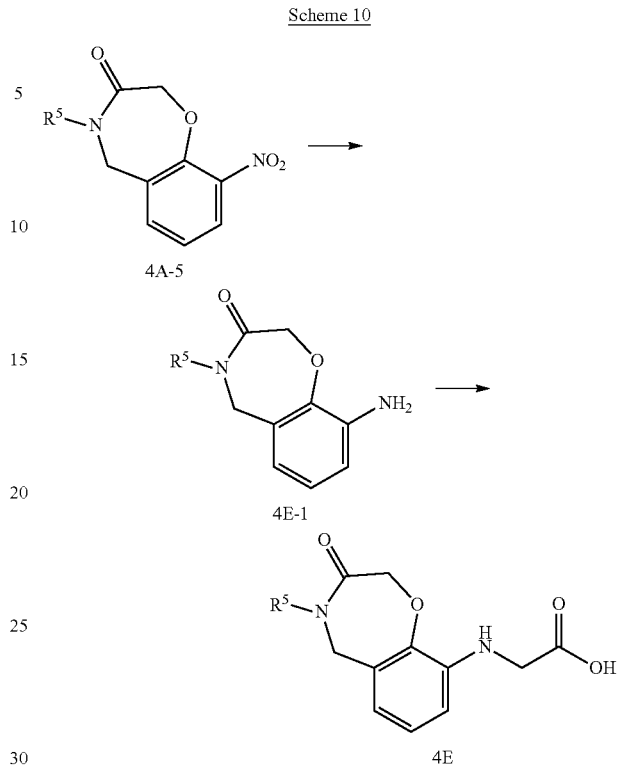

Scheme 10

Compounds of Structure 4E which represent a particular case of compounds of Structure 4 can be prepared by the synthetic pathways described below.

Structure 4E

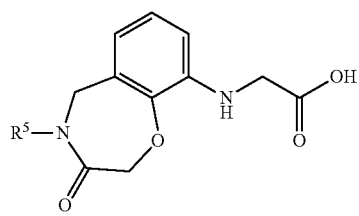

Compounds of Structure 4E may be prepared by the procedure illustrated in Scheme 10, using the intermediate 4A-5 described in Scheme 3. Derivatives 4A-5 can be reduced into the compounds 4E-1 wherein: in a typical experiment, a compound 4E-1 can be obtained from a compound 4A-5 by reaction at 0° C. or RT with a metal powder such as Zn or Fe in presence of a mild acid proton source such as ammonium chloride in a solvent such as acetone according to a reaction well known by a person skilled in the art. Compound 4D-1 can also be obtained by treatment of a Compound of Structure 4A-5 with stannous chloride in a solvent like MeOH at refluxing temperature. Compound 4E-1 can also be prepared according to conditions well-known in the art, like treatment with $H_2$ of 4A-5 in a solvent like MeOH, EtOH, EtOAc or THF in the presence of an hydrogenation catalyst like Pd/C. Compounds 4E can be obtained by treatment of 4E-1 with glyoxylic acid monohydrate in presence of $NaBH_3CN$ in a solvent such as MeOH or the like; alternatively the mixture of compound 4E-1 and glyoxylic acid can be treated with Pd/C in a solvent such as MeOH, EtOH, EtOAc or the like at RT in presence of $H_2$ or with the help of an H-Cube® hydrogen generator to yield Structure 4D.

Compounds of Structure 4F which represent a particular case of compounds of Structure 4 can be prepared by the synthetic pathways described below.

Structure 4F

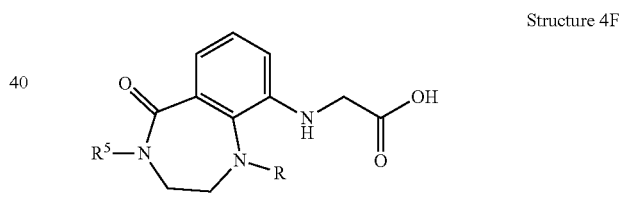

Compounds of Structure 4F wherein $Y^2$ represents CO may be prepared by the procedure illustrated in Scheme 11, using the intermediate 4B-6 described in Scheme 5. Derivatives 4B-6 can be reduced into the compounds 4F-1 wherein $Y^2$ represents CO: in a typical experiment, a compound 4F-1 can be obtained from a compound 4B-6 by reaction at 0° C. or RT with a metal powder such as Zn or Fe in presence of a mild acid proton source such as ammonium chloride in a solvent such as acetone according to a reaction well known by a person skilled in the art. Compound 4F-1 can also be obtained by treatment of a Compound of Structure 4B-6 with stannous chloride in a solvent like MeOH at refluxing temperature. Compounds of Structure 4F-2 can then be obtained by reaction of a compound 4F-1 with benzylbromoacetate in a solvent like DMF or MeCN at temperature between RT and 100° C. Removal of the protective group according to conditions well-known in the art, like treatment with $H_2$ of 4F-2 in a solvent like MeOH, EtOH, EtOAc or THF in the presence of an hydrogenation catalyst like Pd/C delivers Compounds 4F. Alternatively compounds 4F can be obtained by treatment of 4F-1 with glyoxylic acid monohydrate in presence of NaBH₃CN in a solvent such as MeOH or the like; alternatively the mixture of compound 4F-1 and glyoxylic acid can be treated with Pd/C in a solvent such as MeOH, EtOH, EtOAc or the like at RT in presence of H₂ or with the help of an H-Cube® hydrogen generator to yield Structure 4F.

Scheme 11

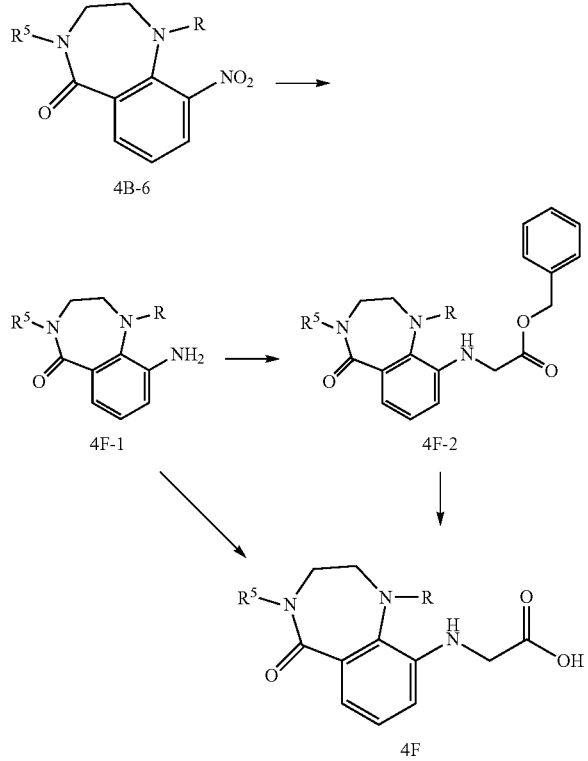

Preparation of Compounds of Formula (V)

Compounds of Formula (I) wherein the seven-membered ring is as in the compounds of Formula (V) can be prepared according to the general sequence of reactions outlined below.

Formula (V)

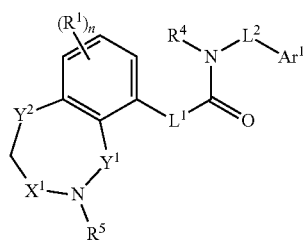

Preparation of Compounds of Structure 5A

Compounds of Structure 5A which represent a particular case of compounds of Formula (V) can be prepared by one of the synthetic pathways described below.

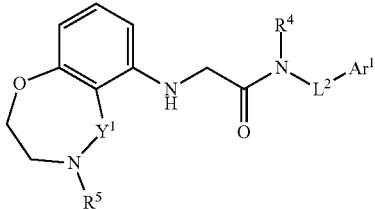

Structure 5A

Compounds of Structure 5A may be prepared by the procedure illustrated in Scheme 12. The synthesis reaction sequence starts with tert-butyl 6-bromo-2,3-dihydrobenzo[f][1,4]oxazepine-4(5H)-carboxylate (EP2123644). Compounds of structure 5A-1 are obtained from the (tert-butoxycarbonyl)glycine and an amine of Structure B using HATU or another amide coupling reagent in a solvent such as DCM or DMF at RT or 0° C. in the presence of a base like TEA or DIPEA. Deprotection of derivatives 5A-1 according to conditions well-known in the art, such as treatment with TFA or HCl in an organic solvent such as dioxane or DCM at 0° C. or RT yields compounds 5A-2.

Derivative 5A-3 can be obtained through a Buchwald reaction or its like. In a typical experiment, tert-butyl 6-bromo-2,3-dihydrobenzo[f][1,4]oxazepine-4(5H)-carboxylate is treated with the amine 5A-2 in presence of a palladium(0) source such as Pd₂(dba)₃ or Pd(PPh₃)₄, an appropriate ligand such as Josiphos® or X-Phos®, a base such as Cs₂CO₃ or tert-BuOK in a solvent such as DMF or NMP at RT or higher temperature, typically at 100° C. Deprotection of derivatives 5A-3 according to conditions commonly known to those skilled in the art, such as treatment with TFA or HCl in an organic solvent such as dioxane or DCM at 0° C. or RT yields compounds 5A-4. Derivatives of Formula 5A are then obtained by further functionalization of compounds 5A-4: the final R⁵ groups may be introduced to generate new compounds of Formula (IV): these manipulations may include, but are not limited to, alkylation, acylation, carbamate or urea formation which are commonly known to those skilled in the art; in a typical experiment, 5A-4 is alkylated by treatment with commercial aldehydes in the presence of a reductive reagent like NaBH₄, NaBH₃CN, NaBH(OAc)₃ in a solvent like DCM, MeOH, THF to give the corresponding compound of Formula (5A). In an alternative approach, tert-butyl 6-bromo-2,3-dihydrobenzo[f][1,4]oxazepine-4(5H)-carboxylate is treated with well-known ammonia analogues, such as benzophenone imine or KHMDS in presence of a palladium(0) source such as Pd₂(dba)₃ or Pd(PPh₃)₄, an appropriate ligand such as Josiphos or X-Phos, a base such as Cs₂CO₃ or KOᵗBu in a solvent such as DMF or NMP at RT or higher temperature, typically at 100° C.; well-known treatment such as an excess of hydrazine in a solvent such as MeOH at RT in the case of the benzophenone imine exposes the amine to yield derivative 5A-5. Compounds 5A-6 can then be obtained by reaction of a compound 5A-5 with glyoxylic acid monohydrate in presence of NaBH₃CN in a solvent such as MeOH or the like; alternatively the mixture of compound 5A-5 and glyoxylic acid can be treated with Pd/C in a solvent such as MeOH, EtOH, EtOAc or the like at RT in presence of H₂ or with the help of an H-Cube® hydrogen generator to yield 5A-6. Reaction of 5A-6 with an amine of Structure B in presence of HATU or another amide coupling reagent in a solvent such as DCM or DMF at RT or 0° C. in the presence of a base like TEA or DIPEA yields 5A-3 derivatives described above.

Scheme 12

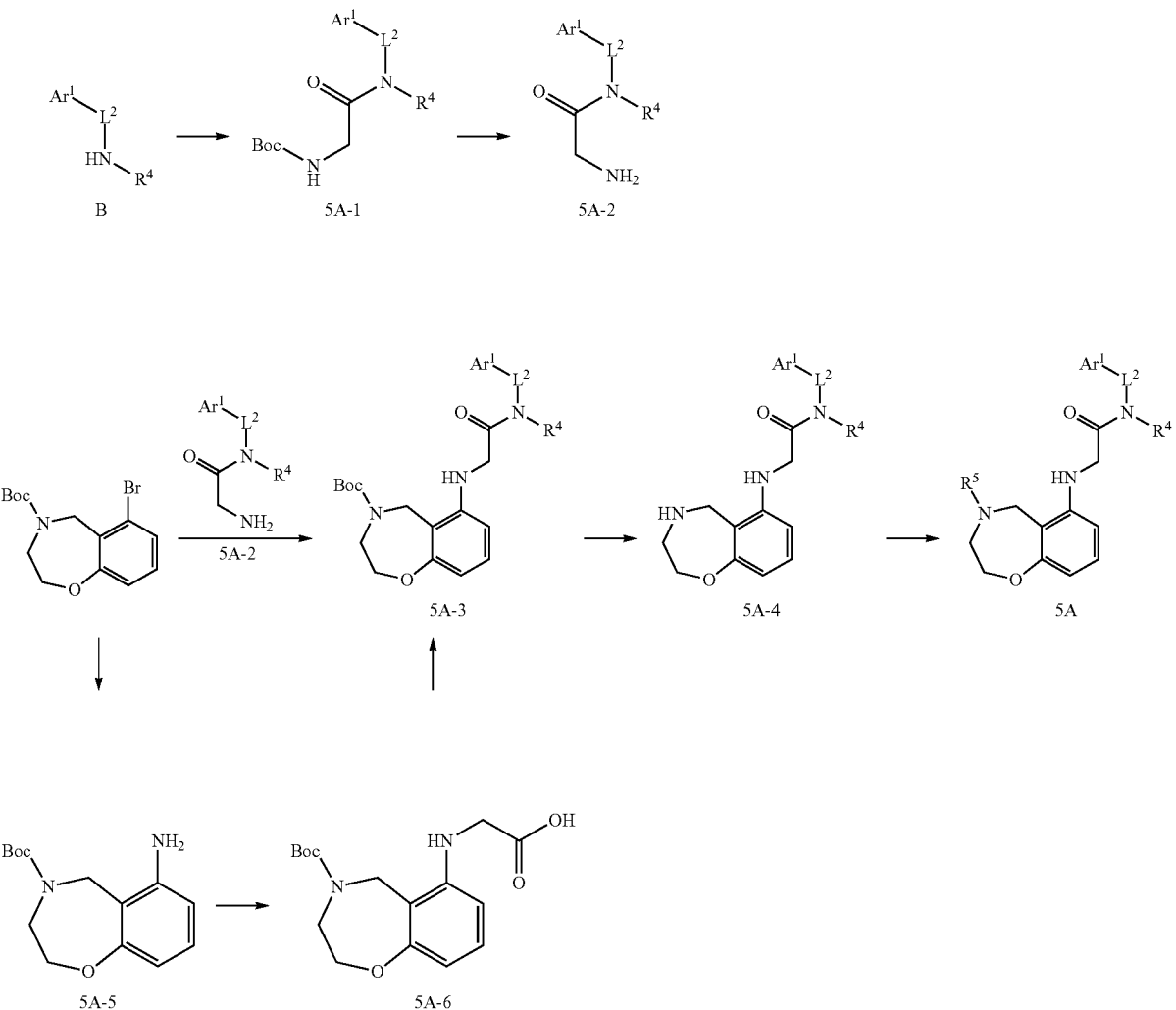

Alternatively compounds of Structure 5A can be synthesized via a chemical sequence described in the Scheme 13 below.

Thus a compound of Structure 5A-7 is synthesized from 2-nitro-6-fluorobenzoic acid and $R^5NCH_2CH_2OH$ following a amide coupling reaction well known by a person skilled in the art. A compound of Structure 5A-7 is then cyclized in a intramolecular nucleophilic aromatic substitution to a compound of Structure 5A-8 by treatment with a base such as NaH or $Cs_2CO_3$ in a solvent such as DMF, THF or the like. The carbonyle function of the amide group is then removed to yield a compound of Structure 5A-9 following a reduction with borane such as $BH_3$-THF as described previously for the transformation of amide 4A-10 to amine 4A-6. Then the aromatic nitro function of compound 5A-9 is transformed into the corresponding aniline by reduction using a metal such as zinc dust in a solvent such as acetone, or following a typical reduction with palladium/charcoal under an hydrogen atmosphere. Subsequently a compound of Structure 5A-11 is then obtained by reaction of 5A-10 with glyoxylic acid in a reductive amination reaction using a solvent such as methanol with a reducing agent such as $NaBH_3CN$ or the like. Finally a compound of structure 5A can be obtained from a compound of Structure 5A-11 and an amine of Structure B as described hereinabove. Similarly, by selective reduction of the nitro group, the compounds of structure 5A-8 can be converted directly to compounds of structure 5A-10 and then subsequently to a compound of structure 5A wherein $Y^1$ represents CO.

Scheme 13

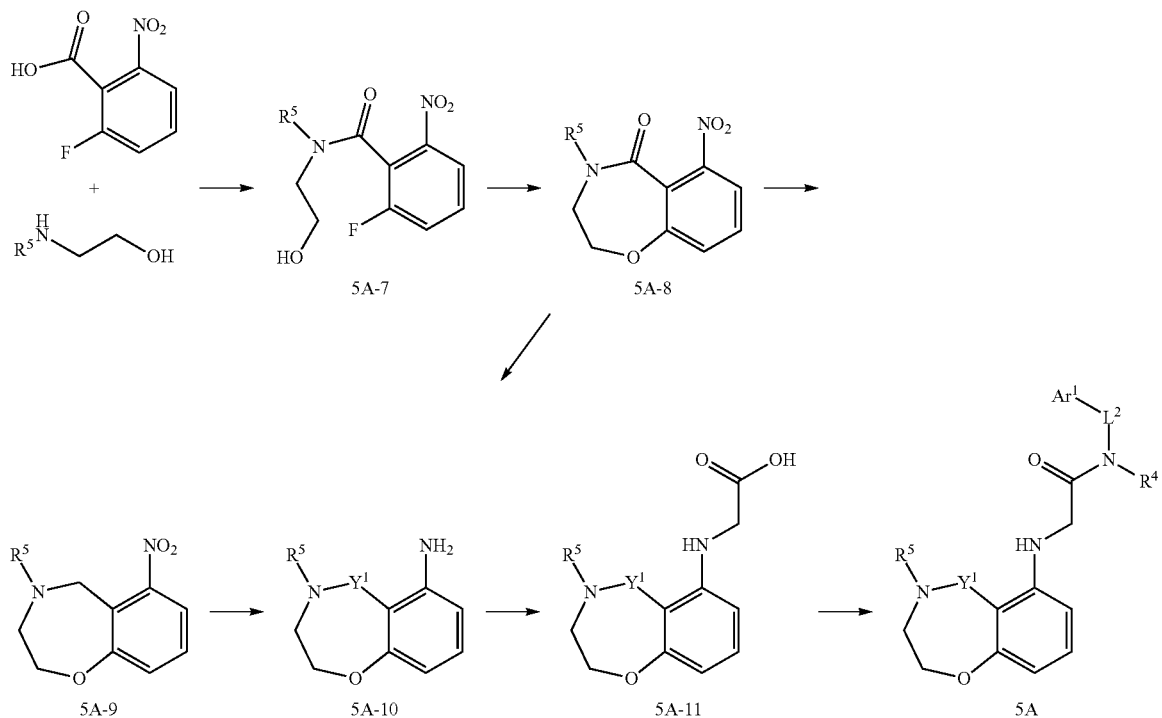

Synthesis of Compounds of Structure B

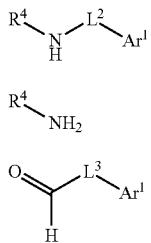
Structure B

Structure B-1

Structure B-2

Compounds of Structure B are commercially available or are made by condensation of a primary amine of Structure B-1 with an aldehyde of Structure B-2 in a typical reductive amination reaction with a reducing agent such as NaBH(OAc)$_3$, NaBH$_3$CN or NaBH$_4$ in a solvent such as THF, DCM, MeOH, water or the like at temperatures between 0° C. and reflux, preferentially at RT. In this case L$^2$ corresponds to —CH$_2$-L$^3$.

EXPERIMENTAL PART

I. Chemistry

All temperatures are stated in ° C. Commercially available starting materials were used as received without further purification. Unless otherwise specified, all reactions were carried out in oven-dried glassware under an atmosphere of nitrogen. All compounds were purified by a method described below: flash column chromatography on silica-gel or preparative HPLC. Compounds described in the invention are characterized by LC-MS data (retention time $t_R$ is given in min; molecular weight obtained from the mass spectrum is given in g/mol) using the conditions listed below. In cases where compounds of the present invention appear as a mixture of conformational isomers, particularly visible in their LC-MS spectra, the retention time of the most abundant conformer is given.

In case an Example compound's or Precursor's name is preceded with the mention rac- this means this Example compound or Precursor is obtained as a racemic mixture of two enantiomers.

NMR Spectroscopy:

Bruker Avance II spectrometer equipped with a 400 MHz Ultrashield™ Magnet and a BBO 5 mm probehead or a PAXTI 1 mm probehead. Chemical shifts (δ) are reported in parts per million (ppm) relative to proton resonances resulting from incomplete deuteration of the NMR solvent, e.g. for dimethylsulfoxide δ(H) 2.49 ppm, for chloroform δ(H) 7.24 ppm. The abbreviations s, d, t, q and m refer to singlet, doublet, triplet, quartet, multiplet and br to broad, respectively. Coupling constants J are reported in Hz. In case NMR spectra are measured using 1 mm Microprobe® tubes and a PAXTI 1 mm probehead, the compounds are dissolved in non-deuterated DMSO. The spectra are then measured with double irradiation for suppression of the DMSO and H$_2$O peaks. In that case only a selection of representative NMR peaks of the compound is given.

LC-MS Equipment and Conditions

Method LC-A: Agilent 1100 series with mass spectrometry detection (MS: Finnigan single quadrupole). Column: Zorbax SB-aq (3.5 m, 4.6×50 mm). Conditions: MeCN [eluent A]; water+0.04% TFA [eluent B]. Gradient: 95% B→5% B over 1.5 min (flow: 4.5 mL/min). Detection: UV/Vis+MS.

Method LC-B: Waters Acquity Binary, Solvent Manager, MS: Waters SQ Detector, DAD: Acquity UPLC PDA Detector, ELSD: Acquity UPLC ELSD. Column: Acquity UPLC BEH C18 1.7 um 2.1×50 mm from Waters, thermostated in the Acquity UPLC Column Manager at 60° C. Conditions: MeCN+0.045% TFA [eluent A]; water+0.05% TFA [eluent B]. Method: Gradient: 98% B→2% B over 2.0 min. Flow: 1.2 mL/min.

Detection: UV 214 nm and ELSD, and MS, $t_R$ is given in min.

Preparative HPLC Equipment:

Gilson 333/334 HPLC pump equipped with Gilson LH215, Dionex SRD-3200 degasser, Dionex ISO-3100A make-up pump, Dionex DAD-3000 DAD detector, Single quadrupole mass analyzer MS detector, Thermo Finnigan MSQ Plus, MRA100-000 flow splitter, Polymer Laboratories PL-ELS1000 ELS detector Preparative HPLC with Basic Conditions Method LC-C:

Column: Waters XBridge (10 m, 75×30 mm). Conditions: MeCN [eluent A]; water+0.5% NH$_4$OH (25% aq.) [eluent B]; Gradient see Table 1 (flow: 75 mL/min), the starting percentage of Eluent A (x) is determined depending on the polarity of the compound to purify. Detection: UV/Vis+MS

TABLE 1

|  | t (min) | | | | |
| --- | --- | --- | --- | --- | --- |
|  | 0 | 0.01 | 4.0 | 6.0 | 6.2 | 6.6 |
| Eluent A (%) | x | x | 95 | 95 | x | x |
| Eluent B (%) | 100 − x | 100 − x | 5 | 5 | 100 − x | 100 − x |

Preparative HPLC with Acidic Conditions

Method LC-D: Column: Waters Atlantis T3 (10 μm, 75×30 mm). Conditions: MeCN [eluent A]; water+0.5% HCO$_2$H [eluent B]; Gradient see Table 1 (flow: 75 mL/min), the starting percentage of Eluent A (x) is determined depending on the polarity of the compound to purify. Detection: UV/Vis+MS

TABLE 1

|  | t (min) | | | | |
| --- | --- | --- | --- | --- | --- |
|  | 0 | 0.01 | 4.0 | 6.0 | 6.2 | 6.6 |
| Eluent A (%) | x | x | 95 | 95 | x | x |
| Eluent B (%) | 100 − x | 100 − x | 5 | 5 | 100 − x | 100 − x |

Abbreviations (as Used Hereinbefore or Hereinafter)
AcOH acetic acid
aq. aqueous
Ar argon
BINAP racemic 2,2'-bis(diphenylphosphino)-1,1'-binaphthyl
Brettphos® 2-(Dicyclohexylphosphino)3,6-dimethoxy-2',4',6'-triisopropyl-1,1'-biphenyl
BSA bovine serum albumin
DABCO 1,4-diazabicyclo[2.2.2]octane
DCC N,N'-dicyclohexylcarbodiimide
DCE 1,2-dichloroethane
DCM dichloromethane
DEAD diethylazadicarboxylate
deion. deionized
DIPEA diisopropyl-ethylamine, Hünig's base, ethyl-diisopropylamine
dioxane 1,4-dioxane
DMAP 4-dimethylaminopyridine
DMF dimethylformamide
DMSO dimethylsulfoxide
eq. equivalent(s)
Ether diethyl ether
EtOAc ethyl acetate
EtOH ethanol
g gram(s)
h hour(s)
HATU 2-(7-aza-1H-benzotriazole-1-yl)-, 1,3,3-tetramethyl-uronium hexafluorophosphate
HBTU N,N,N',N'-Tetramethyl-O-(1H-benzotriazol-1-yl) uronium hexafluorophosphate
HCl hydrogen chloride
HPLC high performance liquid chromatography
HV high vacuum conditions
Josiphos (R)-1-[(S$_P$)-2-(Dicyclohexylphosphino)ferrocenyl] ethyldi-tert-butylphosphine palladium(II) dichloride
LC-MS liquid chromatography-mass spectrometry
MeCN acetonitrile
MeI methyl iodide
MeOH methanol
mg milligram(s)
mL milliliter(s)
mmol millimole(s)
min minute(s)
N normality of a solution
MS mass spectroscopy
NaBH(OAc)$_3$ sodium triacetoxyborohydride
NaBH$_3$CN sodium cyanoborohydride
NaOAc sodium acetate
NH$_3$ ammonia
NMR nuclear magnetic resonance spectroscopy
OAc acetate
Pd/C 10% Palladium on activated charcoal (10%)
Pd$_2$(dba)$_3$ tris(dibenzylideneacetone)dipalladium(0)
Pd(PPh$_3$)$_4$ Palladium tetrakistriphenylphosphine
PMB para-methoxybenzyl
PPh$_3$ Triphenyphosphine
prep. preparative
rac racemic
RT room temperature
s second(s)
sat. saturated
soln. solution
T temperature
T$_3$P n-propanephosphonic acid anhydride
TBAF tetrabutylammonium fluoride
TBME tert-butyl methyl ether
TBDMS tert-butyldimethylsilyl
TEA triethylamine
Tf trifluoromethane-sulfonyl
TFA trifluoroacetic acid
TFAA trifluoroacetic acid anhydride
THF tetrahydrofuran
$t_R$ retention time
X-Phos 2-dicyclohexylphosphino-2',4',6'-triisopropylbiphenyl Example 1

N-(2-Dimethylamino-ethyl)-2-(4-isobutyl-2,3,4,5-tetrahydro-benzo[f][1,4]oxazepin-9-ylamino)-N-(2-trifluoromethyl-benzyl)-acetamide To a solution of Precursor 4A1 (200 mg, 0.503 mmol), Amine B1 (124 mg, 0.503 mmol) and HATU (229 mg, 0.604 mmol) in 5 mL DCM cooled to 0° C. is added DIPEA (0.129 mL, 0.754 mmol). The reaction mixture is allowed to stir at RT for 4 h. Water is added and the resulting organic phase is washed with sat. aq. NaHCO₃ soln. and brine then dried over Na₂SO₄, filtered and evaporated under reduced pressure. The crude residue is purified by prep. HPLC (Method C) to yield the title compound as a yellow oil. LC-A: $t_R$=0.61 min; [M+H]⁺=507.6; ¹H-NMR (DMSO-d⁶), 2:1 mixture of two rotamers:

Major rotamer spectrum δ: 7.75 (d, J=7.8 Hz, 1 H), 7.62 (t, J=7.8 Hz, 1 H), 7.48 (t, J=7.7 Hz, 1 H), 7.33 (d, J=7.7 Hz, 1 H), 6.84 (t, J=7.8 Hz, 1H), 6.58 (d, J=7.7 Hz, 1H), 6.44 (d, J=7.4 Hz, 1H), 5.37 (m, 1H), 4.79 (s, 2H), 4.18 (d, J=4.6 Hz, 2H), 3.91-3.97 (m, 2H), 3.55-3.63 (m, 1H), 3.45-3.51 (m, 1H), 2.96-3.03 (m, 2H), 2.40-2.45 (m, 2 H), 2.06-2.22 (m, 10 H), 1.70-1.79 (m, 1 H), 0.80-0.89 (m, 6 H)

Minor rotamer spectrum δ: 7.81 (d, J=7.8 Hz, 1 H), 7.70 (t, J=7.8 Hz, 1 H), 7.54 (t, J=7.7 Hz, 1 H), 7.40 (d, J=7.7 Hz, 1 H), 6.74 (t, J=7.8 Hz, 1H), 6.39 (d, J=7.7 Hz, 1H), 6.32 (d, J=7.4 Hz, 1H), 5.37 (m, 1H), 4.86 (s, 2H), 3.88-3.92 (m, 2H), 3.85 (d, J=4.6 Hz, 2H), 3.65-3.71 (m, 1H), 3.39-3.45 (m, 1H), 2.96-3.03 (m, 2H), 2.35-2.41 (m, 2 H), 2.06-2.22 (m, 10 H), 1.70-1.79 (m, 1 H), 0.80-0.89 (m, 6 H)

Examples 2-19 listed in Table 1 are prepared applying the method described for Example 1 using the corresponding Precursor and Amine respectively.

TABLE 1

Examples 2-19

| Example | Compound | $t_R$ [min] (LC-B) | MS Data m/z [M + H]⁺ |
|---|---|---|---|
| 2 | N-(2-Dimethylamino-ethyl)-2-(4-isobutyl-2,3,4,5-tetrahydro-benzo[f][1,4]oxazepin-9-ylamino)-N-(3-trifluoromethyl-pyridin-2-ylmethyl)-acetamide | 0.43 | 508.3 |
| 3 | N-(3-Chloro-pyridin-2-ylmethyl)-N-(2-dimethylamino-ethyl)-2-(4-isobutyl-2,3,4,5-tetrahydro-benzo[f][1,4]oxazepin-9-ylamino)-acetamide | 0.39 | 474.2 |
| 4 | N-(3-Chloro-pyridin-2-ylmethyl)-N-(2-dimethylamino-ethyl)-2-(4-ethyl-2,3,4,5-tetrahydro-benzo[f][1,4]oxazepin-9-ylamino)-acetamide | 0.33 | 446.2 |
| 5 | N-(2-Dimethylamino-ethyl)-2-(4-ethyl-2,3,4,5-tetrahydro-benzo[f][1,4]oxazepin-9-ylamino)-N-(2-trifluoromethyl-benzyl)-acetamide | 0.43 | 479.3 |
| 6 | N-(3-Chloro-pyridin-2-ylmethyl)-N-(2-dimethylamino-ethyl)-2-(4-propyl-2,3,4,5-tetrahydro-benzo[f][1,4]oxazepin-9-ylamino)-acetamide | 0.36 | 460.2 |
| 7 | N-(2-Dimethylamino-ethyl)-2-(4-propyl-2,3,4,5-tetrahydro-benzo[f][1,4]oxazepin-9-ylamino)-N-(2-trifluoromethyl-benzyl)-acetamide | 0.46 | 493.2 |
| 8 | N-(3-Bromo-benzyl)-N-(2-dimethylamino-ethyl)-2-(4-isobutyl-2,3,4,5-tetrahydro-benzo[f][1,4]oxazepin-9-ylamino)-acetamide | 0.49 | 517.2 |
| 9 | N-(2-Dimethylamino-ethyl)-2-(4-isobutyl-2,3,4,5-tetrahydro-benzo[f][1,4]oxazepin-9-ylamino)-N-(4-methoxy-pyridin-2-ylmethyl)-acetamide | 0.34 | 470.3 |
| 10 | N-[2-(Cyclopropyl-methyl-amino)-ethyl]-2-(4-isobutyl-2,3,4,5-tetrahydro-benzo[f][1,4]oxazepin-9-ylamino)-N-(2-trifluoromethyl-benzyl)-acetamide | 0.54 | 533.3 |
| 11 | 2-(4-Isobutyl-2,3,4,5-tetrahydro-benzo[f][1,4]oxazepin-9-ylamino)-N-[2-(2-oxo-pyrrolidin-1-yl)-ethyl]-N-(2-trifluoromethyl-benzyl)-acetamide | 0.72 | 547.3 |
| 12 | N-(2,4-Difluoro-benzyl)-2-(4-isobutyl-2,3,4,5-tetrahydro-benzo[f][1,4]oxazepin-9-ylamino)-N-(2-pyrrolidin-1-yl-ethyl)-acetamide | 0.46 | 501.3 |
| 13 | N-(3-Chloro-pyridin-2-ylmethyl)-N-[2-(4,4-difluoro-piperidin-1-yl)-ethyl]-2-(4-isobutyl-2,3,4,5-tetrahydro-benzo[f][1,4]oxazepin-9-ylamino)-acetamide | 0.47 | 550.3 |
| 14 | N-(2-Dimethylamino-ethyl)-2-(4-isobutyl-2,3,4,5-tetrahydro-benzo[f][1,4]oxazepin-9-ylamino)-N-(4-methyl-pyridin-2-ylmethyl)-acetamide | 0.37 | 454.3 |
| 15 | N-(2-Chloro-benzyl)-2-(4-isobutyl-2,3,4,5-tetrahydro-benzo[f][1,4]oxazepin-9-ylamino)-N-(2-pyrrolidin-1-yl-ethyl)-acetamide | 0.47 | 499.3 |
| 16 | 2-(4-Isobutyl-2,3,4,5-tetrahydro-benzo[f][1,4]oxazepin-9-ylamino)-N-(2-morpholin-4-yl-ethyl)-N-(2-trifluoromethyl-benzyl)-acetamide | 0.52 | 549.3 |
| 17 | N-(2-Dimethylamino-ethyl)-N-(4-fluoro-2-trifluoromethyl-benzyl)-2-(4-isobutyl-2,3,4,5-tetrahydro-benzo[f][1,4]oxazepin-9-ylamino)-acetamide | 0.51 | 525.2 |
| 18 | N-(2-Dimethylamino-ethyl)-2-(4-isobutyl-2,3,4,5-tetrahydro-benzo[f][1,4]oxazepin-9-ylamino)-N-(3-trifluoromethyl-benzyl)-acetamide | 0.51 | 507.3 |
| 19 | N-(2,6-Difluoro-benzyl)-N-(2-dimethylamino-ethyl)-2-(4-isobutyl-2,3,4,5-tetrahydro-benzo[f][1,4]oxazepin-9-ylamino)-acetamide | 0.43 | 475.3 |
| 69 | {2-[[2-(4-Ethyl-2,3,4,5-tetrahydro-benzo[f][1,4]oxazepin-9-ylamino)-acetyl]-(2-trifluoromethyl-benzyl)-amino]-ethyl}-isopropyl-carbamic acid tert-butyl ester | 0.95 | 593.3 |
| 70 | N-(2-tert-Butylamino-ethyl)-2-(4-ethyl-2,3,4,5-tetrahydro-benzo[f][1,4]oxazepin-9-ylamino)-N-(2-trifluoromethyl-benzyl)-acetamide | 0.47 | 507.3 |

TABLE 1-continued

Examples 2-19

| Example | Compound | $t_R$ [min] (LC-B) | MS Data m/z $[M + H]^+$ |
|---|---|---|---|
| 72 | N-(2-Dimethylamino-ethyl)-2-(4-ethyl-2,3,4,5-tetrahydro-benzo[f][1,4]oxazepin-9-ylamino)-N-(3-trifluoromethyl-pyridin-2-ylmethyl)-acetamide | 0.37 | 480.3 |
| 73 | N-(2-Dimethylamino-ethyl)-2-(4-ethyl-2,3,4,5-tetrahydro-benzo[f][1,4]oxazepin-9-ylamino)-N-(3-methyl-pyridin-2-ylmethyl)-acetamide | 0.32 | 426.3 |
| 74 | 2-(4-Ethyl-2,3,4,5-tetrahydro-benzo[f][1,4]oxazepin-9-ylamino)-N-(2-pyrrolidin-1-yl-ethyl)-N-(3-trifluoromethyl-pyridin-2-ylmethyl)-acetamide | 0.38 | 506.3 |
| 75 | N-(3-Chloro-pyridin-2-ylmethyl)-2-(4-ethyl-2,3,4,5-tetrahydro-benzo[f][1,4]oxazepin-9-ylamino)-N-(2-pyrrolidin-1-yl-ethyl)-acetamide | 0.35 | 472.2 |
| 76 | N-(2-Dimethylamino-ethyl)-2-(4-ethyl-2,3,4,5-tetrahydro-benzo[f][1,4]oxazepin-9-ylamino)-N-(2-trifluoromethyl-thiazol-5-ylmethyl)-acetamide | 0.37 | 486.2 |
| 77 | N-(5-Chloro-1-methyl-3-trifluoromethyl-1H-pyrazol-4-ylmethyl)-N-(2-dimethylamino-ethyl)-2-(4-ethyl-2,3,4,5-tetrahydro-benzo[f][1,4]oxazepin-9-ylamino)-acetamide | 0.38 | 517.2 |
| 82 | 2-(4-Cyclopropylmethyl-2,3,4,5-tetrahydro-benzo[f][1,4]oxazepin-9-ylamino)-N-(2-pyrrolidin-1-yl-ethyl)-N-(3-trifluoromethyl-pyridin-2-ylmethyl)-acetamide | 0.42 | 532.3 |
| 83 | N-(2-tert-Butylamino-ethyl)-2-(4-cyclopropylmethyl-2,3,4,5-tetrahydro-benzo[f][1,4]oxazepin-9-ylamino)-N-(2-trifluoromethyl-benzyl)-acetamide | 0.51 | 533.3 |
| 84 | 2-(4-Cyclopropylmethyl-2,3,4,5-tetrahydro-benzo[f][1,4]oxazepin-9-ylamino)-N-(2-dimethylamino-ethyl)-N-(2-trifluoromethyl-benzyl)-acetamide | 0.48 | 505.3 |

Example 71

2-(4-Ethyl-2,3,4,5-tetrahydro-benzo[f][1,4]oxazepin-9-ylamino)-N-(2-isopropylamino-ethyl)-N-(2-trifluoromethyl-benzyl)-acetamide To a solution of Example 69 (90 mg, 0.15 mmol) in 3 mL DCM is added TFA (69.8.4 µL, 0.911 mmol) at RT. The mixture is stirred for 2 h at RT. After evaporation of the volatiles the crude is purified by prep. HPLC (Method C) to yield the title compound as a yellow oil. LC-B: $t_R$=0.46 min; $[M+H]^+$=493.3

Example 85

2-(4-Cyclopropylmethyl-2,3,4,5-tetrahydro-benzo[f][1,4]oxazepin-9-ylamino)-N-(2-isopropylamino-ethyl)-N-(2-trifluoromethyl-benzyl)-acetamide Step 1) {2-[[2-(4-Cyclopropylmethyl-2,3,4,5-tetrahydro-benzo[f][1,4]oxazepin-9-ylamino)-acetyl]-(2-trifluoromethyl-benzyl)-amino]-ethyl}-isopropyl-carbamic acid tert-butyl ester In analogy to Example 1, condensation of Precursor 4A5 with amine B21 yields {2-[[2-(4-cyclopropylmethyl-2,3,4,5-tetrahydro-benzo[f][1,4]oxazepin-9-ylamino)-acetyl]-(2-trifluoromethyl-benzyl)-amino]-ethyl}-isopropyl-carbamic acid tert-butyl ester as a yellow foam. LC-A: $t_R$=0.87 min; $[M+H]^+$=619.31

Step 2) The title compound is obtained by treatment of {2-[[2-(4-cyclopropylmethyl-2,3,4,5-tetrahydro-benzo[f][1,4]oxazepin-9-ylamino)-acetyl]-(2-trifluoromethyl-benzyl)-amino]-ethyl}-isopropyl-carbamic acid tert-butyl ester with TFA in analogy to Example 71 as a yellowish oil; LC-A: $t_R$=0.50 min; $[M+H]^+$=519.3

Example 20

2-(4-Acetyl-2,3,4,5-tetrahydro-benzo[f][1,4]oxazepin-9-ylamino)-N-(2-dimethylamino-ethyl)-N-(2-trifluoromethyl-benzyl)-acetamide a) N-(2-(dimethylamino)ethyl)-2-((4-(4-methoxybenzyl)-2,3,4,5-tetrahydrobenzo[f][1,4]-oxazepin-9-yl)amino)-N-(2-(trifluoromethyl)benzyl)acetamide: To a solution of (4-(4-methoxybenzyl)-2,3,4,5-tetrahydrobenzo[f][1,4]oxazepin-9-yl)glycine Precursor 4A4 (430 mg, 0.879 mmol), N-(2-(trifluoromethyl)benzyl)-N',N'-dimethylethane-1,2-diamine Amine B1 (217 mg, 0.879 mmol) and HATU (401 mg, 1.05 mmol) in 8 mL DCM cooled to 0° C. is added DIPEA (0.226 mL, 1.32 mmol). The reaction mixture is allowed to stir at RT for 2 h. Water is added and the recovered organic phase is washed with sat. aq. NaHCO$_3$ soln. and brine then dried over Na$_2$SO$_4$, filtered and evaporated under reduced pressure. The crude residue is purified by flash chromatography over 24 g of silica gel with DCM/MeOH system (1:0 to 4:1 gradient) as eluent to yield the title compound as a dark yellow oil. LC-A: $t_R$=0.63 min; $[M+H]^+$=571.2;

b) N-(2-(dimethylamino)ethyl)-2-((2,3,45-tetrahydrobenzo[f][1,4]oxazepin-9-yl)amino)-N-(2-(trifluoromethyl)benzyl)acetamide: To a degassed solution of N-(2-(dimethylamino)ethyl)-2-((4-(4-methoxybenzyl)-2,3,4,5-tetrahydrobenzo[f][1,4]-oxazepin-9-yl)amino)-N-(2-(trifluoromethyl)benzyl)acetamide (143 mg, 0.15 mmol, 1 eq) and AcOH (0.3 mL) in 3 mL of MeOH (3 mL) at RT is added Palladium, 10 wt. % on activated carbon (16 mg, 0.015 mmol) and the well stirred suspension is put under an atmospheric pressure of H$_2$ for the night. The mixture is filtered over Celite and washed three times with MeOH. The solvent is removed under reduced pressure. The crude residue is purified by prep. HPLC (Method C) to yield the title compound as a yellow oil. LC-A: $t_R$=0.54 min; [M+H]$^+$=451.1 c) 2-(4-Acetyl-2,3,4,5-tetrahydro-benzo[f][1,4]oxazepin-9-ylamino)-N-(2-dimethylamino-ethyl)-N-(2-trifluoromethyl-benzyl)-acetamide (Example 20): To a solution of N-(2-(dimethylamino)ethyl)-2-((2,3,4,5-tetrahydrobenzo[f][1,4]oxazepin-9-yl)amino)-N-(2-(trifluoromethyl)benzyl)acetamide (7 mg, 0.016 mmol) in 0.5 mL DMF is added acetic anhydride (0.0022 mL, 0.023 mmol) followed by DIPEA (0.0054 mL, 0.031 mmol) and DMAP (1 mg, 0.0078 mmol). The reaction mixture is allowed to stir at RT overnight. Water is added and the mixture is extracted with EtOAc. The resulting organic phase is washed with sat. aq. NH$_4$Cl soln. and brine then dried over Na$_2$SO$_4$, filtered and evaporated under reduced pressure. The crude residue is purified by prep. HPLC (Method C) to yield the title compound as a colorless oil. LC-A: $t_R$=0.68 min; [M+H]$^+$=493.1

Precursor 4A1

(4-isobutyl-2,3,4,5-tetrahydrobenzo[f][1,4]oxazepin-9-yl)glycine a) 2-((Isobutylamino)methyl)-6-nitrophenol (Precursor 4A1-2): to a solution of 2-hydroxy-3-nitrobenzaldehyde (2600 mg, 15.6 mmol) in 60 mL of MeOH at RT under Ar is added isobutylamine (1.55 mL, 15.6 mmol). The resulting mixture is stirred at RT for 30 min at which time the reacting mixture is cooled down to 5° C. and NaBH$_4$ (677 mg, 17.9 mmol) is added portionwise. After the end of the addition, the reacting mixture is stirred at 0° C. for 90 minutes. Water (60 ml) is added and a part of MeOH is distilled off under reduced pressure. The resulting aqueous phase is extracted with EtOAc; the combined organic layers are dried over Mg$_2$SO$_4$, filtered and evaporated under reduced pressure to yield the title compound as a crude yellow solid of appropriate purity for the next step. LC-A: $t_R$=0.54 min; [M+H]$^+$=225; $^1$H-NMR (400 MHz, CDCl$_3$) δ: 8.04 (dd, $J_1$=1.7 Hz, $J_2$=8.6 Hz, 1 H), 7.28 (m, 1 H), 6.50 (t, J=7.9 Hz, 1 H), 4.18 (s, 2 H), 2.70 (d, J=6.8 Hz, 2 H), 1.90 (m, 1 H), 0.93 (d, J=6.7 Hz, 6 H)

b) 2-Hydroxy-N-(2-hydroxy-3-nitrobenzyl)-N-isobutylacetamide (Precursor 4A1-3): To a solution of Precursor 4A1-2 (2.880 g, 10.3 mmol) in 75 mL of DCM at RT are added 0.89 mL of a glycolic acid solution, 70 wt. % in H$_2$O (10.3 mmol) and DIPEA (2.64 mL, 15.4 mmol) followed by HBTU (4.29 mg, 11.3 mmol). The reaction mixture is stirred at RT overnight. As some starting material is still present, 0.45 mL of glycolic acid solution (5.14 mmol), 1.32 ml of DIPEA (7.71 mmol) and finally HBTU (2.34 g, 6.16 mmol) are added and the mixture is stirred at RT for 2 h to reach completion. Water is added and the reaction mixture is extracted with DCM/NaHCO$_3$; the combined organic layers are dried over Na$_2$SO$_4$, filtered and evaporated under reduced pressure to yield the title compound with a fair purity compatible with the next step without requiring further purification. LC-A: $t_R$=0.77 min; [M+H]$^+$=283.3 c) 4-Isobutyl-9-nitro-4,5-dihydrobenzo[f][1,4]oxazepin-3(2H)-one (Precursor 4A1-5): to a solution of Precursor 4A1-3 (3.09 g, 10.9 mmol) in 100 mL anhydrous THF at 0° C. is added PPh$_3$ (3.48 g, 13.1 mmol) followed by DEAD solution 40% in toluene (8.97 mL, 19.7 mmol). The reaction mixture is stirred at 0° C. for 2 h. Saturated NH$_4$Cl aq (100 mL) is added and the mixture is extracted with EtOAc. The combined organic layers are dried over Na$_2$SO$_4$, filtered and evaporated under reduced pressure. The crude residue is purified by flash chromatography over 80 g of silica gel with heptane/EtOAc system (4:1 to 1:1 gradient) as eluent to yield the title compound as a yellow solid. LC-A: $t_R$=0.79 min; [M+H+MeCN]$^+$=306.0; $^1$H-NMR (500 MHz, CDCl$_3$) δ: 7.84 (dd, $J_1$=1.5 Hz, $J_2$=8.2 Hz, 1 H), 7.48 (m, 1 H), 7.22 (m, 1 H), 4.89 (s, 2 H), 4.55 (s, 2 H), 3.40 (d, J=7.5 Hz, 2 H), 2.03 (m, 1 H), 0.92 (d, J=6.7 Hz, 6 H)

d) 4-Isobutyl-9-nitro-2,3,4,5-tetrahydrobenzo[f][1,4]oxazepine (Precursor 4A1-6): to a solution of Precursor 4A1-5 (2.93 g, 11.1 mmol) in 40 mL of THF at RT is added a (1M) solution of BH$_3$.THF complex in THF (22.1 mL, 22.1 mmol). The reaction mixture is refluxed overnight. As starting material is still present in major proportions, more (1M) solution of BH$_3$.THF complex in THF has to be added at RT regularly and the mixture is further refluxed between check times. After an overall addition of 88.4 mL of (1M) solution of BH$_3$.THF complex in THF (88.4 mmol) and total refluxing time of 44 h, starting material is not noticeable anymore and the reaction is complete. The mixture is cooled to RT and evaporated under reduced pressure. The residue is dissolved in 40 mL of MeOH and is treated with 5.5 mL of a (4.0M) solution of HCl in 1,4-dioxane (22.1 mmol). The mixture is stirred vigorously at RT overnight and then evaporated under reduced pressure. The crude residue is purified by flash chromatography over 80 g of silica gel with heptane/EtOAc system (4:1 to 0:1 gradient) and then EtOAc/(MeOH+1.5% (7.0M) NH$_3$ solution in MeOH) system (1:0 to 4:1 gradient) as eluents to yield the title compound as an orange oil. LC-A: $t_R$=0.54 min; [M+H]$^+$=251.2 e) 4-Isobutyl-2,3,4,5-tetrahydrobenzo[f][1,4]oxazepin-9-amine (Precursor 4A1-7): to a solution of Precursor 4A1-6 (2.38 g, 9.51 mmol) in 50 mL of acetone at RT is added 19 mL of a sat. ammonium chloride solution (19 mL, 9.51 mmol). The reaction mixture is cooled to 0° C. then zinc dust (6.54 g, 100.0 mmol) is added portionwise. The reaction mixture is warmed up to RT and the suspension is stirred vigorously at RT for 24 h. EtOAc (25 ml) is added followed by Na$_2$SO$_4$ (10 g). The suspension is stirred for 15 min then filtered through a Celite pad and washed with EtOAc then EtOAc/MeOH (9:1). The combined organic phases are evaporated under reduced pressure to afford the crude product with a purity level compatible with the next step. LC-A: $t_R$=0.39 min; [M+H]$^+$=221.2; $^1$H-NMR (400 MHz, CDCl$_3$) δ: 6.82 (t, J=7.6 Hz, 1 H), 6.69 (d, J=7.8 Hz, 1 H), 6.53 (d, J=7.5 Hz, 1 H), 4.09 (t, J=4.1 Hz, 2 H), 3.88 (s, 2 H), 3.19 (t, J=4.1 Hz), 2.28 (d, J=7.2 Hz, 2 H), 1.81 (m, 1 H), 0.92 (d, J=6.6 Hz, 6 H)

f) (4-Isobutyl-2,3,4,5-tetrahydrobenzo[f][1,4]oxazepin-9-yl)glycine (Precursor 4A1): to a solution of 4-isobutyl-2,3,4,5-tetrahydrobenzo[f][1,4]oxazepin-9-amine (2.61 g, 9.48 mmol) in 100 mL of anhydrous MeOH is added glyoxylic acid monohydrate (1.05 g, 11.4 mmol). The reaction mixture is degassed and purged with Argon then Pearlman's catalyst Pd(OH)$_2$ (20% Pd/C) is added (50.4 mg, 0.095 mmol). The well stirred suspension is put under an atmospheric pressure of H$_2$ and left reacting at RT for 48 h. As substantial amount of starting material can still be observed, the reaction kinetic is boosted up by adding more Pearlman's catalyst (252 mg, 0.474 mmol). The reaction mixture is put back under atmospheric pressure of H$_2$ and stirred further at RT for 5 h. The mixture is purged with Ar and filtered over Celite and washed three times with MeOH. The solvent is removed under reduced pressure. The crude residue is purified by flash chromatography over 40 g of silica gel with EtOAc/

(MeOH+1% TEA) system (1:0 to 4:1 gradient) as eluent to yield the title compound as an orange solid. LC-A: $t_R$=0.51 min; [M+H]$^+$=279.4

Precursor 4A2

(4-ethyl-2,3,4,5-tetrahydrobenzo[f][1,4]oxazepin-9-yl)glycine a) N-(2-((tert-Butyldimethylsilyl)oxy)ethyl)-N-ethyl-2-fluoro-3-nitrobenzamide (Precursor 4A2-9): a solution of 2-fluoro-3-nitrobenzoic acid (520 mg, 2.81 mmol) in thionyl chloride (6 mL, 82.3 mmol) is refluxed for 2 h. The mixture is cooled to RT and extensively evaporated under reduced pressure. The residue is dissolved back in 1 mL of anhydrous DCM and is slowly added to a solution of 2-((tert-butyldimethylsilyl)oxy)-N-ethylethan-1-amine (571 mg, 2.81 mmol) in 10% NaOH (3 mL) and DCM (2 mL) at 0° C. The mixture is left returning to RT and stirred at RT for 3 h. The mixture is extracted with DCM/H$_2$O and the combined organic layers are dried over Na$_2$SO$_4$, filtered and evaporated under reduced pressure to yield the title compound as yellow oil which is used in the next step without further purification. LC-A: $t_R$=1.00 min; [M+H]$^+$=371.2 b) 4-Ethyl-9-nitro-3,4-dihydrobenzo[f][1,4]oxazepin-5(2H)-one (Precursor 4A2-10): to a solution of Precursor 4A2-9 (900 mg, 2.43 mmol) in 5 mL of anhydrous THF at 0° C. is added 3.04 mL of a (1M) solution of TBAF in THF (3.04 mL, 3.04 mmol). The reaction mixture is left returning to RT and stirred at RT for 20 h. Water (5 mL) is added to the mixture and THF is partially distilled off under reduced pressure. The resulting aqueous phase is extracted with EtOAc. The combined organic layers are dried over Na$_2$SO$_4$, filtered and extensively evaporated under reduced pressure. The crude residue is purified by flash chromatography over 24 g of silica gel with Heptane/EtOAc system (3:2 to 2:3 gradient) as eluent to yield the title compound as yellow oil. LC-A: $t_R$=0.68 min; [M+H]$^+$=237.2; $^1$H-NMR (400 MHz, CDCl$_3$) δ: 8.01 (dd, $J_1$=1.6 Hz, $J_2$=7.8 Hz, 1 H), 7.90 (dd, $J_1$=1.5 Hz, $J_2$=8.0 Hz), 7.30 (t, J=7.9 Hz, 1 H), 4.59 (t, J=5.2 Hz, 2 H), 3.71 (q, J=7.1 Hz, 2 H), 3.58 (t, J=5.2 Hz, 2 H), 1.30 (t, J=7.1 Hz)

c) 4-Ethyl-9-nitro-2,3,4,5-tetrahydrobenzo[f][1,4]oxazepine (Precursor 4A2-6): to a solution of Precursor 4A2-10 (440 mg, 1.86 mmol) in 6.5 mL of THF at RT is added 7.45 mL of (1M) solution of BH$_3$.THF complex in THF (7.45 mL, 7.45 mmol). The reaction mixture is refluxed overnight. The mixture is cooled down to 0° C. and MeOH (18 mL) and sodium hydroxide (1.67 g, 41 mmol) are added and the mixture is vigorously stirred at RT for 24 h. The mixture is concentrated and the residue is extracted with EtOAc/H$_2$O. The combined organic layers are dried over Na$_2$SO$_4$, filtered and evaporated under reduced pressure to yield the title compound as yellow oil with a purity compatible with the next chemical step. LC-A: $t_R$=0.42 min; [M+H]$^+$=223.1 c2) 4-Ethyl-9-nitro-2,3,4,5-tetrahydrobenzo[f][1,4]oxazepine (Precursor 4A2-6): to a 2M solution of LiALH$_4$ in THF (9.1 mL, 18.2 mmol) in 30 mL of dry THF is added sulfuric acid 98% (0.484 mL, 9.08 mmol) at 0° C. under Ar. The mixture is stirred at RT for 2 h then a solution of 4-ethyl-9-nitro-3,4-dihydro-2H-benzo[f][1,4]oxazepin-5-one (715 mg, 3.03 mmol) in 5 mL THF is added dropwise at RT. The resulting mixture is stirred overnight at RT. Water (20 mL) is carefully added at 0° C. Salts are removed by filtration and DCM (100 mL) is added. The mixture is stirred for 15 min, the organic phase is separated and the aqueous phase is extracted twice with DCM (2×40 mL). The combined organic phases are dried over MgSO$_4$, filtered and evaporated to yield the title compound as a yellow oil with a purity compatible with the next chemical step. LC-A: $t_R$=0.44 min; [M+H]$^+$=223.1 d) & e) (4-Ethyl-2,3,4,5-tetrahydrobenzo[f][1,4]oxazepin-9-yl)glycine (Precursor 4A2): these transformations are achieved according to the methodology described for Precursor 4A1, starting from Precursor 4A2-6 instead of Precursor 4A1-6, to yield the title compound as a brownish oil. LC-A: $t_R$=0.42 min; [M+H]$^+$=251.2. Intermediate analytical details can be found in Table 2.

Precursor 4A3 ((4-propyl-2,3,4,5-tetrahydrobenzo[f][1,4]oxazepin-9-yl)glycine) LC-A: $t_R$=0.47 min; [M+H]$^+$=265.3 and Precursor 4A4 ((4-(4-methoxybenzyl)-2,3,4,5-tetrahydrobenzo[f][1,4]oxazepin-9-yl)glycine) LC-A: $t_R$=0.58 min; [M+H]$^+$=343.3 are prepared applying the method described for Precursor 4A1 using n-propylamine and 4-methoxybenzylamine in the first sequence step instead of isobutylamine respectively. Intermediate analytical details can be found in Table 2.

TABLE 2

Analytical data of the precursor synthesis intermediates

| Alias | Name | Aspect | $t_R$ [min] (LC-A) | MS Data m/z [M + H]$^+$ | $^1$H-NMR |
|---|---|---|---|---|---|
| 4A2-7 | 4-Ethyl-2,3,4,5-tetrahydro-benzo[f][1,4]oxazepin-9-amine | Brown oil | 0.23 | 193.3 | |
| 4A3-2 | 2-Nitro-6-((propyl-amino)methyl)phenol | Yellow solid | 0.48 | 211.2 | (500 MHz, DMSO) δ: 7.69 (dd, $J_1$ = 1.9 Hz, $J_2$ = 8.5 Hz, 1 H), 7.16 (dd, $J_1$ = 1.8 Hz, $J_2$ = 6.9 Hz, 1 H), 6.13 (dd, $J_1$ = 6.9 Hz, $J_2$ = 8.4 Hz, 1 H), 3.97 (s, 2 H), 2.78 (t, J = 7.4 Hz, 2 H), 1.61 (h, J = 7.5 Hz, 2 H), 0.91 (t, J = 7.4 Hz, 3 H) |
| 4A3-3 | 2-Hydroxy-N-(2-hydroxy-3-nitrobenzyl)-N-propylacetamide | Red oil | 0.71 | 269.2 | |
| 4A3-5 | 9-Nitro-4-propyl-4,5-dihydro-benzo[f][1,4]oxazepin-3(2H)-one | Yellow oil | 0.75 | 251.2 | (400 MHz, CDCl$_3$) δ: 7.85 (dd, J1 = 1.5 Hz, J2 = 8.2 Hz, 1 H), 7.49 (dd, J1 = 1.4 Hz, J2 = 7.5 Hz, 1 H), 7.24 (dd, J1 = 7.5 Hz, |

TABLE 2-continued

Analytical data of the precursor synthesis intermediates

| Alias | Name | Aspect | $t_R$ [min] (LC-A) | MS Data m/z $[M + H]^+$ | $^1$H-NMR |
|---|---|---|---|---|---|
| | | | | | J2 = 8.3 Hz, 1 H), 4.88 (s, 2 H), 4.55 (s, 2 H), 3.55 (dd, J1 = 7.4 Hz, J2 = 8.6 Hz, 2 H), 1.64 (m, 2 H), 0.93 (t, J = 7.4 Hz, 3 H) |
| 4A3-6 | 9-Nitro-4-propyl-2,3,4,5-tetrahydro-benzo[f][1,4]oxazepine | Brown oil | 0.50 | 237.3 | |
| 4A3-7 | 4-Propyl-2,3,4,5-tetrahydro-benzo[f][1,4]oxazepin-9-amine | Brown oil | 0.33 | 207.2 | |
| 4A4-2 | 2-(((4-Methoxy-benzyl)amino)methyl)-6-nitrophenol | Yellow solid | 0.61 | 289.1 | (400 MHz, DMSO) δ: 7.70 (m, 1 H), 7.37 (d, J = 8.5 Hz, 2 H), 7.17 (d, J = 6.9 Hz, 1 H), 6.97 (d, J = 8.6 Hz, 2 H), 6.27 (t, J = 7.7 Hz, 1 H), 3.93 (s, 2 H), 3.92 (s, 2 H), 3.77 (s, 3 H) |
| 4A4-3 | 2-Hydroxy-N-(2-hydroxy-3-nitrobenzyl)-N-(4-methoxy-benzyl)acetamide | Orange oil | 0.79 | 347.1 | |
| 4A4-5 | 4-(4-Methoxybenzyl)-9-nitro-4,5-dihydro-benzo[f][1,4]oxazepin-3(2H)-one | Yellow solid | 0.83 | 329.1 | |
| 4A4-6 | 4-(4-Methoxybenzyl)-9-nitro-2,3,4,5-tetrahydro-benzo[f][1,4]oxazepine | Yellow oil | 0.60 | 315.2 | (400 MHz, CDCl$_3$) δ: 7.64 (dd, J$_1$ = 1.6 Hz, J$_2$ = 8.1 Hz, 1 H), 7.23 (m, 3 H), 7.09 (t, J = 7.8 Hz, 1 H), 6.90 (d, J = 8.6 Hz, 2 H), 4.24 (m, 2 H), 3.88 (s, 2 H), 3.84 (s, 3 H), 3.62 (s, 2 H), 3.17 (m, 2 H) |
| 4A4-7 | 4-(4-Methoxybenzyl)-S2,3,4,5-tetrahydro-benzo[f][1,4]oxazepin-9-amine | Orange oil | 0.51 | 285.2 | |

Precursor 4A5

(4-(Cyclopropylmethyl)-2,3,4,5-tetrahydrobenzo[f][1,4]oxazepin-9-yl)glycine a) In analogy to the preparation of precursor 4A2 step c2) above, 4-cyclopropylmethyl-9-nitro-2,3,4,5-tetrahydro-benzo[f][1,4]oxazepine 4A5-6 is obtained from 4-cyclopropylmethyl-9-nitro-3,4-dihydro-2H-benzo[f][1,4]oxazepin-5-one 4A5-10 by treatment with borane THF complex; LC-A: $t_R$=0.51 min; [M+H]$^+$=249.24.

b) In analogy to the preparation of precursor 4A1 step e) above, 4-cyclopropylmethyl-2,3,4,5-tetrahydro-benzo[f][1,4]oxazepin-9-ylamine 4A5-7 is obtained from 4-cyclopropylmethyl-9-nitro-2,3,4,5-tetrahydro-benzo[f][1,4]oxazepine 4A5-6 by treatment with Pd/C 10%; LC-A: $t_R$=0.35 min; [M+H]$^+$=219.28 c) in analogy to the preparation of precursor 4A1 step f) above, (4-(cyclopropylmethyl)-2,3,4,5-tetrahydrobenzo[f][1,4]oxazepin-9-yl)glycine 4A5 is obtained from 4-cyclopropylmethyl-2,3,4,5-tetrahydro-benzo[f][1,4]oxazepin-9-ylamine 4A5-7 by treatment with glyoxylic acid monohydrate and Pd/C 10% LC-A: $t_R$=0.48 min; [M+H]$^+$=277.24

Example 67

2-(4-Cyclopropylmethyl-3-oxo-2,3,4,5-tetrahydro-benzo[f][1,4]oxazepin-9-ylamino)-N-(2-dimethyl-amino-ethyl)-N-(2-trifluoromethyl-benzyl)-acet-amide a) 2-[(Cyclopropylmethyl-amino)-methyl]-6-nitro-phenol (Precursor 4A5-2) is obtained according to the reaction a) described above for the preparation of Precursor 4A1-2 using 2-hydroxy-3-nitrobenzaldehyde and cyclopropyl-methanamine. LC-A: $t_R$=0.50 min; [M+H]$^+$=223.24.

b) N-Cyclopropylmethyl-2-hydroxy-N-(2-hydroxy-3-nitro-benzyl)-acetamide (Precursor 4A5-3) is obtained according to the reaction b) described above for the preparation of Precursor 4A1-3 using 2-[(cyclopropylmethyl-amino)-methyl]-6-nitro-phenol and glycolic acid. LC-A: $t_R$=0.72 min; [M+H]$^+$=281.19.

c) 4-Cyclopropylmethyl-9-nitro-4,5-dihydro-benzo[f][1,4]oxazepin-3-one (Precursor 4A5-5): is obtained according to the reaction c) described above for the preparation of Precursor 4A1-5 by treating N-cyclopropylmethyl-2-hydroxy-N-(2-hydroxy-3-nitro-benzyl)-acetamide with DEAD and PPh$_3$. LC-A: $t_R$=0.77 min; [M+H+MeCN]$^+$=304.2.

d) 9-Amino-4-cyclopropylmethyl-4,5-dihydro-benzo[f][1,4]oxazepin-3-one (Precursor 4E1-1): A flask is charged with Pd/C 10% wet (223 mg, 2.1 mmol). 10 mL MeOH are added under Ar. 4-Cyclopropylmethyl-9-nitro-4,5-dihydrobenzo[f][1,4]oxazepin-3-one (1100 mg, 4.19 mmol) is suspended in 10 mL MeOH, the resulting suspension is purged with argon and then added to the Pd suspension. The dark mixture is stirred under $H_2$ at RT overnight. The mixture is filtered and evaporated until dryness under reduced pressure to afford the crude product with a purity level compatible with the next step. LC-A: $t_R$=0.54 min; [M+MeCN]$^+$=274.14.

e) (4-Cyclopropylmethyl-3-oxo-2,3,4,5-tetrahydro-benzo [f][1,4]oxazepin-9-ylamino)-acetic acid (Precursor 4E1) is obtained according to the reaction f) described above for the preparation of Precursor 4A1 by treating 9-amino-4-cyclopropylmethyl-4,5-dihydro-benzo[f][1,4]oxazepin-3-one with glyoxilic acid monohydrate and Pd/C 10% under $H_2$. LC-A: $t_R$=0.67 min; [M+H]$^+$=297.16.

Example 65

In analogy to Example 1, condensation of Precursor 4E1 with amine B24 yields 2-(4-cyclopropylmethyl-3-oxo-2,3,4,5-tetrahydro-benzo[f][1,4]oxazepin-9-ylamino)-N-(2-pyrrolidin-1-yl-ethyl)-N-(3-trifluoromethyl-pyridin-2-ylmethyl)-acetamide. LC-B: $t_R$=0.72 min; [M+H]$^+$=546.3.

Example 66

In analogy to Example 1, condensation of Precursor 4E1 with amine B16 yields N-(2-tert-butylamino-ethyl)-2-(4-cyclopropylmethyl-3-oxo-2,3,4,5-tetrahydro-benzo[f][1,4] oxazepin-9-ylamino)-N-(2-trifluoromethyl-benzyl)-acetamide. LC-B: $t_R$=0.80 min; [M+H]$^+$=547.3.

Example 67

In analogy to Example 1, condensation of Precursor 4E1 with amine B1 yields 2-(4-cyclopropylmethyl-3-oxo-2,3,4,5-tetrahydro-benzo[f][1,4]oxazepin-9-ylamino)-N-(2-dimethylamino-ethyl)-N-(2-trifluoromethyl-benzyl)-acetamide. LC-B: $t_R$=0.76 min; [M+H]$^+$=519.3.

Example 68

2-(4-Cyclopropylmethyl-3-oxo-2,3,4,5-tetrahydro-benzo[f][1,4]oxazepin-9-ylamino)-N-(2-isopropylamino-ethyl)-N-(2-trifluoromethyl-benzyl)-acetamide Step 1) {2-[[2-(4-Cyclopropylmethyl-3-oxo-2,3,4,5-tetrahydro-benzo[f][1,4]oxazepin-9-ylamino)-acetyl]-(2-trifluoromethyl-benzyl)-amino]-ethyl}-isopropyl-carbamic acid tert-butyl ester In analogy to Example 1, condensation of Precursor 4E1 with amine B21 yields {2-[[2-(4-cyclopropylmethyl-3-oxo-2,3,4,5-tetrahydro-benzo[f][1,4]oxazepin-9-ylamino)-acetyl]-(2-trifluoromethyl-benzyl)-amino]-ethyl}-isopropyl-carbamic acid tert-butyl ester as a light yellow solid. LC-A: $t_R$=1.06 min; [M+H]$^+$=633.28.

Step 2) The title compound is obtained by treatment of {2-[[2-(4-cyclopropylmethyl-3-oxo-2,3,4,5-tetrahydro-benzo[f][1,4]oxazepin-9-ylamino)-acetyl]-(2-trifluoromethyl-benzyl)-amino]-ethyl}-isopropyl-carbamic acid tert-butyl ester with TFA in analogy to Example 71 as a yellowish oil; LC-B: $t_R$=0.79 min; [M+H]$^+$=533.3.

Example 21

N-(2-(dimethylamino)ethyl)-2-((4-ethyl-2,3,4,5-tetrahydro-1H-benzo[e][1,4]diazepin-9-yl)amino)-N-(2-(trifluoromethyl)benzyl)acetamide a) N-(2-(dimethylamino)ethyl)-2-((4-ethyl-1-(4-methoxybenzyl)-2,3,4,5-tetrahydro-1H-benzo[e][1,4]diazepin-9-yl)amino)-N-(2-(trifluoromethyl)benzyl) acetamide: to a solution of (4-ethyl-1-(4-methoxybenzyl)-2,3,4,5-tetrahydro-1H-benzo[e][1,4]diazepin-9-yl)glycine Precursor 4B1 (135 mg, 0.347 mmol) and N-(2-(trifluoromethyl)benzyl)-N',N'-dimethylethane-1,2-diamine Amine B1 (85.5 mg, 0.347 mmol) in 3 mL of DCM at RT are added HATU (158 mg, 0.417 mmol) and DIPEA (0.0891 mL, 0.521 mmol). The reaction mixture is allowed to stir at RT for 4 h. Water is added and the resulting organic phase is washed with sat. aq. $NaHCO_3$ soln. and brine then dried over $Na_2SO_4$, filtered and evaporated under reduced pressure to yield the title compound as a yellow oil. The crude is directly used in the next step without further purification. LC-A: $t_R$=0.66 min; [M+H]$^+$=598.1 b) N-(2-(dimethylamino)ethyl)-2-((4-ethyl-2,3,4,5-tetrahydro-1H-benzo[e][1,4]diazepin-9-yl)amino)-N-(2-(trifluoromethyl)benzyl)acetamide (Example 21): N-(2-(dimethylamino)ethyl)-2-((4-ethyl-1-(4-methoxybenzyl)-2,3,4,5-tetrahydro-1H-benzo[e][1,4]diazepin-9-yl)amino)-N-(2-(trifluoromethyl)benzyl)acetamide (320 mg, 0.268 mmol) is dissolved in 4 mL TFA and stirred at 50° C. for 1 h. The mixture is cooled down to 0-5° C. and is carefully quenched with sat. $NaHCO_3$ solution. The resulting aq. phase is extracted with DCM. The combined organic layers are dried over $Na_2SO_4$, filtered and evaporated under reduced pressure. The crude residue is purified by prep. HPLC (Method C) to yield the title compound as a yellow oil. LC-A: $t_R$=0.56 min; [M+H]$^+$=478.1; $^1$H-NMR (400 MHz, CDCl$_3$), 55:45 mixture of two rotamers:

Major rotamer spectrum δ: 7.74 (d, J=7.8 Hz, 1 H), 7.52 (t, J=8.1 Hz, 1 H), 7.43 (t, J=7.9 Hz, 1 H), 7.30 (d, J=8.0 Hz, 1 H), 6.75 (t, J=7.5 Hz, 1 H), 6.66 (d, J=7.7 Hz, 1 H), 6.46 (d, J=7.6 Hz, 1 H), 4.82 (s, 2 H), 4.62 (t, J=4.7 Hz, 1 H), 3.82 (s, 2 H), 3.79 (d, J=4.8 Hz, 2 H), 3.60 (t, J=6.6 Hz, 2 H), 3.13 (m, 2 H), 2.98 (m, 2 H), 2.53 (q, J=7.3 Hz, 2 H), 2.45 (t, J=6.9 Hz, 2 H), 2.26 (s, 6 H), 1.11 (t, J=7.3 Hz, 3 H)

Minor rotamer spectrum δ: 7.68 (d, J=7.8 Hz, 1 H), 7.55 (t, J=7.6 Hz, 1 H), 7.39 (t, J=7.8 Hz, 1 H), 7.30 (d, J=8.0 Hz, 1 H), 6.84 (t, J=7.7 Hz, 1 H), 6.72 (d, J=7.5 Hz, 1 H), 6.66 (d, J=7.7 Hz, 1 H), 4.93 (s, 2 H), 4.68 (t, J=4.8 Hz, 1 H), 4.07 (d, J=4.8 Hz, 2 H), 3.86 (s, 2 H), 3.36 (t, J=6.9 Hz, 2 H), 3.18 (m, 2 H), 2.98 (m, 2 H), 2.56 (q, J=7.3 Hz, 2H), 2.53 (m, 2 H), 2.24 (s, 6 H), 1.14 (t, J=7.3 Hz, 3 H)

Precursor 4B1

(4-Ethyl-1-(4-methoxybenzyl)-2,3,4,5-tetrahydro-1H-benzo[e][1,4]diazepin-9-yl)glycine a) tert-Butyl (4-methoxybenzyl)(2-oxoethyl)carbamate (Precursor 4B-2): to a suspension of Dess-Martin periodinane (1.36 g, 3.19 mmol) in 20 mL of anhydrous DCM is added a solution of tert-butyl (2-hydroxyethyl)(4-methoxybenzyl)carbamate (749 mg, 2.66 mmol) in DCM (15 mL). The reaction mixture is stirred at RT for 150 minutes. Sodium thiosulfate (1M aq) (26.6 mL, 26.6 mmol) is added and the biphasic system is vigorously stirred for 10 minutes. The organic phase is collected and aqueous phase is further extracted with DCM. The combined organic layers are dried over $Mg_2SO_4$, filtered and evaporated under reduced pressure. The crude residue is purified by flash chromatography over 40 g of silica gel with Heptane/EtOAc system (9:1 to 1:1 gradient) as eluent to yield the title compound as a clear yellows oil. LC-A: $t_R$=0.86 min; $[M+H]^+$=280.1 & $[M+H+MeCN^{-t}Bu]^+$=265.2 b) tert-Butyl (2-(ethylamino)ethyl)(4-methoxybenzyl)carbamate (Precursor 4B1-4): to a solution of Precursor 4B-2 (565 mg, 1.42 mmol) in 20 mL of MeOH at RT is added 1.42 mL of a (2.0M) solution of ethylamine in MeOH (1.42 mL, 2.83 mmol). The reaction mixture is refluxed for 4 h then cooled to 0° C. Sodium borohydride (107 mg, 2.83 mmol) is added portionwise then the mixture is allowed to return slowly to RT and is stirred at RT for 90 min. The mixture is concentrated under reduced pressure and the residue is extracted with $DCM/H_2O$. The combined organic layers are dried over $MgSO_4$, filtered and evaporated under reduced pressure to yield the title compound as yellow oil with a purity acceptable for the next step. LC-A: $t_R$=0.65 min; $[M+H]^+$=309.4; $^1$H-NMR (400 MHz, $CDCl_3$) δ: 7.19 (d, J=8.4 Hz, 2 H), 6.87 (d, J=8.4 Hz, 2 H), 4.41 (s, 2 H), 3.82 (s, 3 H), 3.31 (m, 2 H), 2.73 (m, 2 H), 2.62 (q, J=7.2 Hz, 2 H), 1.49 (m, 9 H), 1.08 (t, J=7.1 Hz, 3 H)

c) tert-Butyl (2-(N-ethyl-2-fluoro-3-nitrobenzamido) ethyl) (4-methoxybenzyl) carbamate (Precursor 4B1-5): a solution of 2-fluoro-3-nitrobenzoic acid (285 mg, 1.54 mmol) in thionyl chloride (3.29 mL, 45.1 mmol) is refluxed for 2 h. The mixture is cooled to RT and extensively evaporated under reduced pressure. The residue is dissolved back in 0.6 mL of anhydrous DCM and the resulting solution is slowly added to a solution of Precursor 4B-4 (540 mg, 1.54 mmol) in 10% NaOH (1.6 mL) and DCM (1 mL) at 0° C. The mixture is left returning to RT and stirred at RT for 2 h. The mixture is extracted with $DCM/H_2O$ and the combined organic layers are dried over $Na_2SO_4$, filtered and evaporated under reduced pressure to yield the title compound as yellow oil which is used in the next step without further purification. LC-A: $t_R$=0.96 min; $[M+H]^+$=476.3 d) 4-Ethyl-1-(4-methoxybenzyl)-9-nitro-1, 2,3, 4-tetrahydro-5H-benzo[e][1,4]diazepin-5-one (Precursor 4B1-6): to a solution of Precursor 4B1-5 (843 mg, 1.56 mmol) in 25 mL of 1,4-dioxane at RT is added 10.1 mL of a (4.0M) HCl soln. in dioxane (10.1 mL, 40.4 mmol). The reaction mixture is stirred at RT for 40 h until completion. The mixture is extensively evaporated under reduced pressure. The residue is dissolved back in 25 mL of DMF and DIPEA (0.54 mL, 3.12 mmol) is added at RT. The reaction mixture is then stirred at RT overnight. The mixture is extracted with $EtOAc/NH_4Cl$ sat. The combined organic layers are dried over $Na_2SO_4$, filtered and evaporated under reduced pressure to yield the title compound as an orange oil. The crude is directly used in the next step without further purification. LC-A: $t_R$=0.88 min; $[M+H]^+$=356.2; $^1$H-NMR (400 MHz, $CDCl_3$) δ: 7.92 (dd, $J_1$=1.6 Hz, $J_2$=7.6 Hz, 1 H), 7.86 (dd, $J_1$=1.5 Hz, $J_2$=8.1 Hz, 1 H), 7.21 (t, J=7.8 Hz, 1 H), 7.15 (d, J=8.6 Hz, 2 H), 6.84 (d, J=8.6 Hz, 2 H), 3.94 (s, 2 H), 3.80 (s, 3 H), 3.58 (q, J=7.2 Hz, 2 H), 3.48 (t, J=5.5 Hz, 2 H), 3.29 (t, J=5.6 Hz, 2 H), 1.12 (t, J=7.2 Hz, 3 H)

e) 4-Ethyl-1-(4-methoxybenz yl)-9-nitro-2,3,4,5-tetrahydro-1H-benzo[e][1,4]diazepine (Precursor 4B1-7): to a solution of Precursor 4B1-6 (616 mg, 1.39 mmol) in 5 mL of THF at RT is added 5.55 mL of (1M) solution of $BH_3·THF$ complex in THF (5.55 mL, 5.55 mmol).

The reaction mixture is refluxed for 64 h. The desired compound is obtained but contaminated by some deprotected starting material, 4-ethyl-9-nitro-2,3,4,5-tetrahydro-1H-benzo[e][1,4]diazepine. The mixture is cooled down to 0° C. and MeOH (15 mL) and sodium hydroxide (1.25 g, 31 mmol) are added and the mixture is vigorously stirred at RT for 24 h. The mixture is concentrated and the residue is extracted with $EtOAc/H_2O$. The combined organic layers are dried over $Na_2SO_4$, filtered and evaporated under reduced pressure to yield the title compound as a crude yellow oil. This crude is directly used in the next step. LC-A: $t_R$=0.68 min; $[M+H]^+$=342.2 f) 4-Ethyl-1-(4-methoxybenzyl)-2,3,4,5-tetrahydro-1H-benzo[e][1,4]diazepin-9-amine (Precursor 4B1-8): to a solution of Precursor 4B1-7 (521 mg, 0.763 mmol) in 10 mL of acetone at RT is added 2 mL of a sat. $NH_4Cl$ soln. The reaction mixture is cooled down to 0° C. then zinc dust (524 mg, 8.01 mmol) is added portionwise. The reaction mixture is warmed up to RT and the suspension is stirred vigorously at RT for 16 h. EtOAc (5 ml) is added followed by 2 g $Na_2SO_4$. The suspension is stirred for 15 min then filtered through a Celite pad and washed with EtOAc then EtOAc/MeOH (9:1). The combined organic phase is evaporated under reduced pressure. The crude residue is purified by flash chromatography over 24 g of silica gel with Heptane/EtOAc system (4:1 to 0:1 gradient) as eluent and then a second time by prep. HPLC (Method C) to yield the title compound as a colorless solid. LC-A: $t_R$=0.57 min; $[M+H]^+$=312.2 g) (4-Ethyl-1-(4-methoxybenzyl)-2,3,4,5-tetrahydro-1H-benzo[e][1,4]diazepin-9-yl)glycine (Precursor 4B1): to a solution of Precursor 4B1-8 (115 mg, 0.369 mmol) in 2.5 mL of MeOH is added glyoxylic acid monohydrate (40.8 mg, 0.443 mmol). The reaction mixture is degassed and purged with Argon then Pearlman's catalyst $Pd(OH)_2$ (20% Pd/C) is added (77.8 mg, 0.554 mmol). The well stirred suspension is put under an atmospheric pressure of $H_2$ and left reacting at RT for 24 h. The mixture is purged with Ar and filtered over Celite and washed three times with MeOH. The solvent is removed under reduced pressure to yield the title compound as an orange oil of purity compatible with the next step. LC-A: $t_R$=0.62 min; $[M+H]^+$=370.2; $^1$H-NMR (400 MHz, $CDCl_3$) δ: 7.42 (d, J=8.1 Hz), 7.06 (dd, $J_1$=7.5 Hz, $J_2$=8.3 Hz), 6.82 (d, J=8.2 Hz, 2 H), 6.63 (d, J=8.1 Hz, 1 H), 6.47 (d, J=7.4 Hz, 1 H), 4.33-4.49 (m, 1 H), 4.23 (d, J=13.3 Hz, 1 H), 4.01 (d, J=13.3 Hz, 1 H), 3.75-3.91 (m, 2 H), 3.71 (s, 3 H), 3.51 (s, 2 H), 3.14-3.37 (m, 2 H), 2.75-2.99 (m, 4 H), 1.29 (t, J=7.2 Hz, 3 H)

Example 42

2-(4-Cyclopropylmethyl-1-methyl-5-oxo-2,3,4,5-tetrahydro-1H-benzo[e][1,4]diazepin-9-ylamino)-N-(2-dimethylamino-ethyl)-N-(2-trifluoromethyl-benzyl)-acetamide To a solution of (4-cyclopropylmethyl-1-methyl-5-oxo-2, 3,4,5-tetrahydro-1H-benzo[e][1,4]diazepin-9-ylamino)-acetic acid Precursor 4F1 (55 mg, 0.16 mmol) and N-(2-(trifluoromethyl)benzyl)-N',N'-dimethylethane-1,2-diamine Amine B1 (40 mg, 0.16 mmol) in 3 mL of DCM at RT are added HATU (75 mg, 0.2 mmol) and DIPEA (0.056 mL, 0.33 mmol). The reaction mixture is allowed to stir at RT for 4 h. Water is added and the resulting organic phase is washed with sat. aq. $NaHCO_3$ soln. and brine then dried over $Na_2SO_4$, filtered and evaporated under reduced pressure The crude is purified by prep. HPLC (Method C) to yield the title compound as a beige foam. LC-B: $t_R$=0.74 min; [M+H]$^+$=532.3

Precursor 4F1

(4-Cyclopropylmethyl-1-methyl-5-oxo-2,3,4,5-tetrahydro-1H-benzo[e][1,4]diazepin-9-ylamino)-acetic acid a) [2-(Cyclopropylmethyl-amino)-ethyl]-methyl-carbamic acid tert-butyl ester (Precursor 4B2-4): Cyclopropanecarboxaldehyde (3.43 mL, 45.9 mmol) is added to a solution of N-Boc-N-methylethylenediamine (8.21 mL, 44.5 mmol) in MeOH (100 mL). The reaction mixture is stirred at RT for 1 h and then cooled at 0° C. NaBH$_4$ (1911 mg, 50.5 mmol, 1.1 eq) is then added in 5 portions and the reaction is stirred at rt for 4 h. The mixture is concentrated under reduced pressure and the residue is extracted with DCM/H$_2$O. The combined organic layers are dried over MgSO$_4$, filtered and evaporated under reduced pressure to yield the title compound as yellow oil with a purity acceptable for the next step. LC-A: $t_R$=0.53 min; [M+H]$^+$=229.25 b) {2-[Cyclopropylmethyl-(2-fluoro-3-nitro-benzoyl)-amino]-ethyl}-methyl-carbamic acid tert-butyl ester (Precursor 4B2-5): a solution of 2-fluoro-3-nitrobenzoic acid (1 g, 5.4 mmol) in thionyl chloride (10 mL, 137 mmol) is refluxed for 5 h. The mixture is cooled to RT and extensively evaporated under reduced pressure. The residue is dissolved back in 5 mL of anhydrous DCM and is slowly treated successively with DIPEA (1.4 mL, 8.1 mmol) and Precursor 4B2-4 (1.393 g, 3.78 mmol) at 0° C. The mixture is left returning to RT and stirred at RT for 1 h. The mixture is extracted with DCM/H$_2$O and the combined organic layers are dried over MgSO$_4$, filtered and evaporated under reduced pressure. The crude residue is purified by flash chromatography over 80 g of silica gel with Heptane/EtOAc system (1:0 to 1:4 gradient) as eluent to yield the title compound as a yellow oil. LC-A: $t_R$=0.90 min; [M+H]$^+$=396.13 c) 4-Cyclopropylmethyl-1-methyl-9-nitro-1,2,3,4-tetrahydro-benzo[e][1,4]diazepin-5-one (Precursor 4B2-6): to a solution of Precursor 4B2-5 (1.28 g, 2.78 mmol) in 5 mL of DCM at RT is added 1.28 mL TFA (16.7 mmol) The reaction mixture is stirred at RT for 6 h until completion. The mixture is evaporated under reduced pressure. The residue is dissolved back in 15 mL of AcOEt and aq NaOH 1M is added until the solution has a pH of 14. The mixture is strongly stirred for 10 min. during this time cyclisation occurs. The reaction mixture is extracted three times with 15 mL EtOAc The combined organic layers are washed three times with 15 mL HCl 0.1N, once with 15 mL brine, dried over MgSO$_4$, filtered and evaporated under reduced pressure to yield the title compound as an orange oil. The crude is directly used in the next step without further purification. LC-A: $t_R$=0.82 min; [M+H]$^+$=276.18 d) 9-Amino-4-cyclopropylmethyl-1-methyl-1,2,3,4-tetrahydro-benzo[e][1,4]diazepin-5-one (Precursor 4F1-1): to a solution of Precursor 4B2-6 (792 mg, 2.82 mmol) in 10 mL of acetone at RT is added 4.4 mL of a sat. ammonium chloride solution (2.2 mmol). The reaction mixture is cooled to 0° C. then zinc dust (1933 mg, 29.6 mmol) is added portionwise. The reaction mixture is warmed up to RT and the suspension is stirred vigorously at RT for 24 h. EtOAc (10 ml) is added followed by Na$_2$SO$_4$ (3 g). The suspension is stirred for 15 min then filtered through a Celite pad and washed with EtOAc then EtOAc/MeOH (9:1). The combined organic phases are evaporated under reduced pressure to afford the crude product with a purity level compatible with the next step. LC-A: $t_R$=0.51 min; [M+H]$^+$=246.21 e) (4-Cyclopropylmethyl-1-methy-5-oxo-2,3,4,5-tetrahydro-1H-benzo[e][1,4]diazepin-9-ylamino)-acetic acid benzyl ester (Precursor 4F1-2): to a solution of Precursor 4F1-1 (286 mg, 1.17 mmol) in 3 mL MeCN is added benzyl bromoacetate (267 mg, 1.17 mmol). The reaction mixture is stirred at RT for 24 h. Benzyl bromoacetate (53 mg, 0.23 mmol) is added again and the mixture is stirred for 72 h. The mixture is evaporated under reduced pressure and the residue is taken up in 20 mL DCM and washed with 20 mL NaOH. The aqueous phase is extracted twice with 20 mL DCM. The combined organic phases are dried over MgSO$_4$, filtered and evaporated. The crude is purified by prep. HPLC (Method C) to yield the title compound as an orange gum. LC-A: $t_R$=0.92 min; [M+H]$^+$=394.19 f) (4-Cyclopropylmethyl-1-methyl-5-oxo-2,3,4,5-tetrahydro-1H-benzo[e][1,4]diazepin-9-ylamino)-acetic acid (Precursor 4F1): to a suspension of Pd/C 10% (44.6 mg, 0.42 mmol, 50% wet) in MeOH (5 mL) is added a solution of Precursor 4F1-2 (330 mg, 0.84 mmol) in 5 mL MeOH. The reaction mixture is degassed and is put under an atmospheric pressure of H$_2$ and left reacting at RT for 4 h. The mixture is purged with Ar and filtered over Celite® and washed three times with MeOH. The solvent is removed under reduced pressure to yield the title compound as an orange oil of purity compatible with the next step. LC-A: $t_R$=0.66 min; [M+H]$^+$=304.19

Example 43

N-(2-tert-Butylamino-ethyl)-2-(4-cyclopropylmethyl-1-methyl-5-oxo-2,3,4,5-tetrahydro-1H-benzo[e][1,4]diazepin-9-ylamino)-N-(2-trifluoromethyl-benzyl)-acetamide In analogy to Example 1, condensation of Precursor 4F1 with N-tert-butyl-N'-(2-trifluoromethyl-benzyl)-ethane-1,2-diamine (amine B16) yields N-(2-tert-butylamino-ethyl)-2-(4-cyclopropylmethyl-1-methyl-5-oxo-2,3,4,5-tetrahydro-1H-benzo[e][1,4]diazepin-9-ylamino)-N-(2-trifluoromethyl-benzyl)-acetamide. LC-B: $t_R$=0.79 min; [M+H]$^+$=560.3

Example 44

2-(4-Cyclopropylmethyl-1-methyl-5-oxo-2,3,4,5-tetrahydro-1H-benzo[e][1,4]diazepin-9-ylamino)-N-(2-dimethylamino-ethyl)-N-(3-methyl-pyridin-2-ylmethyl)-acetamide In analogy to Example 1, condensation of Precursor 4F1 with N,N-dimethyl-N'-(6-methyl-pyridin-2-ylmethyl)-ethane-1,2-diamine (amine B20) yields 2-(4-cyclopropylmethyl-1-methyl-5-oxo-2,3,4,5-tetrahydro-1H-benzo[e][1,4]diazepin-9-ylamino)-N-(2-dimethylamino-ethyl)-N-(3-methyl-pyridin-2-ylmethyl)-acetamide. LC-B: $t_R$=0.61 min; [M+H]$^+$=479.3

Example 45

N-(3-Chloro-pyridin-2-ylmethyl)-2-(4-cyclopropylmethyl-1-methyl-5-oxo-2,3,4,5-tetrahydro-1H-benzo[e][1,4]diazepin-9-ylamino)-N-(2-dimethylamino-ethyl)-acetamide In analogy to Example 1, condensation of Precursor 4F1 with N'-(3-chloro-pyridin-2-ylmethyl)-N,N-dimethyl-ethane-1,2-diamine (amine B2) yields N-(3-chloro-pyridin-2-ylmethyl)-2-(4-cyclopropylmethyl-1-methyl-5-oxo-2,3,4,5-tetrahydro-1H-benzo[e][1,4]diazepin-9-ylamino)-N-(2-dimethylamino-ethyl)-acetamide LC-B: $t_R$=0.64 min; $[M+H]^+$=499.3

Example 46

2-(4-Cyclopropylmethyl-1-methyl-5-oxo-2,3,4,5-tetrahydro-1H-benzo[e][1,4]diazepin-9-ylamino)-N-(2-isopropylamino-ethyl)-N-(2-trifluoromethyl-benzyl)-acetamide Step 1) {2-[[2-(4-Cyclopropylmethyl-1-methyl-5-oxo-2,3,4,5-tetrahydro-1H-benzo[e][1,4]diazepin-9-ylamino)-acetyl]-(2-trifluoromethyl-benzyl)-amino]-ethyl}-isopropyl-carbamic acid tert-butyl ester In analogy to Example 1, condensation of Precursor 4F1 with amine B21 yields {2-[[2-(4-cyclopropylmethyl-1-methyl-5-oxo-2,3,4,5-tetrahydro-1H-benzo[e][1,4]diazepin-9-ylamino)-acetyl]-(2-trifluoromethyl-benzyl)-amino]-ethyl}-isopropyl-carbamic acid tert-butyl ester as a yellow solid. LC-A: $t_R$=1.06 min; $[M+H]^+$=646.33

Step 2) The title compound is obtained by treatment of {2-[[2-(4-cyclopropylmethyl-1-methyl-5-oxo-2,3,4,5-tetrahydro-1H-benzo[e][1,4]diazepin-9-ylamino)-acetyl]-(2-trifluoromethyl-benzyl)-amino]-ethyl}-isopropyl-carbamic acid tert-butyl ester with TFA in analogy to Example 71 as a yellowish oil; LC-B: $t_R$=0.77 min; $[M+H]^+$=546.3

Example 47

2-(1,4-Diethyl-5-oxo-2,3,4,5-tetrahydro-1H-benzo[e][1,4]diazepin-9-ylamino)-N-(2-morpholin-4-yl-ethyl)-N-(3-trifluoromethyl-pyridin-2-ylmethyl)-acetamide In analogy to Example 1, condensation of Precursor 4F2 with (2-morpholin-4-yl-ethyl)-(3-trifluoromethyl-pyridin-2-ylmethyl)-amine (amine B27) yields 2-(1,4-diethyl-5-oxo-2,3,4,5-tetrahydro-1H-benzo[e][1,4]diazepin-9-ylamino)-N-(2-morpholin-4-yl-ethyl)-N-(3-trifluoromethyl-pyridin-2-ylmethyl)-acetamide. LC-B: $t_R$=0.65 min; $[M+H]^+$=563.3

Precursor 4F2

(1,4-Diethyl-5-oxo-2,3,4,5-tetrahydro-1H-benzo[e][1,4]diazepin-9-ylamino)-acetic acetate sodium salt a) 1,4-Diethyl-9-nitro-1,2,3,4-tetrahydro-benzo[e][1,4]diazepin-5-one (Precursor 4B3-6). To a solution of methyl 2-fluoro-3-nitrobenzoate (6 g, 28.6 mmol) in n-butanol (25 mL) are added $Na_2CO_3$ (3034 mg, 28.6 mmol) and N,N'-diethylethylenediamine (4.32 mL, 28.6 mmol). The reaction is heated at 80° C. for 18 h. The reaction mixture is cooled and diluted with water (100 mL). The resulting mixture is extracted with EtOAc (3×150 mL) dried over $MgSO_4$, and concentrated. The crude product is purified by flash chromatography over 80 g of silica gel with Heptane/EtOAc (9:1 to 0:10 gradient) as eluent to yield the title compound as a yellow oil. LC-A: $t_R$=0.79 min; $[M+H]^+$=264.25 b) 9-Amino-1,4-diethyl-1,2,3,4-tetrahydro-benzo[e][1,4]diazepin-5-one (Precursor 4F2-1): In analogy to reaction d) to precursor 4F1-1, 9-amino-1,4-diethyl-1,2,3,4-tetrahydro-benzo[e][1,4]diazepin-5-one is obtained from precursor 4B3-6 by treatment with Zn and ammonium chloride. LC-A: $t_R$=0.46 min; $[M+H]^+$=234.27 c) (1,4-Diethyl-5-oxo-2,3,4,5-tetrahydro-1H-benzo[e][1,4]diazepin-9-ylamino)-acetic acid methyl ester (Precursor 4F2-2): In analogy to reaction e) to precursor 4F1-2, (1,4-diethyl-5-oxo-2,3,4,5-tetrahydro-1H-benzo[e][1,4]diazepin-9-ylamino)-acetic acid methyl ester is obtained from precursor 4F1-1 by treatment with methyl bromoacetate. LC-A: $t_R$=0.74 min; $[M+H]^+$=306.11 d) ((1,4-diethyl-5-oxo-2,3,4,5-tetrahydro-1H-benzo[e][1,4]diazepin-9-ylamino)-acetate sodium salt (Precursor 4F2): In analogy to reaction f) to precursor 4F1, the title compound is obtained from precursor 4F2-2 by treatment with sodium hydroxide in water/THF. LC-A: $t_R$=0.62 min; $[M+H]^+$=292.25

Example 48

2-(1,4-Diethyl-5-oxo-2,3,4,5-tetrahydro-1H-benzo[e][1,4]diazepin-9-ylamino)-N-(2-pyrrolidin-1-yl-ethyl)-N-(3-trifluoromethyl-pyridin-2-ylmethyl)-acetamide In analogy to Example 1, condensation of Precursor 4F2 with (2-pyrrolidin-1-yl-ethyl)-(3-trifluoromethyl-pyridin-2-ylmethyl)-amine (amine B24) yields the title compound. LC-B: $t_R$=0.66 min; $[M+H]^+$=547.3

Example 49

2-(4-Cyclopropylmethyl-1-methyl-2,3,4,5-tetrahydro-1H-benzo[e][1,4]diazepin-9-ylamino)-N-(2-dimethylamino-ethyl)-N-(2-trifluoromethyl-benzyl)-acetamide In analogy to Example 1, condensation of Precursor 4B2 with N,N-dimethyl-N'-(3-trifluoromethyl-benzyl)-ethane-1,2-diamine (amine B1) yields the title compound as a yellow gum. LC-B: $t_R$=0.51 min; $[M+H]^+$=518.3

Precursor 4B2

(4-Cyclopropylmethyl-1-methyl-2,3,4,5-tetrahydro-1H-benzo[e][1,4]diazepin-9-ylamino)-acetic acid a) 4-Cyclopropylmethyl-1-methyl-9-nitro-2,3,4,5-tetrahydro-1H-benzo[e][1,4]diazepine (Precursor 4B2-7): In analogy to the synthesis of Precursor 4B1-7 described above, the title compound is obtained by treatment of Precursor 4B2-6 with borane THF complex. LC-A: $t_R$=0.57 min; $[M+H]^+$=262.26 b) 4-Cyclopropylmethyl-1-methyl-2,3,4,5-tetrahydro-1H-benzo[e][1,4]diazepin-9-ylamine (Precursor 4B2-8): In analogy to reaction f) of the synthesis to precursor 4B1-8 described above the title compound is obtained from precursor 4B2-7 by treatment with Zn and ammonium chloride. LC-A: $t_R$=0.37 min; $[M+H]^+$=232.32 c) (4-Cyclopropylmethyl-1-methyl-2,3,4,5-tetrahydro-1H-benzo[e][1,4]diazepin-9-ylamino)-acetic acid (Precursor 4B2): In analogy to reaction g) of the synthesis to precursor 4B1 described above the title compound is obtained from precursor 4B2-8 by treatment with glyoxylic acid monohydrate under hydrogen atmosphere. LC-A: $t_R$=0.53 min; [M+H]$^+$=290.13

Example 50

{2-[[2-(4-Cyclopropylmethyl-1-methyl-2,3,4,5-tetrahydro-1H-benzo[e][1,4]diazepin-9-ylamino)-acetyl]-(2-trifluoromethyl-benzyl)-amino]-ethyl}-isopropylcarbamic acid tert-butyl ester In analogy to Example 1, condensation of Precursor 4B2 with isopropyl-[2-(2-trifluoromethyl-benzylamino)-ethyl]-carbamic acid tert-butyl ester (amine B21) yields the title compound as a yellow gum. LC-B: $t_R$=1.01 min; [M+H]$^+$=632.4

Example 51

2-(4-Cyclopropylmethyl-1-methyl-2,3,4,5-tetrahydro-1H-benzo[e][1,4]diazepin-9-ylamino)-N-(2-pyrrolidin-1-yl-ethyl)-N-(3-trifluoromethyl-pyridin-2-ylmethyl)-acetamide In analogy to Example 1, condensation of Precursor 4B2 with (2-pyrrolidin-1-yl-ethyl)-(3-trifluoromethyl-pyridin-2-ylmethyl)-amine (amine B24) yields the title compound as a yellow gum. LC-B: $t_R$=0.46 min; [M+H]$^+$=545.3

Example 52

2-(4-Cyclopropylmethyl-1-methyl-2,3,4,5-tetrahydro-1H-benzo[e][1,4]diazepin-9-ylamino)-N-(2-isopropylamino-ethyl)-N-(2-trifluoromethyl-benzyl)-acetamide In analogy to Example 71, treatment of Example 50 with TFA in DCM yields the title compound as a yellowish oil. LC-B: $t_R$=0.53 min; [M+H]$^+$=532.3

Example 55

2-(4-Cyclopropylmethyl-1-methyl-2,3,4,5-tetrahydro-1H-benzo[e][1,4]diazepin-9-ylamino)-N-(2-morpholin-4-yl-ethyl)-N-(3-trifluoromethyl-pyridin-2-ylmethyl)-acetamide In analogy to Example 1, condensation of Precursor 4B2 with (2-morpholin-4-yl-ethyl)-(3-trifluoromethyl-pyridin-2-ylmethyl)-amine (amine B27) yields the title compound as a yellow gum. LC-B: $t_R$=0.46 min; [M+H]$^+$=560.3

Example 22

2-(4-Cyclopropylmethyl-2,3,4,5-tetrahydro-benzo[f][1,4]oxazepin-6-ylamino)-N-(2-dimethylamino-ethyl)-N-(2-trifluoromethyl-benzyl)-acetamide Step 1) N-Cyclopropylmethyl-2-fluoro-N-(2-hydroxy-ethyl)-6-nitro-benzamide (Precursor 5A1-7)

A mixture of 2-bromo-6-fluorobenzoic acid (1000 mg, 5.4 mmol) and thionyl chloride (5.92 mL, 15.11 eq) is refluxed for 2 h. The mixture is cooled down to RT then concentrated. The residue is dissolved in toluene and concentrated again to remove the remaining any excess thionyl chloride. The residue is dissolved in 10 mL THF and the resulting solution is cooled to 0° C. then a solution of 2-[(cyclopropylmethyl) amino]ethan-1-ol (622 mg, 1 eq) and TEA (1.13 mL, 1.5 eq) dissolved in 10 mL THF is added. The mixture is then allowed to warm up to RT and is further stirred at this temperature for 72 h. The mixture is then poured into water and the resulting aq. phase is extracted twice with EtOAc. The combined organic layers are dried over Na$_2$SO$_4$, filtered and concentrated under reduced pressure to afford the subtitle compound as a light grey oil. This compound is a mixture of rotamers which are separable by LC-MS but equilibrate slowly on standing. LC-A: $t_R$=0.63 and 0.65 min; [M+H]$^+$=283.3

Step 2) 4-Cyclopropylmethyl-6-nitro-3, 4-dihydro-2H-benzo[f][1,4]oxazepin-5-one (Precursor 5A1-8)

To a solution of Precursor 5A1-7 (1200 mg, 4.25 mmol) in 100 mL THF stirred at 0° C. in an ice bath is added in small portions NaH (187 mg, 1.1 eq). The light brown suspension is stirred at RT for 2 h. Then more NaH (200 mg, 1.2 eq). is added and the stirring is continued at RT overnight. The brown solution is poured onto water and the resulting aq. solution is extracted twice with EtOAc. The combined organic layers are washed with sat. aq. NaHCO$_3$ soln., with brine, dried over MgSO4, filtered then evaporated under reduced pressure to afford after silica gel flash chromatography (Biotage, SNAP 50 g, gradient Hept/EtOAc 100:0 to 60:40) yields the sub title compound as a yellow oil. LC-A: $t_R$=0.75 min; [M+H]$^+$=263.2; $^1$H NMR (400 MHz, d$_6$-DMSO) δ: 7.73 (m, 1 H), 7.65 (t, J=8.1 Hz, 1 H), 7.41 (dd, J$_1$=0.9 Hz, J$_2$=8.1 Hz, 1 H), 4.40 (t, J=5.4 Hz, 2 H), 3.73 (t, J=5.4 Hz, 2 H), 3.43 (d, J=7.0 Hz, 2 H), 1.09 (m, 1 H), 0.52 (m, 2 H), 0.32 (m, 2 H)

Step 3) 4-Cyclopropylmethyl-6-nitro-2,3, 4,5-tetrahydro-benzo[f][1,4]oxazepine (Precursor 5A1-9)

To a solution of Precursor 5A1-8 (291 mg, 0.821 mmol) in 10 mL THF stirred at RT is added 1M BH$_3$.THF complex soln. in THF (3.92 mL, 4.7 eq). The mixture is refluxed overnight, then 1M BH$_3$.THF complex soln. in THF (1 mL, 1.2 eq) is added and the reflux is continued for 8 h, then 1M BH$_3$.THF complex soln. in THF (2 mL, 2.4 eq) is added again and the resulting mixture is refluxed overnight. The mixture is then cooled to 0° C. and 10 mL MeOH and solid NaOH (996 mg, 22 eq) are added and the mixture is stirred at RT for 4 h. The MeOH is then concentrated under reduced pressure and the residue is dissolved in EtOAc. After addition of water the resulting aq. phase is extracted twice with EtOAc. The combined organic phase is washed with water and brine, then dried over MgSO$_4$. Filtration and evaporation of the solvent under reduced pressure followed by purification of the crude residue by silica gel flash chromatography (Biotage, SNAP 25 g, gradient Hept/EtOAc 95:5 to 50:50) yields the sub title compound as a yellow oil. LC-A: $t_R$=0.49 min; [M+H]$^+$=249.2; $^1$H NMR (400 MHz, DMSO) δ: 7.54 (dd, J$_1$=1.0 Hz, J$_2$=8.0 Hz, 1 H), 7.40 (t, J=8.1 Hz, 1 H), 7.29 (dd, J$_1$=1.0 Hz, J$_2$=8.0 Hz, 1 H), 4.14 (m, 2 H), 3.89 (s, 2 H), 3.07 (m, 2 H), 2.39 (d, J=6.5 Hz, 2 H), 0.81 (m, 1 H), 0.44 (m, 2 H), 0.04 (m, 2 H)

Step 4) 4-Cyclopropylmethyl-2,3,4,5-tetrahydro-benzo[f][1,4]oxazepin-6-ylamine (Precursor 5A1-10)

To a solution of Precursor 5A1-9 (165 mg, 0.545 mmol) in 10 mL acetone stirred at RT are added 2 mL sat. aq. NH$_4$Cl soln. and Zn dust (558 mg, 15.6 eq). The reaction mixture is stirred at RT for 2 h. Then EtOAc is added and the resulting organic phase is dried over Na$_2$SO$_4$. After filtration through celite and rinsing of the filter cake with EtOAc, the mixture is concentrated in vacuo and dried under high vacuum to yield the sub title compound as a yellow oil which is used as such in the next step. LC-A: $t_R$=0.45 min; [M+H]$^+$=219.3

Step 5): (4-Cyclopropylmethyl-2,3,4,5-tetrahydro-benzo[f][1,4]oxazepin-6-ylamino)-acetic acid (Precursor 5A1-11)

To a solution of Precursor 5A1-10 (115 mg, 0.5 mmol) in 3 mL MeOH are added successively 50% aq. glyoxylic acid soln. (0.0755 mL, 1.1 eq) and TEA (0.0766 mL, 1.1 eq). The reaction mixture is stirred for 20 min then NaBH$_3$CN (34.6 mg, 1.1 eq) is added and the resulting mixture is stirred for 1 h. The mixture is then poured into water (pH 6-7) and the resulting aq phase is extracted twice with DCM. The organics are washed with brine, dried over MgSO$_4$ and filtered. Evaporation of the solvents under reduced pressure afford a small amount of crude product which is dissolved in the aqueous. The aq. phase is then evaporated under reduced pressure and the crude solid obtained is suspended in MeOH/DCM. After filtration and drying under high vacuum, this affords the sub title compound as a white solid. LC-A: $t_R$=0.50 min; [M+H]$^+$=277.3

Step 6)

To a solution of Precursor 5A1-11 (79 mg, 0.14 mmol) in 2 mL DMF stirred at RT are added Amine B1 (42.2 mg, 1.1 eq), HATU (63.9 mg, 1.2 eq) and DIPEA (48 µL, 2 eq). The yellow suspension is stirred for 1 h at rt. The organic phase is washed with sat. aq. NaHCO$_3$ soln. and with brine. The organic layer is dried over MgSO$_4$ then filtered and the solvent is evaporated under reduced pressure. The crude is purified by prep. HPLC (Method C) to yield the title compound as a yellow oil. LC-A: $t_R$=0.61 min; [M+H]$^+$=505.2

Examples 86-88 and 91-94 listed in Table 3 are prepared applying the method described for Example 22 using Precursor 5A1-11 and Amine respectively.

Example 89

2-(4-Cyclopropylmethyl-2,3,4,5-tetrahydro-benzo[f][1,4]oxazepin-6-ylamino)-N-(2-isopropylamino-ethyl)-N-(2-trifluoromethyl-benzyl)-acetamide Step a): tert-butyl (2-(2-((4-(cyclopropylmethyl)-2,3,4,5-tetrahydrobenzo[f][1,4]oxazepin-6-yl)amino)-N-(2-(trifluoromethyl)benzyl)acetamido)ethyl) (isopropyl)carbamate As described for the synthesis of Example 22, Precursor 5A1-11 is reacted with amine B21 to yield the subtitle compound as a white solid after purification by preparative HPLC. LC-A: $t_R$=1.23 min; [M+H]$^+$=633.2.

Step b) The product of Step a) is dissolved in DCM and 2 eq. TFA are added. The resulting solution is allowed to stir at rt for 2 h. Evaporation of the solvent in vacuo followed by thorough crying under high vacuum yields the pure title compound as a yellow oil. LC-B: $t_R$=0.51 min; [M+H]$^+$=519.3

Example 90

2-(4-Cyclopropylmethyl-2,3,4,5-tetrahydro-benzo[f][1,4]oxazepin-6-ylamino)-N-(2-isopropylamino-ethyl)-N-(3-trifluoromethyl-pyridin-2-ylmethyl)-acetamide Is obtained as described above for Example 89 using in the first step amine B28 instead of amine B21 to yield tert-butyl (2-(2-((4-(cyclopropylmethyl)-2,3,4,5-tetrahydrobenzo[f][1,4]oxazepin-6-yl)amino)-N-((3-(trifluoromethyl)pyridin-2-yl)methyl)acetamido)ethyl)(isopropyl)carbamate as a yellow oil LC-A: $t_R$=1.01 min; [M+H]$^+$=620.2 and then in a second step the title compound as a yellow oil LC-B: $t_R$=0.44 min; [M+H]$^+$=520.3

TABLE 3

Examples 86-88 and 91-94

| Example | Compound | $t_R$ [min] (LC-B) | MS Data m/z [M + H]$^+$ |
|---|---|---|---|
| 86 | N-(2-Chloro-benzyl)-2-(4-cyclopropylmethyl-2,3,4,5-tetrahydro-benzo[f][1,4]oxazepin-6-ylamino)-N-(2-dimethylamino-ethyl)-acetamide | 0.46 | 471.2 |
| 87 | 2-(4-Cyclopropylmethyl-2,3,4,5-tetrahydro-benzo[f][1,4]oxazepin-6-ylamino)-N-(2-dimethylamino-ethyl)-N-(3-methyl-pyridin-2-ylmethyl)-acetamide | 0.38 | 452.3 |
| 88 | 2-(4-Cyclopropylmethyl-2,3,4,5-tetrahydro-benzo[f][1,4]oxazepin-6-ylamino)-N-(2,3-dichloro-benzyl)-N-(2-dimethylamino-ethyl)-acetamide | 0.51 | 505.2 |
| 91 | N-(2-tert-Butylamino-ethyl)-N-(2-chloro-benzyl)-2-(4-cyclopropylmethyl-2,3,4,5-tetrahydro-benzo[f][1,4]oxazepin-6-ylamino)-acetamide | 0.49 | 499.3 |
| 92 | N-(2-tert-Butylamino-ethyl)-N-(3-chloro-pyridin-2-ylmethyl)-2-(4-cyclopropylmethyl-2,3,4,5-tetrahydro-benzo[f][1,4]oxazepin-6-ylamino)-acetamide | 0.43 | 500.3 |
| 93 | N-(2-tert-Butylamino-ethyl)-2-(4-cyclopropylmethyl-2,3,4,5-tetrahydro-benzo[f][1,4]oxazepin-6-ylamino)-N-(2-trifluoromethyl-benzyl)-acetamide | 0.52 | 533.3 |
| 94 | N-(2-tert-Butylamino-ethyl)-2-(4-cyclopropylmethyl-2,3,4,5-tetrahydro-benzo[f][1,4]oxazepin-6-ylamino)-N-(3-trifluoromethyl-pyridin-2-ylmethyl)-acetamide | 0.46 | 534.3 |

Example 23

2-(3-Cyclopropylmethyl-2,3,4,5-tetrahydro-1H-benzo[d]azepin-6-yloxy)-N-(2-dimethylamino-ethyl)-N-(2-trifluoromethyl-benzyl)-acetamide

Step 1): 2,2,2-Trifluoro-1-(6-methoxy-1,2,4,5-tetra-hydro-benzo[d]azepin-3-yl)-ethanone 6-Methoxy-2,3,4,5-1H-benzoazepine (1 g, 5.64 mmol) is dissolved in 10 mL DCM. The solution is cooled to 0° C. then TEA (2.36 mL, 3 eq) and TFAA (0.877 mL, 1.1 eq) are added. The reaction mixture is stirred at 0° C. for 3 h then allowed to warm to rt. The mixture is washed with water then brine. The organic layer is dried over $MgSO_4$, filtered and evaporated, then dried under high vacuum to yield the subtitle compound as a yellow oil which is used as such in the next step. LC-A: $t_R$=0.89 min; $[M+H]^+$=nd; $^1$H-NMR (400 MHz, $d_6$-DMSO) δ: 7.14 (td, $J_1$=1.8 Hz, $J_2$=8.1 Hz, 1 H), 6.90 (d, J=8.3 Hz, 1 H), 6.80 (t, J=6.6 Hz, 1H), 3.78 (m, 3 H), 3.67 (m, 4 H), 3.01 (m, 4 H).

Step 2): 2,2,2-Trifluoro-1-(6-hydroxy-1,2,4,5-tetra-hydro-benzo[d]azepin-3-yl)-ethanone (Precursor 3A1-1)

To a solution of 1M $BBr_3$ soln. in DCM (9.25 mL, 9.25 mol, 1.6 eq), cooled at 0° C., is added dropwise a solution of 2,2,2-trifluoro-1-(6-methoxy-1,2,4,5-tetrahydro-benzo[d]azepin-3-yl)-ethanone from Step 1) (1.58 g, 5.78 mol) in 5 mL DCM while maintaining the temperature between 0° C. and 10° C. in an ice water bath. The brown solution is then allowed to warmed up to RT and is further stirred for 2 h 30 at this temperature. The crude is poured into ice water and the resulting aq. phase is then extracted thrice with EtOAc. The organic layer is washed with sat. aq. $NaHCO_3$ soln. and brine, dried over $MgSO_4$. After filtration, the solvent is evaporated under reduced pressure to yield the sub-title compound as yellow solid which is used as such in the next step. LC-A: $t_R$=0.78 min; $[M+H]^+$=nd

Step 3):) [3-(2, 2, 2-Trifluoro-acetyl)-2,3, 4,5-tetra-hydro-1H-benzo[d]azepin-6-yloxy]-acetic acid methyl ester (Precursor 3A1-2)

To a solution of Precursor 3A1-1 (700 mg, 2.7 mmol) in 8 mL acetone stirred at RT are added $K_2CO_3$ (560 mg, 1.5 eq) and methylbromoacetate (0.256 mL, 1 eq). The reaction is stirred for 5 h 30 at 80° C. After filtration of the white solid formed, the filtrate is evaporated under reduced pressure, dried with HV to yield the expected crude sub-title compound as a yellow oil which is used as such in the next step. LC-A: $t_R$=0.87 min; $[M+H]^+$=332.2; $^1$H NMR (400 MHz, $d_6$-DMSO) δ: 7.10 (td, $J_1$=2.9 Hz, $J_2$=7.9 Hz, 1 H), 6.83 (m, 2 H), 4.80 (m, 2 H), 3.69 (m, 7 H), 3.10 (m, 2 H), 2.99 (m, 2 H)

Step 4): (2,3,4,5-Tetrahydro-1H-benzo[d]azepin-6-yloxy)-acetic acid

To a solution of Precursor 3A1-2 (960 mg, 2.9 mmol) in 10 mL MeOH stirred at RT is added 1M NaOH aq. soln. (5.8 mL, 2 eq). The yellow mixture is stirred at RT for 2 h, then 1N aq. HCl soln. is added until pH>7. The aq. phase is then evaporated under reduced pressure and then dried under high vacuum to yield the subtitle compound as yellow solid containing 2 eq NaCl. LC-A: $t_R$=0.43 min; $[M+H]^+$=222.6

Step 5): (3-(tert-Butoxycarbonyl)-2,3, 4,5-tetra-hydro-1H-benzo[d]azepin-6-yl)glycine (Precursor 3A1-3)

To a stirring solution of (2,3,4,5-tetrahydro-1H-benzo[d]azepin-6-yloxy)-acetic acid from Step 4) (990 mg, 3.08 mmol) in 6 mL THF and 10 mL water stirred at RT are added NaOH (246 mg, 2 eq) and $Boc_2O$ (739 mg, 1.1 eq). The reaction mixture is stirred overnight at rt. The mixture is diluted with EtOAc and water. The layers are separated and the aq. layer is extracted twice with EtOAc. The aq. layer is then acidified with HCl 1M (pH 6) then evaporated to give the title compound mixed with 2 eq NaCl as a yellow solid which is used as such in the next step. LC-A: $t_R$=0.82 min; $[M+H]^+$=322.1

Step 6): tert-Butyl 6-{[(2-dimethylamino-ethyl)-(2-trifluoromethyl-benzyl)-carbamoyl]-methoxy}-1,2,4,5-tetrahydro-benzo[d]azepine-3-acetate (Precursor 3A1-4)

To a solution of Precursor 3A1-3 (1.41 g, 3.49 mmol) and Amine B1 (953 mg, 1.05 eq) in 20 mL DCM is added HATU (1682 mg, 1.2 eq) and DIPEA (1.26 mL, 2 eq). The yellow suspension is stirred for 2 h at rt. The organic phase is washed with sat. aq. $NaHCO_3$ soln. then with brine. The organic layer is dried over $MgSO_4$, filtered and evaporated under reduced pressure. The crude is purified by silica gel flash chromatography (Biotage, SNAP 25 g, gradient Hept/EtOAc 30:70 to 80:20 to 0:100). The obtained product is dissolved in EtOAc and washed with sat. aq. $NaHCO_3$ soln. then water and brine, dried over $MgSO_4$, filtered and the solvent evaporated. This yields the sub title compound as a yellow oil. LC-A: $t_R$=0.81 min; $[M+H]^+$=550.2

Step 7): N-(2-Dimethylamino-ethyl)-2-(2,3,4,5-tet-rahydro-1H-benzo[d]azepin-6-yloxy)-N-(2-trifluo-romethyl-benzyl)-acetamide (Precursor 3A1)

To a solution of Precursor 3A1-4 (750 mg, 1.19 mmol) dissolved in 10 mL DCM is added 4N HCl in dioxane soln. (1.18 mL, 4 eq) and the resulting mixture is allowed to stir at RT for 2 h, then 4N HCl in dioxane soln. (0.59 mL, 2 eq) is added again and the resulting mixture is allowed to stir at RT for 4 h. Then sat. aq. $NaHCO_3$ soln. is added until pH>9 and the phases are separated. The organic phase is washed with water and brine then dried over $MgSO_4$ and evaporated under reduced pressure to afford the sub-title compound as a yellow oil which is used as such in the next step. LC-A: $t_R$=0.54 min; $[M+H]^+$=449.9

Step 8) To a solution of Precursor 3A1 (100 mg, 0.206 mmol) in 2 mL DCM is added at RT cyclopropanecarbox-aldehyde (31 μL, 2.331 eq) and DIPEA (70.5 μL, 2.314 eq). The yellow suspension is stirred for 10 mn at RT then $NaBH(OAc)_3$ (75.4 mg, 2 eq) is added and the resulting mixture is stirred for overnight at rt. Cyclopropanecarbox-aldehyde (31 μL, 2.331 eq) and $NaBH(OAc)_3$ (75.4 mg, 2 eq) are added again and the stirring is continued for 2 h. Water is added and the resulting aq. phase extracted thrice with DCM. The combined organic phase is washed with sat. aq. $NaHCO_3$ soln. then brine and dried with $MgSO_4$. The organic phase is filtered and evaporated under reduced pressure. The crude is purified by two successive prep. HPLC (Method C, then Method D) to yield the title compound as a colorless oil. LC-B: $t_R$=0.59 min; [M+H]$^+$=504.1; $^1$H NMR (d$_6$-DMSO) 64:36 mixture of rotamers δ: 7.79 (d, J=7.8 Hz, 0.36 H), 7.72 (d, J=7.8 Hz, 0.64 H), 7.67 (m, 0.36 H), 7.62 (t, J=7.7 Hz, 0.64 H), 7.53 (t, J=7.7 Hz, 0.36 H), 7.47 (t, J=7.5 Hz, 0.64 H), 7.32 (d, J=7.8 Hz, 1 H), 7.12 (t, J=7.9 Hz, 0.64 H), 7.05 (t, J=7.9 Hz, 0.36 H), 6.92 (d, J=8.3 Hz, 0.64 H), 6.80 (m, 1 H), 6.70 (d, J=8.4 Hz, 0.36 H), 5.10 (s, 1.28 H), 4.84 (s, 0.72 H), 4.74 (m, 2 H), 3.49 (t, J=6.3 Hz, 2 H), 3.27-2.90 (m, 8 H), 2.85 (d, J=6.9 Hz, 1.28 H), 2.79 (d, J=6.9 Hz, 0.72 H), 2.70 (t, J=6.2 Hz, 0.72 H), 2.57 (t, J=6.1 Hz, 1.28 H), 2.35 (s, 2.16 H), 2.25 (s, 3.84 H), 1.01 (m, 1 H), 0.58 (m, 2 H), 0.27 (m, 2 H).

Example 24

N-(2-Dimethylamino-ethyl)-2-[3-(2-methoxy-acetyl)-2,3,4,5-tetrahydro-1H-benzo[d]azepin-6-yloxy]-N-(2-trifluoromethyl-benzyl)-acetamide To a solution of Precursor 3A1 (100 mg, 0.146 mmol) in 2 mL DCM is added at RT methoxyacetic acid (13.4 μL, 1.2 eq), HATU (66.5 mg, 1.2 eq) and DIPEA (49.9 μL, 2 eq). The mixture is stirred overnight at rt, then water is added and the resulting aq. phase extracted three times with DCM using phase separator cartridges. The organic phase is evaporated under reduced pressure and the crude product is purified by prep. HPLC (Method D). After purification the obtained solid is dissolved in DCM and sat. aq. NaHCO$_3$ soln. is added, the two layers are separated and the organic layer is dried over MgSO$_4$ and evaporated under reduced pressure to yield the title compound as a yellow oil. LC-A: $t_R$=0.69 min; [M+H]$^+$=522.2

Example 25

2-(3-Acetyl-2,3,4,5-tetrahydro-1H-benzo[d]azepin-6-yloxy)-N-(2-dimethylamino-ethyl)-N-(2-trifluoromethyl-benzyl)-acetamide Is obtained from Precursor 3A1 using the same procedure as described for Example 24 with acetic acid instead of methoxyacetic acid yielding the title compound as a yellow oil. LC-A: $t_R$=0.70 min; [M+H]$^+$=492.2

Example 26

N-(2-Dimethylamino-ethyl)-2-[3-(2,2,2-trifluoro-acetyl)-2,3,4,5-tetrahydro-1H-benzo[d]azepin-6-ylamino]-N-(2-trifluoromethyl-benzyl)-acetamide Step 1): Trifluoro-methanesulfonic acid 3-(2,2,2-trifluoro-acetyl)-2,3,4,5-tetrahydro-1H-benzo[d]azepin-6-yl ester (Precursor 3B1-1)

To a solution of Precursor 3A1-1 (500 mg, 1.93 mmol) in 5 mL DCM cooled to 0° C. in an ice bath are added TEA (0.591 mL, 2.2 eq) and trifluoromethanesulfonic anhydride (0.409 mL, 1.26 eq). The ice bath is removed and the reaction is stirred overnight at rt. The mixture is then poured into water and extracted twice with DCM. The organic extracts are washed with brine, dried over MgSO$_4$, filtered, and evaporated. The crude is purified by silica gel flash chromatography (Biotage, SNAP 15 g, gradient Hept/EtOAc 90:10 to 70:30). This yields the sub title compound as a yellow oil. LC-A: $t_R$=0.97 min; [M+H]$^+$=nd; $^1$H NMR (400 MHz, d$_6$-DMSO) δ: 7.36 (m, 3 H), 3.73 (m, 4 H), 3.12 (m, 4 H).

Step 2): {[(2-Dimethylamino-ethyl)-(2-trifluoromethyl-benzyl)-carbamoyl]-methyl}-carbamic acid tert-butyl ester (Precursor 5A1-1)

To a solution of Amine B1 (1 g, 4.06 mmol) and BOC-Glycine (0.782 g, 1.1 eq) in 10 mL DCM at RT is added HATU (2.32 g, 1.5 eq) followed by DIPEA (2.09 mL, 3 eq). The yellow solution is stirred at RT for 1 h 30. Then sat. aq. NaHCO$_3$ is added and the mixture is extracted with DCM. The combined organic layer is dried over MgSO$_4$, filtered and concentrated. The crude is purified by silica gel flash chromatography (Biotage, SNAP 15 g, gradient Hept/EtOAc 80:20 to 0:100). This yields the subtitle compound as a yellow oil. LC-A: $t_R$=0.67 min; [M+H]$^+$=404.3

Step 3): 2-Amino-N-(2-dimethylamino-ethyl)-N-(2-trifluoromethyl-benzyl)-acetamide (Precursor 5A1-2)

To a solution of Precursor 5A1-1 (2.24 g, 3.61 mmol) in 10 mL DCM at RT is added 4M HCl soln. in dioxane (6.6 mL, 3 eq) and the resulting mixture is stirred overnight at rt. The mixture is concentrated, co-evaporated with DCM and dried under high vacuum to yield the sub title compound as light yellow foam which is used as such in the next step. LC-A: $t_R$=0.40 min; [M+H]$^+$=304.2

Step 4) To a microwave tube containing Precursor 5A1-2 (375 mg, 2 eq), Cs$_2$CO$_3$ (386 mg, 3.4 eq), Pd$_2$(dba$_2$)$_3$ (63.9 mg, 0.2 eq), Brettphos (74.9 mg, 0.4 eq) is added a solution of Precursor 3B1-1 (150 mg, 0.349 mmol) in 2 mL degassed toluene. The brown mixture is stirred for 20 mn at 140° C. under microwave irradiation. It is then cooled to RT and poured into water/DCM (1:1) mixture, the layers are separated and the resulting aq. phase is extracted twice with DCM. The combined organic layers are washed with sat. aq. NaHCO$_3$ soln., with brine, dried over MgSO$_4$, filtered and the volatiles are removed under reduced pressure. The crude is purified by silica gel flash chromatography (Biotage, SNAP 15 g, gradient Hept/EtOAc/MeOH 50:50:0 to 0:100:0 to 0:90:10). This yields the title compound as a yellow oil. LC-A: $t_R$=0.77 min; [M+H]$^+$=545.1

Example 27

2-(3-Cyclopropylmethyl-2,3,4,5-tetrahydro-1H-benzo[d]azepin-6-ylamino)-N-(2-dimethylamino-ethyl)-N-(2-trifluoromethyl-benzyl)-acetamide Step 1): N-(2-Dimethylamino-ethyl)-2-(2,3,4,5-tetrahydro-1H-benzo[d]azepin-6-ylamino)-N-(2-trifluoromethyl-benzyl)-acetamide (Precursor 3B1)

To a solution of Example 26 (80 mg, 0.141 mmol) in 2 mL MeOH and 1 mL water stirred at RT is added K$_2$CO$_3$ (117 mg, 6 eq). The yellow solution is stirred at 60° C. for 1 h. After cooling, water is added and extracted thrice with DCM. The combined organic phase is washed with NaHCO$_3$, with brine, dried over MgSO$_4$. Filtration and evaporation under reduced pressure yield the sub-title compound as a yellow oil which is used as such in the next step. LC-A: $t_R$=0.55 min; [M+H]$^+$=449.1

Step 2) Example 2 is obtained from Precursor 3B1 as described in the synthesis of Example 23 (Step 8). This yields the title compound as colorless oil. LC-A: $t_R$=0.60 min; [M+H]$^+$=503.2; $^1$H-NMR (400 MHz, d$_6$-DMSO) 66:34 mixture of rotamers δ: 7.78 (d, J=7.5 Hz, 0.34 H), 7.72 (d, J=7.8 Hz, 0.66 H), 7.67 (s, 0.34 H), 7.60 (t, J=7.5 Hz, 1 H), 7.52 (d, J=0.3 Hz, 0.34 H), 7.46 (t, J=7.7 Hz, 0.66 H), 7.37 (d, J=7.7 Hz, 0.34 H), 7.33 (d, J=7.7 Hz, 0.66H), 6.91 (t, J=7.7 Hz, 0.66 H), 6.82 (t, J=7.7 Hz, 0.34 H), 6.48 (d, J=8.1 Hz, 0.66 H), 6.44 (d, J=7.4 Hz, 0.66 H), 6.41 (d, J=7.6 Hz, 0.34 H), 6.24 (d, J=8.1 Hz, 0.34 H), 5.22 (bs, 0.66 H), 5.17 (bs, 0.34 H), 4.88 (s, 0.68 H), 4.77 (s, 1.32 H), 4.13 (bs, 1.32 H), 3.81 (bs, 0.68 H), 2.86-2.54 (m, 8 H), 2.41 (t, J=5.9 Hz, 1.32 H), 2.36 (m, 0.68 H), 2.29 (m, 2 H), 2.16 (s, 3.96 H), 2.10 (s, 2.04 H), 0.83 (m, 1 H), 0.44 (d, J=7.8 Hz, 2 H), 0.05 (m, 2 H).

Example 28

2-(2-Cyclopropylmethyl-2,3,4,5-tetrahydro-1H-benzo[c]azepin-6-ylamino)-N-(2-dimethylamino-ethyl)-N-(2-trifluoromethyl-benzyl)-acetamide Step 1): 2,2,2 Trifluoro-1-(6-methoxy-1,3,4,5-tetrahydro-2H-benzo[c]azepin-2-yl) ethan-1-one Precursor 4C1-1

To a solution of 6-methoxy-2,3,4,5-tetrahydro-1H-benzo[c]azepine (293 mg, 1.59 mmol) in 5 mL DCM cooled to 0° C. are added TEA (0.442 mL, 3.17 mmol) and TFAA (0.243 mL, 1.75 mmol). The reaction mixture is stirred between 0-5° C. for 2 h. The organic phase is washed with water then brine. The organic layer is dried over MgSO$_4$, filtered and evaporated under reduced pressure then dried with high vacuum. LC-A: $t_R$=0.88 min; [M+MeCN+H]$^+$=315.1

Step 2): 2,2,2-Trifluoro-1-(6-hydroxy-1,3, 4,5-tetrahydro-2H-benzo[c]azepin-2-yl)ethan-1-one Precursor 4C1-2 is obtained from Precursor 4C1-1 following the procedure described for the synthesis of Precursor 3A1-1 from 2,2,2-trifluoro-1-(6-methoxy-1,2,4,5-tetrahydro-benzo[d]azepin-3-yl)-ethanone. LC-A: $t_R$=0.76 min; [M+H]$^+$=n.d.

Step 3): 2-(2,2,2-Trifluoroacetyl)-2,3,4,5-tetrahydro-1H-benzo[c]azepin-6-yl trifluoromethanesulfonate Precursor 4C1-3 is obtained from Precursor 4C1-2 following the procedure described for the synthesis of Precursor 3B1-1 from Precursor 3A1-1. LC-A: $t_R$=0.96 min; [M+H]$^+$=n.d.; $^1$H NMR (500 MHz, d$_6$-DMSO) δ: 7.48 (dd, J$_1$=1.5 Hz, J$_2$=7.1 Hz, 1H), 7.37 (m, 2 H), 4.75 (bs, 2 H), 3.90 (bs, 3 H), 3.11 (dd, J$_1$=5.0 Hz, J$_2$=6.1 Hz, 2H), 1.85 (m, 2 H)

Step 4): N-(2-(dimethylamino)ethyl)-2-((2-(2,2,2-trifluoroacetyl)-2,3,4,5-tetrahydro-1H-benzo[c]azepin-6-yl)amino)-N-(2-(trifluoromethyl)benzyl)acetamide Precursor 4C1-4 is made according to the procedure described in the formation of Example 26 Step 4) using Precursor 5A1-2 and Precursor 4C1-3 as starting materials. LC-A: $t_R$=0.90 min; [M+H]$^+$=545.0

Step 5): N-(2-(dimethylamino)ethyl)-2-((2,3,4,5-tetrahydro-1H-benzo[c]azepin-6-yl)amino)-N-(2-(trifluoromethyl)benzyl)acetamide Precursor 4C1

To a solution of Precursor 4C1-4 (75 mg, 0.11 mmol) in 2 mL MeOH and 1 mL water at RT is added K$_2$CO$_3$ (43.5 mg, 0.22 mmol). The yellow suspension is stirred for 1 h at 60° C. After cooling the suspension is poured into a mixture of water and DCM, the layers are separated and the aqueous phase is extracted twice with DCM. The combined organic layers are washed with sat. aq. NaHCO$_3$ sol. and brine then dried over MgSO$_4$. Filtration and evaporation of the volatiles under reduced pressure yield the sub-title compound which is pure enough for further for the next step. LC-A: $t_R$=0.63 min; [M+H]$^+$=449.0

Step 6) To a solution of Precursor 4C1 (45 mg, 0.0831 mmol) in 2 mL DCM is added at RT cyclopropanecarboxaldehyde (12.4 μL, 0.166 mmol) and DIPEA (28.4 μL, 0.166 mmol). The yellow suspension is stirred for 10 min at RT then NaBH$_3$CN (35.2 mg, 0.166 mmol) is added and the mixture is stirred for a further 2 h at this temperature. Water is added and the resulting aq. phase is extracted thrice with DCM. The combined organic phase is washed with sat. aq. NaHCO$_3$ soln. and brine then dried over MgSO$_4$. After filtration and evaporation under reduced pressure the crude is purified by 2 prep. HPLC (Method C then Method D) to yield the title compound as a yellow oil. LC-A: $t_R$=0.60 min; [M+H]$^+$=503.2

Example 29

N-(2-tert-Butylamino-ethyl)-2-(4-cyclopropylmethyl-5-oxo-2,3,4,5-tetrahydro-benzo[f][1,4]oxazepin-6-ylamino)-N-(2-trifluoromethyl-benzyl)-acetamide Step 1): 6-amino-4-(cyclopropylmethyl)-3, 4-dihydrobenzo[f][1,4]oxazepin-5(2H)-one (Precursor 5A2-10)

To a solution of Precursor 5A1-8 (730 mg, 2.45 mmol) in 10 mL acetone are added at RT 2 mL sat. aq. NH$_4$Cl soln. and Zn powder (2508 mg, 38.4 mmol). The reaction mixture is stirred at rt. EtOAc is added followed by solid Na$_2$SO$_4$. The mixture is filtered through celite and the filtrate is rinsed with EtOAc. The combined organic mixture is concentrated under reduced pressure to yield the sub-title compound as a yellow solid. LC-A: $t_R$=0.64 min; [M+H]$^+$=233.2; $^1$H NMR (400 MHz, d$_6$-DMSO) δ: 7.07 (t, J=8.0 Hz, 1 H), 6.51 (d, J=8.2 Hz, 1 H), 6.21 (d, J=7.8 Hz, 1 H), 5.75 (s, 2 H), 4.20 (t, J=5.5 Hz, 2 H), 3.48 (t, J=5.5 Hz, 2 H), 3.40 (d, J=7.0 Hz, 2 H), 1.06 (m, 1 H), 0.49 (m, 2 H), 0.31 (m, 2 H)

Step 2): (4-(Cyclopropylmethyl)-5-oxo-2,3,4,5-tetrahydrobenzo[f][1,4]oxazepin-6-yl)glycine (Precursor 5A2-11)

To a solution of Precursor 5A2-10 (670 mg, 2.17 mmol) in 10 mL MeOH are added glyoxylic acid solution in water (0.595 mL, 4.34 mmol) and TEA (0.453 mL, 3.25 mmol). The reaction mixture is stirred for 20 min then is added NaBH$_3$CN (272 mg, 4.33 mmol) and stirred the resulting mixture is stirred for for 2 h. It is then poured into water and the resulting neutral aq. phase is then extracted twice with DCM. The organics are washed with brine, dried over MgSO$_4$, filtered and evaporated to yield the sub-title compound as a yellow oil which is used as such in the next step without any purification. LC-A: $t_R$=0.67 min; [M+H]$^+$=291.1

Step 3) To a solution of Precursor 5A2-11 (82 mg, 0.261 mmol) in 1.4 mL DMF are added at RT Amine B16 (71.6 mg, 0.261 mmol), HATU (119 mg, 0.313 mmol) and DIPEA (89.4 μL, 0.522 mmol). The yellow suspension is stirred for 2 h at rt, poured into sat. aq. NaHCO$_3$ solution. The resulting aq. phase is extracted twice with EtOAc, the combined organic phase is then washed with brine, dried over MgSO$_4$, filtered and evaporated under reduced pressure. The resulting crude is purified by prep. HPLC (Method C) to yield the title compound as a yellow oil. LC-A: t$_R$=0.93 min; [M+H]$^+$=547.1; $^1$H NMR (400 MHz, d$_6$-DMSO) 75:25 mixture of rotamers δ: 7.79 (d, J=7.7 Hz, 0.25 H), 7.73 (d, J=7.8 Hz, 0.75H), 7.68 (d, J=7.5 Hz, 0.25 H), 7.61 (t, J=7.5 Hz, 0.75 H), 7.48 (m, 1 H), 7.37 (d, J=7.7 Hz, 1 H), 7.23 (t, J=8.1 Hz, 0.75 H), 7.14 (t, J=8.1 Hz, 0.25 H), 6.97 (bs, 1 H), 6.56 (d, J=8.3 Hz, 0.75 H), 6.31 (m, 1 H), 6.27 (d, J=7.9 Hz, 0.25 H), 4.90 (s, 0.5H), 4.80 (s, 1.5 H), 4.22 (s, 3.5 H), 3.88 (d, J=3.4 Hz, 0.5 H), 2.64 (d, J=4.3 Hz, 2 H), 1.05 (m, 1 H), 0.97 (m, 9 H), 0.48 (m, 2 H), 0.30 (d, J=4.3 Hz, 2 H).

Example 30-33 and 35-38 from Table 4 below are made according in analogy to the procedure described for the synthesis of Example 29

TABLE 4

| Example | Compound | t$_R$ [min] (LC-A) | MS Data m/z [M + H]$^+$ |
|---|---|---|---|
| 30 | 2-(4-Cyclopropylmethyl-5-oxo-2,3,4,5-tetrahydro-benzo[f][1,4]oxazepin-6-ylamino)-N-(2,3-dichloro-benzyl)-N-(2-dimethylamino-ethyl)-acetamide | 0.90 | 519.0 |
| 31 | 2-(4-Cyclopropylmethyl-5-oxo-2,3,4,5-tetrahydro-benzo[f][1,4]oxazepin-6-ylamino)-N-(2,6-dichloro-benzyl)-N-(2-dimethylamino-ethyl)-acetamide | 0.89 | 519.0 |
| 32 | N-(2-Chloro-benzyl)-2-(4-cyclopropylmethyl-5-oxo-2,3,4,5-tetrahydro-benzo[f][1,4]oxazepin-6-ylamino)-N-(2-dimethylamino-ethyl)-acetamide | 0.85 | 485.1 |
| 33 | 2-(4-Cyclopropylmethyl-5-oxo-2,3,4,5-tetrahydro-benzo[f][1,4]oxazepin-6-ylamino)-N-(2-dimethylamino-ethyl)-N-(6-methyl-pyridin-2-ylmethyl)-acetamide | 0.66 | 466.1 |
| 35 | {2-[[2-(4-Cyclopropylmethyl-5-oxo-2,3,4,5-tetrahydro-benzo[f][1,4]oxazepin-6-ylamino)-acetyl]-(2-trifluoromethyl-benzyl)-amino]-ethyl}-isopropyl-carbamic acid tert-butyl ester | 1.23 | 633.2 |
| 37 | {2-[[2-(4-Cyclopropylmethyl-5-oxo-2,3,4,5-tetrahydro-benzo[f][1,4]oxazepin-6-ylamino)-acetyl]-(2-trifluoromethyl-benzyl)-amino]-ethyl}-methyl-carbamic acid tert-butyl ester | 1.17 | 605.1 |
| 38 | 2-(4-Cyclopropylmethyl-5-oxo-2,3,4,5-tetrahydro-benzo[f][1,4]oxazepin-6-ylamino)-N-(2-dimethylamino-ethyl)-N-(2-trifluoromethyl-benzyl)-acetamide | 0.75 | 519.4 |

Example 34

2-(4-Cyclopropylmethyl-5-oxo-2,3,4,5-tetrahydro-benzo[f][1,4]oxazepin-6-ylamino)-N-(2-isopropylamino-ethyl)-N-(2-trifluoromethyl-benzyl)-acetamide To a solution Example 35 in 2 mL DCM is added TFA (46.4 µL, 0.606 mmol) at RT. The mixture is stirred for 2 h at RT. After evaporation of the volatiles the crude is purified by prep. HPLC (Method C) the yield the title compound as a yellow foam. LC-A: t$_R$=0.91 min; [M+H]$^+$=533.1

Example 36

2-(4-Cyclopropylmethyl-5-oxo-2,3,4,5-tetrahydro-benzo[f][1,4]oxazepin-6-ylamino)-N-(2-methyl-amino-ethyl)-N-(2-trifluoromethyl-benzyl)-acetamide is made from Example 37 as described in the synthesis of Example 34 from Example 35. LC-A: t$_R$=0.88 min; [M+H]$^+$=505.1

Example 39

N-(2-Dimethylamino-ethyl)-2-(4-ethyl-5-oxo-2,3,4,5-tetrahydro-benzo[f][1,4]oxazepin-9-ylamino)-N-(3-methyl-pyridin-2-ylmethyl)-acetamide Step 1): N-ethyl-2-fluoro-N-(2-hydroxyethyl)-3-nitrobenzamide (Precursor 4A1-9)

To a solution of 2-fluoro-3-nitrobenzoic acid (2 g, 10.8 mmol) and COMU (5724 mg, 13 mmol) in 100 mL of DCM are added 2-(ethylamino)ethanol (1.08 mL, 10.8 mmol) and DIPEA (5.55 mL, 32.4 mmol) at RT under Ar. The resulting mixture is stirred at RT for 18 h. The reaction mixture is treated with 50 mL aq. sat. NaHCO$_3$ solution. The organic phase is separated. The aqueous phase is extracted twice with 50 mL DCM. The combined organic phase is washed with 100 mL brine, dried over MgSO$_4$, filtered and evaporated under reduced pressure. The crude residue is purified by flash chromatography over 80 g of silica gel with heptane/EtOAc system (1:1 to 0:1 gradient) as eluent to yield the title compound as a brownish oil. LC-A: t$_R$=0.59 min; [M+H]$^+$=257.2

Step 2): 4-Ethyl-9-nitro-3,4-dihydrobenzo[f][1,4]oxazepin-5(2H)-one (Precursor 4A1-10)

A solution of Precursor 4A1-9 (1238 mg, 4.83 mmol) in 20 mL DMF is treated at once with cesium carbonate (4723 mg, 14.5 mmol) at 0° C. under Ar. The mixture is stirred overnight at 60° C. The mixture is cooled to RT and filtered. The filter cake is washed with 20 mL ACN and the resulting solution is evaporated until dryness under reduced pressure to afford the crude product with a purity level compatible with the next step. LC-A: t$_R$=0.68 min; [M+H]$^+$=237.1

Step 3): 9-Amino-4-ethyl-3,4-dihydro-2H-benzo[f][1,4]oxazepin-5-one (Precursor 4D1-1)

To a solution of Precursor 4A2-10 (3.05 g, 12.9 mmol) in 40 mL of acetone at RT is added 20 mL of a sat. aq. NH$_4$Cl solution. The reaction mixture is cooled to 0° C. then Zn dust (10.14 g, 155.0 mmol) is added portionwise. The reaction mixture is warmed up to RT and the suspension is stirred vigorously at RT for 24 h. EtOAc (30 ml) is added followed by MgSO$_4$ (10 g). The suspension is stirred for 15 min then filtered through a Celite pad and washed with 80 mL EtOAc. The combined filtrates are evaporated under reduced pressure to afford the crude subtitle product with a purity level compatible with the next step. LC-A: t$_R$=0.41 min; [M+H]$^+$=207.1

Step 4): (4-ethyl-5-oxo-2,3,4,5-tetrahydrobenzo[f][1,4]oxazepin-9-yl)glycine) (Precursor 4D1)

To a solution of 9-amino-4-ethyl-3,4-dihydro-2H-benzo[f][1,4]oxazepin-5-one from Step 3) (200 mg, 0.97 mmol) and TEA (147 mg, 1.45 mmol) in 10 mL of anhydrous MeOH is added glyoxylic acid monohydrate (182 mg, 1.94 mmol). The reaction mixture is stirred at RT for 30 min then treated with NaBH$_3$CN (122 mg, 1.94 mmol). The stirred reaction mixture is left reacting at RT for 2 h. The mixture is treated with 15 mL water and 20 mL 1N HCl aq. soln. then extracted three times with 25 mL EtOAc. The combined organic phase is washed with 25 mL brine, dried over MgSO$_4$, filtered and evaporated under reduced pressure to afford the crude sub-title product with a purity level compatible with the next step. LC-A: t$_R$=0.53 min; [M+H]$^+$=265.1

Step 5) To a solution of Precursor 4D1 (150 mg, 0.568 mmol) in 5 mL DMF is added Amine B23 (110 mg, 0.568 mmol), HATU (259 mg, 0.681 mmol) and DIPEA (0.243 mL, 1.42 mmol). The resulting mixture is stirred overnight at RT then 5 mL sat. NaHCO$_3$ sol. are added and the resulting aq. phase is extracted twice with DCM, dried over MgSO$_4$, filtered and evaporated. The residue is purified by prep. HPLC (Method C) then by preparative TLC using as eluent DCM/MeOH 95:5 to yield the title compound. LC-A: t$_R$=0.54 min; [M+H]$^+$=440.2

Example 61

2-(4-Cyclopropylmethyl-5-oxo-2,3,4,5-tetrahydro-benzo[f][1,4]oxazepin-9-ylamino)-N-(2-dimethyl-amino-ethyl)-N-(2-trifluoromethyl-benzyl)-acetamide Step 1): N-Cyclopropylmethyl-2-fluoro-N-(2-hydroxy-ethyl)-3-nitro-benzamide (Precursor 4A1-9)

A solution of 2-fluoro-3-nitrobenzoic acid (0.5 g, 2.7 mmol) in 1.6 mL of thionylchloride is heated under reflux for 5 h. The resulting solution is concentrated under reduced pressure The residue is dissolved in 5 mL toluene and concentrated again under reduced pressure. The crude 2-fluoro-3-nitro-benzoyl chloride is dissolved in 25 mL DCM, the resulting solution is cooled to 0° C. and treated with 0.7 mL DIPEA under argon. A solution of cyclopropylmethyl-[2-(4-methoxy-benzyloxy)-ethyl]-amine (636 mg, 2.7 mmol) in 10 mL DCM is added dropwise. The mixture is stirred at RT for 18 h. The reaction mixture is treated with 50 mL aq. sat. NaHCO$_3$ solution. The organic phase is separated. The aqueous phase is extracted twice with 50 mL DCM. The combined organic phase is washed with 100 mL brine, dried over MgSO$_4$, filtered and evaporated under reduced pressure. The crude residue is purified by flash chromatography over 80 g of silica gel with heptane/EtOAc (4:1 to 1:1 gradient) as eluent to yield N-cyclopropylmethyl-2-fluoro-N-[2-(4-methoxy-benzyloxy)-ethyl]-3-nitro-benzamide as a yellowish oil. LC-A: t$_R$=0.92 min; [M+H]$^+$=403.15.

A solution of N-cyclopropylmethyl-2-fluoro-N-[2-(4-methoxy-benzyloxy)-ethyl]-3-nitro-benzamide (609 mg, 1.51 mmol, 1 eq) in DCM (10 mL) at 0° C. is treated with a solution of boron tribromide solution 1M in DCM (1.55 mL, 9.08 mmol, 6 eq). The mixture is stirred at 0° C. for 45 min. Then 15 mL of saturated aqueous NaHCO$_3$ solution are added and the aqueous phase is extracted with DCM (2×30 mL), dried over MgSO$_4$, filtered and evaporated. The title compound is obtained as a yellowish oil. LC-A: t$_R$=0.67 min; [M+H]$^+$=283.18.

Step 2): 4-Cyclopropylmethyl-9-nitro-3,4-dihydro-2H-benzo[f][1,4]oxazepin-5-one (Precursor 4A5-10)

A solution of N-cyclopropylmethyl-2-fluoro-N-(2-hydroxy-ethyl)-3-nitro-benzamide (804 mg, 2.85 mmol) in 15 mL DMF is treated at once with cesium carbonate (2784 mg, 8.55 mmol) at 0° C. under Ar. The mixture is stirred overnight at 60° C. The mixture is cooled to RT and filtered. The filter cake is washed with 20 mL ACN and the resulting solution is evaporated until dryness under reduced pressure to afford the crude product with a purity level compatible with the next step. LC-A: t$_R$=0.77 min; [M+H]$^+$=263.21.

Step 3): 9-Amino-4-cyclopropylmethyl-3, 4-dihydro-2H-benzo[f][1,4]oxazepin-5-one (Precursor 4D2-1)

A flask is charged with Pd/C 10% wet (50.7 mg, 0.477 mmol) then 25 mL MeOH are added under Ar. Then 4-cyclopropylmethyl-9-nitro-3,4-dihydro-2H-benzo[f][1,4]oxazepin-5-one (250 mg, 0.953 mmol, 1 eq) is suspended in 10 mL MeOH and the resulting suspension is purged with argon and then added to the Pd suspension. The dark mixture is stirred under H$_2$ at RT overnight. The mixture is filtered and evaporated until dryness under reduced pressure to afford the crude product with a purity level compatible with the next step. LC-A: t$_R$=0.50 min; [M+H]$^+$=233.24.

Step 4): (4-Cyclopropylmethyl-5-oxo-2,3,4,5-tetrahydro-benzo[f][1,4]oxazepin-9-ylamino)-acetic acid (Precursor 4D2)

To a solution of 9-amino-4-cyclopropylmethyl-3,4-dihydro-2H-benzo[f][1,4]oxazepin-5-one from Step 3) (209 mg, 0.9 mmol) in 10 mL of anhydrous MeOH is added glyoxylic acid monohydrate (166 mg, 1.8 mmol). The reaction mixture is stirred at RT for 30 min. The reaction mixture is degassed and purged with Ar then treated with Pd/C 10% (67 mg, 0.63 mmol). The well stirred suspension is put under an atmospheric pressure of H$_2$ and left reacting at RT for 18 h. The mixture is purged with Ar, filtered and evaporated until dryness under reduced pressure. Purification of the crude by prep. HPLC (Method LC-C) affords the title compound as a light brownish oil. LC-A: t$_R$=0.61 min; [M+H]$^+$=291.16

Step 5)

To a solution of Precursor 4D2 (80 mg, 0.276 mmol) in 2 mL DCM is added Amine B1 (68 mg, 0.276 mmol), T$_3$P (351 mg of a 50% sol. In DCM, 0.55 mmol) in DCM and DIPEA (0.118 mL, 0.69 mmol). The resulting mixture is stirred overnight at RT then 5 mL sat. NaHCO$_3$ sol. are added and the resulting aq. phase is extracted twice with DCM. The organic phase is dried over MgSO4, filtered and evaporated. The residue is purified by Prep (Method LC-C) to yield the title compound. LC-B: t$_R$=0.70 min; [M+H]$^+$=519.3

Example 40, 41, 57, 58, 59, 60, 63 and 64 from Table 5 are made from Precursor 4D1 or 4D2 as described for the synthesis of Example 39

TABLE 5

| Example | Compound | $t_R$ [min] (LC-) | MS Data m/z $[M + H]^+$ |
|---|---|---|---|
| 40 | N-(2-tert-Butylamino-ethyl)-2-(4-ethyl-5-oxo-2,3,4,5-tetrahydro-benzo[f][1,4]oxazepin-9-ylamino)-N-(2-trifluoromethyl-benzyl)-acetamide | 0.71 (LC-A) | 521.3 |
| 41 | N-(2-Dimethylamino-ethyl)-2-(4-ethyl-5-oxo-2,3,4,5-tetrahydro-benzo[f][1,4]oxazepin-9-ylamino)-N-(2-trifluoromethyl-benzyl)-acetamide | 0.67 (LC-A) | 493.2 |
| 57 | 2-(4-Ethyl-5-oxo-2,3,4,5-tetrahydro-benzo[f][1,4]oxazepin-9-ylamino)-N-(2-pyrrolidin-1-yl-ethyl)-N-(3-trifluoromethyl-pyridin-2-ylmethyl)-acetamide | 0.58 (LC-B) | 520.2 |
| 58 | N-(2-Dimethylamino-ethyl)-2-(4-ethyl-5-oxo-2,3,4,5-tetrahydro-benzo[f][1,4]oxazepin-9-ylamino)-N-(3-trifluoromethyl-pyridin-2-ylmethyl)-acetamide | 0.56 (LC-B) | 494.2 |
| 59 | N-(3-Chloro-pyridin-2-ylmethyl)-2-(4-ethyl-5-oxo-2,3,4,5-tetrahydro-benzo[f][1,4]oxazepin-9-ylamino)-N-(2-pyrrolidin-1-yl-ethyl)-acetamide | 0.54 (LC-B) | 486.2 |
| 60 | N-(3-Chloro-pyridin-2-ylmethyl)-N-(2-dimethylamino-ethyl)-2-(4-ethyl-5-oxo-2,3,4,5-tetrahydro-benzo[f][1,4]oxazepin-9-ylamino)-acetamide | 0.52 (LC-B) | 460.2 |
| 63 | N-(2-tert-Butylamino-ethyl)-2-(4-cyclopropylmethyl-5-oxo-2,3,4,5-tetrahydro-benzo[f][1,4]oxazepin-9-ylamino)-N-(2-trifluoromethyl-benzyl)-acetamide | 0.74 (LC-B) | 547.3 |
| 64 | 2-(4-Cyclopropylmethyl-5-oxo-2,3,4,5-tetrahydro-benzo[f][1,4]oxazepin-9-ylamino)-N-(2-pyrrolidin-1-yl-ethyl)-N-(3-trifluoromethyl-pyridin-2-ylmethyl)-acetamide | 0.65 (LC-B) | 546.3 |

Example 56

2-(4-Ethyl-5-oxo-2,3,4,5-tetrahydro-benzo[f][1,4]oxazepin-9-ylamino)-N-(2-isopropylamino-ethyl)-N-(2-trifluoromethyl-benzyl)-acetamide Step 1) {2-[[2-(4-Ethyl-5-oxo-2,3,4,5-tetrahydro-benzo[f][1,4]oxazepin-9-ylamino)-acetyl]-(2-trifluoromethyl-benzyl)-amino]-ethyl}-isopropyl-carbamic acid tert-butyl ester To a solution of Precursor 4D (200 mg, 0.76 mmol) in 5 mL DMF is added Amine B21 (273 mg, 0.76 mmol), HATU (345 mg, 0.91 mmol) and DIPEA (0.324 mL, 1.89 mmol). The resulting mixture is stirred overnight at RT then 5 mL sat. NaHCO₃ sol. are added and the resulting aq. phase is extracted twice with 10 mL DCM, dried over MgSO4, filtered and evaporated. The residue is purified by prep. HPLC (Method C) then by prep. TLC using as eluent DCM/MeOH 95:5 to yield the title compound. LC-A: $t_R$=1.01 min; [M+H]⁺=607.2

Step 2)

To a solution of {2-[[2-(4-ethyl-5-oxo-2,3,4,5-tetrahydro-benzo[f][1,4]oxazepin-9-ylamino)-acetyl]-(2-trifluoromethyl-benzyl)-amino]-ethyl}-isopropyl-carbamic acid tert-butyl ester (185 mg, 0.305 mmol) in 5 mL DCM is added TFA (0.14 mL, 1.83 mmol) at RT. The mixture is stirred for 2 h at RT. After evaporation of the volatiles the crude is purified by prep. HPLC (Method LC-C) to yield the title compound as a yellow foam. LC-B: $t_R$=0.66 min; [M+H]⁺=507.3

Example 62

2-(4-Cyclopropylmethyl-5-oxo-2,3,4,5-tetrahydro-benzo[f][1,4]oxazepin-9-ylamino)-N-(2-isopropylamino-ethyl)-N-(2-trifluoromethyl-benzyl)-acetamide Step 1) {{2-[[2-(4-Cyclopropylmethyl-5-oxo-2,3,4,5-tetrahydro-benzo[f][1,4]oxazepin-9-ylamino)-acetyl]-(2-trifluoromethyl-benzyl)-amino]-ethyl}-isopropyl-carbamic acid tert-butyl ester To a solution of Precursor 4D2 (100 mg, 0.34 mmol) in 3 mL DCM is added Amine B21 (124 mg, 0.34 mmol), T₃P (438 mg of a 30% solution in DCM, 0.7 mmol) and DIPEA (0.15 mL, 0.86 mmol). The resulting mixture is stirred overnight at RT then 5 mL sat. NaHCO₃ sol. are added and the resulting aq. phase is extracted twice with 10 mL DCM, dried over MgSO₄, filtered and evaporated. The residue is purified by prep. HPLC (Method C) then by prep. TLC using as eluent DCM/MeOH 95:5 to yield the title compound. LC-A: $t_R$=1.04 min; [M+H]⁺=633.28

Step 2) To a solution of {{2-[[2-(4-cyclopropylmethyl-5-oxo-2,3,4,5-tetrahydro-benzo[f][1,4]oxazepin-9-ylamino)-acetyl]-(2-trifluoromethyl-benzyl)-amino]-ethyl}-isopropyl-carbamic acid tert-butyl ester (54 mg, 0.085 mmol) in 3 mL DCM is added TFA (0.04 mL, 0.51 mmol) at RT. The mixture is stirred for 2 h at RT. After evaporation of the volatiles the crude is purified by prep. HPLC (Method LC-C) to yield the title compound as a yellow foam. LC-B: $t_R$=0.73 min; [M+H]⁺=533.3

Amine Building Blocks

Amines B1-B31 are either commercially available or are prepared following of the method A described below:

Amine B2

Method A

N'-(3-Chloro-pyridin-2-ylmethyl)-N,N-dimethyl-ethane-1,2-diamine

To a solution of 3-chloro-2-formylpyridine (1.5 g, 10.6 mmol) in 25 mL DCM are added 2-dimethylamino-ethylamine (1.27 mL, 11.7 mmol) and DIPEA (3.6 mL, 21.2 mmol). The resulting solution is treated portionwise with NaBH(OAc)$_3$ (3.37 g, 15.9 mmol) and allowed to stir for 18 h at RT. The reaction mixture is diluted with 10 mL DCM and washed with 25 mL aq. sat. NaHCO$_3$ solution. The aqueous phase is extracted twice with 20 mL DCM. The combined organic phase is washed with 70 mL brine, dried over MgSO$_4$, filtered and evaporated under reduced pressure. This yields the title compound (1.6 g, 71%) as a colourless liquid. LC-A: $t_R$=0.20 min; [M+H]$^+$=214.17

Amines listed in Table 6 below are commercially available or are prepared by applying the above-mentioned methods A using commercially available starting materials. Prepared amines are characterized by their LC-MS data.

II. Biological Assays

In Vitro Assay

The CXCl12 receptor and CXCR7 agonistic activities of the compounds of formula (I) are determined in accordance with the following experimental method.

The assay is using the PathHunter™ CHO-K1 CXCR7 β-arrestin cell line from DiscoverX. The system is based on the Enzyme Fragment Complementation Technology. Two complementing fragments of the β-galactosidase enzyme are expressed within stably transfected cells. The larger portion of β-gal, termed EA for Enzyme Acceptor, is fused to the C-terminus of b-arrestin 2. The smaller fragment, termed ProLink™ tag, is fused to CXCR7 at the C-terminus. Upon activation, b-arrestin is recruited which forces the interaction of ProLink and EA, allowing complementation

TABLE 6

| Amine No | Compound name |
|---|---|
| B1 | N,N-Dimethyl-N'-(2-trifluoromethyl-benzyl)-ethane-1,2-diamine |
| B3 | N,N-Dimethyl-N'-(3-trifluoromethyl-benzyl)-ethane-1,2-diamine |
| B4 | N'-(4-Fluoro-2-trifluoromethyl-benzyl)-N,N-dimethyl-ethane-1,2-diamine; LC-A: $t_R$ = 0.42 min; [M + H]$^+$ = 265.1 |
| B5 | (2-Morpholin-4-yl-ethyl)-(2-trifluoromethyl-benzyl)-amine |
| B6 | 1-[2-(2-Trifluoromethyl-benzylamino)-ethyl]-pyrrolidin-2-one; LC-A: $t_R$ = 0.51 min; [M + H]$^+$ = 287.2 |
| B7 | (2-Chloro-benzyl)-(2-pyrrolidin-1-yl-ethyl)-amine |
| B8 | (2,4-Difluoro-benzyl)-(2-pyrrolidin-1-yl-ethyl)-amine |
| B9 | N,N-Dimethyl-N'-(3-trifluoromethyl-pyridin-2-ylmethyl)-ethane-1,2-diamine; LC-A: $t_R$ = 0.25 min; [M + H]$^+$ = 248.1 |
| B10 | N'-(2,6-Difluoro-benzyl)-N,N-dimethyl-ethane-1,2-diamine;: LC-G: $t_R$ = 1.12 min; [M + H]$^+$ = 215.2 |
| B11 | N-Cyclopropyl-N-methyl-N'-(2-trifluoromethyl-benzyl)-ethane-1,2-diamine; LC-A: $t_R$ = 0.42 min; [M + H]$^+$ = 273.2 |
| B12 | N'-(3-Bromo-benzyl)-N,N-dimethyl-ethane-1,2-diamine; LC-A: $t_R$ = 0.36 min; [M + H]$^+$ = 257.1 |
| B13 | (3-Chloro-pyridin-2-ylmethyl)-[2-(4,4-difluoro-piperidin-1-yl)-ethyl]-amine; LC-A: $t_R$ = 0.42 min; [M + H]$^+$ = 290.1 |
| B14 | N'-(4-Methoxy-pyridin-2-ylmethyl)-N,N-dimethyl-ethane-1,2-diamine; LC-A: $t_R$ = 0.19 min; [M + H]$^+$ = 210.2 |
| B15 | N,N-Dimethyl-N'-(4-methyl-pyridin-2-ylmethyl)-ethane-1,2-diamine; LC-A: $t_R$ = 0.19 min; [M + H]$^+$ = 194.2 |
| B16 | N-tert-Butyl-N'-(2-trifluoromethyl-benzyl)-ethane-1,2-diamine; LC-A: $t_R$ = 0.44 min; [M + H]$^+$ = 275.2 |
| B17 | N'-(2,3-Dichloro-benzyl)-N,N-dimethyl-ethane-1,2-diamine; LC-C: $t_R$ = 0.95 min; [M + H]$^+$ = 247.1 |
| B18 | N'-(2,6-Dichloro-benzyl)-N,N-dimethyl-ethane-1,2-diamine; LC-C: $t_R$ = 0.94 min; [M + H]$^+$ = 247.0 |
| B19 | N'-(2-Chloro-benzyl)-N,N-dimethyl-ethane-1,2-diamine; LC-A: $t_R$ = 0.30 min; [M + H]$^+$ = 212.1 |
| B20 | N,N-Dimethyl-N'-(6-methyl-pyridin-2-ylmethyl)-ethane-1,2-diamine; LC-A: $t_R$ = 0.20 min; [M + H]$^+$ = 194.4 |
| B21 | Isopropyl-[2-(2-trifluoromethyl-benzylamino)-ethyl]-carbamic acid tert-butyl ester; LC-A: $t_R$ = 0.74 min; [M + H]$^+$ = 361.3 |
| B22 | Methyl-[2-(2-trifluoromethyl-benzylamino)-ethyl]-carbamic acid tert-butyl ester; LC-A: $t_R$ = 0.65 min; [M + H]$^+$ = 333.1 |
| B23 | N,N-Dimethyl-N'-(3-methyl-pyridin-2-ylmethyl)-ethane-1,2-diamine; LC-A: $t_R$ = 0.20 min; [M + H]$^+$ = 194.3 |
| B24 | (2-Pyrrolidin-1-yl-ethyl)-(3-trifluoromethyl-pyridin-2-ylmethyl)-amine; LC-A: $t_R$ = 0.31 min; [M + H]$^+$ = 274.08 |
| B25 | N,N-Dimethyl-N'-(2-trifluoromethyl-thiazol-5-ylmethyl)-ethane-1,2-diamine; LC-A: $t_R$ = 0.29 min; [M + H]$^+$ = 254.17 |
| B26 | N'-(5-Chloro-1-methyl-3-trifluoromethyl-1H-pyrazol-4-ylmethyl)-N,N-dimethyl-ethane-1,2-diamine; LC-A: $t_R$ = 0.31 min; [M + H]$^+$ = 285.17 |
| B27 | (2-Morpholin-4-yl-ethyl)-(3-trifluoromethyl-pyridin-2-ylmethyl)-amine; LC-A: $t_R$ = 0.33 min; [M + H]$^+$ = 290.07 |
| B28 | Isopropyl-[2-(3-trifluoromethyl-pyridin-2-ylmethyl)amino-ethyl]-carbamic acid tert-butyl ester; LC-A: $t_R$ = 0.81 min; [M + H]$^+$ = 362.3 |
| B29 | N-tert-Butyl-N'-(2-chloro-benzyl)-ethane-1,2-diamine; $t_R$ = 0.41 min; [M + H]$^+$ = 241.1 |
| B30 | N-tert-Butyl-N'-(3-chloro-pyridin-2-ylmethyl)-ethane-1,2-diamine; $t_R$ = 0.31 min; [M + H]$^+$ = 242.1 |
| B31 | N-tert-Butyl-N'-(3-trifluoromethyl-pyridin-2-ylmethyl)-ethane-1,2-diamine; $t_R$ = 0.40 min; [M + H]$^+$ = 276.2 | of the two fragments of b-gal and the formation of a functional enzyme which is capable of hydrolysing the substrate and generating a chemiluminescent signal.

CHO-K1 CXCR7 β-arrestin cells are detached from culture dishes with a cell dissociation buffer (Invitrogen, #13151-014) and collected in growing medium (F12 HAMS 90% (v/v)/FCS 10% (v/v), Penicillin/streptomycin 1% (v/v)). 5000 cells per well (in 20 µl) are seeded in a 384 well plate (white-walled, clear bottom; BD Falcon #353274). The plate is incubated at 37° C./5% $CO_2$ for 24 hours. Medium is then replaced by 20 µl OPTIMEM (Invitrogen #31985) for 3 to 4 hours. Test compounds are dissolved at 10 mM in DMSO and serially diluted in DMSO to 200× of the final concentration for dose response curves. Compounds are then diluted 1:33.3 in HBSS1X. 5 µl/well of HBSS1X/20 mM HEPES/0.2% BSA are added to the assay plate followed by addition of 5 µl/well of diluted compounds. CXCL12 (Peprotech #300-28A) may be used as a reference agonist. The plate is incubated for 90 minutes at 37° C. 12 µl of detection reagent (Path Hunter Detection Kit, DiscoveRx, #93-0001) is transferred to the assay plate and to the plate is incubated for 1 hour at room temperature. Luminescent signal is read in a microplate reader (FLUOstar Optima, bmg). The calculated $EC_{50}$ values may fluctuate depending on the daily cellular assay performance. Fluctuations of this kind are known to those skilled in the art. Average $EC_{50}$ values from several measurements are given as geometric mean values.

Agonistic activities of exemplified compounds are displayed in Table 7:

TABLE 7

| Example Number | CXCR7 $EC_{50}$ (nM) |
|---|---|
| 1 | 8 |
| 2 | 3 |
| 3 | 9 |
| 4 | 24 |
| 5 | 7 |
| 6 | 19 |
| 7 | 4 |
| 8 | 36 |
| 9 | 200 |
| 10 | 58 |
| 11 | 190 |
| 12 | 14 |
| 13 | 88 |
| 14 | 76 |
| 15 | 11 |
| 16 | 74 |
| 17 | 59 |
| 18 | 53 |
| 19 | 12 |
| 20 | 73 |
| 21 | 6 |
| 22 | 4 |
| 23 | 1 |
| 24 | 3 |
| 25 | 3 |
| 26 | 4 |
| 27 | 2 |
| 28 | 3 |
| 29 | 3 |
| 30 | 7.8 |
| 31 | 27 |
| 32 | 15 |
| 33 | 24 |
| 34 | 5 |
| 35 | 420 |
| 36 | 12 |
| 37 | 410 |
| 38 | 4 |
| 39 | 400 |

TABLE 7-continued

| Example Number | CXCR7 $EC_{50}$ (nM) |
|---|---|
| 40 | 7 |
| 41 | 22 |
| 42 | 7 |
| 43 | 4 |
| 44 | 130 |
| 45 | 50 |
| 46 | 5 |
| 47 | 430 |
| 48 | 47 |
| 49 | 2 |
| 50 | 340 |
| 51 | 1 |
| 52 | 1 |
| 55 | 10 |
| 56 | 16 |
| 57 | 60 |
| 58 | 74 |
| 59 | 260 |
| 60 | 260 |
| 61 | 9 |
| 62 | 5 |
| 63 | 2 |
| 64 | 7 |
| 65 | 18 |
| 66 | 18 |
| 67 | 37 |
| 68 | 15 |
| 69 | 430 |
| 70 | 4 |
| 71 | 4 |
| 72 | 6 |
| 73 | 59 |
| 74 | 5 |
| 75 | 19 |
| 76 | 430 |
| 77 | 280 |
| 78 | 240 |
| 82 | 2 |
| 83 | 3 |
| 84 | 4 |
| 85 | 3 |
| 86 | 14 |
| 87 | 23 |
| 88 | 15 |
| 89 | 5 |
| 90 | 7 |
| 91 | 8 |
| 92 | 10 |
| 93 | 3 |
| 94 | 4 |

The invention claimed is:
1. A compound of formula (I)

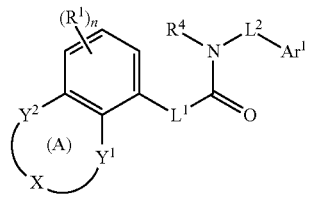

Formula (I)

wherein
ring (A) represents a seven-membered ring, wherein
$Y^1$ represents O,
$Y^2$ represents $CH_2$ or CO; and
X represents *—$CH_2$—$CH_2$—$NR^5$—; or
X represents *—$CH_2$—CO—$NR^5$—;
wherein the asterisks indicate a bond which is attached to the group $Y^1$;

R⁵ represents
(C₁₋₆)alkyl;
(C₁₋₄)alkyl mono-substituted with (C₁₋₃)alkoxy, cyano, vinyl; ethynyl, or (C₁₋₃)alkoxy-carbonyl;
—CO—R¹⁰ wherein R¹⁰ represents (C₁₋₅)alkyl; (C₁₋₅)alkoxy; (C₃₋₆)cycloalkyl-(C₁₋₃)alkyl; (C₃₋₄)alkenoxy; (C₃₋₄)alkynoxy; (C₁₋₃)fluoroalkyl; (C₁₋₃)fluoroalkoxy; (C₁₋₃)alkoxy-(C₂₋₃)alkoxy; hydroxyl-(C₁₋₅)alkyl, (C₁₋₃)alkoxy-(C₁₋₃)alkyl; (C₃₋₆)cycloalkyl optionally comprising one ring oxygen atom, wherein said cycloalkyl is optionally mono- or di-substituted wherein the substituents independently are fluoro or (C₁)fluoroalkyl;
or —NR¹⁰ᵃR¹⁰ᵇ wherein R¹⁰ᵃ and R¹⁰ᵇ independently represent hydrogen, (C₁₋₄)alkyl or (C₃₋₆)cycloalkyl, or R¹⁰ᵃ and R¹⁰ᵇ together with the nitrogen to which they are attached to form a 5- to 7-membered saturated ring;
(C₂₋₄)fluoroalkyl;
(C₃₋₆)cycloalkyl optionally comprises one ring oxygen atom;
(C₃₋₆)cycloalkyl-(C₁₋₃)alkyl, wherein the (C₃₋₆)cycloalkyl group optionally comprises one ring oxygen atom; wherein said cycloalkyl is optionally substituted with one or two methyl substituents;
(R¹)ₙ represents one or two optional substituents independently selected from (C₁₋₄)alkyl, (C₁₋₄)alkoxy, halogen, (C₁₋₃)fluoroalkyl, (C₁₋₃)fluoroalkoxy, or cyano;
L¹ represents a two-membered linker group selected from —NH—CH₂—*; —O—CH₂—*; —CH₂—CH₂—; or —CH═CH—; wherein the asterisks indicate the bond with which the group L¹ is attached to the carbonyl group;
L² represents —(C₁₋₃)alkylene—;
Ar¹ represents phenyl, or 5- or 6-membered heteroaryl; wherein said phenyl or 5- or 6-membered heteroaryl independently is unsubstituted, mono-, di- or tri-substituted, wherein the substituents are independently selected from (C₁₋₄)alkyl; (C₁₋₄)alkoxy; (C₁₋₃)fluoroalkyl; (C₁₋₃)fluoroalkoxy; halogen; or cyano; and
R⁴ represents
(C₂₋₆)alkyl;
(C₂₋₅)alkyl which is mono-substituted with (C₁₋₄)alkoxy, cyano, or hydroxy; or di-substituted wherein the substituents are independently selected from (C₁₋₃)alkoxy, or hydroxy;
(C₂₋₃)fluoroalkyl which is optionally further substituted with one hydroxy;
—(C₂₋₄)alkylene-NR⁶R⁷, wherein R⁶ and R⁷ independently represent hydrogen; (C₁₋₄)alkyl; —CO—(C₁₋₄)alkoxy; —SO₂—(C₁₋₃)alkyl; (C₂₋₃)fluoroalkyl; (C₃₋₆)cycloalkyl or (C₃₋₆)cycloalkyl-(C₁₋₃)alkyl, wherein in the above groups the (C₃₋₆)cycloalkyl group optionally comprises one ring oxygen atom, and wherein said (C₃₋₆)cycloalkyl group is optionally substituted with methyl;
—(C₁₋₃)alkylene-CO—R⁸, wherein R⁸ represents (C₁₋₄)alkoxy; or R⁸ represents NR⁸¹R⁸² wherein R⁸¹ and R⁸² independently represent hydrogen or (C₁₋₄)alkyl, or R⁸¹ and R⁸² together with the nitrogen to which they are attached to form a 4- to 6-membered saturated ring optionally substituted with two fluoro substituents;
(C₃₋₆)cycloalkyl or (C₃₋₆)cycloalkyl-(C₁₋₃)alkyl, wherein in the above groups the cycloalkyl group is optionally mono-substituted with hydroxy;

(C₄₋₇)heterocyclyl or (C₄₋₇)heterocyclyl-(C₁₋₃)alkyl, wherein in the above groups the (C₄₋₇)heterocyclyl independently comprises one or two ring heteroatoms independently selected from nitrogen, sulfur, or oxygen; wherein in the above groups said (C₄₋₇)heterocyclyl independently is unsubstituted, or mono-, or di-substituted, wherein the substituents are independently selected from:
one oxo substituent attached to a ring carbon atom in alpha position to a ring nitrogen; and/or
two oxo substituents at a ring sulfur ring atom (thus forming a —SO₂—group); and/or
(C₁₋₄)alkyl attached to a ring nitrogen atom having a free valency; and/or
two fluoro substituents attached to a ring carbon atom; and/or
in case of a (C₄₋₇)heterocyclyl-(C₁₋₃)alkyl group, methyl attached to a ring carbon atom which is attached to the linking (C₁₋₃)alkyl group;
or a pharmaceutically acceptable salt thereof.

2. The compound according to claim 1; wherein R⁵ represents
(C₁₋₆)alkyl;
(C₁₋₄)alkyl mono-substituted with (C₁₋₃)alkoxy;
—CO—R¹⁰ wherein R¹⁰ represents (C₁₋₅)alkyl; (C₁₋₅)alkoxy; (C₃₋₆)cycloalkyl-(C₁₋₃)alkyl; (C₁₋₃)fluoroalkyl; (C₁₋₃)fluoroalkoxy; (C₁₋₃)alkoxy(C₂₋₃)alkoxy; hydroxy-(C₁₋₃)alkyl; (C₁₋₃)alkoxy-(C₁₋₃)alkyl; or (C₃₋₆)cycloalkyl optionally containing one ring oxygen atom, wherein said cycloalkyl is optionally mono- or di-substituted with fluoro;
(C₂₋₄)fluoroalkyl;
(C₃₋₆)cycloalkyl optionally containing one ring oxygen atom;
(C₃₋₆)cycloalkyl-(C₁₋₃)alkyl, wherein the (C₃₋₆)cycloalkyl group optionally comprises one ring oxygen atom;
or a pharmaceutically acceptable salt thereof.

3. The compound according to claim 1; wherein R⁵ represents
(C₁₋₆)alkyl;
—CO—R¹⁰ wherein R¹⁰ represents (C₁₋₅)alkyl; hydroxy-(C₁₋₃)alkyl; (C₁₋₃)alkoxy-(C₁₋₃)alkyl; or (C₃₋₆)cycloalkyl optionally comprising one ring oxygen atom, wherein said cycloalkyl is unsubstituted, or mono- or di-substituted with fluoro;
(C₂₋₄)fluoroalkyl;
(C₃₋₆)cycloalkyl optionally comprising one ring oxygen atom; or
(C₃₋₆)cycloalkyl-(C₁₋₃)alkyl;
or a pharmaceutically acceptable salt thereof.

4. The compound according to claim 1; wherein (R¹)ₙ represents one optional substituent independently selected from (C₁₋₄)alkyl, (C₁₋₄)alkoxy, halogen, (C₁₋₃)fluoroalkyl, (C₁₋₃)fluoroalkoxy, or cyano;
or a pharmaceutically acceptable salt thereof.

5. The compound according to claim 1; wherein L¹ represents a two-membered linker group selected from —NH—CH₂—*, —O—CH₂—*, or —CH₂CH₂—; wherein the asterisks indicate the bond with which the group L¹ is attached to the carbonyl group;
or a pharmaceutically acceptable salt thereof.

6. The compound according to claim 1; wherein L² represents —CH₂—;
or a pharmaceutically acceptable salt thereof.

7. The compound according to claim 1; wherein Ar¹ represents phenyl which is mono-, or di-substituted, wherein the substituents are independently selected from (C$_{1-4}$)alkyl; (C$_{1-4}$)alkoxy; (C$_{1-3}$)fluoroalkyl; (C$_{1-3}$)fluoroalkoxy; halogen; or cyano; or 6-membered heteroaryl; which is mono-, or di-substituted, wherein the substituents are independently selected from (C$_{1-4}$)alkyl; (C$_{1-4}$)alkoxy; (C$_{1-3}$)fluoroalkyl; (C$_{1-3}$)fluoroalkoxy; halogen; or cyano;

or a pharmaceutically acceptable salt thereof.

8. The compound according to claim 1; wherein R$^4$ represents
- (C$_{2-5}$)alkyl which is mono-substituted with hydroxy; or disubstituted wherein the substituents are independently methoxy or hydroxy;
- —(C$_{2-4}$)alkylene-NR$^6$R$^7$, wherein R$^6$ represents hydrogen or (C$_{1-4}$)alkyl; and R$^7$ represents (C$_{1-4}$)alkyl; (C$_{1-3}$)fluoroalkyl; (C$_{3-6}$)cycloalkyl; or (C$_{3-6}$)cycloalkyl-(C$_{1-3}$)alkyl;
- (C$_{3-6}$)cycloalkyl-(C$_{1-3}$)alkyl, wherein the cycloalkyl group is optionally mono-substituted with hydroxy;
- (C$_{4-7}$)heterocyclyl or (C$_{4-7}$)heterocyclyl-(C$_{1-3}$)alkyl, wherein in the above groups the (C$_{4-7}$)heterocyclyl independently comprises one or two ring heteroatoms independently selected from nitrogen or oxygen; wherein in the above groups said (C$_{4-7}$)heterocyclyl independently is unsubstituted, or mono-, or di-substituted, wherein the substituents are independently selected from:
  - one oxo substituent attached to a ring carbon atom in alpha position to a ring nitrogen; and or
  - (C$_{1-4}$)alkyl attached to a ring nitrogen atom having a free valency; or
  - two fluoro substituents attached to a ring carbon atom;

or a pharmaceutically acceptable salt thereof.

9. The compound according to claim 1; wherein R$^4$ represents
- 2-hydroxy-ethyl, 2-hydroxy-propyl, 2-hydroxy-2-methyl-propyl, 3-hydroxy-3-methyl-butyl, or 2-methoxy-ethyl; 2-hydroxy-3-methoxy-propyl;
- —(C$_{2-4}$)alkylene-NR$^6$R$^7$ selected from 2-amino-ethyl, 2-methylamino-ethyl, 2-dimethylamino-ethyl, 2-diethylamino-ethyl, 3-(dimethylamino)-propyl, 2-ethylamino-ethyl, 2-(ethyl-methylamino)-ethyl, 2-(isopropyl-amino)-ethyl, 2-(isopropyl-methylamino)-ethyl, 2-(diisopropylamino)-ethyl, 2-(tert-butylamino)-ethyl, 2(tert-(butyl-methylamino)-ethyl, 2-[(2-fluoroethyl)-methylamino]-ethyl, 2-[(2,2,2-trifluoroethyl)-amino]-ethyl, 2-[methyl-(2,2,2-trifluoroethyl)-amino]-ethyl, 2-[(2-fluoro-1-methylethyl)-methylamino]-ethyl, 2-[(cyclopropyl)-methylamino]-ethyl, 2-[(cyclopropyl-methyl)-methylamino]-ethyl, 2-[(cyclobutyl)-methyl-amino]-ethyl, or 2-[(cyclopentyl)-methylamino]-ethyl;
- (1-hydroxy-cyclopentyl)-methyl;
- (C$_{4-7}$)heterocyclyl selected from pyrrolidin-3-yl, 1-methyl-pyrrolidin-3-yl, piperidin-3-yl, 1-methyl-piperidin-3-yl, piperidin-4-yl, 1-methyl-piperidin-4-yl, or tetrahydro-pyran-4-yl;
- (C$_{4-7}$)heterocyclyl-(C$_{1-3}$)alkyl selected from 2-(pyrrolidin-1-yl)-ethyl, 2-(1-methyl-pyrrolidin-2-yl)-ethyl, 2-(morpholin-4-yl)-ethyl, pyrrolidin-3-yl-methyl, 3-(pyrrolidin-1-yl)-propyl, 2-(piperazin-1-yl)-ethyl, 2-(piperidin-1-yl)-ethyl, 2-(azepan-1-yl)-ethyl, 2-(3,3-difluoroazetidin-1-yl)-ethyl, 2-(3,3-difluoropyrrolidin-1-yl)-ethyl, 2-(3,3-difluoropiperidin-1-yl)-ethyl, or 2-(4,4-difluoropiperidin-1-yl)-ethyl; or a pharmaceutically acceptable salt thereof.

10. The compound according to claim 1, wherein the compound is:
- N-(2-Dimethylamino-ethyl)-2-(4-isobutyl-2,3,4,5-tetrahydro-benzo[f][1,4]oxazepin-9-ylamino)-N-(2-trifluoromethyl-benzyl)-acetamide;
- N-(2-Dimethylamino-ethyl)-2-(4-isobutyl-2,3,4,5-tetrahydro-benzo[f][1,4]oxazepin-9-ylamino)-N-(3-trifluoromethyl-pyridin-2-ylmethyl)-acetamide;
- N-(3-Chloro-pyridin-2-ylmethyl)-N-(2-dimethylamino-ethyl)-2-(4-isobutyl-2,3,4,5-tetrahydro-benzo[f][1,4]oxazepin-9-ylamino)-acetamide;
- N-(3-Chloro-pyridin-2-ylmethyl)-N-(2-dimethylamino-ethyl)-2-(4-ethyl-2,3,4,5-tetrahydro-benzo[f][1,4]oxazepin-9-ylamino)-acetamide;
- N-(2-Dimethylamino-ethyl)-2-(4-ethyl-2,3,4,5-tetrahydro-benzo[f][1,4]oxazepin-9-ylamino)-N-(2-trifluoromethyl-benzyl)-acetamide;
- N-(3-Chloro-pyridin-2-ylmethyl)-N-(2-dimethylamino-ethyl)-2-(4-propyl-2,3,4,5-tetrahydro-benzo[f][1,4]oxazepin-9-ylamino)-acetamide;
- N-(2-Dimethylamino-ethyl)-2-(4-propyl-2,3,4,5-tetrahydro-benzo[f][1,4]oxazepi9-ylamino)-N-(2-trifluoromethyl-benzyl)-acetamide;
- N-(3-Bromo-benzyl)-N-(2-dimethylamino-ethyl)-2-(4-isobutyl-2,3,4,5-tetrahydro-benzo[f][1,4]oxazepin-9-ylamino)-acetamide;
- N-(2-Dimethylamino-ethyl)-2-(4-isobutyl-2,3,4,5-tetrahydro-benzo[f][1,4]oxazepin-9-ylamino)-N-(4-methoxy-pyridlin-2-ylmethyl)-acetamide;
- N-[2-(Cyclopropyl-methyl-amino)-ethyl]-2-(4-isobutyl-2,3,4,5-tetrahydro-benzo[f][1,4]oxazepin-9-ylamino)-N-(2-trifluoromethyl-benzyl)- acetamide;
- 2-(4-Isobutyl-2,3,4,5-tetrahydro-benzo[f][1,4]oxazepin-9-ylamino)-N-[2-(2-oxo-pyrrolidin-1-yl)-ethyl]-N-(2-trifluoromethyl-benzyl)-acetamide;
- N-(2,4-Difluoro-benzyl)-2-(4-isobutyl-2,3,4,5-tetrahydro-benzo[f][1,4]oxazepin-9-ylamino)-N-(2-pyrrolidin-1-yl-ethyl)-acetamide;
- N-(3-Chloro-pyridin-2-ylmethyl)-N-[2-(4,4-difluoro-piperidin-1-yl)-ethyl]-2-(4-isobutyl-2,3,4,5-tetrahydro-benzo[f][1,4]oxazepin-9-ylamino)-acetamide;
- N-(2,6-Difluoro-benzyl)-N-(2-dimethylamino-ethyl)-2-(4-isobutyl-2,3,4,5-tetrahydro-benzo[f][1,4]oxazepin-9-ylamino)-acetamide;
- 2-(4-Acetyl-2,3,4,5-tetrahydro-benzo[f][1,4]oxazepin-9-ylamino)-N-(2-dimethylamino-ethyl)-N-(2-trifluoromethyl-benzyl)-acetamide;
- N-(2-Dimethylamino-ethyl)-2-(4-ethyl-5-oxo-2,3,4,5-tetrahydro-benzo[f][1,4]oxazepin-9-ylamino)-N-(3-methyl-pyridin-2-ylmethyl)-acetamide;
- N-(2-tert-Butylamino-ethyl)-2-(4-ethyl-5-oxo-2,3,4,5-tetrahydro-benzo[f][1,4]oxazepin-9-ylamino)-N-(2-trifluoromethyl-benzyl)-acetamide;
- N-(2-Dimethylamino-ethyl)-2-(4-ethyl-5-oxo-2,3,4,5-tetrahydro-benzo[f][1,4]oxazepin-9-ylamino)-N-(2-trifluoromethyl-benzyl)-acetamide;
- 2-(4-Ethyl-5-oxo-2,3,4,5-tetrahydro-benzo[f][1,4]oxazepin-9-ylamino)-N-(2-isopropylamino-ethyl)-N-(2-trifluoromethyl-benzyl)-acetamide;
- 2-(4-Ethyl-5-oxo-2,3,4,5-tetrahydro-benzo[f][1,4]oxazepin-9-ylamino)-N-(2-pyrrolidin-1-yl-ethyl)-N-(3-trifluoromethyl-pyridin-2-ylmethyl)-acetamide;
- N-(2-Dimethylamino-ethyl)-2-(4-ethyl-5-oxo-2,3,4,5-tetrahydro-benzo[f][1,4]oxazepin-9-ylamino)-N-(3-trifluoromethyl-pyridin-2-ylmethyl)-acetamide;

N-(3-Chloro-pyridin-2-ylmethyl)-2-(4-ethyl-5-oxo-2,3,4,5-tetrahydro-benzo[f][1,4]oxazepin-9-ylamino)-N-(2-pyrrolidin-1-yl-ethyl)-acetamide;
N-(3-Chloro-pyridin-2-ylmethyl)-N-(2-dimethylamino-ethyl)-2-(4-ethyl-5-oxo-2,3,4,5-tetrahydro-benzo[f][1,4]oxazepin-9-ylamino)-acetamide;
2-(4-Cyclopropylmethyl-5-oxo-2,3,4,5-tetrahydro-benzo[f][1,4]oxazepin-9-ylamino)-N-(2-dimethylamino-ethyl)-N-(2-trifluoromethyl-benzyl)-acetamide;
2-(4-Cyclopropylmethyl-5-oxo-2,3,4,5-tetrahydro-benzo[f][1,4]oxazepin-9-ylamino)-N-(2-isopropylamino-ethyl)-N-(2-trifluoromethyl-benzyl)-acetamide;
N-(2-tert-Butylamino-ethyl)-2-(4-cyclopropylmethyl-5-oxo-2,3,4,5-tetrahydro-benzo[f][1,4]oxazepin-9-ylamino)-N-(2-trifluoromethyl-benzyl)-acetamide;
2-(4-Cyclopropylmethyl-5-oxo-2,3,4,5-tetrahydro-benzo[f][1,4]oxazepin-9-ylamino)-N-(2-pyrrolidin-1-yl-ethyl)-N-(3-trifluoromethyl-pyridin-2-ylmethyl)-acetamide;
2-(4-Cyclopropylmethyl-3-oxo-2,3,4,5-tetrahydro-benzo[f][1,4]oxazepin-9-ylamino)-N-(2-pyrrolidin-1-yl-ethyl)-N-(3-trifluoromethyl-pyridin-2-ylmethyl)-acetamide;
N-(2-tert-Butylamino-ethyl)-2-(4-cyclopropylmethyl-3-oxo-2,3,4,5-tetrahydro-benzo[f][1,4]oxazepin-9-ylamino)-N-(2-trifluoromethyl-benzyl)-acetamide;
2-(4-Cyclopropylmethyl-3-oxo-2,3,4,5-tetrahydro-benzo[f][1,4]oxazepin-9-ylamino)-N-(2-dimethylamino-ethyl)-N-(2-trifluoromethyl-benzyl)-acetamide;
2-(4-Cyclopropylmethyl-3-oxo-2,3,4,5-tetrahydro-benzo[f][1,4]oxazepin-9-ylamino)-N-(2-isopropylamino-ethyl)-N-(2-trifluoromethyl-benzyl)-acetamide;
{2-[[2-(4-Ethyl-2,3,4,5-tetrahydro-benzo[f][1,4]oxazepin-9-ylamino)-acetyl]-(2-trifluoromethyl-benzyl)-amino]-ethyl}-isopropyl-carbamic acid tert-butyl ester;
N-(2-tert-Butylamino-ethyl)-2-(4-ethyl-2,3,4,5-tetrahydro-benzo[f][1,4]oxazepin-9-ylamino)-N-(2-trifluoromethyl-benzyl)-acetamide;
2-(4-Ethyl-2,3,4,5-tetrahydro-benzo[f][1,4]oxazepin-9-ylamino)-N-(2-isopropylamino-ethyl)-N-(2-trifluoromethyl-benzyl)-acetamide;
N-(2-Dimethylamino-ethyl)-2-(4-ethyl-2,3,4,5-tetrahydro-benzo[f][1,4]oxazepin-9-ylamino)-N-(3-trifluoromethyl-pyridin-2-ylmethyl)-acetamide;
N-(2-Dimethylamino-ethyl)-2-(4-ethyl-2,3,4,5-tetrahydro-benzo[f][1,4]oxazepin-9-ylamino)-N-(3-methyl-pyridin-2-ylmethyl)-acetamide;
2-(4-Ethyl-2,3,4,5-tetrahydro-benzo[f][1,4]oxazepin-9-ylamino)-N-(2-pyrrolidin-1-yl-ethyl)-N-(3-trifluoromethyl-pyridin-2-ylmethyl)-acetamide;
N-(3-Chloro-pyridin-2-ylmethyl)-2-(4-ethyl-2,3,4,5-tetrahydro-benzo[f][1,4]oxazepin-9-ylamino)-N-(2-pyrrolidin-1-yl-ethyl)-acetamide;
N-(2-Dimethylamino-ethyl)-2-(4-ethyl-2,3,4,5-tetrahydro-benzo[f][1,4]oxazepin-9-ylamino)-N-(2-trifluoromethyl-thiazol-5-ylmethyl)-acetamide;
N-(5-Chloro-1-methyl-3-trifluoromethyl-1H-pyrazol-4-ylmethyl)-N-(2-dimethylamino-ethyl)-2-(4-ethyl-2,3,4,5-tetrahydro-benzo[f][1,4]oxazepin-9-ylamino)-acetamide;
(2-{(3-Chloro-pyridin-2-ylmethyl)-[2-(4-ethyl-2,3,4,5-tetrahydro-benzo[f][1,4]oxazepin-9-ylamino)-acetyl]-amino}-ethyl)-methyl-carbamic acid tert-butyl ester;
2-(4-Cyclopropylmethyl-2,3,4,5-tetrahydro-benzo[f][1,4]oxazepin-9-ylamino)-N-(2-pyrrolidin-1-yl-ethyl)-N-(3-trifluoromethyl-pyridin-2-ylmethyl)-acetamide;
N-(2-tert-Butylamino-ethyl)-2-(4-cyclopropylmethyl-2,3,4,5-tetrahydro-benzo[f][1,4]oxazepin-9-ylamino)-N-(2-trifluoromethyl-benzyl)-acetamide;
2-(4-Cyclopropylmethyl-2,3,4,5-tetrahydro-benzo[f][1,4]oxazepin-9-ylamino)-N-(2-dimethylamino-ethyl)-N-(2-trifluoromethyl-benzyl)-acetamide; or
2-(4-Cyclopropylmethyl-2,3,4,5-tetrahydro-benzo[f][1,4]oxazepin-9-ylamino)-N-(2-isopropylamino-ethyl)-N-(2-trifluoromethyl-benzyl)-acetamide;

or a pharmaceutically acceptable salt thereof.

11. A pharmaceutical composition comprising, as active principle, the compound according to claim 1, or a pharmaceutically acceptable salt thereof, and at least one therapeutically inert excipient.

12. A method of treating a disease comprising administering to a subject in need thereof an amount of the compound of formula (I) according to claim 1, wherein the disease is a cancer selected from carcinomas, leukemias, adenocarcinomas, malignant glioma, glioblastoma multiforme, brain metastases, multiple myelomas, renal clear cell carcinoma, prostate cancer, pancreatic adenocarcinoma, melanoma, metastatic melanoma, hepatocellular carcinoma, colon tumors, breast cancer, non-small cell lung cancer, colorectal cancer, brain tumors, Ewing's sarcoma, lymphoma, Burkitt's lymphoma, Hodgkin's lymphoma, adult T-cell leukemia, lymphoproliferative disease, and Kaposi's sarcoma;

an autoimmune disorder selected from multiple sclerosis, rheumatoid arthritis, inflammatory bowel disease, systemic lupus erythematosus, lupus nephritis, interstitial cystitis, celiac disease, auto-immune encephalomyelitis, demyelinating diseases, osteoarthritis, and type I diabetes;

an inflammatory disease selected from chronic rhinosinusitis, asthma, chronic obstructive pulmonary disorder, atherosclerosis, myocarditis, and sarcoidosis;

a transplant rejection selected from renal allograft rejection, cardiac allograft rejection, and graft-versus-host diseases brought about by hematopoietic stem cell transplantation; or fibrosis selected from liver fibrosis, liver cirrhosis, and idiopathic pulmonary fibrosis.

13. A method of treating a disease comprising administering to a subject in need thereof an amount of a pharmaceutical composition according to claim 11, wherein the disease is a cancer selected from carcinomas, leukemias, adenocarcinomas, malignant glioma, glioblastoma multiforme, brain metastases, multiple myelomas, renal clear cell carcinoma, prostate cancer, pancreatic adenocarcinoma, melanoma, metastatic melanoma, hepatocellular carcinoma, colon tumors, breast cancer, non-small cell lung cancer, colorectal cancer, brain tumors, Ewing's sarcoma, lymphoma, Burkitt's lymphoma, Hodgkin's lymphoma, adult T-cell leukemia, lymphoproliferative disease, and Kaposi's sarcoma;

an autoimmune disorder selected from multiple sclerosis, rheumatoid arthritis, inflammatory bowel disease, systemic lupus erythematosus, lupus nephritis, interstitial cystitis, celiac disease, auto-immune encephalomyelitis, demyelinating diseases, osteoarthritis, and type I diabetes;

an inflammatory disease selected from chronic rhinosinusitis, asthma, chronic obstructive pulmonary disorder, atherosclerosis, myocarditis, and sarcoidosis;

a transplant rejection selected from renal allograft rejection, cardiac allograft rejection, and graft-versus-host diseases brought about by hematopoietic stem cell transplantation; or a fibrosis selected from liver fibrosis, liver cirrhosis, and idiopathic pulmonary fibrosis.

14. A method of treating a tumor comprising administering to a subject in need thereof an effective amount of the compound of formula (I) according to claim 1, or of a pharmaceutically acceptable salt thereof, wherein said effective amount leads to a change of tumor properties, said change being achieved by modulating a CXCL12 receptor pathway; wherein said subject has a cancer selected from carcinomas, leukemias, adenocarcinomas, malignant glioma, glioblastoma multiforme, brain metastases, multiple myelomas, renal clear cell carcinoma, prostate cancer, pancreatic adenocarcinoma, melanoma, metastatic melanoma, hepatocellular carcinoma, colon tumors, breast cancer, non-small cell lung cancer, colorectal cancer, brain tumors, Ewing's sarcoma, lymphoma, Burkitt's lymphoma, Hodgkin's lymphoma, adult T-cell leukemia, lymphoproliferative disease, and Kaposi's sarcoma.

15. A method of modulating an immune response comprising administering an effective amount of the compound of formula (I) according to claim 1, or a pharmaceutically acceptable salt thereof, wherein said effective amount modulates an inflammatory disease selected from chronic rhinosinusitis, asthma, chronic obstructive pulmonary disorder, atherosclerosis, myocarditis, and sarcoidosis, said modulation being mediated by a CXCL12 receptor pathway.

16. A method of treating cancer comprising administering to a subject in need thereof an effective amount of the compound according to formula (I); wherein said compound is optionally administered in combination with one or more chemotherapy agents having anti-neoplastic activity, selected from alkylating agents selected from mechlorethamine, chlorambucil, cyclophosphamide, ifosfamide, streptozocin, carmustine, lomustine, melphalan, busulfan, dacarbazine, temozolomide, thiotep a or altretamine, platinum drugs selected from cisplatin, carboplatin or oxaliplatin, antimetabolite drugs selected from 5-fluorouracil, capecitabine, 6-mercaptopurine, methotrexate, gemcitabine, cytarabine, fludarabine or pemetrexed, anti-tumor antibiotics selected from daunorubicin, doxorubicin, epirubicin, idarubicin, actinomycin-D, bleomycin, mitomycin-C or mitoxantrone, mitotic inhibitors selected from paclitaxel, docetaxel, ixabepilone, vinblastine, vincristine, vinorelbine, vindesine or estramustine, or topoisomerase inhibitors selected from etoposide, teniposide, topotecan, irinotecan, diflomotecan or elomotecan;

radiotherapy; or targeted therapy;

wherein said cancer is selected from carcinomas, leukemias, adenocarcinomas, malignant glioma, glioblastoma multiforme, brain metastases, multiple myelomas, renal clear cell carcinoma, prostate cancer, pancreatic adenocarcinoma, melanoma, metastatic melanoma, hepatocellular carcinoma, colon tumors, breast cancer, non-small cell lung cancer, colorectal cancer, brain tumors, Ewing's sarcoma, lymphoma, Burkitt's lymphoma, Hodgkin's lymphoma, adult T-cell leukemia, lymphoproliferative disease, and Kaposi's sarcoma.

* * * * *